United States Patent
Canan et al.

(10) Patent No.: US 10,420,772 B2
(45) Date of Patent: Sep. 24, 2019

(54) ANIMAL AND HUMAN ANTI-TRYPANOSOMONAL AND ANTI-LEISHMANIA AGENTS

(71) Applicant: Celgene Corporation, Summit, NJ (US)

(72) Inventors: Stacie S. Canan, La Jolla, CA (US); Natalie Anne Hawryluk, San Diego, CA (US); Michael John Witty, Dover (GB)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 16/000,969

(22) Filed: Jun. 6, 2018

(65) Prior Publication Data

US 2018/0280399 A1 Oct. 4, 2018

Related U.S. Application Data

(62) Division of application No. 15/611,061, filed on Jun. 1, 2017, now Pat. No. 1,001,055.

(60) Provisional application No. 62/344,759, filed on Jun. 2, 2016.

(51) Int. Cl.
| | | |
|---|---|---|
| A61K 31/52 | (2006.01) | |
| A61K 45/06 | (2006.01) | |
| G01N 33/569 | (2006.01) | |
| C07C 211/36 | (2006.01) | |
| C07C 211/57 | (2006.01) | |
| C07C 13/06 | (2006.01) | |
| C07C 13/10 | (2006.01) | |
| C07C 217/02 | (2006.01) | |
| C07D 413/02 | (2006.01) | |
| C07D 473/32 | (2006.01) | |

(52) U.S. Cl.
CPC ............. *A61K 31/52* (2013.01); *A61K 45/06* (2013.01); *C07C 211/36* (2013.01); *C07C 211/57* (2013.01); *C07D 413/02* (2013.01); *C07D 473/32* (2013.01); *C07C 13/06* (2013.01); *C07C 13/10* (2013.01); *C07C 217/02* (2013.01); *G01N 33/56905* (2013.01)

(58) Field of Classification Search
CPC ........ A61K 31/52; A61K 45/06; C07C 13/06; C07C 13/10; C07C 211/36; C07C 211/57; C07C 217/02; C07D 413/02; C07D 473/32; G01N 3/56905
See application file for complete search history.

(56) References Cited

U.S. PATENT DOCUMENTS

| | | |
|---|---|---|
| 7,521,446 B2 | 4/2009 | Albers et al. |
| 7,723,340 B2 | 5/2010 | Albers et al. |
| 7,759,342 B2 | 7/2010 | Bennett et al. |
| 8,158,635 B2 | 4/2012 | Beauchamps et al. |
| 8,440,661 B2 | 5/2013 | Bennett et al. |
| 9,512,124 B2 | 12/2016 | Alexander et al. |
| 9,725,450 B2 | 8/2017 | Clareen et al. |
| 2010/0056494 A1 | 3/2010 | Winzeler et al. |
| 2016/0039822 A1 | 2/2016 | Clareen et al. |

FOREIGN PATENT DOCUMENTS

| | | | |
|---|---|---|---|
| WO | WO 2006/076595 | * | 7/2006 |
| WO | WO 2010/059418 | | 5/2010 |

OTHER PUBLICATIONS

Wilen et al., (1977) "Strategies in optical resolutions," *Tetrahedron*, 33.21 (1977): 2725-2736.

* cited by examiner

*Primary Examiner* — Erich A Leeser
(74) *Attorney, Agent, or Firm* — Jones Day

(57) ABSTRACT

Provided herein are Aminopurine compounds of Formula I:

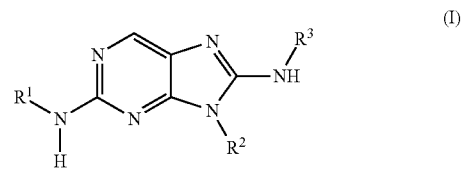

or pharmaceutically acceptable salts, tautomers, isotopologues, or stereoisomers thereof, wherein $R^1$, $R^2$, and $R^3$ are as defined herein, compositions comprising an effective amount of an Aminopurine Compound, and methods for treating or preventing animal and human protozoal infections.

35 Claims, No Drawings

ANIMAL AND HUMAN ANTI-TRYPANOSOMONAL AND ANTI-LEISHMANIA AGENTS

This application is a divisional of U.S. patent application Ser. No. 15/611,061, filed Jun. 1, 2017, currently allowed, which claims the benefit of U.S. Provisional Application No. 62/344,759, filed Jun. 2, 2016, the entire contents of which is incorporated herein by reference.

FIELD

Provided herein are certain aminopurine compounds, compositions comprising an effective amount of such compounds, and methods for treating or preventing trypanosomosis, trypanosomiasis, or leishmaniasis, comprising administering an effective amount of such aminopurine compounds to a subject in need thereof. Accordingly, also provided herein are such compounds for use in said methods for treating or preventing trypanosomosis, trypanosomiasis, or leishmaniasis.

BACKGROUND

Protozoa of the genus *Trypanosoma* and *Leishmania* are known to cause a number of diseases in animals and humans. These protozoa can be transmitted by blood feeding invertebrates, by mechanical vectors or venereally, and are responsible for a number of diseases known as trypanosomosis or trypanosomiasis and leishmaniasis. Animal African Trypanosomosis (AAT), Human African Trypanosomiasis (HAT), Chagas disease and leishmaniasis are such parasitic diseases, which result in significant morbidity and mortality.

Animal trypanosomosis or African animal trypanosomosis (AAT) is one of the most significant infectious threats to cattle and other livestock in sub-Saharan Africa, and it also is also widespread in Asia and South America. African animal trypanosomosis (AAT) remains one of the biggest infectious disease constraints to productive livestock rearing in sub-Saharan Africa. AAT is also becoming increasingly prevalent beyond this region and is an established threat to animal health in South America and Asia. Trypanosomes are spread by the bite of infected tsetse flies (*Glossina* species). Certain *Trypanoxome* species can be mechanically transmitted by biting flies or by venereal transmission. Animal trypanosomosis clinical symptoms vary from per-acute to chronic and include intermittent fever, anaemia, weight loss, hypertrophy of lymph nodes, oedema, hemorrhages, rough hair coat, lacrimation, abortion, sterility, and reduction in draught power. Death often follows in animals not treated effectively. There are veterinary trypanocidal drugs, based on several families of compounds, however, most were developed more than 50 years ago, that are used for treatment and chemoprophylaxis. Widespread resistance is reported against the available trypanocidal drugs. Many of the current drugs for animal trypanosomosis have poor therapeutic indices and there are concerns about their human safety (meat and milk residues and exposure of administrators to the drug). All of these current therapies have deficiencies, including resistance and safety, and new trypanocidal agents are urgently needed.

Human African trypanosomiasis (HAT), also known as sleeping sickness, is transmitted by the tsetse fly (*Glossina* genus) which have acquired their infection from human beings or from animals harboring the human pathogenic parasites. In the early stages of HAT, the trypanosomes multiply in subcutaneous tissues, blood and lymph. This is also called the hemo-lymphatic stage, which produces bouts of fever, headaches, joint pains and itching. In the advanced stage of HAT, the parasites cross the blood-brain barrier to infect the central nervous system, known as the neurological or meningo-encephalic stage. Symptoms include changes of behavior, confusion, sensory disturbances, poor coordination and sleep disturbances. Without treatment, sleeping sickness is considered fatal. Several drugs are used to treat the early and advanced stages of HAT, however, the treatments are marred by toxicities (including fatalities), complex and difficult administration, low response rates, resistance and narrow therapeutic indices.

A different form of human trypanosomiasis occurs mainly in Latin America and is known as American trypanosomiasis or Chagas disease, caused by the *T. cruzi* trypanosome species. Chagas is vector-borne by contact with feces or urine of blood-sucking triatomine bugs (insects), known as kissing bugs. Chagas disease occurs mainly in the continental part of Latin America, but has been increasingly detected in the United States, Canada, and many European and some Western Pacific countries. Chagas disease presents itself in two phases. The initial, acute phase lasts for about 2 months after infection. During the acute phase, a high number of parasites circulate in the blood but in most cases symptoms are absent or mild. In less than 50% of people bitten by a triatomine bug, characteristic first visible signs may be a skin lesion or a purplish swelling of the lids of one eye. Additionally patients may present with fever, headache, enlarged lymph glands, pallor, muscle pain, difficulty in breathing, swelling, and abdominal or chest pain. During the chronic phase, the parasites are hidden mainly in the heart and digestive muscles. Up to 30% of patients suffer from cardiac disorders and up to 10% suffer from digestive (typically enlargement of the esophagus or colon), neurological or mixed alterations. In later years the infection may lead to sudden death or heart failure caused by progressive destruction of the heart muscle and the nervous system. Chagas disease can be treated with benznidazole and also nifurtimox. Both medicines are effective in curing the disease if given soon after infection at the onset of the acute phase including the cases of congenital transmission. The efficacy of both drugs diminishes, however, the longer a person has been infected.

Leishmaniasis is a disease caused by protozoa of the genus *Leishmania*. Primary hosts are mammals, including human and rodents. Typically, Leishmaniasis results from *Leishmania* transmission by the bite of certain species of sand fly (e.g. *Phiebotominae* and *Lutzomyi*). The human disease is zoonotic (i.e transmissible from non-human animals), but some can be spread between humans. There are three main forms of leishmaniases—visceral (the most serious form of the disease), cutaneous (the most common), and mucocutaneous. Visceral leishmaniasis (VL; caused by *L. donovani*), also known as kala-azar is fatal if left untreated in over 95% of cases. It is characterized by irregular bouts of fever, weight loss, enlargement of the spleen and liver, and anemia. It is highly endemic in the Indian subcontinent and in East Africa. An estimated 200,000 to 400,000 new cases of VL occur worldwide each year. Over 90% of new cases occur in six countries: Bangladesh, Brazil, Ethiopia, India, South Sudan and Sudan. Post-kala-azar dermal leishmaniasis (PKDL) is a sequel of visceral leishmaniasis that appears as macular, papular or nodular rash usually on face, upper arms, trunks and other parts of the body. It occurs mainly in East Africa and the Indian subcontinent. It usually appears 6 months to 1 or more years after kala-azar has apparently been cured, but may occur earlier. People with PKDL are considered to be a potential source of kala-azar infection. Cutaneous leishmaniasis (CL) is the most common form of leishmaniasis and causes skin lesions, mainly ulcers, on exposed parts of the body, leaving life-long scars and serious disability. About 95% of CL cases occur in the Americas, the Mediterranean basin, the Middle East and Central Asia. Over two thirds of new CL cases occur in 6 countries: Afghanistan, Algeria, Brazil, Colombia, Iran and the Syrian Arab Republic. Mucocutaneous leishmaniasis leads to partial or total destruction of mucous membranes of the nose, mouth and throat. Almost 90% of mucocutaneous leishmaniasis cases occur in Bolivia, Brazil and Peru. The current treatments suffer from safety/toxicity concerns (including cardiotoxicty), incomplete cure rates, difficult administration, long duration of treatment, lack of compliance and developing resistance. (Disease descriptions and facts were obtained from www.who.org).

Consequently, there remains a need to develop effective therapeutic agents for the infectious diseases and their symptoms described above.

Citation or identification of any reference in this application is not to be construed as an admission that the reference is prior art to the present application.

SUMMARY

Provided herein are Aminopurine Compounds of formula (I)

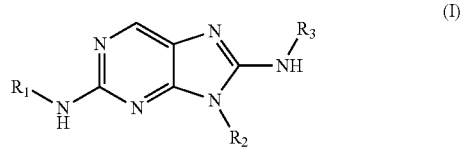

wherein $R^1$, $R^2$ and $R^3$ are as defined herein.

In one aspect, provided herein are Aminopurine Compounds as described in the instant disclosure, such as, for example, an Aminopurine Compound of formula (I), or a compound from Table 1 or Table 2.

In one aspect, provided herein are pharmaceutical compositions comprising an effective amount of an Aminopurine Compound, as described herein, and a pharmaceutically acceptable carrier, excipient or vehicle. In some embodiments the pharmaceutical composition is suitable for oral, parenteral, mucosal, transdermal or topical administration.

In one aspect, provided herein are uses of Aminopurine Compounds for treating or preventing trypanosomosis, trypanosomiasis, and/or leishmaniasis, wherein the methods comprise administering to a subject in need thereof an effective amount of an Aminopurine Compound as described herein. In another aspect, provided herein are uses of Aminopurine Compounds for treating or preventing trypanosomosis, trypanosomiasis, and/or leishmaniasis, wherein the methods comprise administering to a subject in need thereof an effective amount of an Aminopurine Compound as described herein.

In one aspect, provided herein is an Aminopurine Compound for use as a medicament. Provided is the Aminopurine Compound for use in a method for the treatment or prevention of trypanosomosis, trypanosomiasis, or leishmaniasis, the method comprising administering to a subject in need thereof an effective amount of the Aminopurine Compound. Provided herein is an Aminopurine Compound for use in a method of treating or preventing Animal trypanosomosis or African animal trypanosomosis (AAT), the method comprising administering to a subject in need thereof an effective amount of the Aminopurine Compound. Provided herein is an Aminopurine Compound for use in a method of treating or preventing Human African trypanosomiasis (HAT), comprising administering to a subject in need thereof an effective amount of the Aminopurine Compound. Provided herein is an Aminopurine Compound for use in a method of treating or preventing American trypanosomiasis or Chagas disease, comprising administering to a subject in need thereof an effective amount of the Aminopurine Compound. Provided herein is an Aminopurine Compound for use in a method of treating or preventing Leishmaniasis, comprising administering to a subject in need thereof an effective amount of the Aminopurine Compound.

In another aspect provided herein are methods for preparing Aminopurine Compounds as described herein.

The present embodiments can be understood more fully by reference to the detailed description and examples, which are intended to exemplify non-limiting embodiments.

DETAILED DESCRIPTION

Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. Examples of unsaturated alkyl groups include, but are not limited to, vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_2$CH$_3$), among others. An alkyl group can be substituted or unsubstituted. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; $B(OH)_2$, or O(alkyl)aminocarbonyl.

A "cycloalkyl" group is a saturated, or partially saturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d]oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-one or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indolyl-2-onyl or isoindolin-1-onyl), indolinyl, isoindolyl, isoindolinyl, azaindolyl (pyrrolopyridyl or 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (i.e., benzo[d]oxazolyl), benzothiazolyl, benzothiadiazolyl, benzo[1,3]dioxolyl, pyrazolopyridyl (for example, 1H-pyrazolo[3,4-b]pyridyl, 1H-pyrazolo[4,3-b]pyridyl), imidazopyridyl (e.g., azabenzimidazolyl or 1H-imidazo[4,5-b]pyridyl), triazolopyridyl, isoxazolopyridyl, purinyl, xanthinyl, adeninyl, guaninyl, quinolinyl, isoquinolinyl (e.g., 3,4-dihydroisoquinolin-1(2H)-onyl), quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-only or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

A "cycloalkylalkyl" group is a radical of the formula: -alkyl-cycloalkyl, wherein alkyl and cycloalkyl are as defined above. Substituted cycloalkylalkyl groups may be substituted at the alkyl, the cycloalkyl, or both the alkyl and the cycloalkyl portions of the group. Representative cycloalkylalkyl groups include but are not limited to methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopentyl, propylcyclohexyl and the like.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

An "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyridin-3-yl methyl, tetrahydrofuran-2-yl ethyl, and indol-2-yl propyl.

A "halogen" is fluorine, chlorine, bromine or iodine.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amino" group is a radical of the formula: —NH$_2$.

An "alkylamino" group is a radical of the formula: —NH-alkyl or —N(alkyl)$_2$, wherein each alkyl is independently as defined above.

A "carboxy" group is a radical of the formula: —C(O)OH.

An "aminocarbonyl" group is a radical of the formula: —C(O)N(R#)$_2$, —C(O)NH(R$^#$) or —C(O)NH$_2$, wherein each R$^#$ is independently a substituted or unsubstituted alkyl, cycloalkyl, aryl, aralkyl, heterocyclyl or heterocyclyl group as defined herein.

An "acylamino" group is a radical of the formula: —NHC(O)(R$^#$) or —N(alkyl)C(O)(R$^#$), wherein each alkyl and R$^#$ are independently as defined above.

A "sulfonylamino" group is a radical of the formula: —NHSO$_2$(R$^#$) or —N(alkyl)SO$_2$(R$^#$), wherein each alkyl and R$^#$ are defined above.

A "urea" group is a radical of the formula: —N(alkyl)C(O)N(R$^#$)$_2$, —N(alkyl)C(O)NH(R$^#$), —N(alkyl)C(O)NH$_2$, —NHC(O)N(R$^#$)$_2$, —NHC(O)NH(R$^#$), or —NH(CO)NHR#, wherein each alkyl and R$^#$ are independently as defined above.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl) aryloxy; aralkyloxy; heterocyclyloxy; and heterocyclyl alkoxy.

As used herein, the term "Aminopurine Compound" refers to compounds of formula (I) as well as to further embodiments of compounds of formula (I) provided herein. For example, the term "Aminopurine Compound" refers to deuterated compounds of formula (I). In one embodiment, an "Aminopurine Compound" is a compound set forth in Table 1 or Table 2. In certain embodiments, the term "Aminopurine Compound" includes pharmaceutically acceptable salts, tautomers, isotopologues, and/or stereoisomers of the Aminopurine Compounds provided herein.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride and mesylate salts. Others are well-known in the art, see for example, *Remington's Pharmaceutical Sciences,* 18$^{th}$ eds., Mack Publishing, Easton Pa. (1990) or *Remington: The Science and Practice of Pharmacy,* 19$^{th}$ eds., Mack Publishing, Easton Pa. (1995).

As used herein and unless otherwise indicated, the term "stereoisomer" or "stereomerically pure" means one stereoisomer of an Aminopurine Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Aminopurine Compounds can have chiral centers and can occur as racemates, individual enantiomers or diastereomers, and mixtures thereof. All such isomeric forms are included within the embodiments disclosed herein, including mixtures thereof.

The use of stereomerically pure forms of such Aminopurine Compounds, as well as the use of mixtures of those forms, are encompassed by the embodiments disclosed herein. For example, mixtures comprising equal or unequal amounts of the enantiomers of a particular Aminopurine Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Aminopurine Compounds can include E and Z isomers, or a mixture thereof, and cis and trans isomers or a mixture thereof. In certain embodiments, the Aminopurine Compounds are isolated as either the E or Z isomer. In other embodiments, the Aminopurine Compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

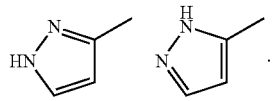

As readily understood by one skilled in the art, a wide variety of functional groups and other structures may exhibit tautomerism and all tautomers of compounds of formula (I) are within the scope of the present invention.

It should also be noted the Aminopurine Compounds can contain unnatural proportions of atomic isotopes at least one of the atoms. For example, the compounds may be radiolabeled with radioactive isotopes, such as for example tritium ($^3$H), iodine-125 ($^{125}$I) sulfur-35 ($^{35}$S), or carbon-14 ($^{14}$C), or may be isotopically enriched, such as with carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the Aminopurine Compounds as described herein, whether radioactive or not, are intended to be encompassed within the scope of the embodiments provided herein. In some embodiments, there are provided isotopologues of the Aminopurine Compounds, for example, the isotopologues are carbon-13, or nitrogen-15 enriched Aminopurine Compounds. As used herein, "deuterated", means a compound wherein at least one hydrogen (H) has been replaced by deuterium (indicated by D or $^2$H), that is, the compound is enriched in deuterium in at least one position.

It should be noted that if there is a discrepancy between a depicted structure and a name for that structure, the depicted structure is to be accorded more weight.

As used herein, "inhibit" and "inhibition" mean that a specified response of a designated activity (e.g., parasite growth) is comparatively decreased in the presence of an Aminopurine Compound. Inhibition of parasite growth, for example growth of *T. congolensce, T. vivax* and/or *T. evansi*, can be determined by the assays described herein.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition.

The term "effective amount" in connection with an Aminopurine Compound means an amount capable of treating or preventing a disorder, disease or condition, or symptoms thereof, disclosed herein.

The term "subject" or "patient" includes an animal, including, but not limited to, an animal such a bull, camel, cat, cattle, chicken, cow, deer, dog, donkey, duck, elephant, gerbil, goat, goose, guinea fowl, guinea pig, honey bee, horse, ostrich, otter, pig, pigeon, rabbit, reindeer, sheep, swan, turkey, water buffalo, or yak, in one embodiment a mammal, in another embodiment a human, in another embodiment a cell from any one of the foregoing subjects. In one embodiment, a subject or patient is a non-human animal. In another embodiment, a subject or patient is a non-human mammal.

The term "combination" or administration "in combination" includes administration as a mixture, simultaneous administration using separate formulations, and consecutive administration in any order.

The term "consecutive" means that more than 10 minutes have passed between the administration of the anti-MIF antibody and the administration of the chemotherapeutic agent. The time period can then be more than 10 minutes, more than 30 minutes, more than 1 hour, more than 3 hours, more than 6 hours or more than 12 hours.

In one embodiment, a subject or patient is a human having or at risk for having trypanosomiasis, and/or leishmaniasis.

In some such embodiments, the subject or patient is a human having or at risk for having leishmaniasis. In some such embodiments, the subject or patient is a human having or at risk for having Chagas Disease. In another embodiment, a subject is a bull, camel, cat, cattle, chicken, cow, deer, dog, donkey, duck, elephant, gerbil, goat, goose, guinea fowl, guinea pig, honey bee, horse, ostrich, otter, pig, pigeon, rabbit, reindeer, sheep, swan, turkey, water buffalo, or yak having or at risk for having trypanosomosis. In another embodiment a subject is cattle, having or at risk for having trypanosomosis.

Compounds

Provided herein are Aminopurine Compounds having the following formula (I):

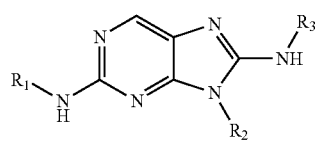

(I)

wherein:

$R^1$ is $CR^{1a}R^{1b}R^{1c}$, wherein each of $R^{1a}$, $R^{1b}$ and $R^{1c}$ is independently $(C_{1-4})$alkyl, or $(C_{1-4})$alkyl(OR); or $R^{1a}$ and $R^{1b}$ and the carbon to which they are attached form a 3-6 membered cycloalkyl or 3-6 membered heterocyclyl, and $R^{1c}$ is $(C_{1-4})$alkyl;

$R^2$ is cycloalkyl or aryl, substituted with at least one $NR_2$, OR, CN, NRC(O)R, $CH_2OR$, $CH_2NR_2$, $CH_2NRCOR$, $CH_2NRCOOR'$, or heterocyclylalkyl;

$R^3$ is phenyl or pyridyl, optionally substituted with at least one halogen, CN, $(C_{1-2})$alkyl, or $O(C_{1-2})$alkyl, wherein the alkyl is optionally fluorinated;

R is H or $(C_{1-4})$ alkyl; and

R' is $(C_{1-4})$alkyl;

provided the Aminopurine Compound is not 4-(2-(tert-butylamino)-8-((2,6-difluorophenyl)amino)-9H-purin-9-yl)cyclohexan-1-ol

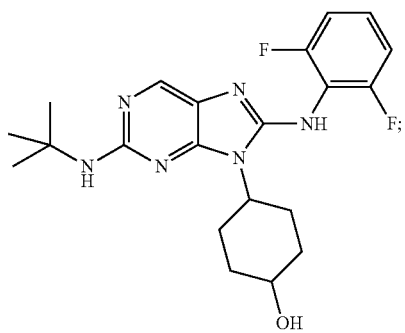 [SMILES: CC(C)(C)Nc1ncc2nc(Nc3c(F)cccc3F)n(C3CCC(O)CC3)c2n1]

4-(2-(tert-butylamino)-8-((2,4,6-trifluorophenyl)amino)-9H-purin-9-yl)cyclohexan-1-ol

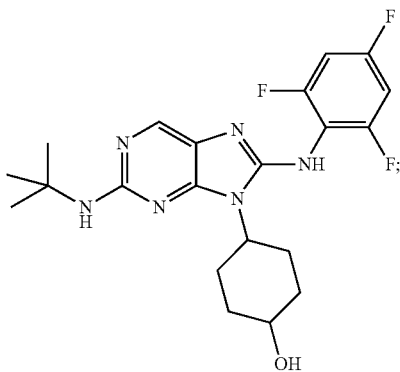 [SMILES: CC(C)(C)Nc1ncc2nc(Nc3c(F)cc(F)cc3F)n(C3CCC(O)CC3)c2n1]

or 4-(2-(tert-butyl amino)-8-((2,4-difluorophenyl)amino)-9H-purin-9-yl)cyclohexan-1-ol

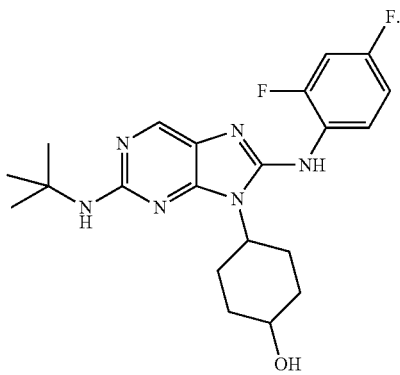 [SMILES: CC(C)(C)Nc1ncc2nc(Nc3ccc(F)cc3F)n(C3CCC(O)CC3)c2n1]

In some embodiments of compounds of formula (I), $R^1$ is $CR^{1a}R^{1b}R^{1c}$, wherein each of $R^{1a}$, $R^{1b}$ and $R^{1c}$ is independently $(C_{1-2})$alkyl. For example, $R^1$ is t-butyl, $C(CH_3)_2CH_2CH_3$, or $C(CH_3)_2CH_2OH$. In other embodiment, $R^1$ is t-butyl. In other embodiment, $R^1$ is $C(CH_3)_2CH_2CH_3$. In other embodiment, $R^1$ is $C(CH_3)_2CH_2OH$. In other embodiments of compounds of formula (I), $R^1$ is $CR^{1a}R^{1b}R^{1c}$, wherein $R^{1a}$ and $R^{1b}$ and the carbon to which they are attached form a 3-6 membered cycloalkyl or 3-6 membered heterocyclyl, and $R^{1c}$ is $(C_{1-4})$alkyl. In some such embodiments, $R^{1a}$ and $R^{1b}$ and the carbon to which they are attached form a cyclopropyl, cyclobutyl, cyclohexyl, or tetrahydropyranyl. In some such embodiments, $R^{1c}$ is $CH_3$. For example, $R^1$ is 1-methylcyclopropyl, 1-methylcyclobutyl, 1-methylcyclpentyl, 1-methyl-tetrahydropyranyl, 4-methyltetrahydropyranyl or 2,2-dimethyltetrahydropyranyl. In one embodiment, $R^1$ is 1-methylcyclopropyl. In one embodiment, $R^1$ is 1-methylcyclobutyl. In one embodiment, $R^1$ is 1-methylcyclpentyl. In one embodiment, $R^1$ is 1-methyltetrahydropyranyl. In one embodiment, $R^1$ is 4-methyltetrahydropyranyl. In a specific embodiment, $R^1$ is 4-methyl-tetrahydropyran-4-yl. In one embodiment, $R^1$ is 2,2-dimethyltetrahydropyranyl. In a specific embodiment, $R^1$ is 2,2-dimethyltetrahydropyran-4-yl.

In some embodiments of compounds of formula (I), $R^2$ is $(C_{3-7})$cycloalkyl, substituted with at least one $NR_2$, OR, CN, NRC(O)R, $CH_2OR$, $CH_2NR_2$, $CH_2NRC(O)R$, $CH_2NRC(O)OR'$ or heterocyclylalkyl. In some such embodiments, $R^2$ is cyclobutyl, cyclopentyl, or cyclohexyl. In some other such embodiments, $R^2$ is substituted with at least one $NH_2$, $NHCH_3$, $N(CH_3)_2$, OH, $OCH_3$, CN, $NHC(O)CH_3$, $N(CH_3)C(O)CH_3$, $CH_2OH$, $CH_2OCH_3$, $CH_2NH_2$, $CH_2NHCH_3$, $CH_2N(CH_3)_2$, $CH_2NHC(O)CH_3$, $CH_2N(CH_3)C(O)CH_3$, $CH_2NHC(O)OCH_3$, $CH_2N(CH_3)C(O)OCH_3$, $CH_2$-piperidyl, or $CH_2$-morpholinyl. In some such embodiments, $R^2$ is cyclobutyl, substituted with $NH_2$. In some embodiments, $R^2$ is cyclohexyl, substituted with $NH_2$, OH, CN, $NHC(O)CH_3$, $CH_2OH$, $CH_2NH_2$, $CH_2NHCH_3$, $CH_2N(CH_3)_2$, $CH_2NHC(O)CH_3$, $CH_2NHC(O)OCH_3$, $CH_2$-piperidyl, or $CH_2$-morpholinyl. In one embodiments, $R^2$ is cyclobutyl substituted with $NH_2$. In one embodiment, $R^2$ is cyclohexyl, substituted with OH. In one embodiment, $R^2$ is cyclohexyl, substituted with CN, $NHC(O)CH_3$. In one embodiment, $R^2$ is cyclohexyl, substituted with $CH_2OH$. In one embodiment, $R^2$ is cyclohexyl, substituted with $CH_2NH_2$. In one embodiment, $R^2$ is cyclohexyl, substituted with $CH_2NHCH_3$. In one embodiment, $R^2$ is cyclohexyl, substituted with $CH_2N(CH_3)_2$. In one embodiment, $R^2$ is cyclohexyl, substituted with $CH_2NHC(O)CH_3$. In one embodiment, $R^2$ is cyclohexyl, substituted with $CH_2NHC(O)OCH_3$. In one embodiment, $R^2$ is cyclohexyl, substituted with $CH_2$-piperidyl. In one embodiment, $R^2$ is cyclohexyl, substituted with $CH_2$-morpholinyl. In yet other embodiments of compounds of formula (I), $R^2$ is aryl, substituted with at least one $NR_2$, OR, CN, NRC(O)R, $CH_2OR$, $CH_2NR_2$, $CH_2NRCOR$, or $CH_2NRCOOR'$. For example, $R^2$ is phenyl, substituted with at least one $NH_2$, $NHCH_3$, $N(CH_3)_2$, OH, $OCH_3$, CN, $NHC(O)CH_3$, $N(CH_3)C(O)CH_3$, $CH_2OH$, $CH_2OCH_3$, $CH_2NH_2$, $CH_2NHCH_3$, $CH_2N(CH_3)_2$, $CH_2NHC(O)CH_3$, $CH_2N(CH_3)C(O)CH_3$, $CH_2NHC(O)OCH_3$, or $CH_2N(CH_3)C(O)OCH_3$. in some embodiments, $R^2$ is phenyl, substituted with $CH_2NH_2$.

In some embodiments of compounds of formula (I), $R^3$ is phenyl, substituted with at least one halogen, fluorinated $(C_{1-2})$alkyl, or O-fluorinated$(C_{1-2})$alkyl. In some such embodiments, $R^3$ is substituted with at least one F, Cl, $CHF_2$, $CF_3$, or $OCF_3$. In other such embodiments, $R^3$ is meta-substituted phenyl, for example, $R^3$ is meta-F-phenyl, meta-Cl-phenyl, meta-$CF_3$-phenyl, or meta-$OCF_3$-phenyl. In one embodiment, $R^3$ is meta-F-phenyl. In one embodiment, $R^3$ is meta-Cl-phenyl. In one embodiment, $R^3$ is meta-$CF_3$-phenyl. In one embodiment, $R^3$ is meta-$OCF_3$-phenyl. In still other embodiments, $R^3$ is bis-meta-substituted phenyl, wherein each substituent is independently F, Cl, or $CF_3$. In one embodiment, $R^3$ is bis-meta-substituted phenyl, wherein each substituent is F. In one embodiment, $R^3$ is bis-meta-substituted phenyl, wherein each substituent is Cl. In one embodiment, $R^3$ is bis-meta-substituted phenyl, wherein one substituent is F and one substituent is Cl. In one embodiment, $R^3$ is bis-meta-substituted phenyl, wherein one substituent is F and one substituent is $CF_3$. In one embodiment, $R^3$ is bis-meta-substituted phenyl, wherein one substituent is Cl and one substituent is $CF_3$. In some embodiments, $R^3$ is para-substituted phenyl, for example, para-$OCF_3$-phenyl, para-$CF_3$-phenyl or para-Cl-phenyl. In one embodiment, $R^3$ is para-Cl-phenyl. In one embodiment, $R^3$ is para-$CF_3$-phenyl. In one embodiment, $R^3$ is para-$OCF_3$-phenyl. In some embodiments, $R^3$ is ortho-F, meta-$CF_3$-phenyl, ortho-F, meta-Cl-phenyl, or ortho-Cl, para-Cl-phenyl. In one embodiment, $R^3$ is ortho-F, meta-F-phenyl. In one embodiment, $R^3$ is ortho-F, meta-$CF_3$-phenyl. In one embodiment, $R^3$ is ortho-F, meta-Cl-phenyl. In one embodiment, $R^3$ is meta-Cl, para-Cl-phenyl. In some other embodiments of formula (I), $R^3$ is pyridyl substituted with at least one halogen, fluorinated $(C_{1-2})$alkyl, O-fluorinated$(C_{1-2})$alkyl or $CF_3$. In one embodiment, $R^3$ is pyridyl substituted with Cl. In one embodiment, $R^3$ is pyridyl substituted with $CF_3$. In some such embodiments, $R^3$ is substituted with at least one F, Cl, $CHF_2$, $CF_3$, or $OCF_3$. In one embodiment, $R^3$ is substituted with at least one Cl, or $CF_3$.

In some embodiments of compounds of formula (I), wherein $R^1$ is $CR^{1a}R^{1b}R^{1c}$, wherein $R^{1a}$ and $R^{1b}$ and the carbon to which they are attached form a 3-6 membered cycloalkyl or 3-6 membered heterocyclyl, and $R^{1c}$ is $(C_{1-4})$alkyl, $R^2$ is cyclohexyl, substituted with $NH_2$, OH, CN, $NHC(O)CH_3$, $CH_2OH$, $CH_2NH_2$, $CH_2NHCH_3$, $CH_2N(CH_3)_2$, $CH_2NHC(O)CH_3$, $CH_2NHC(O)OCH_3$, $CH_2$-piperidyl, or $CH_2$-morpholinyl. In some such embodiments, $R^3$ is meta-substituted phenyl, or bis-meta-substituted phenyl. In some such embodiments, $R^1$ is 1-methylcyclopropyl, 1-methylcyclobutyl, 1-methylcyclpentyl or 1-methyl-tetrahydropyranyl. In others, $R^3$ is meta-F-phenyl, meta-Cl-phenyl, meta-$CF_3$-phenyl, or meta-$OCF_3$-phenyl, or $R^3$ is bis-meta-substituted phenyl, wherein each substituent is independently F, Cl, or $CF_3$.

Further embodiments provided herein include combinations of at least one of the particular embodiments set forth above.

Representative compounds of formula (I) are set forth in Table 1.

In one embodiment, the compound is 9-((1s,4s)-4-(aminomethyl)cyclohexyl)-N8-(3-chlorophenyl)-N2-(4-methyltetrahydro-2H-pyran-4-yl)-9H-purine-2,8-diamine.

In one embodiment, the compound is 9-((1s,4s)-4-(aminomethyl)cyclohexyl)-N8-(3-chlorophenyl)-N2-(1-methylcyclobutyl)-9H-purine-2,8-diamine.

In one embodiment, the compound is 9-((1s,4s)-4-(aminomethyl)cyclohexyl)-N8-(3-chlorophenyl)-N2-tert-pentyl-9H-purine-2,8-diamine.

In one embodiment, the compound is 9-((1s,4s)-4-(aminomethyl)cyclohexyl)-N8-(3-chlorophenyl)-N2-(1-methylcyclopentyl)-9H-purine-2,8-diamine.

In one embodiment, the compound is N8-(3-chlorophenyl)-9-((1s,4s)-4-((dimethylamino)methyl)cyclohexyl)-N2-(4-methyltetrahydro-2H-pyran-4-yl)-9H-purine-2,8-diamine.

In one embodiment, the compound is 9-((1s,4s)-4-(aminomethyl)cyclohexyl)-N2-tert-butyl-N8-(pyridin-2-yl)-9H-purine-2,8-diamine.

In one embodiment, the compound is 9-((1r,4r)-4-(aminomethyl)cyclohexyl)-N8-(3-chlorophenyl)-N2-(4-methyltetrahydro-2H-pyran-4-yl)-9H-purine-2,8-diamine.

In one embodiment, the compound is 9-((1s,4s)-4-(aminomethyl)cyclohexyl)-N2-(4-methyltetrahydro-2H-pyran-4-yl)-N8-(pyridin-2-yl)-9H-purine-2,8-diamine.

In one embodiment, the compound is 9-((1s,4s)-4-(aminomethyl)cyclohexyl)-N8-(2,3-difluorophenyl)-N2-(4-methyltetrahydro-2H-pyran-4-yl)-9H-purine-2,8-diamine, In one embodiment, the compound is (1s,4s)-4-(8-(3-chlorophenylamino)-2-(1-methylcyclopentylamino)-9H-purin-9-yl)cyclohexanol.

In one embodiment, the compound is N-(((1s,4s)-4-(8-(3-chlorophenylamino)-2-(4-methyltetrahydro-2H-pyran-4-ylamino)-9H-purin-9-yl)cyclohexyl)methyl)acetamide.

In one embodiment, the compound is 9-((1s,4s)-4-(aminomethyl)cyclohexyl)-N2-(1-methylcyclopentyl)-N8-(3-(trifluoromethyl)phenyl)-9H-purine-2,8-diamine.

In one embodiment, the compound is 9-((1s,4s)-4-(aminomethyl)cyclohexyl)-N2-tert-pentyl-N8-(3-(trifluoromethyl)phenyl)-9H-purine-2,8-diamine.

In one embodiment, the compound is methyl ((1s,4s)-4-(8-(3-chlorophenylamino)-2-(4-methyltetrahydro-2H-pyran-4-ylamino)-9H-purin-9-yl)cyclohexyl)methylcarbamate.

In one embodiment, the compound is 9-((1s,4s)-4-(aminomethyl)cyclohexyl)-N2-tert-butyl-N8-(3-(trifluoromethyl)phenyl)-9H-purine-2,8-diamine.

In one embodiment, the compound is 9-((1s,4s)-4-(aminomethyl)cyclohexyl)-N2-(1-methylcyclopentyl)-N8-(4-(trifluoromethyl)phenyl)-9H-purine-2,8-diamine.

In one embodiment, the compound is 9-((1r,4r)-4-(aminomethyl)cyclohexyl)-N2-tert-butyl-N8-(3-(trifluoromethyl)phenyl)-9H-purine-2,8-diamine.

In one embodiment, the compound is 9-((1r,4r)-4-(aminomethyl)cyclohexyl)-N2-tert-butyl-N8-p-tolyl-9H-purine-2,8-diamine.

In one embodiment, the compound is ((1s,4s)-4-(8-(3-chlorophenylamino)-2-(4-methyltetrahydro-2H-pyran-4-ylamino)-9H-purin-9-yl)cyclohexyl)methanol.

In one embodiment, the compound is 9-((1R,3S)-3-(aminomethyl)cyclohexyl)-N8-(3-chlorophenyl)-N2-(4-methyltetrahydro-2H-pyran-4-yl)-9H-purine-2,8-diamine.

In one embodiment, the compound is N8-(3-chlorophenyl)-9-((1s,4s)-4-((methylamino)methyl)cyclohexyl)-N2-(4-methyltetrahydro-2H-pyran-4-yl)-9H-purine-2,8-diamine.

In one embodiment, the compound is 9-((1s,4s)-4-(aminomethyl)cyclohexyl)-N2-tert-butyl-N8-(4-(trifluoromethyl)phenyl)-9H-purine-2,8-diamine.

In one embodiment, the compound is 9-((1s,4s)-4-(aminomethyl)cyclohexyl)-N2-tert-pentyl-N8-(4-(trifluoromethyl)phenyl)-9H-purine-2,8-diamine.

In one embodiment, the compound is (1s,4s)-4-(2-(4-methyltetrahydro-2H-pyran-4-ylamino)-8- In one embodiment, the compound is (3-(trifluoromethyl)phenylamino)-9H-purin-9-yl)cyclohexanecarbonitrile.

In one embodiment, the compound is N-((1s,4s)-4-(8-(3-chlorophenylamino)-2-(4-methyltetrahydro-2H-pyran-4-ylamino)-9H-purin-9-yl)cyclohexyl)acetamide.

In one embodiment, the compound is ((1r,4r)-4-(8-(3-chlorophenylamino)-2-(4-methyltetrahydro-2H-pyran-4-ylamino)-9H-purin-9-yl)cyclohexyl)methanol.

In one embodiment, the compound is 9-((1s,4s)-4-aminocyclohexyl)-N8-(3-chlorophenyl)-N2-(4-methyltetrahydro-2H-pyran-4-yl)-9H-purine-2,8-diamine.

In one embodiment, the compound is 9-((1s,4s)-4-(aminomethyl)cyclohexyl)-N2-(4-methyltetrahydro-2H-pyran-4-yl)-N8-(3-(trifluoromethyl)phenyl)-9H-purine-2,8-diamine.

In one embodiment, the compound is 9-((1s,4s)-4-aminocyclohexyl)-N2-tert-butyl-N8-(3-(trifluoromethyl)phenyl)-9H-purine-2,8-diamine.

In one embodiment, the compound is 9-((1r,4r)-4-aminocyclohexyl)-N2-tert-butyl-N8-(3-(trifluoromethyl)phenyl)-9H-purine-2,8-diamine.

In one embodiment, the compound is 9-((1s,4s)-4-(aminomethyl)cyclohexyl)-N2-(4-methyltetrahydro-2H-pyran-4-yl)-N8-(4-(trifluoromethyl)phenyl)-9H-purine-2,8-diamine.

In one embodiment, the compound is 9-(4-(aminomethyl)phenyl)-N8-(3-chlorophenyl)-N2-(4-methyltetrahydro-2H-pyran-4-yl)-9H-purine-2,8-diamine.

In one embodiment, the compound is 9-((1s,4s)-4-(aminomethyl)cyclohexyl)-N8-(5-chloropyridin-3-yl)-N2-(4-methyltetrahydro-2H-pyran-4-yl)-9H-purine-2,8-diamine.

In one embodiment, the compound is 9-((1s,4s)-4-(aminomethyl)cyclohexyl)-N2-(4-methyltetrahydro-2H-pyran-4-yl)-N8-(2-(trifluoromethyl)pyridin-4-yl)-9H-purine-2,8-diamine.

9-(3-aminocyclobutyl)-N8-(3-chlorophenyl)-N2-(4-methyltetrahydro-2H-pyran-4-yl)-9H-purine-2,8-diamine.

In one embodiment, the compound is 9-((1s,4s)-4-(aminomethyl)cyclohexyl)-N8-(3-chloro-5-(trifluoromethyl)phenyl)-N2-(4-methyltetrahydro-2H-pyran-4-yl)-9H-purine-2,8-diamine.

In one embodiment, the compound is 9-((1s,4s)-4-(aminomethyl)cyclohexyl)-N2-(4-methyltetrahydro-2H-pyran-4-yl)-N8-(3-(trifluoromethoxy)phenyl)-9H-purine-2,8-diamine.

In one embodiment, the compound is 9-((1s,4s)-4-(aminomethyl)cyclohexyl)-N2-(4-methyltetrahydro-2H-pyran-4-yl)-N8-(4-(trifluoromethoxy)phenyl)-9H-purine-2,8-diamine.

In one embodiment, the compound is 9-(3-aminocyclobutyl)-N2-tert-butyl-N8-(3,4-dichlorophenyl)-9H-purine-2,8-diamine.

In one embodiment, the compound is N8-(3-chlorophenyl)-N2-(4-methyltetrahydro-2H-pyran-4-yl)-9-((1s,4s)-4-(piperidin-1-ylmethyl)cyclohexyl)-9H-purine-2,8-diamine.

In one embodiment, the compound is N8-(3-chlorophenyl)-N2-(4-methyltetrahydro-2H-pyran-4-yl)-9-((1s,4s)-4-(morpholinomethyl)cyclohexyl)-9H-purine-2,8-diamine.

In one embodiment, the compound is 9-((1s,4s)-4-(aminomethyl)cyclohexyl)-N8-(2-fluoro-5-(trifluoromethyl)phenyl)-N2-(4-methyltetrahydro-2H-pyran-4-yl)-9H-purine-2,8-diamine.

In one embodiment, the compound is 9-((1s,4s)-4-(aminomethyl)cyclohexyl)-N8-(3,5-dichlorophenyl)-N2-(4-methyltetrahydro-2H-pyran-4-yl)-9H-purine-2,8-diamine.

In one embodiment, the compound is 9-((1s,4s)-4-(aminomethyl)cyclohexyl)-N8-(3,5-difluorophenyl)-N2-(4-methyltetrahydro-2H-pyran-4-yl)-9H-purine-2,8-diamine.

In one embodiment, the compound is 9-((1s,4s)-4-(aminomethyl)cyclohexyl)-N2-(4-methyltetrahydro-2H-pyran-4-yl)-N8-(6-(trifluoromethyl)pyridin-2-yl)-9H-purine-2,8-diamine.

In one embodiment, the compound is 9-((1s,4s)-4-(aminomethyl)cyclohexyl)-N8-(2-fluoro-3-(trifluoromethyl)phenyl)-N2-(4-methyltetrahydro-2H-pyran-4-yl)-9H-purine-2,8-diamine.

In one embodiment, the compound is 9-((1s,4s)-4-(aminomethyl)cyclohexyl)-N8-(3-chloro-5-fluorophenyl)-N2-(4-methyltetrahydro-2H-pyran-4-yl)-9H-purine-2,8-diamine In one embodiment, the compound is 9-((1s,4s)-4-(aminomethyl)cyclohexyl)-N2-tert-butyl-N8-(3,5-dichlorophenyl)-9H-purine-2,8-diamine.

In one embodiment, the compound is 9-((1s,4s)-4-(aminomethyl)cyclohexyl)-N8-(3-chloro-2-fluorophenyl)-N2-(4-methyltetrahydro-2H-pyran-4-yl)-9H-purine-2,8-diamine.

In one embodiment, the compound is 9-((1s,4s)-4-(aminomethyl)cyclohexyl)-N8-(5-chloro-2-fluorophenyl)-N2-(4-methyltetrahydro-2H-pyran-4-yl)-9H-purine-2,8-diamine.

In one embodiment, the compound is 9-((1s,4s)-4-(aminomethyl)cyclohexyl)-N8-(3-chlorophenyl)-N2-(1-methylcyclopropyl)-9H-purine-2,8-diamine.

In one embodiment, the compound is 3-(9-((1r,4r)-4-aminocyclohexyl)-2-(tert-butylamino)-9H-purin-8-ylamino)benzonitrile.

In one embodiment, the compound is 9-((1r,4r)-4-aminocyclohexyl)-N2-tert-butyl-N8-(3-chloro-5-(trifluoromethyl)phenyl)-9H-purine-2,8-diamine.

In one embodiment, the compound is 2-(9-((1s,4s)-4-(aminomethyl)cyclohexyl)-8-(3-chlorophenylamino)-9H-purin-2-ylamino)-2-methylpropan-1-ol.

In one embodiment, the compound is 9-((1s,4s)-4-(aminomethyl)cyclohexyl)-N8-(3-chloro-5-(trifluoromethyl)phenyl)-N2-(1-methylcyclobutyl)-9H-purine-2,8-diamine.

In one embodiment, the compound is 9-((1s,4s)-4-((dimethylamino)methyl)cyclohexyl)-N2-(4-methyltetrahydro-2H-pyran-4-yl)-N8-(3-(trifluoromethyl)phenyl)-9H-purine-2,8-diamine.

In one embodiment, the compound is 9-((1s,4s)-4-(aminomethyl)cyclohexyl)-N2-(1-methylcyclobutyl)-N8-(3-(trifluoromethyl)phenyl)-9H-purine-2,8-diamine.

In one embodiment, the compound is 9-((1s,4s)-4-((methylamino)methyl)cyclohexyl)-N2-(4-methyltetrahydro-2H-pyran-4-yl)-N8-(3-(trifluoromethyl)phenyl)-9H-purine-2,8-diamine.

In one embodiment, the compound is 9-(4-aminocyclohexyl)-N8-(2-fluoro-5-(trifluoromethyl)phenyl)-N2-(4-methyltetrahydro-2H-pyran-4-yl)-9H-purine-2,8-diamine.

In one embodiment, the compound is N2-tert-butyl-N8-(3-chloro-2-fluorophenyl)-9-((1s,4s)-4-((dimethylamino)methyl)cyclohexyl)-9H-purine-2,8-diamine.

In one embodiment, the compound is 9-((1s,4s)-4-(aminomethyl)cyclohexyl)-N8-(2-fluoro-5-(trifluoromethyl)phenyl)-N2-(1-methylcyclobutyl)-9H-purine-2,8-diamine.

Also provided herein are compounds selected from Table 2.

In one embodiment, the compound is 9-((1s,4s)-4-(aminomethyl)cyclohexyl)-N8-(3-chlorophenyl)-N2-(tetrahydro-2H-pyran-4-yl)-9H-purine-2,8-diamine.

In one embodiment, the compound is 9-((1r,4r)-4-aminocyclohexyl)-N8-(3-chlorophenyl)-N2-cyclopropyl-9H-purine-2,8-diamine.

In one embodiment, the compound is 9-((1r,4r)-4-aminocyclohexyl)-N8-(3-chlorophenyl)-N2-(cyclopropylmethyl)-9H-purine-2,8-diamine.

In one embodiment, the compound is 9-((1r,4r)-4-aminocyclohexyl)-N8-(3-chlorophenyl)-N2-(2,2,2-trifluoroethyl)-9H-purine-2,8-diamine.

In one embodiment, the compound is 9-((1s,4s)-4-(aminomethyl)cyclohexyl)-N8-(3-chlorophenyl)-N2-methyl-N2-(tetrahydro-2H-pyran-4-yl)-9H-purine-2,8-diamine.

In one embodiment, the compound is ((1s,4s)-4-(8-(3-chlorophenylamino)-2-(tetrahydro-2H-pyran-4-ylamino)-9H-purin-9-yl)cyclohexyl)methanol.

In one embodiment, the compound is 9-((1s,4s)-4-(aminomethyl)cyclohexyl)-N8-(3-chlorophenyl)-N2,N2-dimethyl-9H-purine-2,8-diamine.

In one embodiment, the compound is 9-((1s,4s)-4-(aminomethyl)cyclohexyl)-N8-(3-chlorophenyl)-N2-(2,2-dimethyltetrahydro-2H-pyran-4-yl)-9H-purine-2,8-diamine.

In one embodiment, the compound is 9-((1s,4s)-4-(aminomethyl)cyclohexyl)-N8-(3-chlorophenyl)-N2-methyl-9H-purine-2,8-diamine.

In one embodiment, the compound is 9-((1s,4s)-4-(aminomethyl)cyclohexyl)-N8-(3-chlorophenyl)-N2-(2,2,2-trifluoroethyl)-9H-purine-2,8-diamine.

In one embodiment, the compound is 4-(9-((1s,4s)-4-(aminomethyl)cyclohexyl)-8-(3-chlorophenylamino)-9H-purin-2-ylamino)-1-methylcyclohexanol.

In one embodiment, the compound is 9-((1s,4s)-4-(aminomethyl)cyclohexyl)-N8-(3-chloro-5-(trifluoromethyl)phenyl)-N2-(tetrahydro-2H-pyran-4-yl)-9H-purine-2,8-diamine.

In one embodiment, the compound is 9-((1s,4s)-4-(aminomethyl)cyclohexyl)-N8-(3-chloro-2-fluorophenyl)-N2-(tetrahydro-2H-pyran-4-yl)-9H-purine-2,8-diamine.

In one embodiment, the compound is 9-((1s,4s)-4-(aminomethyl)cyclohexyl)-N8-(2-fluoro-5-(trifluoromethyl)phenyl)-N2,N2-dimethyl-9H-purine-2,8-diamine.

In one embodiment, the compound is 9-((1s,4s)-4-(aminomethyl)cyclohexyl)-N-(2-fluoro-5-(trifluoromethyl)phenyl)-2-(pyrrolidin-1-yl)-9H-purin-8-amine.

In one embodiment, the compound is 9-((1s,4s)-4-(aminomethyl)cyclohexyl)-N8-(2-fluoro-5-(trifluoromethyl)phenyl)-N2-(tetrahydro-2H-pyran-4-yl)-9H-purine-2,8-diamine.

In one embodiment, the compound is 9-((1s,4s)-4-(aminomethyl)cyclohexyl)-N8-(5-chloro-2-fluorophenyl)-N2-(tetrahydro-2H-pyran-4-yl)-9H-purine-2,8-diamine.

Each of the compounds in Table 1 and Table 2 was tested in one or more of the in vitro parasite growth assays and was found to have activity therein.

Methods for Making Compounds

The Aminopurine Compounds of Formula I can be made using conventional organic syntheses and commercially available starting materials. By way of example and not limitation, Aminopurine Compounds of formula (I) can be prepared as described in U.S. Pats. No. 7,723,340, and 8,158,635, or as outlined in Scheme 1, shown below, as well as in the examples set forth herein. It should be noted that one skilled in the art would know how to modify the procedures set forth in the illustrative schemes and examples to arrive at the desired products.

Scheme 1

-continued

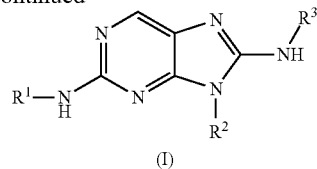

As shown in Scheme 1, compounds of formula (I), wherein $R^1$, $R^2$ and $R^3$ are as defined herein, can be prepared starting from an appropriately derivatized nitropyrimidine, wherein $Hal^1$ is Cl, and $Hal^2$ is Cl. Treatment of the dihalogenated nitropyrimidine with the appropriate $R^2NH_2$ amine derivative, in the presence of a base, such as, for example, DIEA, TEA, sodium carbonate, sodium bicarbonate or pyridine, in a solvent, such as for example, DCM, DMF, dioxane or THF, at reduced temperature (for example, −78° C.), provided incorporation of the $R^2$ sidechain. Treatment of this product with $R^1NH_2$, in the presence of a base, such as, for example, DIEA, TEA, sodium carbonate, sodium bicarbonate or pyridine, in a solvent, such as for example, DCM, DMF, dioxane or THF, at temperatures ranging from 0-60° C., resulted in incorporation of the $R^1$ sidechain. Reduction of the nitro moiety, using, a reducing agent in a solvent (for example, hydrogen in the presence of a catalyst such as Pd/C, in a solvent, such as MeOH or ethyl acetate, or iron in the presence of ammonium chloride in a solvent, such as for example, EtOH, MeOH or water) provided the aminopyrimidine derivative. The aminopyrimidine derivative was treated with $R^3NCS$, in a solvent, such as THF, DMF, NMP, dioxane, or EtOH, to obtain the (optionally isolated) thiourea derivative, which was cyclized, using for example, EDC or DIC, in a solvent, for example, THF, dioxane, NMP or DMF, optionally at elevated temperature (for example, 40-80° C.), to provide compounds of formula (I).

In one aspect, provided herein are methods for preparing an Aminopurine Compound of formula (I):

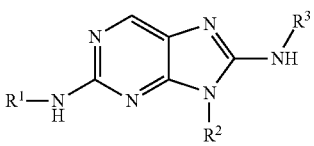

the methods comprising contacting a compound of formula (Ia)

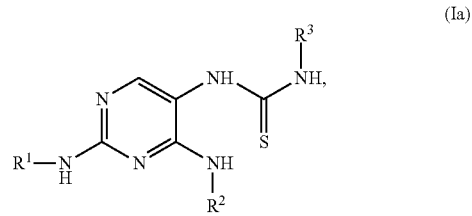

with EDC or DIC, in a solvent, under conditions suitable to provide an Aminopurine Compound of formula (I), wherein:

$R^1$ is $CR^{1a}R^{1b}R^{1c}$, wherein each of $R^{1a}$, $R^{1b}$ and $R^{1c}$ is independently $(C_{1-4})$alkyl, or $(C_{1-4})$alkyl(OR); or $R^{1a}$ and $R^{1b}$ and the carbon to which they are attached form a 3-6 membered cycloalkyl or 3-6 membered heterocyclyl, and $R^{1c}$ is $(C_{1-4})$alkyl;

$R^2$ is cycloalkyl or aryl, substituted with at least one $NR_2$, OR, CN, NRC(O)R, $CH_2OR$, $CH_2NR_2$, $CH_2NRCOR$, $CH_2NRCOOR'$, or heterocyclylalkyl;

$R^3$ is phenyl or pyridyl, optionally substituted with at least one halogen, CN, $(C_{1-2})$alkyl, or $O(C_{1-2})$alkyl, wherein the alkyl is optionally fluorinated;

R is H or $(C_{1-4})$ alkyl; and

R' is $(C_{1-4})$alkyl;

provided the Aminopurine Compound of formula (I) is not 4-(2-(tert-butylamino)-8-((2,6-difluorophenyl)amino)-9H-purin-9-yl)cyclohexan-1-ol;

4-(2-(tert-butylamino)-8-((2,4,6-trifluorophenyl)amino)-9H-purin-9-yl)cyclohexan-1-ol; or 4-(2-(tert-butylamino)-8-((2,4-difluorophenyl)amino)-9H-purin-9-yl)cyclohexan-1-ol.

In one embodiment, the solvent is THF, dioxane, NMP or DMF. In some embodiments, the contacting is optionally performed at elevated temperature, for example, from about 40° C. to about 80° C.

In some embodiments, the methods further comprise preparing a compound of formula (Ia):

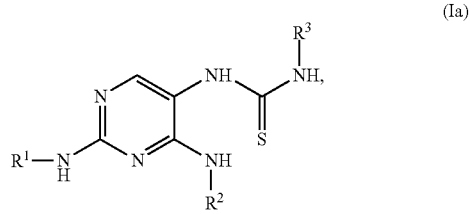

the methods comprising contacting a compound of formula (Ib)

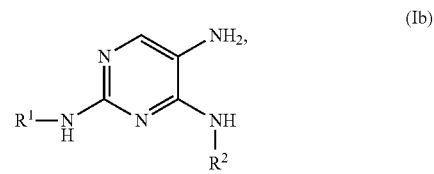

with $R^3NCS$, in a solvent, under conditions suitable to provide a compound of formula (Ia).

In one embodiment, the solvent is THF, DMF, NMP, dioxane, or EtOH.

In some embodiments, the methods further comprise preparing a compound of formula (Ib):

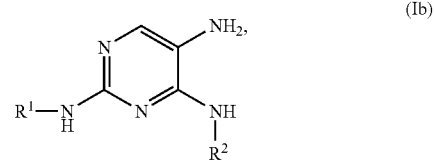

the methods comprising reducing a compound of formula (Ic)

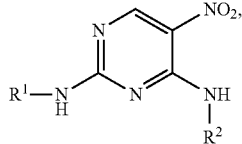

(Ic)

with a reducing agent, in a solvent, under conditions suitable to provide a compound of formula (Ib).

In one embodiment, the reducing agent is $H_2$ in the presence of a catalyst. In some such embodiments, the catalyst Pd/C. In some such embodiments, the solvent is MeOH or ethyl acetate. In other embodiments, the reducing agent is iron in the presence of ammonium chloride. In some such embodiments, the solvent is EtOH, MeOH or water.

In some embodiments, the methods further comprise preparing a compound of formula (Ic):

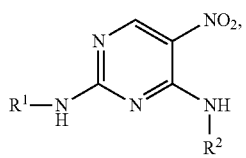

(Ic)

the methods comprising contacting a compound of formula (Id)

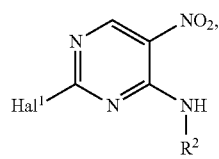

(Id)

with $R^1NH_2$, in the presence of a base, in a solvent under conditions suitable to provide a compound of formula (Ic), wherein $Hal^1$ is Cl.

In some embodiments, the base is DIEA, TEA, sodium carbonate, sodium bicarbonate, or pyridine. In other embodiments, the solvent is DCM, DMF, dioxane or THF. In some embodiments, the contacting is performed at elevated temperature, for example, from about 0° C. to about 60° C.

In some embodiments, the methods further comprise preparing a compound of formula (Id):

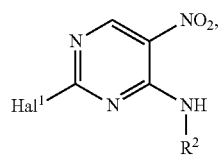

(Id)

the methods comprising contacting a compound of formula (Ie)

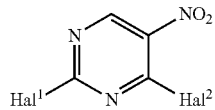

(Ie)

with $R^2NH_2$, in the presence of a base, in a solvent, under conditions suitable to provide a compound of formula (Id), wherein $Hal^2$ is Cl.

In some embodiments, the base is DIEA, TEA, sodium carbonate, sodium bicarbonate, or pyridine. In other embodiments, the solvent is DCM, DMF, dioxane or THF. In some embodiments, the contacting is performed at reduced temperature, for example, about −78° C.

Methods of Use

The Aminopurine Compounds, including compounds of formula (I), Table 1 and Table 2, have utility as pharmaceuticals to treat, prevent or improve conditions in animals or humans. The Aminopurine Compounds provided herein are intended for use in the treatment or prevention of all diseases, disorders or conditions disclosed herein. Accordingly, the Aminopurine Compounds provided herein are for use as a medicament. Accordingly, provided herein are the Aminopurine Compounds for use in methods of treatment or prevention of trypanosomosis, trypanosomiasis and/or leishmaniasis. The methods provided herein comprise the administration of an effective amount of at least one Aminopurine Compound(s) to a subject in need thereof.

The Aminopurine Compounds provided herein can be administered in combination with a second active agent. Accordingly, the Aminopurine Compounds provided herein and the second active agent provided herein can be used in the treatment or prevention of all diseases, disorders or conditions provided herein.

In one aspect, provided herein are methods of treating or preventing trypanosomosis, trypanosomiasis and/or leishmaniasis, comprising administering to a subject in need thereof an effective amount of an Aminopurine Compound, as described herein. In one aspect, provided herein are Aminopurine Compounds for use in methods of treating or preventing trypanosomosis, trypanosomiasis and/or leishmaniasis, comprising administering to a subject in need thereof an effective amount of an Aminopurine Compound, as described herein. In another aspect provided herein are compounds for treating or preventing trypanosomosis, trypanosomiasis and/or leishmaniasis, comprising administering to a subject in need thereof an effective amount of an Aminopurine Compound, as described herein.

In one embodiment, the trypanosomosis or trypanosomiasis is caused by *Trypanosoma avium, T. boissoni, T. brucei, T. b. gambiense, T. b. rhodesiense, T. b. evansi, T. carassii, T. cruzi, T. congolense, T. equinum, T. equiperdum, T. evansi, T. godfreyi, T. hosei, T. levisi, T. melophagium, T. parroti, T. percae, T. rangeli, T. rotatorium, T. rugosae, T. sergenti, T. simiae, T. sinipercae, T. suis, T. theileri, T. triglae* and *T. vivax*. In some embodiments, the trypanosomosis or trypanosomiasis is caused by *T. congolense, T. vivax* or *T. evansi*. In some embodiments, the subject is an animal, and the trypanosomosis or trypanosomiasis is caused by *T. congolense, T. vivax, T. brucei brucei, T. evansi* or *T. simiae*. In some embodiments, the subject is a human, and the trypanosomosis or trypanosomiasis is caused by *T. brucei rhodesiense, T. brucei gambiense* or *T. cruzi*.

In some embodiments, the leishmaniasis is caused by *L. donovani, L. infantum, L. chagasi; L. mexicana, L. amazonensis, L. venezuelensis, L. tropica, L. major, L. aethiopica, L.* (V.) *braziliensis, L.* (V.) *guyanensis, L.* (V.) *panamensis*, or *L.* (V.) *peruviana*. In one embodiment, the subject is a human and the leishmaniasis is caused by *L. major, L. tropica, L. aethiopica, L. mexicana, L. donovani* or *L. infantum*.

In some embodiments, the trypanosomosis is Animal trypanosomosis or African animal trypanosomosis (AAT). In other embodiments, the trypanosomiasis is Human African trypanosomiasis (HAT, also known as sleeping sickness). In other embodiments, the trypanosomiasis is American trypanosomiasis or Chagas disease.

Also provided herein are methods of treating or preventing Animal trypanosomosis or African animal trypanosomosis (AAT), comprising administering to a subject in need thereof an effective amount of an Aminopurine Compound, as described herein. Also provided herein are Aminopurine Compounds, as described herein, for use in methods of treating or preventing Animal trypanosomosis or African animal trypanosomosis (AAT), comprising administering to a subject in need thereof an effective amount of an Aminopurine Compound, as described herein. In some such embodiments, the subject is selected from cattle, sheep, goats, pigs, and dogs, and the Animal trypanosomosis or African animal trypanosomosis is caused by *T. vivax, T. congolense, T. brucei*, or *T. evansi*. In other such embodiments, the subject is selected from horses and donkeys, and the Animal trypanosomosis or African animal trypanosomosis is caused by *T. equiperdum*. In yet other embodiments, the subject is selected from dogs, horses and cats, and the Animal trypanosomosis or African animal trypanosomosis is caused by *T. brucei brucei*. In still other embodiments, the subject is selected from horses, camels, water buffalo and cattle, and the Animal trypanosomosis or African animal trypanosomosis is caused by *T. brucei evansi*.

In some embodiments, the trypanosomosis is Nagana and is caused by *T. congolense* or *T. vivax*. In other embodiments, the trypanosomosis is Surra and is caused by *T. evansi*. In yet other embodiments, the trypanosomosis is Dourine and is caused by *T. equiperdum*.

Also provided herein are methods of treating or preventing Animal trypanosomosis or African animal trypanosomosis (AAT), comprising administering to a subject in need thereof an effective amount of an Aminopurine Compound, as described herein, in combination with a second active agent. Also provided herein are Aminopurine Compounds, as described herein, for use in methods of treating or preventing Animal trypanosomosis or African animal trypanosomosis (AAT), comprising administering to a subject in need thereof an effective amount of an Aminopurine Compound, as described herein, in combination with a second active agent. In one embodiment, the second active agent is at least one of diminazene in various salt forms, including diminazene di-aceturate (i.e. Berenil®, Veriben®, Trypan®, Trypadim®, Trypazene®, Trypamyl®, Diamyl® Diminazen®); quinapyramine sulphate (Triquin®, Anthrycide®, Trypacide®, Trybexin®, Noroquin®); melarsomine (Cymelarsan®); isometamidium (Trypamidium®, Samorin®, Veridium®, Securidium); homidium chloride or bromide (Novidium®, Ethidium®). In another embodiment, the methods additionally may comprise administering at least one of an antibiotic, an anti-parasitic, an anti-inflammatory and/or a vitamin.

Also provided herein are methods of treating or preventing Human African trypanosomiasis (HAT), comprising administering to a subject in need thereof an effective amount of an Aminopurine Compound, as described herein. Also provided herein are Aminopurine Compounds, as described herein, for use in methods of treating or preventing Human African trypanosomiasis (HAT), comprising administering to a subject in need thereof an effective amount of an Aminopurine Compound, as described herein. In some such embodiments, the Human African trypanosomiasis is caused by *T. brucei gambiense, T. brucei brucei*, or *T. brucei rhodesiense*.

Also provided herein are methods of treating or preventing Human African trypanosomiasis (HAT), comprising administering to a subject in need thereof an effective amount of an Aminopurine Compound, as described herein, in combination with a second active agent. Also provided herein are Aminopurine Compounds, as described herein, for use in methods of treating or preventing Human African trypanosomiasis (HAT), comprising administering to a subject in need thereof an effective amount of an Aminopurine Compound, as described herein, in combination with a second active agent. In some embodiments, the second active agent is selected from pentamidine, suramin, melarsoprol (arsenic-derived), eflornithine and nifurtimox.

Also provided herein are methods of treating or preventing American trypanosomiasis or Chagas disease, comprising administering to a subject in need thereof an effective amount of an Aminopurine Compound, as described herein. Also provided herein are Aminopurine Compounds, as described herein, for use in methods of treating or preventing American trypanosomiasis or Chagas disease, comprising administering to a subject in need thereof an effective amount of an Aminopurine Compound, as described herein. In some such embodiments, the American trypanosomiasis or Chagas disease is caused by *T. cruzi*.

Also provided herein are methods of treating or preventing the American trypanosomiasis or Chagas disease, comprising administering to a subject in need thereof an effective amount of an Aminopurine Compound, as described herein, in combination with a second active agent. Also provided herein are Aminopurine Compounds, as described herein, for use in methods of treating or preventing the American trypanosomiasis or Chagas disease, comprising administering to a subject in need thereof an effective amount of an Aminopurine Compound, as described herein, in combination with a second active agent. In some embodiments, the second active agent is selected from benznidazole and nifurtimox.

Also provided herein are methods of treating or preventing leishmaniasis, comprising administering to a subject in need thereof an effective amount of an Aminopurine Compound, as described herein. Also provided herein are Aminopurine Compounds, as described herein, for use in methods of treating or preventing leishmaniasis, comprising administering to a subject in need thereof an effective amount of an Aminopurine Compound, as described herein. In some such embodiments, the leishmaniasis is caused by *Leishmania*. In some such embodiments, the subject is a mammal, for example, a human or a rodent. In some embodiments, the leishmaniasis is visceral leishmaniasis (also known as kala-azar) and is caused by *L. donovani* or *L. infantum*. In another embodiment the Leishmaniasis is post-kala-azar dermal leishmaniasis (PKDL). In yet other embodiments, the Leishmaniasis is cutaneous and is caused by *L. major, L. tropica, L. aethiopica* or *L. Mexicana*. In still other embodiments, the leishmaniasis is mucocutaneous leishmaniasis.

Also provided herein are methods of treating or preventing Leishmaniasis, comprising administering to a subject in need thereof an effective amount of an Aminopurine Compound, as described herein, in combination with a second active agent. Also provided herein are Aminopurine Compounds, as described herein, for use in methods of treating or preventing Leishmaniasis, comprising administering to a subject in need thereof an effective amount of an Aminopurine Compound, as described herein, in combination with a second active agent. In some embodiments, the second active agent is selected from pentavalent antimonials (meglumine antimoniate and sodium stibogluconate; Pentostam®), Amphotericin B deoxycholate (also AmBisome®), pentamidine, paromomycin sulfate (aminosidine), miltefosine (hexadecylphosphocholine) and ketoconazole.

Pharmaceutical Compositions and Routes of Administration

Provided herein are pharmaceutical compositions comprising an effective amount of an Aminopurine compound, as described herein, and a pharmaceutically acceptable carrier, excipient or vehicle. The Aminopurine Compounds can be administered to a subject enterally (for example, orally, rectally), topically, or parenterally (for example, intravenously, intramuscularly, subcutaneously), in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrrolidone or aluminum stearate), a dispersing agent (e.g., hydroxypropylmethylcellulose), a diluent (e.g., water), a cosolvent (e.g. propylene glocyl/glycofurol), a buffer, a copolymer (e.g. poly(lactic-co-glycolic acid, i.e PLGA), and base wax (e.g., cocoa butter, white petrolatum or polyethylene glycol). The effective amount of the Aminopurine Compounds in the pharmaceutical composition may be at a level that will exercise the desired effect; for example, about 0.005 mg/kg of a subject's body weight to about 20 mg/kg of a subject's body weight in unit dosage for both oral and parenteral administration.

The dose of an Aminopurine Compound to be administered to a subject is rather widely variable and can be subject to the judgment of a health-care practitioner. In general, the Aminopurine Compounds can be administered one to four times a day in a dose of about 0.005 mg/kg of a subject's body weight to about 20 mg/kg of a subject's body weight in a subject, but the above dosage may be properly varied depending on the age, body weight and medical condition of the subject and the type of administration. In one embodiment, the dose is about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, the dose is about 0.01 mg/kg of a subject's body weight to about 5 mg/kg of a subject's body weight. In one embodiment, the dose is about 0.05 mg/kg of a subject's body weight to about 1 mg/kg of a subject's body weight. In one embodiment, the dose is about 0.1 mg/kg of a subject's body weight to about 0.75 mg/kg of a subject's body weight. In one embodiment, the dose is about 0.25 mg/kg of a subject's body weight to about 0.5 mg/kg of a subject's body weight. In one embodiment, one dose is given per day. In any given case, the amount of the Aminopurine Compound administered will depend on such factors as the solubility of the active component, the formulation used and the route of administration. In one embodiment, application of a topical concentration provides intracellular exposures or concentrations of about 0.01-10 µM.

In another embodiment, provided herein are methods for the treatment or prevention of a disease or disorder comprising the administration of about 1 mg/day to about 1200 mg/day. In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of an Aminopurine Compound to a subject in need thereof. In one embodiment, the methods for the treatment of a disease or disorder comprise the administration of about 0.375 mg/day to about 750 mg/day of an Aminopurine Compound to a subject in need thereof. In one embodiment, the methods for the treatment of a disease or disorder comprise the administration of about 0.75 mg/day to about 375 mg/day of an Aminopurine Compound to a subject in need thereof. In one embodiment, the methods for the treatment of a disease or disorder comprise the administration of about 3.75 mg/day to about 75 mg/day of an Aminopurine Compound to a subject in need thereof. In one embodiment, the methods for the treatment of a disease or disorder comprise the administration of about 7.5 mg/day to about 55 mg/day of an Aminopurine Compound to a subject in need thereof. In one embodiment, the methods for the treatment of a disease or disorder comprise the administration of about 18 mg/day to about 37 mg/day of an Aminopurine Compound to a subject in need thereof.

In another embodiment, provided herein are methods for the treatment or prevention of a disease or disorder comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of an Aminopurine Compound to a subject in need thereof. In a particular embodiment, the methods disclosed herein comprise the administration of 400 mg/day, 600 mg/day or 800 mg/day of an Aminopurine Compound to a subject in need thereof. The methods for the treatment of a disease or disorder comprise the administration of about 1 mg/day to about 1200 mg/day of an Aminopurine Compound to a subject in need thereof. The methods for the treatment of a disease or disorder comprise the administration of about 10 mg/day to about 1200 mg/day of an Aminopurine Compound to a subject in need thereof. The methods for the treatment of a disease or disorder comprise the administration of about 100 mg/day to about 1200 mg/day of an Aminopurine Compound to a subject in need thereof. The methods for the treatment of a disease or disorder comprise the administration of about 400 mg/day to about 1200 mg/day of an Aminopurine Compound to a subject in need thereof. The methods for the treatment of a disease or disorder comprise the administration of about 600 mg/day to about 1200 mg/day of an Aminopurine Compound to a subject in need thereof. The methods for the treatment of a disease or disorder comprise the administration of about 400 mg/day to about 800 mg/day of an Aminopurine Compound to a subject in need thereof. The methods for the treatment of a disease or disorder comprise the administration of about 600 mg/day to about 800 mg/day of an Aminopurine Compound to a subject in need thereof. In a particular embodiment, the methods disclosed herein comprise the administration of 400 mg/day of an Aminopurine Compound to a subject in need thereof. In another particular embodiment, the methods disclosed herein comprise the administration of 600 mg/day of an Aminopurine Compound to a subject in need thereof. In another particular embodiment, the methods disclosed herein comprise the administration of 800 mg/day of an Aminopurine Compound to a subject in need thereof. In another embodiment, provided herein are unit dosage formulations that comprise between about 1 mg and 500 mg, or between about 500 mg and about 1000 mg of an Aminopurine Compound. In one embodiment, provided herein is a unit dosage formulation that comprise between about 1 mg and 500 mg of an Aminopurine Compound. In one embodiment, provided herein is a unit dosage formulation that comprise between about 500 mg and about 1000 mg of an Aminopurine Compound.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of an Aminopurine Compound. In one embodiment, the unit dosage formulations comprises between about 1 mg and 200 mg of an Aminopurine Compound. In one embodiment, the unit dosage formulations comprises between about 35 mg and about 1400 mg of an Aminopurine Compound. In one embodiment, the unit dosage formulations comprises between about 125 mg and about 1000 mg of an Aminopurine Compound. In one embodiment, the unit dosage formulations comprises between about 250 mg and about 1000 mg of an Aminopurine Compound. In one embodiment, the unit dosage formulations comprises between about 500 mg and about 1000 mg of an Aminopurine Compound.

In a particular embodiment, provided herein are unit dosage formulations comprising about 100 mg or 400 mg of an Aminopurine Compound.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of an Aminopurine Compound. In one embodiment the unit dosage formulations comprise 1 mg of an Aminopurine Compound. In one embodiment the unit dosage formulations comprise 5 mg of an Aminopurine Compound. In one embodiment the unit dosage formulations comprise 10 mg of an Aminopurine Compound. In one embodiment the unit dosage formulations comprise 15 mg of an Aminopurine Compound. In one embodiment the unit dosage formulations comprise 20 mg of an Aminopurine Compound. In one embodiment the unit dosage formulations comprise 25 mg of an Aminopurine Compound. In one embodiment the unit dosage formulations comprise 30 mg of an Aminopurine Compound. In one embodiment the unit dosage formulations comprise 35 mg of an Aminopurine Compound. In one embodiment the unit dosage formulations comprise 40 mg of an Aminopurine Compound. In one embodiment the unit dosage formulations comprise 50 mg of an Aminopurine Compound. In one embodiment the unit dosage formulations comprise 70 mg of an Aminopurine Compound. In one embodiment the unit dosage formulations comprise 100 mg of an Aminopurine Compound. In one embodiment the unit dosage formulations comprise 125 mg of an Aminopurine Compound. In one embodiment the unit dosage formulations comprise 140 mg of an Aminopurine Compound. In one embodiment the unit dosage formulations comprise 175 mg of an Aminopurine Compound. In one embodiment the unit dosage formulations comprise 200 mg of an Aminopurine Compound. In one embodiment the unit dosage formulations comprise 250 mg of an Aminopurine Compound. In one embodiment the unit dosage formulations comprise 280 mg of an Aminopurine Compound. In one embodiment the unit dosage formulations comprise 350 mg of an Aminopurine Compound. In one embodiment the unit dosage formulations comprise 500 mg of an Aminopurine Compound. In one embodiment the unit dosage formulations comprise 560 mg of an Aminopurine Compound. In one embodiment the unit dosage formulations comprise 700 mg of an Aminopurine Compound. In one embodiment the unit dosage formulations comprise 750 mg of an Aminopurine Compound. In one embodiment the unit dosage formulations comprise 1000 mg of an Aminopurine Compound. In one embodiment the unit dosage formulations comprise 1400 mg of an Aminopurine Compound.

An Aminopurine Compound can be administered once, twice, three, four or more times daily. In a particular embodiment, doses of 600 mg or less are administered as a once daily dose and doses of more than 600 mg are administered twice daily in an amount equal to one half of the total daily dose.

An Aminopurine Compound can be administered orally for reasons of convenience. In one embodiment, when administered orally, an Aminopurine Compound is administered with a meal and water. In another embodiment, the Aminopurine Compound is dispersed in water or juice (e.g., apple juice or orange juice) and administered orally as a suspension.

The Aminopurine Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing an Aminopurine Compound without an additional carrier, excipient or vehicle.

In another embodiment, provided herein are compositions comprising an effective amount of an Aminopurine Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories, suspensions, gels, intra-ruminal devices (e.g. for prolonged prophylaxis or controlled release), implants, topical pour-ons, transdermal delivery gels, spot-ons, implants (including devices, gels, liquids (e.g. PLGA), and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing an Aminopurine Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer an Aminopurine Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Aminopurine Compound can be delayed or prolonged by proper formulation. For example, a slowly soluble pellet of the Aminopurine Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Aminopurine Compound in oily or emulsified vehicles, or adding amounts of PLGA, that allow it to disperse slowly in the serum.

EXAMPLES

The following Examples are presented by way of illustration, not limitation. Compounds are named using the automatic name generating tool provided in Chemdraw Ultra 9.0 (Cambridgesoft), which generates systematic names for chemical structures, with support for the Cahn-Ingold-Prelog rules for stereochemistry. One skilled in the art can modify the procedures set forth in the illustrative examples to arrive at the desired products.

Abbreviations Used

| | |
|---|---|
| Boc | t-Butyloxycarbonyl |
| Cbz | Carboxybenzyl |
| CDI | Carbonyldiimidazole |
| DAST | Diethylaminosulfur trifluoride |
| DBU | 1 8-Diazabicyclo 5.4.0 undec-7-ene |
| DCM | Dichloromethane |
| DEA | Diethylamine |
| DIC | Diisopropylcarbodiimide |
| DIPEA | Diisopropylethylamine |
| DMA | N,N-Dimethylacetamide |
| DME | 1,2-Dimethoxyethane |
| DMF | N,N-Dimethylformamide |
| DMSO | Dimethylsulfoxide |
| DPPA | Diphenylphosphoryl azide |
| EDCI | Ethyl-(N',N'-dimethylamino)propylcarbodiimide hydrochloride |
| ESI | Electrospray ionization |
| EtOH | Ethanol |
| HATU | O-(7-Azabenzotriazol-1-yl)-N,N,N',N'-tetramethyluronium hexafluorophosphate |
| HBTU | O-(Benzotriazol-1-yl)-N,N,N',N'-tetramethyluronium hexafluorophosphate |
| HCl | Hydrochloric acid |
| HMPA | Hexamethylphosphoramide |
| HOBt | 1-Hydroxybenzotriazole |
| HPLC | High performance liquid chromatography |
| HTRF | Homogeneous time resolved fluorescence |
| KOAc | Potassium acetate |
| LAH | Lithium aluminum hydride |
| LCMS | Liquid chromatography mass spectrometry |
| mCPBA | Meta-chloroperoxybenzoic acid |
| MeOH | Methanol |
| MS | Mass spectrometry |
| MTBE | tert-Butyl Methyl ether |
| NaOH | Sodium hydroxide |
| NMM | N-Methylmorpholine |
| NMP | N-methylpyrrolidone |
| NMR | Nuclear magnetic resonance |
| $POCl_3$ | Phosphorus trichloride |
| pTSA | p-Toluenesulfonic acid |
| SEM | 2-Trimethylsilylethoxymethoxy |
| SFC | Supercritical fluid chromatography |
| TBTU | O-Benzotriazol-1-yl-N,N,N',N'-tetra-methyluronium tetrafluoroborate |
| t-BuOH | Tert-butanol |
| TEA | Triethylamine |
| TFA | Trifluoracetic acid |
| THF | Tetrahydrofuran |
| THP | Tetrahydropyran |
| TLC | Thin layer chromatography |
| TMS | Trimethylsilane |
| UPLC | Ultra Performance Liquid Chromatography |

Compound Synthesis

Example 1: N8-(3-Chlorophenyl)-N2-(4-methyltetrahydro-2H-pyran-4-yl)-9-((1S, 4S)-4-(piperidin-1-ylmethyl)cyclohexyl)-9H-purine-2,8-diamine

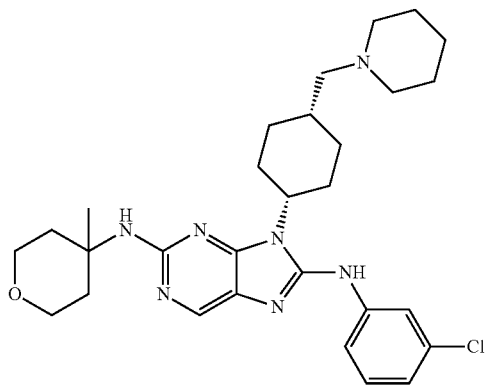 [SMILES: CC1(Nc2ncc3nc(Nc4cccc(Cl)c4)n([C@H]4CC[C@@H](CN5CCCCC5)CC4)c3n2)CCOCC1]

tert-Butyl (1S, 4S)-4-(piperidine-1-carbonyl)cyclohexyl) carbamate. To a stirred solution of (1S, 4S)-4-((tert-butoxycarbonyl)amino)cyclohexane-1-carboxylic acid (1.5 g, 6.0 mmol) in DMF (20 mL) was added DIPEA (2 ml, 12.5 mmol), piperidine (0.63 g, 7.5 mmol), EDCI (2.35 g, 12.5 mmol) and HOBT (1.88 g, 12.5 mmol) at ambient temperature. The reaction mixture was stirred for 16 h. Completion of the reaction was confirmed by UPLC. The product was isolated and triturated with petroleum ether to afford tert-butyl ((1S, 4S)-4-(piperidine-1-carbonyl)cyclohexyl)carbamate (1.9 g) as an off-white solid. MS (ESI) m/z 311 [M+1]$^+$.

((1S, 4S)-4-Aminocyclohexyl)(piperidin-1-yl)methanone. To a stirred solution of tert-butyl ((1S, 4S)-4-(piperidine-1-carbonyl)cyclohexyl)carbamate (1.9 g, 6.5 mmol) in DCM (20 mL) was added HCl in dioxane (2 mL) at 0° C. The reaction mixture was stirred at ambient temperature for 5 h. Completion of the reaction was confirmed by UPLC. The product was isolated to afford ((1S, 4S)-4-aminocyclohexyl)(piperidin-1-yl)methanone. MS (ESI) m/z 211 [M+1]$^+$.

((1S, 4S)-4-((2-Chloro-5-nitropyrimidin-4-yl)amino)cyclohexyl)(piperidin-1-yl)methanone. To a stirred solution of 2, 4-dichloro-5-nitropyrimidine (1 g, 5.5 mmol) and DIPEA (6.5 mL, 57 mmol) in IPA (20 mL) was added ((1S, 4S)-4-aminocyclohexyl)(piperidin-1-yl)methanone (1.2 g, 6 mmol) portionwise at 0° C. under nitrogen. The reaction mixture was slowly warmed to ambient temperature and stirred for 5 h. Completion of the reaction was confirmed by TLC. The product was isolated to afford ((1S, 4S)-4-((2-chloro-5-nitropyrimidin-4-yl)amino)cyclohexyl)(piperidin-1-yl)methanone (0.5 g, 30%) as yellow solid. MS (ESI) m/z 369, 370 [M, M+1]$^+$.

((1S, 4S)-4-((2-((4-Methyltetrahydro-2H-pyran-4-yl)amino)-5-nitropyrimidin-4-yl)amino)cyclohexyl)(piperidin-1-yl)methanone. To a stirred solution of ((1S, 4S)-4-((2-chloro-5-nitropyrimidin-4-yl)amino)cyclohexyl)(piperidin-1-yl)methanone (0.5 g 1.5 mmol) in DMF (10 mL) was added 4-methyltetrahydro-2H-pyran-4-amine (0.25 g, 2 mmol) and sodium bicarbonate (0.43 g, 4 mmol) at ambient temperature. The reaction mixture was stirred at 60° C. for 2 h. Completion of the reaction was confirmed by UPLC. The product was isolated and triturated with petroleum ether to afford ((1S, 4S)-4-((2-((4-methyltetrahydro-2H-pyran-4-yl)amino)-5-nitropyrimidin-4-yl)amino)cyclohexyl)(piperidin-1-yl)methanone. (0.4 g, 66%) as yellow solid. MS (ESI) m/z 447 [M+1]$^+$.

((1S, 4S)-4-((5-Amino-2-((4-methyltetrahydro-2H-pyran-4-yl)amino)pyrimidin-4-yl)amino)cyclohexyl)(piperidin-1-yl)methanone. To a stirred solution of ((1S, 4S)-4-((2-((4-methyltetrahydro-2H-pyran-4-yl)amino)-5-nitropyrimidin-4-yl)amino)cyclohexyl)(piperidin-1-yl)methanone (0.4 g, 1 mmol) in ethanol:water (20 mL, 3:1) was added iron powder (0.5 g, 10 mmol) and ammonium chloride (0.05 g, 1 mmol) at ambient temperature. The reaction mixture was heated to 85° C. for 5 h. Completion of the reaction was confirmed by UPLC. The resulting reaction mixture was filtered through a bed of celite, washed with ethyl acetate and concentrated to afford ((1S, 4S)-4-((5-amino-2-((4-methyltetrahydro-2H-pyran-4-yl)amino)pyrimidin-4-yl)amino)cyclohexyl)(piperidin-1-yl)methanone (0.35 g, 93%) as a brown solid. MS (ESI) m/z 417.4 [M+1]$^+$.

(4-(8-((3-Chlorophenyl)amino)-2-((4-methyltetrahydro-2H-pyran-4-yl)amino)-9H-purin-9-yl)cyclohexyl)(piperidin-1-yl)methanone. To a stirred solution of ((1S, 4S)-4-((5-amino-2-((4-methyltetrahydro-2H-pyran-4-yl)amino)pyrimidin-4-yl)amino)cyclohexyl)(piperidin-1-yl)methanone (0.2 g, 0.5 mmol) and 1-chloro-3-isothiocyanatobenzene (0.1 g, 0.6 mmol) in THF (10 mL) was added EDCI (0.19 g, 1 mmol) at ambient temperature. The reaction mixture was heated to 60° C. for 5 h. Completion of the reaction was confirmed by UPLC. The product was isolated and purified via standard methods to afford (4-(8-((3-chlorophenyl)amino)-2-((4-methyltetrahydro-2H-pyran-4-yl)amino)-9H-purin-9-yl)cyclohexyl)(piperidin-1-yl)methanone (0.1 g, 38%) as an off-white solid. MS (ESI) m/z 553, 554 [M, M+1]$^+$.

N8-(3-Chlorophenyl)-N2-(4-methyltetrahydro-2H-pyran-4-yl)-9-(4-(piperidin-1-ylmethyl)cyclohexyl)-9H-purine-2, 8-diamine. To a stirred solution of (4-(8-((3-chlorophenyl)amino)-2-((4-methyltetrahydro-2H-pyran-4-yl)amino)-9H-purin-9-yl)cyclohexyl)(piperidin-1-yl)methanone (0.1 g, 0.2 mmol) in THF (15 mL) was added dropwise lithium aluminium hydride in THF (1.6 M, 0.5 mL) at 0° C. for 2 h. Completion of the reaction was confirmed by TLC. The product was isolated and purified via standard methods to afford N8-(3-chlorophenyl)-N2-(4-methyltetrahydro-2H-pyran-4-yl)-9-(4-(piperidin-1-ylmethyl)cyclohexyl)-9H-purine-2,8-diamine. (8 mg, 10%). MS (ESI) m/z 538, 539 [M, M+1]+. $^1$H NMR (400 MHz, CD$_3$OD): δ 8.21 (s, 1H), 7.90 (s, 1H), 7.59 (s, 1H), 7.35-7.39 (m, 1H), 7.14 (d, J=7.6 Hz, 1H), 4.49-4.52 (m, 1H), 3.78-3.83 (m, 5H), 3.64-3.67 (m, 3H), 3.02-3.08 (m, 2H), 2.42-2.59 (m, 5H), 1.82-2.10 (m, 14H), 1.66 (s, 3H).

Example 2: N8-(3-Chlorophenyl)-N2-(4-methyltetrahydro-2H-pyran-4-yl)-9-((1S, 4S)-4-(morpholinemethyl)cyclohexyl)-9H-purine-2,8-diamine

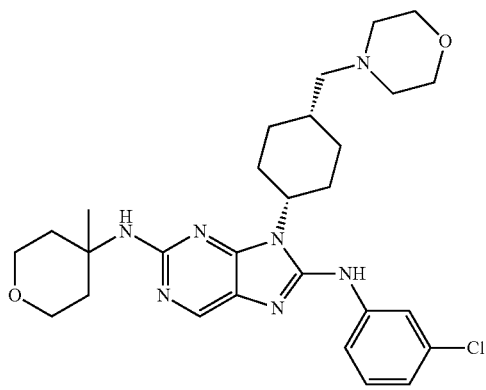 [SMILES: CC1(Nc2ncc3nc(Nc4cccc(Cl)c4)n([C@H]4CC[C@@H](CN5CCOCC5)CC4)c3n2)CCOCC1]

tert-Butyl((1S, 4S)-4-(morpholine-4-carbonyl)cyclohexyl)carbamate. To a stirred solution of (1S, 4S)-4-((tert-butoxycarbonyl)amino)cyclohexane-1-carboxylic acid (3 g, 12 mmol) in DMF (30 mL) was added DIPEA (4.5 mL, 24 mmol), morpholine (1.28 g, 14.76 mmol), EDCI (4.70 g, 24.6 mmol) and HOBT (3.76 g, 24.6 mmol) at ambient temperature. The reaction mixture was stirred for 16 h. Completion of the reaction was confirmed by UPLC. The product was isolated and triturated with petroleum ether to afford tert-butyl ((1S, 4S)-4-(morpholine-4-carbonyl)cyclohexyl)carbamate (2.65 g, 75%) as an off-white solid. MS (ESI) m/z 313 [M+1]$^+$.

((1S, 4S)-4-Aminocyclohexyl)(morpholino)methanone. To a stirred solution of tert-butyl ((1S, 4S)-4-(morpholine-4-carbonyl)cyclohexyl)carbamate (2.65 g, 8.5 mmol) in DCM (50 mL) was added HCl in dioxane (5 mL) at 0° C. The reaction mixture was stirred at ambient temperature for 5 h. Completion of the reaction was confirmed by UPLC. The product was isolated to afford ((1S, 4S)-4-aminocyclohexyl)(morpholino)methanone.

((1S, 4S)-4-((2-Chloro-5-nitropyrimidin-4-yl)amino)cyclohexyl)(morpholino)methanone. To a stirred solution of 2,4-dichloro-5-nitropyrimidine (1.2 g, 6 mmol) and DIPEA (2 mL, 12 mmol) in IPA (50 mL) was added ((1S, 4S)-4-aminocyclohexyl)(morpholino)methanone (1.57 g, 7 mmol) portionwise at 0° C. under nitrogen. The reaction mixture was slowly warmed to ambient temperature and stirred for 5 h. Completion of the reaction was confirmed by TLC. The product was isolated to afford ((1S, 4S)-4-((2-chloro-5-nitropyrimidin-4-yl)amino)cyclohexyl)(morpholino)methanone (1 g, 44%) as yellow solid.

((1S, 4S)-4-((2-((4-Methyltetrahydro-2H-pyran-4-yl)amino)-5-nitropyrimidin-4-yl)amino)cyclohexyl)(morpholino)methanone. To a stirred solution of ((1S, 4S)-4-((2-chloro-5-nitropyrimidin-4-yl)amino)cyclohexyl)(morpholino)methanone (0.5 g 1 mmol) in DMF (10 mL) was added 4-methyltetrahydro-2H-pyran-4-amine (0.24 g, 1 mmol) and sodium bicarbonate (0.29 g, 4 mmol) at ambient temperature. The reaction mixture was stirred at ambient temperature for 5 h. Completion of the reaction was confirmed by UPLC. The product was isolated and triturated with petroleum ether to afford ((1S, 4S)-4-((2-((4-methyltetrahydro-2H-pyran-4-yl)amino)-5-nitropyrimidin-4-yl)amino)cyclohexyl)(morpholino)methanone (0.45 g, 70%) as yellow solid. MS (ESI) m/z 449 [M+1]$^+$.

((1S, 4S)-4-((5-Amino-2-((4-methyltetrahydro-2H-pyran-4-yl)amino)pyrimidin-4-yl)amino)cyclohexyl)(morpholino)methanone. To a stirred solution of ((1S, 4S)-4-((2-((4-methyltetrahydro-2H-pyran-4-yl)amino)-5-nitropyrimidin-4-yl)amino)cyclohexyl)(morpholino)methanone (0.45 g, 1 mmol) in ethanol:water (20 mL, 3:1) was added iron powder (0.56 g, 10 mmol) and ammonium chloride (0.05 g, 1 mmol) at ambient temperature. The reaction mixture was heated to 85° C. for 5 h. Completion of the reaction was confirmed by UPLC. The resulting reaction mixture was filtered through a bed of celite, washed with ethyl acetate and concentrated to afford ((1S, 4S)-4-((5-amino-2-((4-methyltetrahydro-2H-pyran-4-yl)amino)pyrimidin-4-yl)amino)cyclohexyl)(morpholino)methanone (0.4 g) as a brown solid. MS (ESI) m/z 419.4 [M+1]$^+$.

N8-(3-Chlorophenyl)-N2-(4-methyltetrahydro-2H-pyran-4-yl)-9-((1S, 4S)-4-(morpholinemethyl)cyclohexyl)-9H-purine-2,8-diamine. To a stirred solution of ((1S, 4S)-4-((5-amino-2-((4-methyltetrahydro-2H-pyran-4-yl)amino)pyrimidin-4-yl)amino)cyclohexyl)(morpholino)methanone (0.4 g, 1.0 mmol) and 1-chloro-3-isothiocyanatobenzene (0.19 g, 1.1 mmol) in THF (10 mL) was added EDCI (0.36 g, 2.00 mmol) at ambient temperature. The reaction mixture was heated to 60° C. for 4 h. Completion of the reaction was confirmed by UPLC. The product was isolated and purified via standard methods to afford (4-(8-((3-chlorophenyl)amino)-2-((4-methyltetrahydro-2H-pyran-4-yl)amino)-9H-purin-9-yl)cyclohexyl)(morpholino)methanone (0.2 g, 38%) as an off-white solid. MS (ESI) m/z 553, 554 [M, M+1]$^+$.

N8-(3-Chlorophenyl)-N2-(4-methyltetrahydro-2H-pyran-4-yl)-9-((1S, 4S)-4(morpholinomethyl)cyclohexyl)-9H-purine-2, 8-diamine. To a stirred solution of (4-(8-((3-chlorophenyl)amino)-2-((4-methyltetrahydro-2H-pyran-4-yl)amino)-9H-purin-9-yl)cyclohexyl)(morpholino)methanone (0.2 g, 0.36 mmol) in THF (15 mL) was added lithium aluminium hydride in THF (1.6 M, 1 mL) dropwise at 0° C. The reaction mixture was stirred at ambient temperature for 2 h. Completion of the reaction was confirmed by UPLC. The product was isolated and purified via standard methods to afford N8-(3-chlorophenyl)-N2-(4-methyltetrahydro-2H-pyran-4-yl)-9-((1S, 4S)-4-(morpholinomethyl)cyclohexyl)-9H-purine-2,8-diamine (0.085 g, 43%). MS (ESI) m/z 540, 541 [M, M+1]$^+$. $^1$H NMR (400 MHz, CD$_3$OD): δ 8.30 (s, 1H), 7.70 (s, 1H), 7.45 (d, J=7.6 Hz, 1H), 7.30-7.34 (m, 1H), 7.04 (d, J=7.6 Hz, 1H), 4.27-4.33 (m, 1H), 3.75-3.77 (m, 8H), 2.64-2.70 (m, 2H), 2.54-2.58 (m, 6H), 2.33-2.42 (m, 2H), 2.07 (brs, 1H), 1.97-2.00 (m, 2H), 1.76-1.82 (m, 6H), 1.66 (s, 3H).

Example 3: (1S, 4S)-4-((2-Chloro-5-nitropyrimidin-4-yl)amino)cyclohexane-1-carboxamide

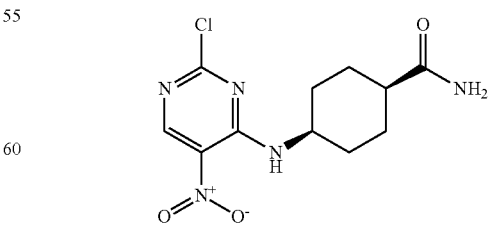

cis-(4-Carbamoyl-cyclohexyl)-carbamic acid tert-butyl ester. cis-4-tert-Butoxycarbonylamino-cyclohexanecarboxylic acid (1 equiv.) and TEA (1.1 equiv.) were dissolved in 0.3 M THF and the mixture was cooled to 0° C. Ethyl chloroformate (1.1 equiv.) was added drop-wise. After stirring at 0° C. for 30 min, NH$_3$ in THF was added. The mixture was allowed to stir at −78° C. for 2 h. The mixture was diluted with water, and the solvent was evaporated until only water remained. The resulting precipitate was collected by filtration and dried under vacuum to give cis (4-carbamoyl-cyclohexyl)-carbamic acid tert-butyl ester (45%) as a white solid. $^1$H NMR (400 MHz, DMSO-d$_6$) δ ppm 7.10 (brs, 1 H), 6.69 (brs, 2 H), 3.41 (brs, 1 H), 2.10 (m, 1 H), 1.72 (m, 2 H), 1.53 (m, 2 H), 1.42 (m, 4 H), 1.36 (s, 9 H).

cis-4-Amino-cyclohexanecarboxylic acid amide hydrochloride. To a solution of cis-(4-carbamoyl-cyclohexyl)-carbamic acid tert-butyl ester (1 equiv.) in 1/1 DCM/TFA. The mixture was stirred for 1 h. The solvents were evaporated under reduced pressure. To the resulting residue was added 2M HCl/ether to give a white solid. The solvent was evaporated. The resulting solid was treated with ether and filtered to give cis-4-amino-cyclohexanecarboxylic acid amide hydrochloride (100%) as a white solid. $^1$H NMR (400 MHz, DMSO-d$_6$) δ ppm: 8.08 (brs, 3 H), 7.28 (s, 1 H), 6.78 (s, 1 H), 3.06 (m, 1 H), 2.22 (m, 1 H), 1.86 (m, 2 . H), 1.66 (m, 4 H), 1.48 (m, 2 H).

(1S, 4S)-4-((2-Chloro-5-nitropyrimidin-4-yl)amino)cyclohexane-1-carboxamide. (1S, 4S)-4-Aminocyclohexanecarboxamide hydrochloride (0.56 mol) and 2,4-dichloro-5-nitropyrimidine (1 equiv.) were dissolved in DCM (0.16 M). The mixture was cooled to −78° C. An addition funnel was charged with DIEA (3 equiv.) and DCM (1.0 M). The DIEA solution was added dropwise via an addition funnel. After the addition was complete, the reaction was stirred for an additional 2 h at −78° C. The reaction was monitored by LCMS. Once the reaction was completed, the reaction mixture was purified by standard methods to give (1S, 4S)-4-((2-chloro-5-nitropyrimidin-4-yl)amino)cyclohexane-1-carboxamide (65%). $^1$H NMR (400 MHz, DMSO-d$_6$) δ ppm: 9.01 (s, 1H), 8.51 (d, J=7.6 Hz, 1H), 7.23 (s, 1H), 6.75 (s, 1H), 4.26 (s, 1H), 2.24 (s, 1H), 1.60-1.83 (m, 8H).

Example 4: -((1S, 4S)-4-(Aminomethyl)cyclohexyl)-N8-(2-fluoro-5-(trifluoromethyl)phenyl)-N2-(4-methyltetrahydro-2H-pyran-4-yl)-9H-purine-2,8-diamine

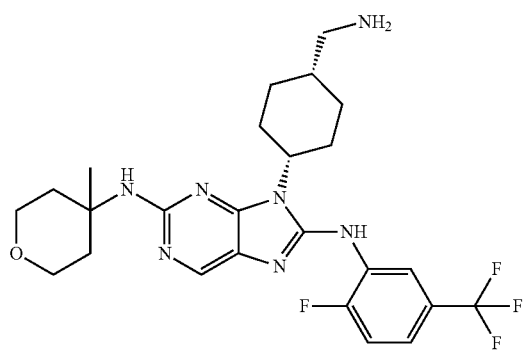 [SMILES: CC1(Nc2ncc3nc(Nc4cc(C(F)(F)F)ccc4F)n([C@H]4CC[C@@H](CN)CC4)c3n2)CCOCC1]

(1S, 4S)-4-((2-((4-Methyltetrahydro-2H-pyran-4-yl)amino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (5 g, 17 mmol) in DMF (10 mL) was added sodium carbonate (5.3 g, 50 mmol) portionwise followed by 2-methylbutane-2-amine (3 g, 20 mmol) at ambient temperature. The reaction mixture was stirred for 16 h. Completion of the reaction was confirmed by LCMS. The product was isolated to afford (1S, 4S)-4-((2-((4-methyltetrahydro-2H-pyran-4-yl)amino)-5-nitropyrimidin-4-yl)amino)cyclohexane-1-carboxamide (3.2 g, 50%) as a yellow solid. MS (ESI) m/z 379 [M+1]$^+$.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl) amino)cyclohexane-1-carboxamide (3.2 g, 8 mmol) in ethanol:water (50 mL, 1:1) was added iron powder (8.4 g, 80 mmol) followed by ammonium chloride (0.80 g, 8 mmol). The reaction mixture was heated to 85° C. for 16 h. Completion of the reaction was confirmed by LCMS. The resulting reaction mixture was filtered through a bed of celite, washed with ethyl acetate and concentrated to afford (1S, 4S)-4-((5-amino-2-((4-methyltetrahydro-2H-pyran-4-yl)amino)pyrimidin-4-yl)amino)cyclohexane-1-carboxamide (2.8 g, 95%) as a violet solid. MS (ESI) m/z 349 [M+1]$^+$.

1-Fluoro-2-isothiocyanato-4-(trifluoromethyl)benzene. To a stirred solution of 2-fluoro-5-(trifluoromethyl)aniline (2 g, 11 mmol) in dichloromethane (25 mL) was added TEA (2.5 g, 22 mmol), then thiophosgene (1.9 g, 16 mmol) was added dropwise at 0° C. The resulting reaction mixture was stirred at ambient temperature for 1 h. Completion of the reaction was confirmed by UPLC. The product was isolated via standard purification methods to afford 1-fluoro-2-isothiocyanato-4-(trifluoromethyl)benzene (0.75 g, 33%) as a pale yellow liquid. MS (ESI) m/z 222 [M+1]$^+$.

(1S, 4S)-4-(8-((2-Fluoro-5-(trifluoromethyl)phenyl)amino)-2-((4-methyltetrahydro-2H-pyran-4-yl)amino)-9H-purin-9-yl)cyclohexane-1-carboxamide. To stirred solution of (1S, 4S)-4-((5-amino-2-((4-methyltetrahydro-2H-pyran-4-yl)amino)pyrimidin-4-yl)amino)cyclohexane-1-carboxamide (0.6 g, 2 mmol) in THF:DMF (20 mL, 1:1) was added 1-ethyl-3-(3-dimethylaminopropyl)carbodiimide (0.7 g, 3 mmol) and 1-fluoro-2-isothiocyanato-4-(trifluoromethyl) benzene (0.45 g, 2 mmol) at ambient temperature. The reaction mixture was heated to 50° C. for 4 h. Completion of the reaction was confirmed by UPLC. The product was isolated via standard purification methods to afford (1S, 4S)-4-(8-((2-fluoro-5-(trifluoromethyl)phenyl)amino)-2-((4-methyltetrahydro-2H-pyran-4-yl)amino)-9H-purin-9-yl) cyclohexane-1-carboxamide (0.4 g, 43%) as an off-white solid. MS (ESI) m/z 536 [M+1]$^+$.

9-((1S, 4S)-4-(Aminomethyl)cyclohexyl)-N8-(2-fluoro-5-(trifluoromethyl)phenyl)-N2-(4-methyltetrahydro-2H-pyran-4-yl)-9H-purine-2,8-diamine.

To a stirred solution of (1S, 4S)-4-(8-((2-fluoro-5-(trifluoromethyl)phenyl)amino)-2-((4-methyltetrahydro-2H-pyran-4-yl)amino)-9H-purin-9-yl)cyclohexane-1-carboxamide (0.4 g, 1 mmol) in diethyl ether (10 mL) was added lithium aluminum hydride in THF (2.4 M; 5 mL) at 0° C. The reaction mixture was stirred at ambient temperature for 2 h. Completion of the reaction was confirmed by UPLC. The product was isolated and purified by standard methods to afford 9-((1S, 4S)-4-(aminomethyl)cyclohexyl)-N8-(2-fluoro-5-(trifluoromethyl)phenyl)-N2-(4-methyltetrahydro-2H-pyran-4-yl)-9H-purine-2,8-diamine (0.05 g, 10%). MS (ESI) m/z 522 [M+1]$^+$. $^1$H NMR (400 MHz, CD$_3$OD): δ 8.14 (brs, 1H), 7.93 (brs, 1H), 7.32-7.40 (m, 2H), 4.33-4.36 (m, 1H), 3.75-3.81 (m, 4H), 2.94-2.98 (m, 2H), 2.61-2.68 (m, 2H), 2.33-2.36 (m, 2H), 1.97-1.99 (m, 2H), 1.75-1.85 (m, 4H), 1.60 (s, 3H).

Example 5: 9-((1S, 4S)-4-(Aminomethyl)cyclohexyl)-N8-(3-chloro-5-fluorophenyl)-N2-(4-methyltetrahydro-2H-pyran-4-yl)-9H-purine-2,8-diamine

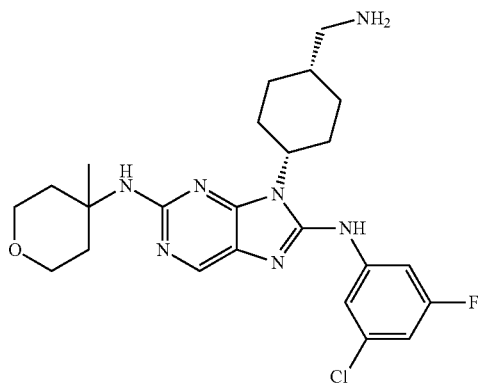 [SMILES: CC1(Nc2ncc3nc(Nc4cc(F)cc(Cl)c4)n([C@H]4CC[C@@H](CN)CC4)c3n2)CCOCC1]

(1S, 4S)-4-((2-((4-Methyltetrahydro-2H-pyran-4-yl)amino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (5 g, 16.7 mmol) in DMF (50 mL) was added 4-methyltetrahydro-2H-pyran-4-amine (2.1 g, 18.3 mmol) and sodium carbonate (3.5 g, 33 mmol) at ambient temperature. The reaction mixture was stirred for 12 h. Completion of the reaction was confirmed by UPLC. The product was isolated and triturated with petroleum ether to afford (1S, 4S)-4-((2-((4-methyltetrahydro-2H-pyran-4-yl)amino)-5-nitropyrimidin-4-yl)amino)cyclohexane-1-carboxamide (2.7 g, 43%) as an off-white solid. MS (ESI) m/z 379.2 [M+1]$^+$.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-(2-((4-methyltetrahydro-2H-pyran-4-yl)amino)-5-nitropyrimidin-4-yl)amino)cyclohexane-1-carboxamide (1 g, 2.64 mmol) in ethanol:water (30 mL, 3:1) was added iron powder (0.74 g, 13.2 mmol) and ammonium chloride (0.7 g, 13.2 mmol) at ambient temperature. The reaction mixture was heated to 85° C. for 16 h. Completion of the reaction was confirmed by LCMS. The resulting reaction mixture was filtered through a bed of celite, washed with ethyl acetate and concentrated to afford (1S, 4S)-4-((5-amino-2-((4-methyltetrahydro-2H-pyran-4-yl)amino)pyrimidin-4-yl)amino)cyclohexane-1-carboxamide (0.8 g, 87%) as a brown solid. MS (ESI) m/z 349 [M+1]$^+$.

(1S, 4S)-4-(8-((3-Chloro-5-flurophenyl)amino)-2-((4-methyltetrahydro-2H-pyran-4-yl) amino)-9H-purin-9-yl)cyclohexane-1-carboxamide. To a stirred solution of (1S, 4S)-4-((5-amino-2-((4-methyltetrahydro-2H-pyran-4-yl)amino)-5-nitropyrimidin-4-yl)amino)cyclohexane-1-carboxamide (0.4 g, 1.15 mmol) and 1-chloro-3-fluoro-5-isothiocyanatobenzene (0.26 g, 1.37 mmol) in ethanol was added DCC (0.71 g, 3.44 mmol) at ambient temperature. The reaction mixture was stirred for 12 h. Completion of the reaction was confirmed by UPLC. The product was isolated and purified via standard methods to afford (1S, 4S)-4-(8-((3-chloro-5-flurophenyl)amino)-2-((4-methyltetrahydro-2H-pyran-4-yl)amino)-9H-purin-9-yl)cyclohexane-1-carboxamide (0.4 g, 69%) as an off-white solid. MS (ESI) m/z 501.2, 502.2 [M, M+1]$^+$.

9-((1S, 4S)-4-(Aminomethyl)cyclohexyl)-N8-(3-chloro-5-fluorophenyl)-N2-(4-methyltetrahydro-2H-pyran-4-yl)-9H-purine-2,8-diamine. To a stirred solution of (1S, 4S)-4-(8-((3-chloro-5-flurophenyl)amino)-2-((4-methyltetrahydro-2H-pyran-4-yl)amino)-9H-purin-9-yl)cyclohexane-1-carboxamide (0.4 g, 0.77 mmol) in THF (20 mL) was added lithium aluminium hydride in THF (2.4 M; 1.27 mL) dropwise at 0° C. and then heated at 50° C. for 8 h. Completion of the reaction was confirmed by TLC. The product was purified via standard methods to afford 9-((1S, 4S)-4-(aminomethyl)cyclohexyl)-N8-(3-chloro-5-fluorophenyl)-N2-(4-methyltetrahydro-2H-pyran-4-yl)-9H-purine-2,8-diamine (0.07 g, 17%). MS (ESI) m/z 488.2, 489.2 [M, M+1]$^+$. $^1$H NMR (400 MHz, CD$_3$OD): δ 8.27 (s, 1H), 7.51 (s, 1H), 7.43-7.46 (m, 1H), 6.82-6.85 (m, 1H), 4.33-4.39 (m, 1H), 3.76-3.83 (m, 4H), 3.13-3.14 (m, 2H), 2.64-2.73 (m, 2H), 2.41-2.44 (m, 2H), 1.76-2.01 (m, 9H and 3H), 1.61 (s, 3H).

Example 6: 9-((1S, 4S)-4-(Aminomethyl)cyclohexyl)-N8-(2-fluoro-3-(trifluoromethyl)phenyl)-N2-(4-methyltetrahydro-2H-pyran-4-yl)-9H-purine-2,8-diamine

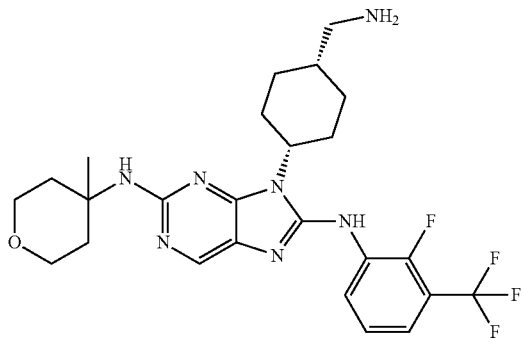 [SMILES: CC1(Nc2ncc3nc(Nc4cccc(C(F)(F)F)c4F)n([C@H]4CC[C@@H](CN)CC4)c3n2)CCOCC1]

(1S, 4S)-4-((2-((4-Methyltetrahydro-2H-pyran-4-yl)amino-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (5 g, 20 mmol) in DMF (50 mL) was added sodium carbonate (5.3 g, 60 mmol) portionwise followed by 4-methyltetrahydro-2H-pyran-4-amine (3 g, 20 mmol) at ambient temperature. The reaction mixture was stirred for 16 h. Completion of the reaction was confirmed by UPLC. The product was isolated via standard purification methods to afford (1S, 4S)-4-((2-((4-methyltetrahydro-2H-pyran-4-yl)amino)-5-nitropyrimidin-4-yl)amino)cyclohexane-1-carboxamide (3.2 g, 50%) as a yellow solid. MS (ESI) m/z 379 [M+1]$^+$.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl)amino)cyclohexane-1-carboxamide (3.2 g, 8 mmol) in ethanol:water (60 mL, 10:1) was added iron powder (8.4 g, 80 mmol) and ammonium chloride (0.5 g, 8 mmol) at ambient temperature. The reaction mixture was heated to 85° C. for 16 h. Completion of the reaction was confirmed by UPLC. The resulting reaction mixture was filtered through a bed of celite, washed with ethyl acetate and concentrated to afford (1S, 4S)-4-((5-amino-2-((4-methyltetrahydro-2H-pyran-4-yl)amino)pyrimidin-4-yl)amino)cyclohexane-1-carboxamide (2.8 g, 90%) as a violet solid. MS (ESI) m/z 349 [M+1]$^+$.

(1S, 4S)-4-(8-((2-Fluoro-3-(trifluoromethyl)phenyl)amino)-2-((4-methyltetrahydro-2H-pyran-4-yl)amino)-9H-purin-9-yl)cyclohexane-1-carboxamide. To a stirred solution of (1S, 4S)-4-((5-Amino-2-((4-methyltetrahydro-2H-pyran-4-yl) amino)pyrimidin-4-yl)amino)cyclohexane-1-carboxamide (0.6 g, 2 mmol) in THF: DMF (1:1; 20 mL) was added 1-ethyl-3-(3-dimethylaminopropyl)carbodiimide (0.6 g, 3 mmol) and 2-fluoro-1-isothiocyanato-3-(trifluoromethyl)benzene (0.5 g, 2 mmol) at ambient temperature. The reaction mixture was heated to 50° C. for 4 h. Completion of the reaction was confirmed by UPLC. The product was isolated and purified via standard purification methods to afford (1S, 4S)-4-(8-((2-fluoro-3-(trifluoromethyl)phenyl)amino)-2-((4-methyltetrahydro-2H-pyran-4-yl)amino)-9H-purin-9-yl)cyclohexane-1-carboxamide (0.4 g, 44%) as an off-white solid. MS (ESI) m/z 536 [M+1]$^+$.

9-((1S, 4S)-4-(Aminomethyl)cyclohexyl)-N8-(2-fluoro-3-(trifluoromethyl)phenyl)-N2-(4-methyltetrahydro-2H-pyran-4-yl)-9H-purine-2,8-diamine.

To a stirred solution of (1S, 4S)-4-(8-((2-fluoro-3-(trifluoromethyl)phenyl)amino)-2-((4-methyltetrahydro-2H-pyran-4-yl)amino)-9H-purin-9-yl)cyclohexane-1-carboxamide (0.3 g, 1 mmol) in THF (3 mL) was added lithium aluminum hydride in THF (1.6 M; 5 mL) at 0° C. The reaction mixture was stirred at ambient temperature for 3 h. Completion of the reaction was confirmed by UPLC. The product was purified by standard methods to afford 9-((1S, 4S)-4-(aminomethyl)cyclohexyl)-N8-(2-fluoro-3-(trifluoromethyl)phenyl)-N2-(4-methyltetrahydro-2H-pyran-4-yl)-9H-purine-2,8-diamine (0.05 g, 10%). MS (ESI) m/z 522.2, 523.2 [M, M+1]$^+$. $^1$H NMR (400 MHz, CD$_3$OD): δ 8.56, 8.12 (s, 1H), 7.81-7.83 (m, 1H), 7.41-7.44 (m, 1H), 7.31-7.35 (m, 1H), 4.35-4.41 (m, 1H), 3.76-3.78 (m, 4H), 2.95-2.97 (d, J=7.6 Hz, 2H), 2.62-2.72 (m, 2H), 2.34-2.37 (m, 2H), 1.97-2.00 (m, 2H), 1.75-1.86 (m, 7H), 1.60 (s, 3H).

Example 7: 9-((1S, 4S)-4-(Aminomethyl)cyclohexyl)-N2-(4-methyltetrahydro-2H-pyran-4-yl)-N8-(6-(trifluoromethyl)pyridin-2-yl)-9H-purine-2,8-diamine

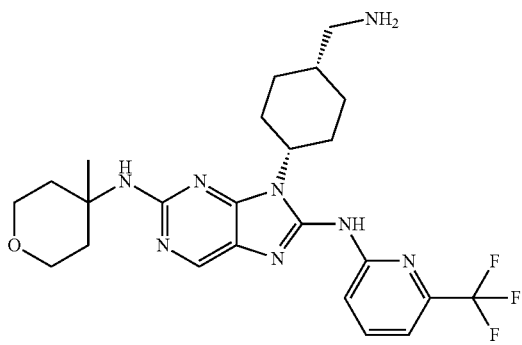 [SMILES: CC1(Nc2ncc3nc(Nc4cccc(C(F)(F)F)n4)n([C@H]4CC[C@@H](CN)CC4)c3n2)CCOCC1]

(1S, 4S)-4-((2-((4-Methyltetrahydro-2H-pyran-4-yl)amino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (5 g, 20 mmol) in DMF (50 mL) was added sodium carbonate (5.3 g, 60 mmol) portionwise followed by 4-methyltetrahydro-2H-pyran-4-amine (3 g, 20 mmol) at ambient temperature. The reaction mixture was stirred for 16 h. Completion of the reaction was confirmed by UPLC. The product was isolated via standard purification methods to afford (1S, 4S)-4-((2-((4-methyltetrahydro-2H-pyran-4-yl)amino)-5-nitropyrimidin-4-yl)amino)cyclohexane-1-carboxamide (3.2 g, 50%) as a yellow solid. MS (ESI) m/z 379 [M+1]$^+$.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl)amino)cyclohexane-1-carboxamide (3.2 g, 8 mmol) in ethanol:water (60 mL, 10:1) was added iron powder (8.4 g, 80 mmol) and ammonium chloride (0.5 g, 8 mmol) at ambient temperature. The reaction mixture was heated to 85° C. for 16 h. Completion of the reaction was confirmed by UPLC. The resulting reaction mixture was filtered through a bed of celite, washed with ethyl acetate and concentrated to afford (1S, 4S)-4-((5-amino-2-((4-methyltetrahydro-2H-pyran-4-yl)amino)pyrimidin-4-yl)amino)cyclohexane-1-carboxamide (2.8 g, 90%) as a violet solid. MS (ESI) m/z 349 [M+1]$^+$.

2-Isothiocyanato-6-(trifluoromethyl)pyridine. To a stirred solution of 6-(trifluoromethyl)pyridin-2-amine (1 g, 6 mmol) in dichloromethane (25 mL) was added saturated sodium bicarbonate solution (25 mL). Thiophosgene (0.84 g, 7 mmol) was added dropwise at 0° C. The resulting reaction mixture was stirred at ambient temperature for 1 h. Completion of the reaction was confirmed by UPLC. The product was isolated to afford 2-isothiocyanato-6-(trifluoromethyl)pyridine (0.75 g, 60%) as a yellow liquid. MS (ESI) m/z 205 [M+1]$^+$.

(1S,4S)-4-(2-((4-Methyltetrahydro-2H-pyran-4-yl)amino)-8-((6-(trifluoromethyl)pyridin-2-yl)amino)-9H-purin-9-yl)cyclohexane-1-carboxamide. To a stirred solution of (1S, 4S)-4-((5-amino-2-((4-methyltetrahydro-2H-pyran-4-yl)amino)pyrimidin-4-yl)amino)cyclohexane-1-carboxamide (0.6 g, 2 mmol) in THF: DMF (1:1; 20 mL) was added 1-ethyl-3-(3-dimethylaminopropyl)carbodiimide (0.6 g, 3 mmol) and 2-isothiocyanato-6-(trifluoromethyl)pyridine (0.4 g, 2 mmol) at ambient temperature. The reaction mixture was heated to 50° C. for 4 h. Completion of the reaction was confirmed by UPLC. The product was isolated and purified via standard purification methods to afford (1S, 4S)-4-(2-((4-methyltetrahydro-2H-pyran-4-yl)amino)-8-((6-(trifluoromethyl)pyridin-2-yl)amino)-9H-purin-9-yl)cyclohexane-1-carboxamide (0.45 g, 50%) as an off-white solid. MS (ESI) m/z 536 [M+1]$^+$.

9-((1S, 4S)-4-(Aminomethyl)cyclohexyl)-N2-(4-methyltetrahydro-2H-pyran-4-yl)-N8-(6-(trifluoromethyl)pyridin-2-yl)-9H-purine-2,8-diamine. To a stirred solution of (1S, 4S)-4-(2-((4-methyltetrahydro-2H-pyran-4-yl)amino)-8-((6-(trifluoromethyl)pyridin-2-yl)amino)-9H-purin-9-yl)cyclohexane-1-carboxamide (0.3 g, 1 mmol) in THF (3 mL) was added lithium aluminum hydride in THF (1.6 M; 4 mL) at 0° C. The reaction mixture was stirred at ambient temperature for 3 h. Completion of the reaction was confirmed by UPLC. The product was purified via standard methods to afford 9-((1S, 4S)-4-(aminomethyl)cyclohexyl)-N2-(4-methyltetrahydro-2H-pyran-4-yl)-N8-(6-(trifluoromethyl)pyridin-2-yl)-9H-purine-2,8-diamine (0.08 g, 25%). MS (ESI) m/z 505 [M+1]$^+$. $^1$H NMR (400 MHz, CD$_3$OD): δ 8.58, 8.17-8.24 (s, 1H), 7.84-7.88 (m, 1H), 7.65 (brs, 1H), 7.31 (d, J=7.2 Hz, 1H), 3.72-3.82 (m, 4H), 3.03 (d, J=7.2 Hz, 2H), 2.60-2.70 (m, 2H), 2.35-2.39 (m, 2H), 1.91-2.01 (m, 3H), 1.74-1.84 (m, 6H), 1.60 (s, 3H).

Example 8: 9-((1S, 4S)-4-(Aminomethyl)cyclohexyl)-N8-(3,5-difluorophenyl)-N2-(4-methyltetrahydro-2H-pyran-4-yl)-9H-purine-2,8-diamine

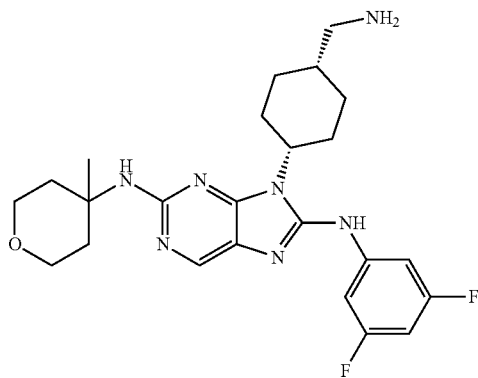 [SMILES: CC1(Nc2ncc3nc(Nc4cc(F)cc(F)c4)n([C@H]4CC[C@@H](CN)CC4)c3n2)CCOCC1]

(1S, 4S)-4-((2-((4-Methyltetrahydro-2H-pyran-4-yl)amino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (5 g, 20 mmol) in DMF (50 mL) was added sodium bicarbonate (5.3 g, 50 mmol) portionwise followed by 4-methyltetrahydro-2H-pyran-4-amine (3 g, 20 mmol) at ambient temperature. The reaction mixture was stirred for 16 h. Completion of the reaction was confirmed by UPLC. The product was isolated to afford (1S, 4S)-4-((2-((4-methyltetrahydro-2H-pyran-4-yl)amino)-5-nitropyrimidin-4-yl)amino)cyclohexane-1-carboxamide (3.2 g, 50%) as a yellow solid. MS (ESI) m/z 379 [M+1]+.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl)amino)cyclohexane-1-carboxamide (3.2 g, 8 mmol) in ethanol:water (66 mL, 10:1) was added iron powder (8.4 g, 80 mmol) and ammonium chloride (0.5 g, 8 mmol) at ambient temperature. The reaction mixture was heated to 85° C. for 16 h. Completion of the reaction was confirmed by UPLC. The resulting reaction mixture was filtered through a bed of celite, washed with ethyl acetate and concentrated to afford (1S, 4S)-4-((5-amino-2-((4-methyltetrahydro-2H-pyran-4-yl)amino)pyrimidin-4-yl)amino)cyclohexane-1-carboxamide (2.8 g, 90%) as a violet solid. MS (ESI) m/z 349 [M+1]+.

(1S, 4S)-4-(8-((3, 5-Difluorophenyl)amino)-2-((4-methyltetrahydro-2H-pyran-4-yl)amino)-9H-purin-9-yl)cyclohexane-1-carboxamide. To a stirred solution of (1S, 4S)-4-((5-amino-2-((4-methyltetrahydro-2H-pyran-4-yl)amino)pyrimidin-4-yl)amino)cyclohexane-1-carboxamide (0.6 g, 2 mmol) in THF:DMF (20 mL, 1:1) was added 1-ethyl-3-(3-dimethylamino propyl)carbodiimide (0.7 g, 3 mmol) and 1,3-difluoro-5-isothiocyanatobenzene (0.35 g, 2 mmol) at ambient temperature. The reaction mixture was heated to 50° C. for 4 h. Completion of the reaction was confirmed by UPLC. The product was isolated and purified via standard methods to afford (1S, 4S)-4-(8-((3,5-difluorophenyl)amino)-2-((4-methyltetrahydro-2H-pyran-4-yl)amino)-9H-purin-9-yl)cyclohexane-1-carboxamide (0.35 g, 42%) as an off-white solid. MS (ESI) m/z 485 [M+1]+.

9-((1S, 4S)-4-(Aminomethyl)cyclohexyl)-N8-(3,5-difluorophenyl)-N2-(4-methyltetrahydro-2H-pyran-4-yl)-9H-purine-2,8-diamine. To a stirred solution of (1S, 4S)-4-(8-((3,5-difluorophenyl)amino)-2-((4-methyltetrahydro-2H-pyran-4-yl)amino)-9H-purin-9-yl)cyclohexane-1-carboxamide (0.35 g, 1 mmol) in diethyl ether (5 mL) was added lithium aluminum hydride in THF (1.6 M; 4 mL) at 0° C. The reaction mixture was stirred at ambient temperature for 2 h. Completion of the reaction was confirmed by UPLC. The product was purified via standard methods to afford 9-((1S, 4S)-4-(aminomethyl)cyclohexyl)-N8-(3,5-difluorophenyl)-N2-(4-methyltetrahydro-2H-pyran-4-yl)-9H-purine-2,8-diamine (0.05 g, 15%). MS (ESI) m/z 472.2 [M+1]+. 1H NMR (400 MHz, CD3OD): δ 8.25 (s, 1H), 7.27-7.30 (m, 2H), 6.55-6.66 (m, 1H), 4.32-4.39 (m, 1H), 3.77-3.79 (m, 4H), 2.96-2.98 (d, J=7.2 Hz, 2H), 2.67-2.74 (m, 2H), 2.34-2.38 (m, 2H), 1.98-2.01 (m, 2H), 1.75-1.87 (m, 5H), 1.71-1.75 (m, 2H), 1.62 (s, 3H).

Example 9: 9-((1S, 4S)-4-(Aminomethyl)cyclohexyl)-N8-(3,5-dichlorophenyl)-N2-(4-methyltetrahydro-2H-pyran-4-yl)-9H-purine-2,8-diamine

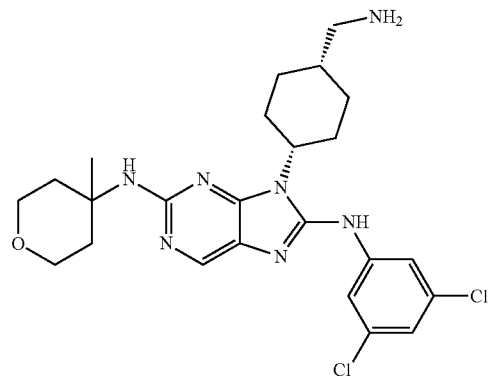 [SMILES: CC1(Nc2ncc3nc(Nc4cc(Cl)cc(Cl)c4)n([C@H]4CC[C@@H](CN)CC4)c3n2)CCOCC1]

(1S, 4S)-4-((2-((4-Methyltetrahydro-2H-pyran-4-yl)amino)-5-nitropyrimidin-4-yl) amino)cyclohexane-1-carboxamide. To a stirred solution of (1S, 4S)-4-((2-chloro-5-nitropyrimidin-4-yl)amino)cyclohexane-1-carboxamide (5 g, 16.7 mmol) in DMF (50 mL) was added 4-methyltetrahydro-2H-pyran-4-amine (2.1 g, 18.3 mmol) and sodium carbonate (3.5 g, 33 mmol) at ambient temperature. The reaction mixture was stirred for 12 h. Completion of the reaction was confirmed by UPLC. The product was isolated and triturated with petroleum ether to afford (1S, 4S)-4-((2-((4-methyltetrahydro-2H-pyran-4-yl)amino)-5-nitropyrimidin-4-yl)amino)cyclohexane-1-carboxamide (2.74 g, 43%) as an off-white solid. MS (ESI) m/z 379.2 [M+1]+.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-(2-((4-methyltetrahydro-2H-pyran-4-yl)amino)-5-nitropyrimidin-4-yl)amino)cyclohexane-1-carboxamide (1 g, 2.64 mmol) in ethanol:water (30 mL, 3:1) was added iron powder (0.74 g, 13.2 mmol) and ammonium chloride (0.7 g, 13.2 mmol) at ambient temperature. The reaction mixture was heated to 85° C. for 16 h. Completion of the reaction was confirmed by LCMS. The resulting reaction mixture was filtered through a bed of celite, washed with ethyl acetate and concentrated to afford (is 4s)-4-((5-amino-2-((4-methyltetrahydro-2H-pyran-4-yl)amino)pyrimidin-4-yl)amino)cyclohexane-1-carboxamide (0.8 g, 87%) as a brown solid. MS (ESI) m/z 349 [M+1]+.

(1S, 4S)-4-(8-((3, 5-Dichlorophenyl)amino-2-((4-methyltetrahydro-2H-pyran-4-yl)amino)-9H-purin-9-yl)cyclohexane-1-carboxamide. To a stirred solution of (1S, 4S)-4-((5-amino-2-((4-methyltetrahydro-2H-pyran-4-yl)amino)pyrimidin-4-yl)amino)cyclohexane-1-carboxamide (0.4 g, 1.2 mmol) and 1,3-dichloro-5-isothiocyanatobenzene (0.28 g, 1.4 mmol) in ethanol was added DCC (0.71 g, 3.4 mmol) at ambient temperature. The reaction mixture was stirred for 12 h. Completion of the reaction was confirmed by UPLC. The product was isolated and purified via standard methods to afford (1S, 4S)-4-(8-((3,5-dichlorophenyl)amino)-2-((4methyltetrahydro-2H-pyran-4-yl)amino)-9H-purin-9-yl)cyclohexane-1-carboxamide. (0.4 g, 67%) as an off-white solid. MS (ESI) m/z 520.2 [M+2]$^+$.

9-((1S, 4S)-4-(Aminomethyl)cyclohexyl)-N8-(3,5-dichlorophenyl)-N2-(4-methyltetrahydro-2H-pyran-4-yl)-9H-purine-2,8-diamine. To a stirred solution of (1S, 4S)-4-(8-((3,5-dichlorophenyl)amino)-2-((4-methyltetrahydro-2H-pyran-4-yl)amino)-9H-purin-9-yl)cyclohexane-1-carboxamide (0.4 g, 0.77 mmol) in THF (20 mL) was added dropwise lithium aluminium hydride in THF (2.4 M; 1.28 mL) at 0° C. and heated at 50° C. for 8 h. Completion of the reaction was confirmed by TLC. The product was purified by standard methods to afford 9-((1S, 4S)-4-(aminomethyl)cyclohexyl)-N8-(3,5-dichlorophenyl)-N2-(4-methyltetrahydro-2H-pyran-4-yl)-9H-purine-2,8-diamine (0.09 g, 23%). MS (ESI) m/z 504.46, 505.2 [M, M+2]$^+$. $^1$H NMR (400 MHz, CD$_3$OD): δ 8.27 (s, 1H), 7.65 (s, 2H), 7.07 (s, 1H), 4.34-4.40 (m, 1H), 3.75-3.83 (m, 4H), 3.19-3.21 (m, 2H), 2.62-2.72 (m, 2H), 2.43-2.47 (m, 2H), 2.00-2.10 (m, 1H), 2.0-2.02 (m, 2H), 1.87-1.92 (m, 1H), 1.75-1.85 (m, 5H), 1.61 (s, 3H).

Example 10: 9-((1S, 4S)-4-(Aminomethyl)cyclohexyl)-N8-(3-chlorophenyl)-N2-(1-methylcyclopropyl)-9H-purine-2,8-diamine

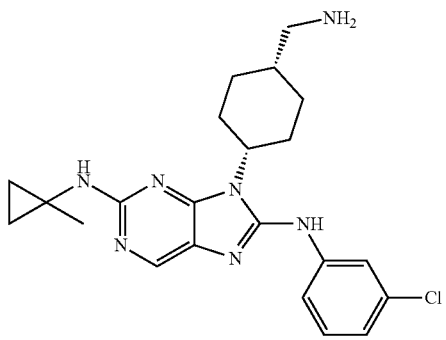 [SMILES: CC1(Nc2ncc3nc(Nc4cccc(Cl)c4)n([C@H]4CC[C@@H](CN)CC4)c3n2)CC1]

(1S, 4S)-4-((2-((1-Methylcyclopropyl)amino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (1 g, 3 mmol) in DMF (10 mL) was added sodium carbonate (1 g, 10 mmol) portionwise followed by 1-methylcyclopropan-1-amine hydrochloride (0.4 g, 3 mmol) at ambient temperature. The reaction mixture was stirred for 16 h. Completion of the reaction was confirmed by LCMS. The product was isolated to afford (1S, 4S)-4-((2-((1-methylcyclopropyl)amino)-5-nitropyrimidin-4-yl)amino)cyclohexane-1-carboxamide (0.9 g, 81%) as a yellow solid. MS (ESI) m/z 335 [M+1]$^+$.

(1S, 4S)-4-((5-Amino-2-((1-methylcyclopropyl)amino)pyrimidin-4-yl)amino)cyclohexane-1-carboxamide. To a stirred solution of (1S, 4S)-4-((2-((1-methylcyclopropyl)amino)-5-nitropyrimidin-4-yl)amino)cyclohexane-1-carboxamide (0.9 g, 2.7 mmol) in ethanol:water (20 mL, 1:1) was added iron powder (1.5 g, 26 mmol) followed by ammonium chloride (0.145 g, 2.7 mmol). The reaction mixture was heated to 85° C. for 16 h. Completion of the reaction was confirmed by LCMS. The resulting reaction mixture was filtered through a bed of celite, washed with ethyl acetate and concentrated to afford (1S, 4S)-4-((5-amino-2-((1-methylcyclopropyl)amino)pyrimidin-4-yl)amino)cyclohexane-1-carboxamide (0.8 g, 97%) as a violet solid. MS (ESI) m/z 305 [M+1]$^+$.

(1S, 4S)-4-(8-((3-Chlorophenyl)amino)-2-((1-methylcyclopropyl)amino)-7,8-dihydro-9H-purin-9-yl)cyclohexane-1-carboxamide. To stirred solution of (1S, 4S)-4-((5-amino-2-((1-methylcyclopropyl)amino)pyrimidin-4-yl)amino)cyclohexane-1-carboxamide (0.85 g, 2.8 mmol) in THF: DMF (20 mL, 1:1) was added 1-ethyl-3-(3-dimethylaminopropyl)carbodiimide (1 g, 5.6 mmol) and 1-chloro-3-isothiocyanatobenzene (0.6 g, 3.3 mmol) at ambient temperature. The reaction mixture was heated to 50° C. for 4 h. Completion of the reaction was confirmed by UPLC. The product was isolated via standard purification method to afford (1S, 4S)-4-(8-((3-chlorophenyl)amino)-2-((1-methylcyclopropyl)amino)-7,8-dihydro-9H-purin-9-yl)cyclohexane-1-carboxamide (0.65 g, 58%) as a brown solid. MS (ESI) m/z 439, 440 [M, M+1]$^+$.

9-((1S, 4S)-4-(Aminomethyl)cyclohexyl)-N8-(3-chlorophenyl)-N2-(1-methylcyclopropyl)-9H-purine-2,8-diamine. To a stirred solution of (1S, 4S)-4-(8-((3-chlorophenyl)amino)-2-((1-methylcyclopropyl)amino)-7,8-dihydro-9H-purin-9-yl)cyclohexane-1-carboxamide (0.4 g, 1 mmol) in diethyl ether (10 mL) was added lithium aluminum hydride in THF (2.4 M; 5 mL) at 0° C. The reaction mixture was stirred at ambient temperature for 2 h. Completion of the reaction was confirmed by UPLC. The product was purified via standard methods to afford 9-((1S, 4S)-4-(aminomethyl)cyclohexyl)-N8-(3-chlorophenyl)-N2-(1-methylcyclopropyl)-9H-purine-2,8-diamine (0.1 g, 30%). MS (ESI) m/z 425.2, 426.2 [M, M+1]$^+$. $^1$HNMR (400 MHz, CD$_3$OD): δ 8.25 (s, 1H), 8.01 (s, 1H), 7.66-7.68 (d, J=8 Hz, 1H), 7.31-7.35 (m, 1H), 6.98-7.00 (m, 1H), 4.34-4.40 (m, 1H), 2.89 (d, J=6.8 Hz, 2H), 2.70-2.79 (m, 2H), 1.89-1.92 (m, 2H), 1.68-1.73 (m, 1H), 1.58-1.64 (m, 4H), 1.42 (s, 3H) 0.64-0.70 (m, 4H).

Example 11: 9-((1S, 4S)-4-(Aminomethyl)cyclohexyl)-N8-(5-chloro-2-fluorophenyl)-N2-(4-methyltetrahydro-2H-pyran-4-yl)-9H-purine-2,8-diamine

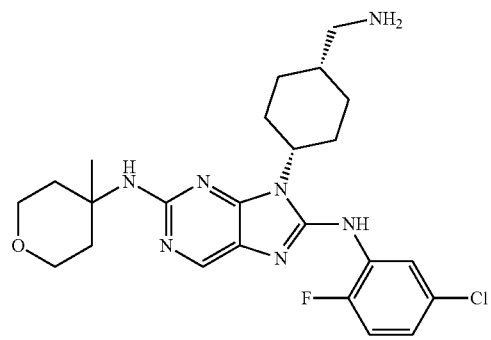 [SMILES: CC1(Nc2ncc3nc(Nc4cc(Cl)ccc4F)n([C@H]4CC[C@@H](CN)CC4)c3n2)CCOCC1]

(1S, 4S)-4-((2-((4-Methyltetrahydro-2H-pyran-4-yl)amino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (1 g, 3.33 mmol) in DMF (30 mL) was added 4-methyltetrahydro-2H-pyran-4-amine (0.42 g, 3.67 mmol) and sodium bicarbonate (0.56 g, 6.67 mmol) at ambient temperature. The reaction mixture was heated to 60° C. for 4 h. Completion of the reaction was confirmed by UPLC. The product was isolated and triturated with petroleum ether to afford (1S, 4S)-4-((2-((4-methyltetrahydro-2H-pyran-4-yl)amino)-5-nitropyrimidin-4-yl)amino)cyclohexane-1-carboxamide (0.8 g, 63%) as an off-white solid. MS (ESI) m/z 379, 380 [M, M+1]$^+$.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl)amino)cyclohexane-1-carboxamide (1.18 g, 2.11 mmol) in ethanol:water (30 mL, 10:1) was added iron powder (0.8 g, 21.13 mmol) and ammonium chloride (0.13 g, 2.53 mmol) at ambient temperature. The reaction mixture was heated at 80° C. Completion of the reaction was confirmed by TLC. The resulting reaction mixture was filtered through bed of celite, washed with methanol and concentrated to afford (1S, 4S)-4-((5-amino-2-((4-methyltetrahydro-2H-pyran-4-yl)amino)pyrimidin-4-yl)amino)cyclohexane-1-carboxamide (0.6 g, 82%) as a black solid. MS (ESI) m/z 349, 350 [M, M+1]$^+$.

(1S, 4S)-4-(8-((5-Chloro-2-fluorophenyl)amino)-2-((4-methyltetrahydro-2H-pyran-4-yl)amino)-9H-purin-9-yl)cyclohexane-1-carboxamide. To a stirred solution of (1S, 4S)-4-((5-amino-2-((4-methyltetrahydro-2H-pyran-4-yl)amino)pyrimidin-4-yl)amino)cyclohexane-1-carboxamide (0.6 g, 1.72 mmol) and 4-chloro-1-fluoro-2-isothiocyanatobenzene (0.35 g, 1.89 mmol) in THF was added EDCI (0.66 g, 3.44 mmol) at ambient temperature. The reaction mixture was heated to 60° C. for 4 h. Completion of the reaction was confirmed by UPLC. The product was isolated and purified via standard methods to afford (1S, 4S)-4-(8-((3-chloro-2-fluorophenyl)amino)-2-((4-methyltetrahydro-2H-pyran-4-yl)amino)-9H-purin-9-yl)cyclohexane-1-carboxamide (0.3 g, 34%) as an off-white solid. MS (ESI) m/z 502, 503 [M, M+1]$^+$.

9-((1S, 4S)-4-(Aminomethyl)cyclohexyl)-N8-(5-chloro-2-fluorophenyl)-N2-(4-methyltetrahydro-2H-pyran-4-yl)-9H-purine-2,8-diamine. To a stirred solution of (1S, 4S)-4-(8-((3-chloro-2-fluorophenyl)amino)-2-((4-methyltetrahydro-2H-pyran-4-yl)amino)-9H-purin-9-yl)cyclohexane-1-carboxamide (0.3 g, 0.59 mmol) in THF (10 mL) was added dropwise lithium aluminium hydride in THF (1.6 M; 3 mL) at 0° C. The reaction was heated at 50° C. for 8 h. Completion of the reaction was confirmed by TLC. The product was purified via standard methods to afford 9-((1S, 4S)-4-(aminomethyl)cyclohexyl)-N8-(3-chloro-2-fluorophenyl)-N2-(4-methyltetrahydro-2H-pyran-4-yl)-9H-purine-2,8-diamine (0.015 g, 5%). MS (ESI) m/z 488, 489 [M, M+1]$^+$. $^1$H NMR (400 MHz, CD$_3$OD): δ 8.57 NH proton (brs, 0.5H), 8.19 (brs, 1H), 7.67 (brs, 1H), 7.13-7.22 (m, 2H), 4.35-4.45 (m, 1H), 3.74-3.78 (m, 4H), 3.16-3.18 (m, 2H), 2.64-2.68 (m, 2H), 2.42-2.46 (m, 2H), 1.97-2.06 (m, 3H), 1.74-1.89 (m, 6H), 1.60 (s, 3H).

Example 12: 9-((1S, 4S)-4-(Aminomethyl)cyclohexyl)-N8-(3-chlorophenyl)-N2-(2,2-dimethyltetrahydro-2H-pyran-4-yl)-9H-purine-2,8-diamine

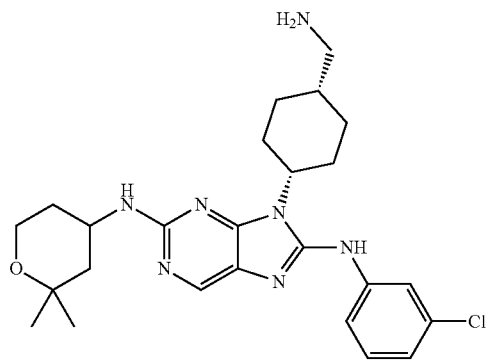 [SMILES: CC1(C)CC(Nc2ncc3nc(Nc4cccc(Cl)c4)n([C@H]4CC[C@@H](CN)CC4)c3n2)CCO1]

2,2-Dimethyltetrahydro-2H-pyran-4-amine. To a stirred solution of 2,2-dimethyltetrahydro-4H-pyran-4-one (2 g, 20 mmol) in MeOH (40 mL) and H$_2$O (5 mL) was added ammonium formate (10.33 g, 160 mmol) and pallidum on carbon (0.5 g). The reaction was stirred under atmospheric hydrogen atmosphere for 5 h. The reaction mixture was filtered through bed of celite and washed with methanol. The resulting filtrate was concentrated under reduced pressure to afford 2, 2-dimethyltetrahydro-2H-pyran-4-amine (2.5 g, 85%) as a colourless gummy material.

(1S, 4S)-4-((2-((2,2-Dimethyltetrahydro-2H-pyran-4-yl)amino)-5-nitropyrimidin-4-yl)amino)cyclohexane-1-carboxamide. To a stirred solution of 4-((2-chloro-5-nitropyrimidin-4-yl)amino)cyclohexane-1-carboxamide (0.5 g, 2.2 mmol) in DMF (10 mL) was added 2,2-dimethyltetrahydro-2H-pyran-4-amine (0.24 g, 1.8 mmol) and sodium carbonate (0.53 g, 5.0 mmol) at ambient temperature. The reaction mixture was stirred at ambient temperature for 16 h. Completion of the reaction was confirmed by UPLC. The product was isolated and triturated with petroleum ether to afford (1S, 4S)-4-((2-((2,2-dimethyltetrahydro-2H-pyran-4-yl)amino)-5-nitropyrimidin-4-yl)amino)cyclohexane-1-carboxamide (0.4 g, 61%) as an yellow solid. MS (ESI) m/z 393.2 [M+1]$^+$.

(1S, 4S)-4-((5-Amino-2-((2,2-dimethyltetrahydro-2H-pyran-4-yl)amino)pyrimidin-4-yl)amino)cyclohexane-1-carboxamide. To a stirred solution of (1S, 4S)-4-((2-((2,2-dimethyltetrahydro-2H-pyran-4-yl)amino)-5-nitropyrimidin-4-yl)amino)cyclohexane-1-carboxamide (0.4 g, 1.01 mmol) in ethanol (24 mL) was added iron powder (0.57 g, 10 mmol) and ammonium chloride (0.053 g, 1 mmol) under an inert atmosphere at ambient temperature. The reaction mixture was stirred at 80° C. for 6 h. Completion of the reaction was confirmed by TLC. The resulting reaction mixture was filtered through bed of celite, washed with ethyl acetate and concentrated to afford (1S, 4S)-4-((5-amino-2-((2,2-dimethyltetrahydro-2H-pyran-4-yl)amino)pyrimidin-4-yl)amino)cyclohexane-1-carboxamide (0.4 g,) as a brown solid. MS (ESI) m/z 363.7 [M+1]$^+$.

(1S, 4S)-4-(8-((3-Chlorophenyl)amino)-2-((2,2-dimethyltetrahydro-2H-pyran-4-yl)amino)-9H-purin-9-yl)cyclohexane-1-carboxamide. To a stirred solution of (1S, 4S)-4-((5-amino-2-((2,2-dimethyltetrahydro-2H-pyran-4-yl)amino)pyrimidin-4-yl)amino)cyclohexane-1-carboxamide (0.4 g, 1.1 mmol) and 1-chloro-3-isothiocyanatobenzene (0.22 g, 1.32 mmol) in THF (8 mL) was added EDCI (0.42 g, 2.2 mmol) at ambient temperature. The reaction mixture was heated to 60° C. for 4 h. Completion of the reaction was confirmed by UPLC. The product was isolated and purified via standard methods to afford (1S, 4S)-4-(8-((3-chlorophenyl)amino)-2-((2,2-dimethyltetrahydro-2H-pyran-4-yl)amino)-9H-purin-9-yl)cyclohexane-1-carboxamide (0.35 g, 64%) as an off-white solid. MS (ESI) m/z 497, 498 [M, M+1]⁺.

9-((1S, 4S)-4-(Aminomethyl)cyclohexyl)-N8-(3-chlorophenyl)-N2-(2,2-dimethyltetrahydro-2H-pyran-4-yl)-9H-purine-2,8-diamine. To a stirred solution of (1S, 4S)-4-(8-((3-chlorophenyl)amino)-2-((2,2-dimethyltetrahydro-2H-pyran-4-yl)amino)-9H-purin-9-yl)cyclohexane-1-carboxamide (0.35 g, 0.70 mmol in THF (10 mL) was added lithium aluminium hydride in THF (1.6 M; 3 mL) dropwise at 0° C. The reaction mixture was stirred at ambient temperature for 18 h. Completion of the reaction was confirmed by TLC. The product was purified via standard methods to afford 9-((1S, 4S)-4-(aminomethyl) cyclohexyl)-N8-(3-chlorophenyl)-N2-(2,2-dimethyltetrahydro-2H-pyran-4-yl)-9H-purine-2,8-diamine (0.035 g, 10%) as an off-white solid. MS (ESI) m/z 484.2, 485.2 [M, M+1]+. ¹H NMR (400 MHz, CD₃OD): δ 8.57, 8.19 (s, 1H), 7.71 (s, 1H), 7.46 (d, J=7.6 Hz, 1H), 7.30-7.34 (m, 1H), 7.04-7.06 (m, 1H), 4.32-4.38 (m, 1H), 4.18-4.24 (m, 1H), 3.84-3.87 (m, 2H), 3.05-3.15 (m, 2H), 2.83-2.86 (m, 1H), 2.69-2.72 (m, 1H), 2.07-2.11 (m, 1H), 1.87-2.00 (m, 8H), 1.49-1.52 (m, 2H), 1.37 (s, 3H), 1.28 (s, 3H).

Example 13: 9-((1S, 4S)-4-(Aminomethyl)cyclohexyl)-N8-(3-chloro-2-fluorophenyl)-N2-(4-methyltetrahydro-2H-pyran-4-yl)-9H-purine-2,8-diamine

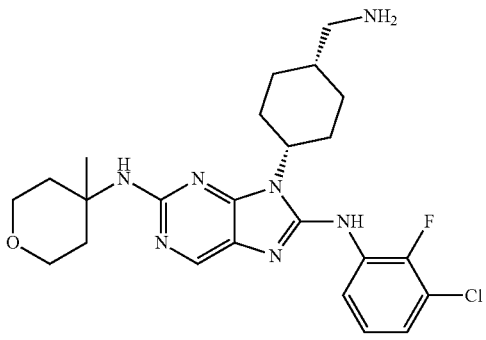 [SMILES: CC1(Nc2ncc3nc(Nc4cccc(Cl)c4F)n([C@H]4CC[C@@H](CN)CC4)c3n2)CCOCC1]

(1S, 4S)-4-((2-((4-Methyltetrahydro-2H-pyran-4-yl)amino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (1 g, 3.3 mmol) in DMF (30 mL) was added 4-methyltetrahydro-2H-pyran-4-amine (0.42 g, 3.67 mmol) and sodium bicarbonate (0.56 g, 6.7 mmol) at ambient temperature. The reaction mixture was heated to 60° C. for 4 h. Completion of the reaction was confirmed by UPLC. The product was isolated and triturated with petroleum ether to afford (1S, 4S)-4-((2-((4-methyltetrahydro-2H-pyran-4-yl)amino)-5-nitropyrimidin-4-yl)amino)cyclohexane-1-carboxamide (0.8 g, 63%) as an off-white solid. MS (ESI) m/z 379, 380 [M, M+1]⁺.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl) amino)cyclohexane-1-carboxamide (1.18 g, 2.11 mmol) in ethanol (24 mL) and water (3 mL) was added iron powder (0.8 g, 21.13 mmol) and ammonium chloride (0.13 g, 2.53 mmol) at ambient temperature. The reaction mixture heated at 80° C. Completion of the reaction was confirmed by UPLC. The resulting reaction mixture was filtered through bed of celite, washed with methanol and concentrated to afford (1S, 4S)-4-((5-amino-2-((4-methyltetrahydro-2H-pyran-4-yl)amino)pyrimidin-4-yl)amino)cyclohexane-1-carboxamide (0.6 g, 82%) as a brown solid. MS (ESI) m/z 349, 350 [M, M+1]⁺.

(1S, 4S)-4-(8-((3-Chloro-2-fluorophenyl)amino)-2-((4-methyltetrahydro-2H-pyran-4-yl)amino)-9H-purin-9-yl)cyclohexane-1-carboxamide. To a stirred solution of (1S, 4S)-4-((5-amino-2-((4-methyltetrahydro-2H-pyran-4-yl)amino)pyrimidin-4-yl)amino)cyclohexane-1-carboxamide (0.6 g, 1.7 mmol) and 1-chloro-2-fluoro-3-isothiocyanatobenzene (0.35 g, 1.89 mmol) in THF (10 mL) was added EDCI (0.66 g, 3.44 mmol) at ambient temperature. The reaction mixture was heated to 60° C. for 4 h. Completion of the reaction was confirmed by UPLC. The product was isolated and purified via standard methods to afford (1S, 4S)-4-(8-((3-chloro-2-fluorophenyl)amino)-2-((4-methyltetrahydro-2H-pyran-4-yl)amino)-9H-purin-9-yl)cyclohexane-1-carboxamide (0.3 g, 34%) as an off-white solid. MS (ESI) m/z 502, 503 [M, M+1]⁺.

9-((1S, 4S)-4-(Aminomethyl)cyclohexyl)-N8-(3-chloro-2-fluorophenyl)-N2-(4-methyltetrahydro-2H-pyran-4-yl)-9H-purine-2,8-diamine. To a stirred solution of (1S, 4S)-4-(8-((3-chloro-2-fluorophenyl)amino)-2-((4-methyltetrahydro-2H-pyran-4-yl)amino)-9H-purin-9-yl)cyclohexane-1-carboxamide (0.3 g, 0.59 mmol in THF (10 mL) was added lithium aluminium hydride in THF (1.6 M; 3 mL) dropwise at 0° C. and heated at 50° C. for 8 h. Completion of the reaction was confirmed by TLC. The product was isolated and purified via standard methods to afford 9-((1S, 4S)-4-(aminomethyl)cyclohexyl)-N8-(3-chloro-2-fluorophenyl)-N2-(4-methyltetrahydro-2H-pyran-4-yl)-9H-purine-2,8-diamine (15 mg, 5%). MS (ESI) m/z 488.2, 489.2 [M, M+1]+. ¹H NMR (400 MHz, CD₃OD): δ 8.22 (brs, 1H), 7.74 (brs, 1H), 7.18-7.23 (m, 1H), 7.14 (brs, 1H), 4.45 (brs, 1H), 3.74-3.84 (m, 4H), 3.20-3.25 (m, 2H), 2.63-2.67 (m, 2H), 2.46-2.50 (m, 2H), 2.00-2.17 (m, 1H), 1.90-1.97 (m, 6H), 1.83-1.89 (m, 2H), 1.60 (s, 3H).

Example 14: 9-((1S, 4S)-4-(Aminomethyl)cyclohexyl)-N2-(tert-butyl)-N8-(3,5-dichlorophenyl)-9H-purine-2,8-diamine

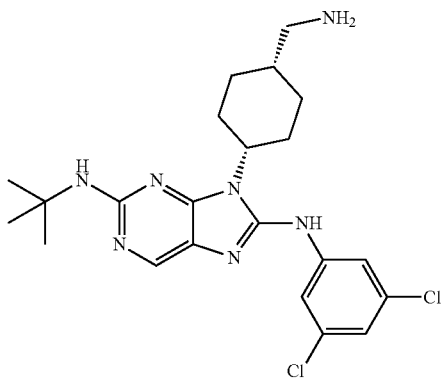 [SMILES: CC(C)(C)Nc1ncc2nc(Nc3cc(Cl)cc(Cl)c3)n([C@H]3CC[C@@H](CN)CC3)c2n1]

(1S, 4S)-4-((2-(tert-Butylamino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (1 g, 3.3 mmol) in DMF (30 mL) was added 2-methylpropan-2-amine (0.27 g, 3.7 mmol) and sodium bicarbonate (0.56 g, 6.7 mmol) at ambient temperature. The reaction mixture was heated to 60° C. for 4 h. Completion of the reaction was confirmed by UPLC. The product was isolated and triturated with petroleum ether to afford (1S, 4S)-4-((2-(tert-butylamino)-5-nitropyrimidin-4-yl)amino)cyclohexane-1-carboxamide (0.8 g, 71%) as an off-white solid. MS (ESI) m/z 337, 338 [M, M+1]$^+$.

(1S, 4S)-4-((5-Amino-2-(tert-butylamino)pyrimidin-4-yl)amino)cyclohexane-1-carboxamide. To a stirred solution of (1S, 4S)-4-((2-(tert-butylamino)-5-nitropyrimidin-4-yl)amino)cyclohexane-1-carboxamide (0.8 g, 2.38 mmol) in ethanol:water (27 mL, 10:1) was added iron powder (1.33 g, 23.78 mmol) and ammonium chloride (0.15 g, 2.85 mmol) at ambient temperature. The reaction mixture heated at 80° C. Completion of the reaction was confirmed by UPLC. The resulting reaction mixture was filtered through bed of celite, washed with methanol and concentrated to afford (1S, 4S)-4-((5-amino-2-(tert-butylamino)pyrimidin-4-yl)amino)cyclohexane-1-carboxamide (0.6 g, 83%) as a brown solid. MS (ESI) m/z 307, 308 [M, M+1]$^+$.

(1S, 4S)-4-(2-(tert-Butylamino)-8-((3,5-dichlorophenyl)amino)-9H-purin-9-yl)cyclohexane-1-carboxamide. To a stirred solution of (1S, 4S)-4-((5-amino-2-(tert-butylamino)pyrimidin-4-yl)amino)cyclohexane-1-carboxamide (0.6 g, 1.95 mmol) and 1,3-dichloro-5-isothiocyanatobenzene (0.43 g, 2.15 mmol) in THF (10 mL) was added EDCI (0.75 g, 3.91 mmol) at ambient temperature. The reaction mixture was heated to 60° C. for 4 h. Completion of the reaction was confirmed by UPLC. The product was isolated and purified via standard methods to afford ((1S, 4S)-4-(2-(tert-butylamino)-8-((3,5-dichlorophenyl)amino)-9H-purin-9-yl)cyclohexane-1-carboxamide (0.3 g, 32%) as an off-white solid. MS (ESI) m/z 477, 478 [M, M+1]$^+$.

9-((1S, 4S)-4-(Aminomethyl)cyclohexyl)-N2-(tert-butyl)-N8-(3,5-dichlorophenyl)-9H-purine-2,8-diamine. To a stirred solution of ((1S, 4S)-4-(2-(tert-butylamino)-8-((3,5-dichlorophenyl)amino)-9H-purin-9-yl)cyclohexane-1-carboxamide (0.3 g, 0.63 mmol) in THF (10 mL) was added lithium aluminium hydride in THF (1.6 M; 3 mL) dropwise at 0° C. and heated at 50° C. for 8 h. Completion of the reaction was confirmed by TLC. The product was isolated and purified via standard methods to afford 9-((1S, 4S)-4-(aminomethyl)cyclohexyl)-N2-(tert-butyl)-N8-(3,5-dichlorophenyl)-9H-purine-2,8-diamine (0.015 g, 6%). MS (ESI) m/z 462.2, 463.2, 464.2, 465.2 [M, M+1, M+2, M+3]$^+$. $^1$H NMR (400 MHz, CD$_3$OD): δ 8.26 (s, 1H), 7.66 (s, 2H), 7.08 (s, 1H), 4.38 (m, 1H), 2.72-2.76 (m, 2H), 2.16-2.20 (m, 1H), 1.91-1.20 (m, 5H), 1.81-1.85 (m, 2H), 1.56 (s, 10H).

Example 15: ((1S, 4S)-4-(8-((3-Chlorophenyl)amino)-2-((4-methyltetrahydro-2H-pyran-4-yl)amino)-9H-purin-9-yl)cyclohexyl)methanol

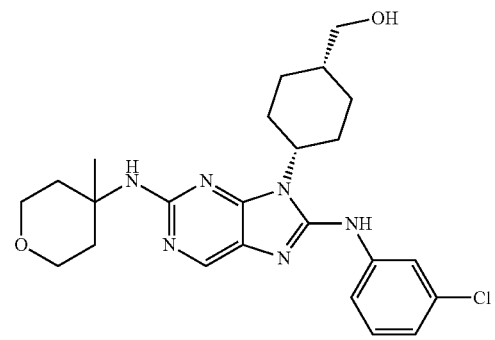 [SMILES: CC1(Nc2ncc3nc(Nc4cccc(Cl)c4)n([C@H]4CC[C@@H](CO)CC4)c3n2)CCOCC1]

((1S, 4S)-4-((2-Chloro-5-nitropyrimidin-4-yl)amino)cyclohexyl)methanol. To a stirred solution of 2,4-dichloro-5-nitropyrimidine (0.4 g, 2 mmol) in THF (10 mL) was added DIPEA (0.2 g, 2 mmol) portionwise followed by ((1S, 4S)-4-aminocyclohexyl)methanol (0.3 g, 2 mmol) at ambient temperature. The reaction mixture was stirred for 4 h. Completion of the reaction was confirmed by UPLC. The product was isolated to afford ((1S, 4S)-4-((2-chloro-5-nitropyrimidin-4-yl)amino)cyclohexyl)methanol (0.2 g, 27%) as a yellow solid. MS (ESI) m/z 287 [M+1]$^+$.

((1S, 4S)-4-((2-((4-Methyltetrahydro-2H-pyran-4-yl)amino)-5-nitropyrimidin-4-yl)amino)cyclohexyl)methanol. To a stirred solution of ((1S, 4S)-4-((2-chloro-5-nitropyrimidin-4-yl)amino)cyclohexyl)methanol (0.05 g, 0.2 mmol) in DMF (10 mL) was added sodium carbonate (0.04 g, 0.4 mmol) portionwise followed by 4-methyltetrahydro-2H-pyran-4-amine hydrochloride (0.03 g, 0.2 mmol) at ambient temperature The reaction mixture was stirred for 4 h. Completion of the reaction was confirmed by UPLC. The product was isolated to afford ((1S, 4S)-4-((2-((4-methyltetrahydro-2H-pyran-4-yl)amino)-5-nitropyrimidin-4-yl)amino)cyclohexyl) methanol (0.03 g, 50%) as a yellowsolid. MS (ESI) m/z 366 [M+1]$^+$.

((1S, 4S)-4-((5-Amino-2-((4-methyltetrahydro-2H-pyran-4-yl)amino)pyrimidin-4-yl)amino)cyclohexyl)methanol. To a stirred solution of ((1S, 4S)-4-((2-((4-methyltetrahydro-2H-pyran-4-yl)amino)-5-nitropyrimidin-4-yl)amino)cyclohexyl)methanol (0.1 g, 3 mmol) in ethanol:water (4 mL, 1:1) was added iron powder (0.2 g, 2.7 mmol) portionwise followed by ammonium chloride (0.02 g, 0.3 mmol) at ambient temperature. The reaction mixture was heated to 80° C. for 4 h. Completion of the reaction was confirmed by UPLC. The product was isolated and purified via standard methods to afford ((1S, 4S)-4-((5-amino-2-((4-methyltetrahydro-2H-pyran-4-yl)amino)pyrimidin-4-yl)amino)cyclohexyl)methanol (0.08 g, 80%) as a yellow solid. MS (ESI) m/z 336 [M+1].

((1S, 4S)-4-(8-((3-Chlorophenyl)amino)-2-((4-methyltetrahydro-2H-pyran-4-yl)amino)-9H-purin-9-yl)cyclohexyl) methanol. To a stirred solution of ((1S, 4S)-4-((5-amino-2-((4-methyltetrahydro-2H-pyran-4-yl)amino)pyrimidin-4-yl)amino)cyclohexyl)methanol (0.1 g, 3 mmol) in THF (100 mL) was added 1-ethyl-3-(3-dimethylaminopropyl)carbodiimide (0.07 g, 3 mmol) and 1-isothiocyanato-3-chloro benzene (0.05 g 3 mmol) at ambient temperature. The reaction mixture was heated to 60° C. for 4 h. Completion of the reaction was confirmed by UPLC. The product was isolated and purified via standard methods to afford ((1S, 4S)-4-(8-((3-chlorophenyl)amino)-2-((4-methyltetrahydro-2H-pyran-4-yl)amino)-9H-purin-9-yl)cyclohexyl)methanol (0.06 g, 40%). MS (ESI) m/z 471 [M+1]+. $^1$H NMR (400 MHz, CD$_3$OD): δ 8.20 (s, 1H), 7.70 (s, 1H), 7.45 (d, J=8.0 Hz, 1H), 7.28-7.32 (m, 1H), 7.03 (d, J=8.0 Hz, 1H), 4.32-4.38 (m, 1H), 3.72-3.80 (m, 4H), 3.47-3.51 (m, 2H), 2.64-2.71 (m, 2H), 2.35-2.38 (m, 2H), 1.93-2.04 (m, 4H), 1.74-1.80 (m, 2H), 1.58-1.63 (m, 1H), 1.57 (s, 3H), 1.20-1.30 (m, 2H).

Example 16: 9-((1R, 4R)-4-(Aminomethyl)cyclohexyl)-N2-(tert-butyl)-N8-(3-(trifluoromethyl) phenyl)-9H-purine-2,8-diamine

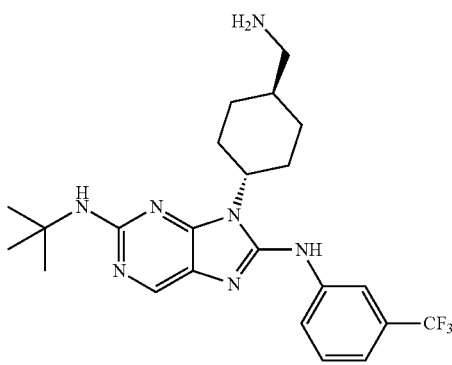 [SMILES: CC(C)(C)Nc1ncc2nc(Nc3cccc(C(F)(F)F)c3)n([C@H]3CC[C@H](CN)CC3)c2n1]

(1R, 4R)-4-((2-Chloro-5-nitropyrimidin-4-yl)amino)cyclohexane-1-carboxamide. To a stirred solution of 2, 4-dichloro-5-nitropyrimidine (1.0 g, 5.15 mmol) and DIPEA (2.75 mL, 15.45 mmol) in IPA (20 mL) was added portionwise (1R, 4R)-4-aminocyclohexane-1-carboxamide (0.73 g, 5.15 mmol) at 0° C. under N2. The reaction mixture was slowly warmed to ambient temperature and stirred for 2 h. Completion of the reaction was confirmed by UPLC. The product was isolated to afford (1r, 4r)-4-((2-chloro-5-nitropyrimidin-4-yl)amino)cyclohexane-1-carboxamide (1.2 g) as pale yellow solid. MS (ESI) m/z 300, 301 [M, M+1]+.

(1R, 4R)-4-((2-(tert-Butylamino)-5-nitropyrimidin-4-yl)amino)cyclohexane-1-carboxamide. To a stirred solution of (1r, 4r)-4-((2-chloro-5-nitropyrimidin-4-yl)amino)cyclohexane-1-carboxamide (1.2 g, 4 mmol), tert-butylamine (0.58 g, 8 mmol) and sodium bicarbonate (0.5 g, 6 mmol) in DMF (10 mL) was heated to 60° C. for 4 h. Completion of the reaction was confirmed by UPLC. The reaction mixture was diluted with water. The solid obtained was filtered, washed with water and dried under vacuum to afford (1r, 4r)-4-((2-(tert-butylamino)-5-nitropyrimidin-4-yl)amino)cyclohexane-1-carboxamide (1.0 g, 75%) as a pale yellow solid. MS (ESI) m/z 337 [M+1]+.

(1R, 4R)-4-((5-Amino-2-(tert-butylamino)pyrimidin-4-yl)amino)cyclohexane-1-carboxamide. To a stirred solution of (1r, 4r)-4-((2-(tert-butylamino)-5-nitropyrimidin-4-yl)amino)cyclohexane-1-carboxamide (1.0 g, 3 mmol) in ethanol:water (20 mL, 3:1) was added iron powder (1.66 g, 30 mmol) and ammonium chloride (0.146 g, 3 mmol) at ambient temperature. The reaction mixture was heated to 85° C. for 2 h. Completion of the reaction was confirmed by UPLC. The resulting reaction mixture was filtered through a bed of celite, washed with ethyl acetate and concentrated to afford (1r, 4r)-4-((5-amino-2-(tert-butylamino)pyrimidin-4-yl)amino)cyclohexane-1-carboxamide (0.9 g) as a brown solid. MS (ESI) m/z 307 [M+1]+.

(1R, 4R)-4-(2-(tert-Butylamino)-8-((3-(trifluoromethyl)phenyl)amino)-9H-purin-9-yl)cyclohexane-1-carboxamide. To a stirred solution of (1r, 4r)-4-((5-amino-2-(tert-butylamino)pyrimidin-4-yl)amino)cyclohexane-1-carboxamide (0.42 g, 1.4 mmol) and 1-isothiocyanato-3-(trifluoromethyl)benzene (0.33 g, 1.6 mmol) in THF was added EDCI (0.5 g, 2.7 mmol) at ambient temperature. The reaction mixture was heated to 60° C. for 4 h. Completion of the reaction was confirmed by UPLC. The product was isolated and purified via standard methods to afford (1r, 4r)-4-(2-(tert-butylamino)-8-((3-(trifluoromethyl)phenyl)amino)-9H-purin-9-yl) cyclohexane-1-carboxamide (0.2 g, 31%) as a brown solid. MS (ESI) m/z 476 [M+1]+.

9-((1R, 4R)-4-(Aminomethyl)cyclohexyl)-N2-(tert-butyl)-N8-(3-(trifluoromethyl)phenyl)-9H-purine-2,8-diamine. To a stirred solution of (1r, 4r)-4-(2-(tert-butylamino)-8-((3-(trifluoromethyl)phenyl)amino)-9H-purin-9-yl)cyclohexane-1-carboxamide (0.18 g, 0.4 mmol) in THF (5 mL) was added 1.5 M solution of lithium aluminium hydride (0.5 mL, 0.75 mmol) at 0° C. The reaction mixture was stirred at 40° C. for 1 h. Completion of the reaction was confirmed by UPLC. The product was isolated and purified via standard methods to afford 9-((1r, 4r)-4-(aminomethyl)cyclohexyl)-N2-(tert-butyl)-N8-(3-(trifluoromethyl)phenyl)-9H-purine-2, 8-diamine (0.05 g, 29%). MS (ESI) m/z 462 [M+1]+. $^1$H NMR (400 MHz, CD$_3$OD): δ 8.56 (s, 1H), 8.19 (s, 1H), 7.93 (s, 1H), 7.83 (d, J=8 Hz, 1H), 7.50-7.54 (m, 1H), 7.32 (d, J=7.6 Hz, 1H), 4.36-4.42 (m, 1H), 2.75-2.87 (m, 4H), 2.02-2.10 (m, 4H), 1.78-1.80 (m, 1H), 1.52 (s, 9H), 1.28-1.36 (m, 2H).

Example 17: 9-((1S, 4S)-4-(Aminomethyl)cyclohexyl)-N2-(tert-pentyl)-N8-(3-(trifluoromethyl)phenyl)-9H-purine-2,8-diamine

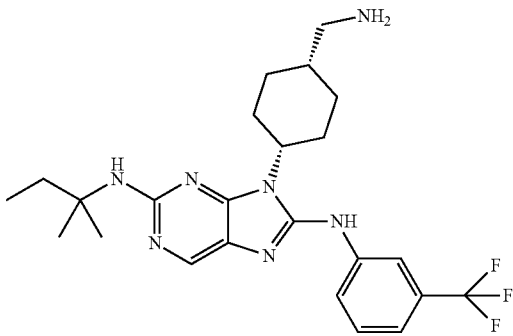 [SMILES: CCC(C)(C)Nc1ncc2nc(Nc3cccc(C(F)(F)F)c3)n([C@H]3CC[C@@H](CN)CC3)c2n1]

(1S, 4S)-4-((5-Nitro-2-(tert-pentylamino)pyrimidin-4-yl)amino)cyclohexane-1-carboxamide. To a stirred solution of (1S, 4S)-4-((2-chloro-5-nitropyrimidin-4-yl)amino)cyclohexane-1-carboxamide (0.6 g, 2 mmol) in DMF (10 mL) was added sodium bicarbonate (0.17 g, 2 mmol) portionwise followed by 2-methylbutane-2-amine (0.22 g, 2 mmol) at ambient temperature. The reaction mixture was heated to 60° C. for 16 h. Completion of the reaction was confirmed by UPLC. The product was isolated to afford (1S, 4S)-4-((5-nitro-2-(tert-pentylamino)pyrimidin-4-yl)amino) cyclohexane-1-carboxamide (0.6 g, 83%) as a yellow solid. MS (ESI) m/z 351 [M+1]+.

(1S, 4S)-4-((5-Amino-2-(tert-pentylamino)pyrimidin-4-yl)amino)cyclohexane-1-carboxamide. To a stirred solution of (1S, 4S)-4-((5-nitro-2-(tert-pentylamino)pyrimidin-4-yl)amino)cyclohexane-1-carboxamide (0.5 g, 2 mmol) in ethanol (10 mL) was added palladium on charcoal (0.06 g, 10% W/M) portionwise under argon atmosphere. The reaction was stirred at ambient temperature under atmospheric hydrogen atmosphere. Completion of the reaction was confirmed by UPLC. The resulting reaction mixture was filtered through a bed of celite, washed with ethyl acetate and concentrated to afford (1S, 4S)-4-((5-amino-2-(tert-pentylamino)pyrimidin-4-yl)amino)cyclohexane-1-carboxamide (0.4 g, 90%) as a yellow solid. MS (ESI) m/z 321 [M+1]$^+$.

(1S, 4S)-4-(2-(tert-Pentylamino)-8-((3-(trifluoromethyl)phenyl)amino)-9H-purin-9-yl)cyclohexane-1-carboxamide. To a stirred solution of (1S, 4S)-4-((5-amino-2-(tert-pentylamino)pyrimidin-4-yl)amino)cyclohexane-1-carboxamide (0.5 g, 1 mmol) in THF (10 mL) was added 1-ethyl-3-(3-dimethylaminopropyl)carbodiimide (0.6 g, 3 mmol) and 1-isothiocyanato-3-(trifluoromethyl)benzene (0.3 g, 2 mmol) at ambient temperature. The reaction mixture was heated to 60° C. for 4 h. Completion of the reaction was confirmed by UPLC. The product was isolated and purified via standard methods to afford (1S, 4S)-4-(2-(tert-pentylamino)-8-((3-(trifluoromethyl)phenyl)amino)-9H-purin-9-yl)cyclohexane-1-carboxamide (0.4 g, 55%) as an off-white solid. MS (ESI) m/z 490 [M+1]$^+$.

9-((1S, 4S)-4-(Aminomethyl)cyclohexyl)-N2-(tert-pentyl)-N8-(3-(trifluoromethyl)phenyl)9H-purine-2,8-diamine. To a stirred solution of (1S, 4S)-4-(2-(tert-pentylamino)-8-((3-(trifluoromethyl)phenyl)amino)-9H-purin-9-yl)cyclohexane-1-carboxamide (0.3 g, 1 mmol) in THF (3 mL) was added lithium aluminum hydride in THF (1.6 M; 2 mL) at 0° C. The reaction mixture was heated to 55° C. for 1 h. Completion of the reaction was confirmed by UPLC. The product was purified via standard methods to afford 9-((1S, 4S)-4-(aminomethyl)cyclohexyl)-N2-(tert-pentyl)-N8-(3-(trifluoromethyl)phenyl)-9H-purine-2,8-diamine (0.09 g, 30%). MS (ESI) m/z 476 [M+1]$^+$. $^1$H NMR (400 MHz, CD$_3$OD): δ 8.50 (s, 1H), 8.20 (s, 1H), 7.95 (s, 1H), 7.85 (d, J=8.0 Hz, 1H), 7.51-7.55 (m, 1H), 7.33 (d, J=8.0 Hz, 1H), 4.38-4.44 (m, 1H), 3.28 (d, J=7.6 Hz, 2H), 2.66-2.76 (m, 2H), 2.17 (m, 1H), 1.83-2.05 (m, 8H), 1.50 (s, 6H), 0.96 (m, 3H).

Example 18: Methyl (((1S, 4S)-4-(8-((3-chlorophenyl) amino)-2-((4-methyltetrahydro-2H-pyran-4-yl) amino)-9H-purin-9-yl)cyclohexyl)methyl)carbamate

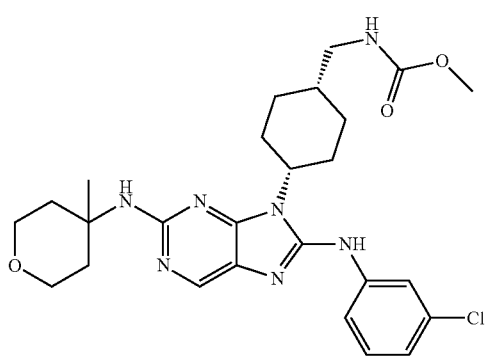 [SMILES: COC(=O)NC[C@H]1CC[C@@H](n2c(Nc3cccc(Cl)c3)nc3cnc(NC4(C)CCOCC4)nc32)CC1]

Methyl (((1S, 4S)-4-(8-((3-chlorophenyl)amino)-2-((4-methyltetrahydro-2H-pyran-4-yl)amino)-9H-purin-9-yl)cyclohexyl)methyl)carbamate. To a stirred solution of 9-((1S, 4S)-4-(aminomethyl)cyclohexyl)-N8-(3-chlorophenyl)-N2-(4-methyltetrahydro-2H-pyran-4-yl)-9H-purine-2,8-di-amine (0.1 g, 0.2 mmol) in methanol (5 mL) was added pyridine (0.02 g, 0.2 mmol) portionwise followed by methylchloroformate (0.02 g, 0.2 mmol) at 0° C. The reaction mixture was stirred for 30 minutes at 0° C. Completion of the reaction was confirmed by UPLC. The product was purified via standard methods to afford methyl(((1S, 4S)-4-(8-((3-chlorophenyl)amino)-2-((4-methyltetrahydro-2H-pyran-4-yl)amino)-9H-purin-9-yl)cyclohexyl)methyl)carbamate (0.02 g, 21%). MS (ESI) m/z 528 [M+1]$^+$. $^1$H NMR (400 MHz, CD$_3$OD): δ 8.20 (s, 1H), 7.71 (s, 1H), 7.46 (d, J=8.0 Hz, 1H), 7.29-7.33 (m, 1H), 7.04 (d, J=8.0 Hz, 1H), 4.30-4.36 (m, 1H), 3.70-3.83 (m, 4H), 3.66 (s, 3H), 3.40-3.50 (m, 2H), 2.70-2.80 (m, 2H), 2.35-2.38 (m, 2H), 1.91-1.95 (m, 3H), 1.71-1.87 (m, 6H), 1.60 (s, 3H).

Example 19: 9-((1S, 4S)-4-(Aminomethyl)cyclohexyl)-N2-(tert-butyl)-N8-(3-(trifluoromethyl)phenyl)-9H-purine-2,8-diamine

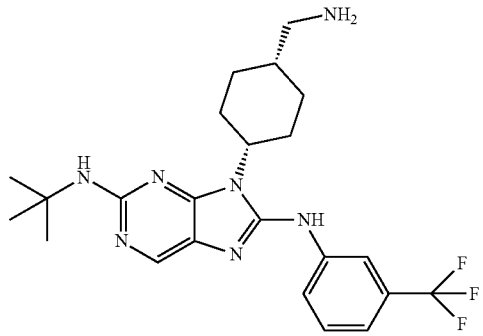 [SMILES: CC(C)(C)Nc1ncc2nc(Nc3cccc(C(F)(F)F)c3)n([C@H]3CC[C@@H](CN)CC3)c2n1]

(1S,4S)-4-((2-(tert-Butylamino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (1.0 g, 3.3 mmol) in DMF (10 mL) was added tert-butylamine (0.3 g, 4 mmol) and sodium bicarbonate (0.84 g, 10 mmol) at ambient temperature. The reaction mixture was heated to 60° C. for 4 h. Completion of the reaction was confirmed by UPLC. The product was isolated and triturated with petroleum ether to afford (1S, 4S)-4-((2-(tert-butylamino)-5-nitropyrimidin-4-yl)amino)cyclohexane-1-carboxamide (0.7 g, 63%) as a yellow solid. MS (ESI) m/z 337 [M+1]$^+$.

(1S, 4S)-4-((5-Amino-2-(tert-butylamino)pyrimidin-4-yl)amino)cyclohexane-1-carboxamide. To a stirred solution of (1S, 4S)-4-((2-(tert-butylamino)-5-nitropyrimidin-4-yl)amino)cyclohexane-1-carboxamide (0.7 g, 2 mmol) in ethanol (24 mL) was added palladium on carbon (0.1 g, W/W) under inert atmosphere at ambient temperature. The reaction mixture was stirred under atmospheric hydrogen pressure at ambient temperature. Completion of the reaction was confirmed by UPLC. The product was isolated via standard methods to afford (1S, 4S)-4-((5-amino-2-(tert-butylamino)pyrimidin-4-yl)amino)cyclohexane-1-carboxamide (0.6 g, 90%) as a brown solid. MS (ESI) m/z 307 [M+1]$^+$.

(1S, 4S)-4-(2-(tert-Butylamino)-8-((3-(trifluoromethyl)phenyl)amino)-7,8-dihydro-9H-purin-9-yl)cyclohexane-1-carboxamide. To a stirred solution of (1S, 4S)-4-((5-amino-2-(tert-butylamino)pyrimidin-4-yl)amino)cyclohexane-1-carboxamide (0.6 g, 2 mmol) and 1-isothiocyanato-3-(trifluoromethyl)benzene (0.5 g, 2.0 mmol) in THF was added 1-ethyl-3-(3-dimethylaminopropyl)carbodiimide (0.75 g, 4 mmol) at ambient temperature. The reaction mixture was heated to 50° C. for 4 h. Completion of the reaction was confirmed by TLC. The product was isolated and purified via standard purification methods to afford (1S, 4S)-4-(2-(tert-butylamino)-8-((3-(trifluoromethyl)phenyl)amino)-7, 8-dihydro-9H-purin-9-yl)cyclohexane-1-carboxamide (0.45 g, 48%) as a yellow solid. MS (ESI) m/z 476 [M-H]⁺.

9-((1S, 4S)-4-(Aminomethyl)cyclohexyl)-N2-(tert-butyl)-N8-(3-(trifluoromethyl)phenyl)-8,9-dihydro-7H-purine-2,8-diamine To a stirred solution of (1S, 4S)-4-(2-(tert-butylamino)-8-((3-(trifluoromethyl)phenyl)amino)-7, 8-dihydro-9H-purin-9-yl)cyclohexane-1-carboxamide (0.3 g, 0.13 mmol) in THF (10 mL) was added dropwise lithium aluminium hydride in THF (1.6 M, 5 mL) at 0° C. and heated at 45° C. for 8 h. Completion of the reaction was confirmed by TLC. The product was purified via standard methods to afford 9-((1S, 4S)-4-(aminomethyl)cyclohexyl)-N2-(tert-butyl)-N8-(3-(trifluoromethyl)phenyl)-8,9-dihydro-7H-purine-2,8-diamine (0.06 g, 20%). MS (ESI) m/z 463 [M+1]+.
¹H NMR (400 MHz, CD₃OD): δ8.56, 8.19 (brs, 1H), 7.88 (brs, 1H), 7.79-7.83 (m, 1H), 7.48-7.52 (m, 1H), 7.30 (d, J=6.8 Hz, 1H), 4.31-4.38 (m, 1H), 3.15 (d, J=6.8 Hz, 2H), 2.72-2.78 (m, 2H), 1.93-2.00 (m, 3H), 1.79-1.89 (m, 4H), 1.54 (s, 9H).

Example 20: 9-((1S, 4S)-4-(Aminomethyl)cyclohexyl)-N8-(3-chlorophenyl)-N2-methyl-N2-(tetrahydro-2H-pyran-4-yl)-9H-purine-2,8-diamine

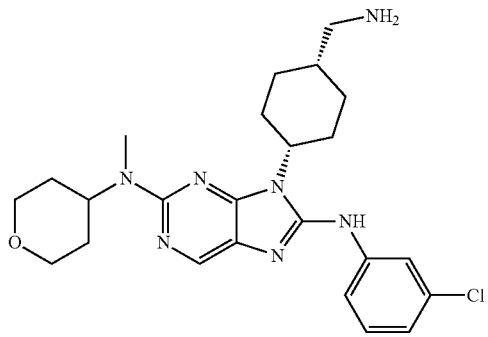 [SMILES: CN(c1ncc2nc(Nc3cccc(Cl)c3)n([C@H]3CC[C@@H](CN)CC3)c2n1)C1CCOCC1]

N-Methyltetrahydro-2H-pyran-4-amine. To a stirred solution of tetrahydro-4H-pyran-4-one (1 g, 10 mmol) in THF (10 mL) was added methylamine (0.62 g, 20 mmol, 2 M solution in THF) dropwise at ambient temperature followed by acetic acid (0.5 mL). The reaction mixture was stirred for 1 h. Sodium cyanoborohydride (0.7 g, 12 mmol) was added to the reaction mixture at 0° C. and continued stirring at ambient temperature for 16 h. Completion of the reaction was confirmed by TLC. The product was isolated to afford N-methyltetrahydro-2H-pyran-4-amine (1 g) as a yellow color liquid. GCMS (ESI) m/z 115 [M]⁺.

(1S, 4S)-4-((2-(Methyl(tetrahydro-2H-pyran-4-yl)amino)-5-nitropyrimidin-4-yl)amino)cyclo hexane-1-carboxamide. To a stirred solution of (1S, 4S)-4-((2-chloro-5-nitropyrimidin-4-yl) amino)cyclohexane-1-carboxamide (5 g, 7 mmol) in DMF (10 mL) was added N-methyl tetrahydro-2H-pyran-4-amine (1 g, 8 mmol) and sodium carbonate (2 g, 20 mmol) under nitrogen atmosphere. The reaction was stirred at ambient temperature for 16 h. Completion of the reaction was confirmed by UPLC. Product was isolated via standard purification methods to afford (1S, 4S)-4-((2-(methyl(tetrahydro-2H-pyran-4-yl)amino)-5-nitropyrimidin-4-yl)amino)cyclohexane-1-carboxamide (0.5 g, 22%) as a yellow solid. MS (ESI) m/z 379 [M+1]⁺.

(1S, 4S)-4-((5-Amino-2-(methyl(tetrahydro-2H-pyran-4-yl)amino)pyrimidin-4-yl)amino) cyclohexane-1-carboxamide. To a stirred solution of (1S, 4S)-4-((2-(methyl(tetrahydro-2H-pyran-4-yl)amino)-5-nitropyrimidin-4-yl)amino) cyclohexane-1-carboxamide (0.4 g, 1 mmol) in ethanol (10 mL) was added palladium on carbon (0.04 g, W/W) under inert atmosphere at ambient temperature. The reaction mixture was stirred under atmospheric hydrogen pressure at ambient temperature. Completion of the reaction was confirmed by UPLC. The product was isolated via standard methods to afford (1S, 4S)-4-((5-amino-2-(methyl(tetrahydro-2H-pyran-4-yl)amino)pyrimidin-4-yl)amino)cyclohexane-1-carboxamide (0.35 g, 94%) as a brown solid. MS (ESI) m/z 349 [M+1]⁺.

(1S, 4S)-4-(8-((3-Chlorophenyl)amino)-2-(methyl(tetrahydro-2H-pyran-4-yl)amino)-9H-purin-9-yl)cyclohexane-1-carboxamide. To a stirred solution of (1S, 4S)-4-((5-amino-2-(methyl (tetrahydro-2H-pyran-4-yl)amino) pyrimidin-4-yl)amino)cyclohexane-1-carboxamide (0.35 g, 1 mmol) in THF (10 mL) was added 1-chloro-3-isothiocyanatobenzene (0.2 g, 1 mmol) and 1-ethyl-3-(3-dimethylaminopropyl)carbodiimide (0.4 g, 2 mmol) at ambient temperature. The reaction mixture was heated to 60° C. for 4 h. Completion of the reaction was confirmed by UPLC. The product was isolated and purified via standard methods to afford (1S, 4S)-4-(8-((3-chlorophenyl)amino)-2-(methyl(tetrahydro-2H-pyran-4-yl)amino)-9H-purin-9-yl)cyclohexane-1-carboxamide (0.23 g, 47%) as pale yellow solid. MS (ESI) m/z 484, 485 [M, M+1]⁺.

9-((1S, 4S)-4-(Aminomethyl)cyclohexyl)-N8-(3-chlorophenyl)-N2-methyl-N2-(tetrahydro-2H-pyran-4-yl)-9H-purine-2,8-diamine. To a stirred solution of (1S, 4S)-4-(8-((3-chlorophenyl)amino)-2-(methyl(tetrahydro-2H-pyran-4-yl) amino)-9H-purin-9-yl)cyclohexane-1-carboxamide (0.23 g, 0.5 mmol) in THF (5 mL) was added lithium aluminum hydride in THF (1.6 M; 4 mL) at 0° C. The reaction mixture was heated to 45° C. for 1 h. Completion of the reaction was confirmed by UPLC. The product was purified via standard methods to afford 9-((1S, 4S)-4-(aminomethyl)cyclohexyl)-N8-(3-chlorophenyl)-N2-methyl-N2-(tetrahydro-2H-pyran-4-yl)-9H-purine-2,8-diamine (0.05 g, 22%). MS (ESI) m/z 470, 471 [M, M+1]⁺. ¹H NMR (400 MHz, CD₃OD): δ 8.57 (s, 1H), 8.27 (s, 1H), 7.65 (s, 1H), 7.42 (d, J=8 Hz, 1H), 7.27-7.31 (t, J=8 Hz, 1H), 7.01-7.03 (dd, J=1.6 Hz & 8 Hz, 1H),4.81-4.87 (m, 1H), 4.31-4.37 (m, 1H), 4.06-4.10 (m, 2H), 3.55-3.61 (m, 2H), 3.15-3.17 (d, J=7.2 Hz 2H), 3.10 (s, 3H) 2.76-2.86 (m, 2H), 1.92-2.00 (m, 5H), 1.66-1.86 (m, 6H).

Example 21: 9-((1S, 4S)-4-(Aminomethyl)cyclohexyl)-N8-(3-chlorophenyl)-N2-(1-methylcyclobutyl)-9H-purine-2,8-diamine

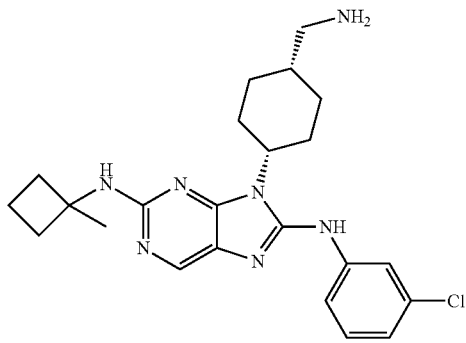 [SMILES: CC1(Nc2ncc3nc(Nc4cccc(Cl)c4)n([C@H]4CC[C@@H](CN)CC4)c3n2)CCC1]

(1S, 4S)-4-((2-((1-Methylcyclobutyl)amino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (1.0 g, 3 mmol) in DMF (10 mL) was added 1-methylcyclobutan-1-amine (0.5 g, 4 mmol) and sodium bicarbonate (0.56 g, 7 mmol) at ambient temperature. The reaction mixture was heated to 60° C. for 4 h. Completion of the reaction was confirmed by UPLC. The product was isolated via standard methods to afford (1S, 4S)-4-((2-((1-methylcyclobutyl) amino)-5-nitropyrimidin-4-yl) amino) cyclohexane-1-carboxamide (0.6 g, 51%) as yellow solid. MS (ESI) m/z 349 [M+1]+.

(1S, 4S)-4-((5-Amino-2-((1-methylcyclobutyl)amino)pyrimidin-4-yl)amino)cyclohexane-1-carboxamide. To a stirred solution (1S, 4S)-4-((2-((1-methylcyclobutyl) amino)-5-nitropyrimidin-4-yl) amino) cyclohexane-1-carboxamide (0.8 g, 2 mmol) in ethanol (24 mL) was added palladium on carbon (0.1 g, 10% w/w) under inert atmosphere at ambient temperature. The reaction mixture was stirred under atmospheric hydrogen pressure at ambient temperature for 16 h. Completion of the reaction was confirmed by UPLC. The product was isolated via standard purification methods to afford (1S, 4S)-4-((5-amino-2-((tetrahydro-2H-pyran-4-yl)amino)pyrimidin-4-yl) amino)cyclohexane-1-carboxamide (0.7 g, 90%) as a brown solid. MS (ESI) m/z 319 [M+1]+.

(1S, 4S)-4-(8-((3-Chlorophenyl)amino)-2-((1-methylcyclobutyl)amino)-9H-purin-9-yl)cyclohexane-1-carboxamide. To a stirred solution of (1S, 4S)-4-((5-amino-2-((tetrahydro-2H-pyran-4-yl) amino) pyrimidin-4-yl) amino) cyclohexane-1-carboxamide (0.4 g, 1 mmol) and 1-chloro-3-isothiocyanatobenzene (0.2 g, 1 mmol) in THF was added 1-ethyl-3-(3-dimethylaminopropyl)carbodiimide (0.5 g, 2 mmol) at ambient temperature. The reaction mixture was heated to 50° C. for 4 h. Completion of the reaction was confirmed by UPLC. The product was isolated via standard methods to afford (1S, 4S)-4-(8-((3-chlorophenyl)amino)-2-((1-methylcyclobutyl)amino)-9H-purin-9-yl)cyclohexane-1-carboxamide (0.3 g, 43%) as an yellow solid. MS (ESI) m/z 454, 455 [M, M+1]+.

9-((1S, 4S)-4-(Aminomethyl)cyclohexyl)-N8-(3-chlorophenyl)-N2-(1-methylcyclobutyl)-9H-purine-2,8-diamine. To a stirred solution of (1S, 4S)-4-(8-((3-chlorophenyl) amino)-2-((1-methylcyclobutyl)amino)-9H-purin-9-yl)cyclohexane-1-carboxamide (0.2 g, 0.4 mmol) in THF (10 mL) was added drop wise lithium aluminium hydride in THF (1.6 M, 3 mL) at 0° C. The reaction mixture was heated to 50° C. for 4 h. Completion of the reaction was confirmed by UPLC. The product was purified via standard methods to afford 9-((1S, 4S)-4-(aminomethyl)cyclohexyl)-N8-(3-chlorophenyl)-N2-(1-methylcyclobutyl)-9H-purine-2,8-diamine (0.040 g, 16%). MS (ESI) m/z 440, 441 [M, M+1]+. ¹H NMR (400 MHz, CD₃OD): δ 8.60, 8.19 (s, 1H), 7.64 (s, 1H), 7.42-7.40 (d, J=8.4 Hz, 1H), 7.26-7.31 (t, J=8 Hz, 1H), 7.01-7.04 (m, 1H), 4.30-4.34 (m, 1H), 3.20-3.22 (d, J=7.6 Hz, 2H), 2.69-2.73 (m, 2H), 2.33-2.37 (m, 2H), 2.15-2.20 (m, 2H), 2.08 (brs, 1H), 1.86-1.98 (m, 4H), 1.77-1.85 (m, 4H), 1.60 (s, 3H).

Example 22: 9-((1S, 4S)-4-(Aminomethyl)cyclohexyl)-N8-(3-chlorophenyl)-N2-(tert-pentyl)-9H-purine-2,8-diamine

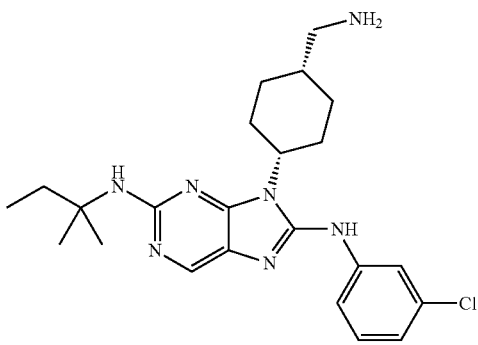 [SMILES: CCC(C)(C)Nc1ncc2nc(Nc3cccc(Cl)c3)n([C@H]3CC[C@@H](CN)CC3)c2n1]

(1S, 4S)-4-((5-Nitro-2-(tert-pentylamino)pyrimidin-4-yl) amino)cyclohexane-1-carboxamide. To a stirred solution of (1S, 4S)-4-((2-chloro-5-nitropyrimidin-4-yl)amino)cyclohexane-1-carboxamide (0.6 g, 2 mmol) in DMF (10 mL) was added sodium bicarbonate (0.17 g, 2 mmol) portionwise followed by 2-methylbutane-2-amine (0.22 g, 2 mmol) at ambient temperature. The reaction mixture was heated to 60° C. for 16 h. Completion of the reaction was confirmed by UPLC. The product was isolated to afford (1S, 4S)-4-((5-nitro-2-(tert-pentylamino)pyrimidin-4-yl)amino) cyclohexane-1-carboxamide (0.6 g, 83%) as a yellow solid. MS (ESI) m/z 351 [M+1]+.

(1S, 4S)-4-((5-Amino-2-(tert-pentylamino)pyrimidin-4-yl)amino)cyclohexane-1-carboxamide. To a stirred solution of (1S, 4S)-4-((5-nitro-2-(tert-pentylamino)pyrimidin-4-yl) amino)cyclohexane-1-carboxamide (0.5 g, 2 mmol) in ethanol (10 mL) was added palladium on charcoal (0.06 g, 10% W/M) portionwise under argon atmosphere. The reaction was stirred at ambient temperature under atmospheric hydrogen. Completion of the reaction was confirmed by UPLC. The resulting reaction mixture was filtered through a bed of celite, washed with ethyl acetate and concentrated to afford (1S, 4S)-4-((5-amino-2-(tert-pentylamino)pyrimidin-4-yl)amino)cyclohexane-1-carboxamide (0.4 g, 90%) as a yellow solid. MS (ESI) m/z 321 [M+1]+.

(1S, 4S)-4-8-((3-Chlorophenyl)amino)-2-(tert-pentylamino)-9H-purin-9-yl)cyclohexane-1-carboxamide. To a stirred solution of (1S, 4S)-4-((5-amino-2-(tert-pentylamino)pyrimidin-4-yl) amino)cyclohexane-1-carboxamide (0.5 g, 1 mmol) in THF (10 mL) was added 1-ethyl-3-(3-dimethylaminopropyl)carbodiimide (0.6 g, 3 mmol) and 1-chloro-3-isothiocyanatobenzene (0.27 g, 2 mmol) at ambient temperature. The reaction mixture was heated to 60° C. for 4 h. Completion of the reaction was confirmed by UPLC. The product was isolated and purified via standard methods to afford (1S, 4S)-4-8-((3-chlorophenyl)amino-2-(tert-pentylamino)-9H-purin-9-yl)cyclohexane-1-carboxamide (0.25 g, 35%) as colorless solid. MS (ESI) m/z 456 [M+1]⁺.

9-((1S, 4S)-4-(Aminomethyl)cyclohexyl)-N8-(3-chlorophenyl)-N2-(tert-pentyl)-9H-purine-2, 8-diamine. To a stirred solution of (1S, 4S)-4-8-((3-chlorophenyl)amino-2-(tert-pentylamino)-9H-purin-9-yl)cyclohexane-1-carboxamide (0.25 g, 1 mmol) in THF (3 mL) was added lithium aluminum hydride in THF (1.6 M; 5 mL) at 0° C. The reaction mixture was heated to 55° C. for 1 h. Completion of the reaction was confirmed by UPLC. The product was purified via standard methods to afford 9-((1S, 4S)-4-(aminomethyl)cyclohexyl)-N8-(3-chlorophenyl)-N2-(tert-pentyl)-9H-purine-2, 8-diamine (0.04 g, 16%). MS (ESI) m/z 442 [M+1]+. ¹H NMR (400 MHz, CD₃OD): δ 8.17 (s, 1H), 7.64 (s, 1H), 7.41 (d, J=8.4 Hz, 1H), 7.26-7.30 (m, 1H), 7.02 (d, J=8.4 Hz, 1H), 4.28-4.38 (m, 1H), 3.10 (d, J=7.2 Hz, 2H), 2.68-2.72 (m, 2H), 1.93-1.99 (m, 6H), 1.75-1.87 (m, 3H), 1.48 (s, 6H), 0.93 (t, J=7.6 Hz, 3H).

Example 23: 9-((1S, 4S)-4-(Aminomethyl)cyclohexyl)-N8-(3-chlorophenyl)-N2-(tetrahydro-2H-pyran-4-yl)-9H-purine-2, 8-diamine

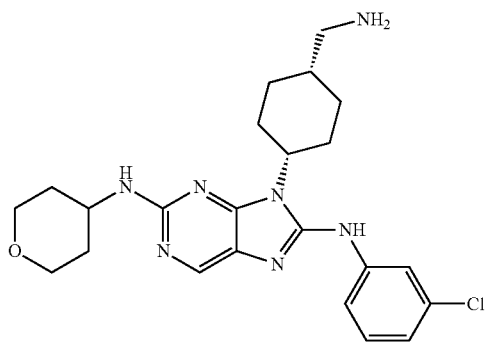 [SMILES: NC[C@H]1CC[C@@H](n2c(Nc3cccc(Cl)c3)nc3cnc(NC4CCOCC4)nc32)CC1]

(1S, 4S)-4-((5-Nitro-2-((tetrahydro-2H-pyran-4-yl)amino)pyrimidin-4-yl)amino)cyclohexane-1-carboxamide. To a stirred solution of (1S, 4S)-4-((2-chloro-5-nitropyrimidin-4-yl)amino)cyclohexane-1-carboxamide (1 g, 3.33 mmol) in DMF (10 mL) was added tetrahydro-2H-pyran-4-amine (0.37 g, 3.67 mmol) and sodium bicarbonate (0.56 g, 6.67 mmol) at ambient temperature. The reaction mixture was heated to 60° C. for 4 h. Completion of the reaction was confirmed by UPLC. The product was isolated and triturated with petroleum ether to afford (1S, 4S)-4-((5-nitro-2-((tetrahydro-2H-pyran-4-yl)amino)pyrimidin-4-yl)amino)cyclohexane-1-carboxamide (0.8 g, 66%) as an off-white solid. MS (ESI) m/z 365, 366 [M, M+1]⁺.

(1S, 4S)-4-((5-Amino-2-((tetrahydro-2H-pyran-4-yl)amino)pyrimidin-4-yl)amino)cyclohexane-1-carboxamide. To a stirred solution of (1S, 4S)-4-((5-nitro-2-((tetrahydro-2H-pyran-4-yl)amino)pyrimidin-4-yl)amino)cyclohexane-1-carboxamide (0.8 g, 2.19 mmol) in methanol (24 mL) was added palladium on carbon under inert atmosphere at ambient temperature. The reaction mixture was stirred under atmospheric hydrogen at ambient temperature. Completion of the reaction was confirmed by UPLC. The resulting reaction mixture was filtered through bed of celite, washed with methanol and concentrated to afford (1S, 4S)-4-((5-amino-2-((tetrahydro-2H-pyran-4-yl)amino)pyrimidin-4-yl)amino)cyclohexane-1-carboxamide (0.6 g, 82%) as a black solid. MS (ESI) m/z 335 [M+1]⁺.

(1S, 4S)-4-(8-((3-Chlorophenyl) amino)-2-((tetrahydro-2H-pyran-4-yl) amino)-9H-purin-9-yl)cyclohexane-1-carboxamide. To a stirred solution of (1S, 4S)-4-((5-amino-2-((tetrahydro-2H-pyran-4-yl)amino)pyrimidin-4-yl)amino) cyclohexane-1-carboxamide (0.6 g, 1.79 mmol) and 1-chloro-3-isothiocyanatobenzene (0.33 g, 1.97 mmol) in THF was added EDCI (0.69 g, 2.04 mmol) at ambient temperature. The reaction mixture was heated to 60° C. for 4 h. Completion of the reaction was confirmed by UPLC. The product was isolated and purified via standard methods to afford (1S, 4S)-4-(8-((3-chlorophenyl)amino)-2-((tetrahydro-2H-pyran-4-yl)amino)-9H-purin-9-yl)cyclohexane-1-carboxamide (0.3 g, 36%) as an off-white solid. MS (ESI) m/z 471, 472 [M, M+1]⁺.

9-((1S, 4S)-4-(Amino methyl)cyclohexyl)-N8-(3-chlorophenyl)-N2-(tetrahydro-2H-pyran-4-yl)-9H-purine-2, 8-diamine. To a stirred solution of (1S, 4S)-4-(8-((3-chlorophenyl) amino)-2-((tetrahydro-2H-pyran-4-yl)amino)-9H-purin-9-yl)cyclohexane-1-carboxamide (0.3 g, 0.64 mmol) in THF (10 mL) was added dropwise lithium aluminium hydride in THF (1.6 M; 3 mL) at 0° C. and the reaction was heated at 50° C. for 8 h. Completion of the reaction was confirmed by TLC. The product was purified via standard methods to afford 9-((1S, 4S)-4-(amino methyl)cyclohexyl)-N8-(3-chlorophenyl)-N2-(tetrahydro-2H-pyran-4-yl)-9H-purine-2, 8-diamine (50 mg, 17%). MS (ESI) m/z 456, 457 [M, M+1]⁺. ¹H NMR (400 MHz, CD₃OD): δ 8.18 (s, 1H), 7.65 (s, 1H), 7.41-7.43 (m, 1H), 7.26-7.30 (m, 1H), 7.01-7.03 (m, 1H), 4.31-4.37 (m, 1H), 3.97-4.02 (m, 3H), 3.56-3.62 (m, 2H), 3.14-3.16 (m, 2H), 2.69-2.80 (m, 2H), 1.93-2.06 (m, 5H), 1.62-1.86 (m, 6H).

Example 24: 1-Methylcyclopentan-1-amine hydrochloride

2-Chloro-N-(1-methylcyclopentyl)acetamide. A mixture of acetic acid (0.7 mL) and sulphuric acid (0.7 mL) was added dropwise to a stirred solution of 1-methylcyclopentan-1-ol (0.5 g, 5 mmol) in chloroacetonitrile (0.54 mL, 6 mmol) at 0° C. The reaction was stirred at ambient temperature for 3 h. Completion of the reaction was confirmed by UPLC. The product was isolated and purified via standard methods to afford 2-chloro-N-(1-methylcyclopentyl) acetamide (0.65 g, 74%) as white solid. GCMS m/z 175.6

1-Methylcyclopentan-1-amine hydrochloride. To the stirred solution of 2-chloro-N-(1-methylcyclopentyl)acetamide (0.63 g, 3.59 mmol) in ethanol (5 mL) and acetic acid (1 mL) mixture was added thiourea (0.28 g, 3.59 mmol) at ambient temperature. The mixture was stirred at 80° C. for 2 h. Completion of the reaction was confirmed by TLC. The product was isolated and purified via standard methods to afford 1-methylcyclopentan-1-amine hydrochloride (0.5 g) as white solid. GCMS m/z 135.64.

Example 25: 9-((1S, 4S)-4-(Amino methyl)cyclohexyl)-N8-(3-chlorophenyl)-N2-(1-methylcyclopentyl)-9H-purine-2, 8-diamine

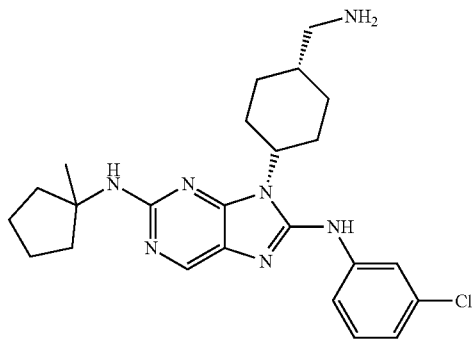

(1S, 4S)-4-((2-((1-Methylcyclopentyl)amino)-5-nitropyrimidin-4-yl)amino)cyclohexane-1-carboxamide. To the stirred solution of (1S, 4S)-4-((2-chloro-5-nitropyrimidin-4-yl) amino) cyclohexane-1-carboxamide (0.7 g, 2.34 mmol) in DMF (10 mL), 1-methylcyclopentan-1-amine hydrochloride (0.35 g, 3.51 mmol) and sodium bicarbonate (1.0 g, 11.71 mmol) were added at ambient temperature and the mixture was heated to 60° C. for 16 h. Completion of the reaction was confirmed by UPLC. The product was isolated to afford (1S, 4 S)-4-((2-((1-methylcyclopentyl)amino)-5-nitropyrimidin-4-yl)amino)cyclohexane-1-carboxamide (0.5 g, 60%) as off-white solid. MS (ESI) m/z 363, 364 [M, M+1]+.

(1S, 4S)-4-((5-Amino-2-((1-methylcyclopentyl)amino) pyrimidin-4-yl)amino)cyclohexane-1-carboxamide. To a stirred solution of (1S, 4S)-4-((2-((1-methylcyclopentyl) amino)-5-nitropyrimidin-4-yl)amino)cyclohexane-1-carboxamide (0.5 g, 1.38 mmol) in methanol (10 mL) was added palladium on carbon (0.15 g) under inert atmosphere at ambient temperature. The reaction mixture was stirred under atmospheric hydrogen. Completion of the reaction was confirmed by TLC. The resulting reaction mixture was filtered through bed of celite, washed with methanol and concentrated to afford (1S, 4S)-4-((5-amino-2-((1-methylcyclopentyl)amino)pyrimidin-4-yl)amino)cyclohexane-1-carboxamide (0.5 g) as brown gummy solid. MS (ESI) m/z 333, 334 [M, M+1]+.

(1S, 4S)-4-(8-((3-Chlorophenyl)amino)-2-((1-methylcyclopentyl)amino)-9H-purin-9-yl) cyclohexane-1-carboxamide. To a stirred solution of (1S, 4S)-4-((5-amino-2-((1-methyl cyclopentyl)amino)pyrimidin-4-yl)amino) cyclohexane-1-carboxamide (0.5 g, 1.51 mmol) and 1-chloro-3-isothiocyanatobenzenes (0.3 g, 1.81 mmol) in THF was added EDCI (1.14 g, 3.01 mmol) at ambient temperature. The reaction mixture was heated to 60° C. for 4 h. Completion of the reaction was confirmed by UPLC. The product was isolated and purified via standard methods to afford (1S, 4S)-4-(8-((3-chlorophenyl) amino)-2-((1-methylcyclopentyl)amino)-9H-purin-9-yl) cyclohexane-1-carboxamide (0.27 g, 39%) as pale yellow solid. MS (ESI) m/z 468, 469 [M, M+1]+.

9-((1S, 4S)-4-(Aminomethyl)cyclohexyl)-N8-(3-chlorophenyl)-N2-(1-methylcyclopentyl)-9H-purine-2, 8-diamine To a stirred solution of (1S, 4S)-4-(8-((3-chlorophenyl) amino)-2-(1-methylcyclopentyl)amino)-9H-purin-9-yl)cyclohexane-1-carboxamide (0.24 g, 0.51 mmol) in THF (10 mL) was added dropwise lithium aluminium hydride in THF (1.6 M; 3 mL) at 0° C. and heated at 50° C. for 8 h. Completion of the reaction was confirmed by TLC. The product was purified via standard methods to afford 9-((1S, 4S)-4-(aminomethyl)cyclohexyl)-N8-(3-chlorophenyl)-N2-(1-methylcyclopentyl)-9H-purine-2, 8-diamine (70 mg; 30%). MS (ESI) m/z 454.2, 455.2 [M, M+1]+. ¹H NMR (400 MHz, CD₃OD): δ 8.56 (brs, 1H), 8.19 (brs, 1H), 7.71 (brs, 1H), 7.45 (d, J=8.4 Hz, 1H), 7.30-7.34 (m, 1H), 7.04 (d, J=8 Hz, 1H), 4.36-4.42 (m, 1H), 3.28 (d, J=7.6 Hz, 2H), 2.71-2.80 (m, 2H), 2.23-2.26 (m, 2H), 2.17 (brs, 1H), 1.94-2.01 (m, 4H), 1.75-1.87 (m, 9H), 1.66 (s, 3H).

Example 26: 9-((1S, 4S)-4-(Aminomethyl)cyclohexyl)-N8-(2, 3-difluorophenyl)-N2-(4-methyltetrahydro-2H-pyran-4-yl)-9H-purine-2, 8-diamine

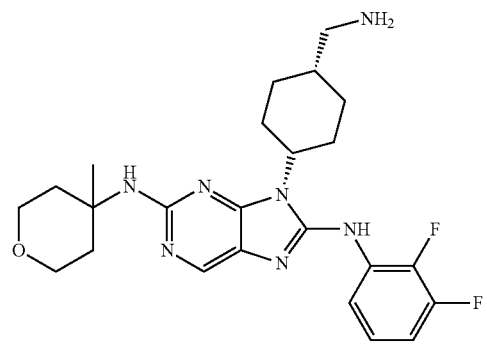

(1S, 4S)-4-((2-((4-Methyltetrahydro-2H-pyran-4-yl) amino)-5-nitropyrimidin-4-yl)amino)cyclohexane-1-carboxamide. To a stirred solution of (1S, 4S)-4-((2-chloro-5-nitropyrimidine-4-yl)amino)cyclohexane-1-carboxamide (2.0 g, 6 mmol) in DMF (10 mL) was added sodium carbonate (1.9 g, 18 mmol) portionwise followed by 4-methyltetrahydro-2H-pyran-4-amine hydrochloride (1.2 g, 8 mmol) at ambient temperature. The reaction mixture was stirred for 4 h. Completion of the reaction was confirmed by UPLC. The product was isolated to afford (1S, 4S)-4-((2-((4-methyltetrahydro-2H-pyran-4-yl)amino)-5-nitropyrimidin-4-yl) amino)cyclohexane-1-carboxamide (1.5 g, 66%) as a yellow solid. MS (ESI) m/z 379 [M+1]+.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl) amino)cyclohexane-1-carboxamide (0.7 g, 2 mmol) in ethanol (10 mL) was added palladium on charcoal (0.07 g, 10% W/M) portionwise under argon atmosphere. The reaction was stirred at ambient temperature under atmospheric hydrogen. Completion of the reaction was confirmed by UPLC. The resulting reaction mixture was filtered through a bed of celite, washed with ethyl acetate and concentrated to afford (1S, 4S)-4-((5-amino-2-((4-methyltetrahydro-2H-pyran-4-yl)amino)pyrimidin-4-yl)amino)cyclohexane-1-carboxamide (0.5 g, 71%) as a yellow solid. MS (ESI) m/z 349 [M+1]+.

(1S, 4S)-4-(8-((2,3-Difluorophenyl)amino)-2-((4-methyltetrahydro-2H-pyran-4-yl)amino)-9H-purin-9-yl)cyclohexane-1-carboxamide. To a stirred solution of (1S, 4S)-4-((5-amino-2-((4-methyltetrahydro-2H-pyran-4-yl)amino) pyrimidin-4-yl)amino)cyclohexane-1-carboxamide (0.25 g, 1 mmol) in THF (10 mL) was added 1-ethyl-3-(3-dimethylaminopropyl)carbodiimide (0.3 g, 1.5 mmol) and 1,2- difluoro-3-isothiocyanatobenzene (0.12 g, 1 mmol) at ambient temperature. The reaction mixture was heated to 60° C. for 4 h. Completion of the reaction was confirmed by UPLC. The product was isolated and purified via standard methods to afford (1S, 4S)-4-(8-((2,3-difluorophenyl)amino)-2-((4-methyltetrahydro-2H-pyran-4-yl)amino)-9H-purin-9-yl)cyclo
hexane-1-carboxamide (0.2 g, 62%) as off-white solid. MS (ESI) m/z 486 [M+1]$^+$.

9-((1S, 4S)-4-(Aminomethyl)cyclohexyl)-N8-(2,3-difluorophenyl)-N2-(4-methyltetrahydro-2H-pyran-4-yl)-9H-purine-2, 8-diamine. To a stirred solution of ((1S, 4S)-4-(8-((2, 3-difluorophenyl)amino)-2-((4-methyltetrahydro-2H-pyran-4-yl)amino)-9H-purin-9-yl)cyclohexane-1-carboxamide (0.2 g, 0.5 mmol) in THF (3 mL) was added lithium aluminum hydride in THF (1.6 M; 1 mL) at 0° C. The reaction mixture was heated to 55° C. for 1 h. Completion of the reaction was confirmed by UPLC. The product was purified via standard methods to afford 9-((1S, 4S)-4-(aminomethyl)cyclohexyl)-N8-(2,3-difluorophenyl)-N2-(4-methyltetrahydro-H-pyran-4-yl)-9H-purine-2,8-diamine (0.03 g, 16%). MS (ESI) m/z 472 [M+1]$^+$. $^1$H NMR (400 MHz, CD$_3$OD): δ 8.10 (s, 1H), 7.30 (m, 1H), 7.08-7.14 (m, 1H), 7.0-7.02 (m, 1H), 4.4-4.6 (m, 1H), 3.7-3.8 (m, 4H), 3.15 (d, J=7.2 Hz, 2H), 2.60-2.69 (m, 2H), 2.40-2.42 (m, 2H), 1.92-2.05 (m, 5H) 1.72-1.80 (m, 5H), 1.6 (s, 3H), Example 27: N-(((1S, 4S)-4-(8-((3-Chlorophenyl)amino)-2-((4-methyltetrahydro-2H-pyran-4-yl)amino)-9H-purin-9-yl)cyclohexyl)methyl)acetamide

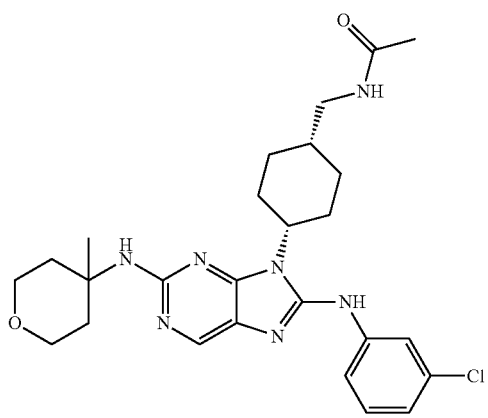 [SMILES: CC(=O)NC[C@H]1CC[C@@H](n2c(Nc3cccc(Cl)c3)nc3cnc(NC4(C)CCOCC4)nc32)CC1]

N-(((1S, 4S)-4-(8-((3-Chlorophenyl)amino)-2-((4-methyltetrahydro-2H-pyran-4-yl)amino)-9H-purin-9-yl)cyclohexyl)methyl)acetamide. To a solution of 9-((1S, 4S)-4-(aminomethyl)cyclohexyl)-N8-(3-chlorophenyl)-N2-(4-methyltetrahydro-2H-pyran-4-yl)-9H-purine-2,8-diamine (0.05 g, 0.1 mmol) in dry chloroform (10 mL) was added acetic anhydride (0.01 g, 0.1 mmol) at 0° C. under nitrogen. The reaction mixture was stirred at ambient temperature for 3 h. Completion of the reaction was confirmed by TLC. The product was purified via standard methods to afford N-(((1S, 4S)-4-(8-((3-chlorophenyl)amino)-2-((4-methyltetrahydro-2H-pyran-4-yl)amino)-9H-purin-9-yl)cyclohexyl)methyl) acetamide (0.04 g, 74%). MS (ESI) m/z 512.2, 513.4 [M, M+1]$^+$. $^1$H NMR (400 MHz, CD$_3$OD): δ 8.20 (s, 1H), 7.70 (s, 1H), 7.45 (d, J=8 Hz, 1H), 7.29-7.33 (m, 1H), 7.04 (d, J=8 Hz, 1H), 4.29-4.36 (m, 1H), 3.77-3.79 (m, 4H), 3.47-3.49 (d, J=7.6 Hz 2H), 2.75-2.78 (m, 2H), 2.33-2.37 (m, 2H), 1.83-1.99 (m, 6H), 1.72-1.82 (m, 6H), 1.61 (s, 3H).

Example 28: 9-((1S, 4S)-4-(Aminomethyl)cyclohexyl)-N8-(5-chloropyridin-3-yl)-N2-(4-methyltetrahydro-2H-pyran-4-yl)-9H-purine-2,8-diamine

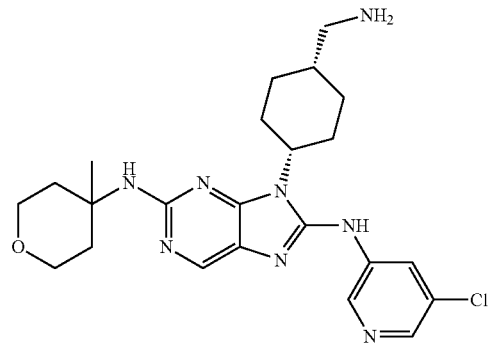 [SMILES: CC1(Nc2ncc3nc(Nc4cncc(Cl)c4)n([C@H]4CC[C@@H](CN)CC4)c3n2)CCOCC1]

(1S, 4S)-4-((2-((4-Methyltetrahydro-2H-pyran-4-yl)amino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (5 g, 20 mmol) in DMF (50 mL) was added sodium carbonate (5.3 g, 50 mmol) portionwise followed by 4-methyl-tetrahydro-2H-pyran-4-amine (3 g, 20 mmol) at ambient temperature. The reaction mixture was stirred for 16 h. Completion of the reaction was confirmed by UPLC. The product was isolated via standard purification methods to afford (1S, 4S)-4-((2-((4-methyltetrahydro-2H-pyran-4-yl)amino)-5-nitropyrimidin-4-yl)amino)cyclohexane-1-carboxamide (3.2 g, 50%) as a yellow solid. MS (ESI) m/z 379 [M+1]$^+$.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl) amino)cyclohexane-1-carboxamide (3.2 g, 8 mmol) in ethanol:water (70 mL, 9:1) was added iron powder (8.4 g, 80 mmol) and ammonium chloride (0.5 g, 8 mmol) at ambient temperature. The reaction mixture was heated to 85° C. for 16 h. Completion of the reaction was confirmed by UPLC. The product was isolated via standard purification methods to afford (1S, 4S)-4-((5-amino-2-((4-methyltetrahydro-2H-pyran-4-yl)amino)pyrimidin-4-yl)amino)cyclohexane-1-carboxamide (2.8 g, 90%) as a violet solid. MS (ESI) m/z 349 [M+1]$^+$.

3-Chloro-5-isothiocyanatopyridine. To a stirred solution of 5-chloropyridin-3-amine (1 g, 8 mmol) in dichloromethane (25 ml) and saturated sodium bicarbonate solution (25 mL) was added dropwise thiophosgene (1 g, 9 mmol) at 0° C. The reaction mixture was stirred at ambient temperature for 1 h. Completion of the reaction was confirmed by UPLC. The product was isolated and purified via standard purification methods to afford 3-chloro-5-isothiocyanatopyridine (0.6 g, 46%) as a pale yellow liquid. MS (ESI) m/z 170 [M+1]$^+$.

(1S, 4S)-4-(8-((5-Chloropyridin-3-yl)amino)-2-((4-methyltetrahydro-2H-pyran-4-yl) amino)-9H-purin-9-yl)cyclohexane-1-carboxamide. To a stirred solution of (1S, 4S)-4-((5-amino-2-((4-methyltetrahydro-2H-pyran-4-yl)amino) pyrimidin-4-yl)amino)cyclohexane-1-carboxamide (0.6 g, 2 mmol) in THF:DMF (20 mL, 1:1) was added 1-ethyl-3-(3- dimethylaminopropyl)carbodiimide (0.6 g, 3 mmol) and 3-chloro-5-isothiocyanatopyridine (0.4 g, 2 mmol) at ambient temperature. The reaction mixture was heated to 50° C. for 4 h. Completion of the reaction was confirmed by UPLC. The product was isolated via standard purification methods to afford (1S, 4S)-4-(8-((5-chloropyridin-3-yl)amino)-2-((4-methyltetrahydro-2H-pyran-4-yl)amino)-9H-purin-9-yl)cyclohexane-1-carboxamide (0.27 g, 33%) as pale yellow solid. MS(ESI) m/z 485, 486 [M, M+1]$^+$.

9-((1S, 4S)-4-(Aminomethyl)cyclohexyl)-N8-(5-chloropyridin-3-yl)-N2-(4-methyltetrahydro-2H-pyran-4-yl)-9H-purine-2,8-diamine. To a stirred solution of (1S, 4S)-4-(8-((5-chloropyridin-3-yl)amino)-2-((4-methyltetrahydro-2H-pyran-4-yl)amino)-9H-purin-9-yl)cyclohexane-1-carboxamide (0.27 g, 1 mmol) in THF (3 mL) was added lithium aluminum hydride in THF (1.6 M; 5 mL) at 0° C. The reaction mixture was heated to 50° C. for 3 h. Completion of the reaction was confirmed by UPLC. The product was purified via standard methods to afford 9-((1S, 4S)-4-(aminomethyl)cyclohexyl)-N8-(5-chloropyridin-3-yl)-N2-(4-methyltetrahydro-2H-pyran-4-yl)-9H-purine-2, 8-diamine (0.045 g, 18%). MS (ESI) m/z 471.2, 472.2 [M, M+1]$^+$. $^1$H NMR (400 MHz, CD$_3$OD): δ 8.67 (m, 1H), 8.41 (s, 1H), 8.26 (s, 1H), 8.20 (m, 1H), 4.35-4.41 (m, 1H), 3.77-3.80 (m, 4H), 3.08 (d, J=7.4 Hz, 2H), 2.65-2.74 (m, 2H), 2.39-2.42 (m, 2H), 2.02-1.99 (m, 3H), 1.77-1.88 (m, 6H), 1.62 (s, 3H).

Example 29: 9-((1S, 4S)-4-(Aminomethyl)cyclohexyl)-N2-(4-methyltetrahydro-2H-pyran-4-yl)-N8-(2-(trifluoromethyl)pyridin-4-yl)-9H-purine-2,8-diamine

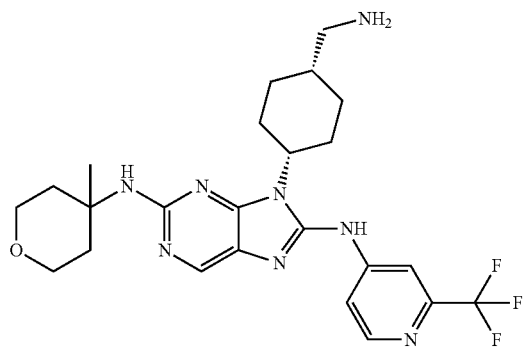 [SMILES: CC1(Nc2ncc3nc(Nc4ccnc(C(F)(F)F)c4)n([C@H]4CC[C@@H](CN)CC4)c3n2)CCOCC1]

(1S, 4S)-4-((2-((4-Methyltetrahydro-2H-pyran-4-yl) amino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (5 g, 17 mmol) in DMF (10 mL) was added sodium carbonate (5.3 g, 50 mmol) portionwise followed by 2-methylbutane-2-amine (3 g, 20 mmol) at ambient temperature. The reaction mixture was stirred same temperature for 16 h. Completion of the reaction was confirmed by LCMS. The product was isolated to afford (1S, 4S)-4-((2-((4-methyltetrahydro-2H-pyran-4-yl)amino)-5-nitropyrimidin-4-yl)amino)cyclohexane-1-carboxamide (3.2 g, 50%) as a yellow solid. MS (ESI) m/z 379 [M+1]$^+$.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl) amino)cyclohexane-1-carboxamide (3.2 g, 8 mmol) in ethanol:water (50 mL, 1:1) was added iron powder (8.4 g, 80 mmol) followed by ammonium chloride (0.8 g, 8 mmol). The reaction mixture was heated to 85° C. Completion of the reaction was confirmed by LCMS. The resulting reaction mixture was filtered through a bed of celite, washed with ethyl acetate and concentrated to afford (1S, 4S)-4-((5-amino-2-((4-methyltetrahydro-2H-pyran-4-yl)amino)pyrimidin-4-yl)amino)cyclohexane-1-carboxamide (2.8 g, 95%) as a violet solid. MS (ESI) m/z 349 [M+1]$^+$.

4-Isothiocyanato-2-(trifluoromethyl)pyridine. To a stirred solution of 2-(trifluoromethyl)pyridine-4-amine (1 g, 6 mmol) in dichloromethane (25 mL) was added saturated sodium bicarbonate solution (25 mL). Thiophosgene (0.84 g, 7 mmol) was added dropwise and the resulting reaction mixture was stirred at ambient temperature for 1 h. Completion of the reaction was confirmed by UPLC. The product was isolated to afford 4-isothiocyanato-2-(trifluoromethyl) pyridine (0.6 g, 50%) as a light yellow liquid. MS (ESI) m/z 205 [M+1]$^+$.

(1S, 4S)-4-(2-((4-Methyltetrahydro-2H-pyran-4-yl) amino)-8-((2-(trifluoromethyl)pyridin-4-yl)amino)-9H-purin-9-yl)cyclohexane-1-carboxamide. To stirred solution of (1S, 4S)-4-((5-amino-2-((4-methyltetrahydro-2H-pyran-4-yl)amino)pyrimidin-4-yl)amino)cyclohexane-1-carboxamide (0.6 g, 2 mmol) in THF:DMF (20 mL, 1:1) was added 1-ethyl-3-(3-dimethylaminopropyl)carbodiimide (0.7 g, 3 mmol) and 4-isothiocyanato-2-(trifluoromethyl)pyridine (0.35 g, 2 mmol) at ambient temperature. The reaction mixture was heated to 50° C. for 4 h. Completion of the reaction was confirmed by UPLC. The product was isolated via standard purification method to afford (1S, 4S)-4-(2-((4-methyltetrahydro-2H-pyran-4-yl)amino)-8-((2-(trifluoromethyl)pyridin-4-yl)amino)-9H-purin-9-yl)cyclohexane-1-carboxamide (0.3 g, 33%) as an off-white solid. MS (ESI) m/z 519 [M+1]$^+$.

9-((1S, 4S)-4-(Aminomethyl)cyclohexyl)-N8-(2-fluoro-3-(trifluoromethyl)phenyl)-N2-(4-methyltetrahydro-2H-pyran-4-yl)-9H-purine-2, 8-diamine. To a stirred solution of (1S, 4S)-4-(2-((4-methyltetrahydro-2H-pyran- 4-yl)amino)-8-((2-(trifluoromethyl)pyridin-4-yl)amino)-9H-purin-9-yl) cyclohexane-1-carboxamide (0.3 g, 1 mmol) in diethyl ether (10 mL) was added lithium aluminum hydride in THF (2.4 M; 5 mL) at 0° C. The reaction mixture was stirred at ambient temperature for 2 h. Completion of the reaction was confirmed by UPLC. The product was purified via standard methods to afford 9-((1S, 4S)-4-(aminomethyl)cyclohexyl)-N8-(2-fluoro-3-(trifluoromethyl)phenyl)-N2-(4-methyltetrahydro-2H-pyran-4-yl)-9H-purine-2, 8-diamine. MS (ESI) m/z 506 [M+1]$^+$. $^1$H NMR (400 MHz, CD$_3$OD): δ 8.50 (d, J=8 Hz, 1H), 8.38 (s, 1H), 8.13 (s, 1H), 7.87-7.89 (m, 1H), 4.39-4.45 (m, 1H), 3.76-3.84 (m, 4H), 3.24 (d, J=7.6 Hz, 2H), 2.67-2.70 (m, 2H), 2.46-2.50 (m, 2H), 2.14 (brs, 1H), 1.91-2.01 (m, 4H), 1.72-1.84 (m, 4H), 1.61 (s, 3H).

Example 30: 9-(3-Aminocyclobutyl)-N8-(3-chlorophenyl)-N2-(4-methyltetrahydro-2H-pyran-4-yl)-9H-purine-2,8-diamine

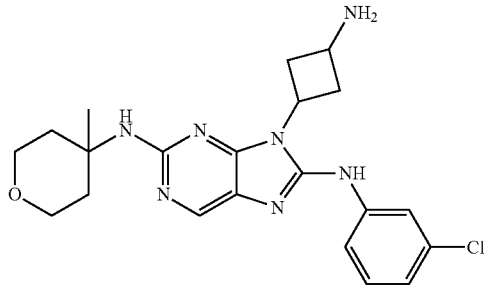 [SMILES: CC1(Nc2ncc3nc(Nc4cccc(Cl)c4)n(C4CC(N)C4)c3n2)CCOCC1]

tert-Butyl (3-((2-chloro-5-nitropyrimidin-4-yl)amino)cyclobutyl)carbamate. To a stirred solution of 2, 4-dichloro-5-nitropyrimidine (0.3 g, 2 mmol) and DIPEA (1 mL, 5 mmol) in 2-propanol (10 mL) was added tert-butyl (3-aminocyclobutyl)carbamate (0.31 g, 3 mmol) portionwise at 0° C. under nitrogen. The reaction mixture was slowly warmed to ambient temperature and stirred for 5 h. Completion of the reaction was confirmed by UPLC. The product was isolated to afford tert-butyl(3-((2-chloro-5-nitropyrimidin-4-yl)amino)cyclo butyl)carbamate (0.4 g, 75%) as yellow solid. MS (ESI) m/z 346.2 [M+2]$^+$.

tert-Butyl(3-((2-((4-methyltetrahydro-2H-pyran-4-yl)amino)-5-nitropyrimidin-4-yl)amino)cyclobutyl)carbamate. To a stirred solution of tert-butyl(3-((2-chloro-5-nitropyrimidin-4-yl)amino)cyclobutyl)carbamate (0.40 g 2 mmol) in DMF (10 mL) was added 4-methyltetrahydro-2H-pyran-4-amine (0.14 g, 1 mmol) and sodium bicarbonate (0.292 g, 3 mmol) at ambient temperature. The reaction mixture was stirred at ambient temperature for 5 h. Completion of the reaction was confirmed by UPLC. The product was isolated and triturated with petroleum ether to afford tert-butyl (3-((2-((4-methyltetrahydro-2H-pyran-4-yl)amino)-5-nitropyrimidin-4-yl)amino)cyclobutyl)carbamate (0.38 g, 77%) as yellow solid. MS (ESI) m/z 423 [M+1]$^+$.

tert-Butyl(3-((5-amino-2-((4-methyltetrahydro-2H-pyran-4-yl)amino)pyrimidin-4-yl)amino)cyclobutyl)carbamate. To a stirred solution of tert-butyl (3-((2-((4-methyltetrahydro-2H-pyran-4-yl)amino)-5-nitropyrimidin-4-yl)amino)cyclobutyl)carbamate (0.38 g, 1 mmol) in ethanol:water (50 mL, 3:1) was added iron powder (0.50 g, 1 mmol) and ammonium chloride (0.05 g, 1 mmol) at ambient temperature. The reaction mixture was heated to 80° C. for 6 h. Completion of the reaction was confirmed by UPLC. The resulting reaction mixture was filtered through a bed of celite, washed with ethyl acetate and concentrated to afford tert-butyl(3-((5-amino-2-((4-methyltetrahydro-2H-pyran-4-yl)amino)pyrimidin-4-yl)amino)cyclobutyl)carbamate (0.37 g) as a brown solid. MS (ESI) m/z 394.4 [M+2]$^+$.

tert-Butyl (3-(8-((3-chlorophenyl)amino)-2-((4-methyltetrahydro-2H-pyran-4-yl)amino)-9H-purin-9-yl)cyclobutyl)carbamate. To a stirred solution of tert-butyl (3-((5-amino-2-((4-methyltetrahydro-2H-pyran-4-yl)amino)pyrimidin-4-yl)amino)cyclobutyl)carbamate (0.37 g, 1 mmol) and 1-chloro-3-isothiocyanatobenzene (0.181 g, 1 mmol) in THF was added EDCI (0.340 g, 2 mmol) at ambient temperature. The reaction mixture was heated to 60° C. for 6 h. Completion of the reaction was confirmed by UPLC. The product was isolated and purified via standard methods to afford tert-butyl (3-(8-((3-chlorophenyl) amino)-2-((4-methyltetrahydro-2H-pyran-4-yl)amino)-9H-purin-9-yl)cyclobutyl)carbamate (0.11 g, 27%) as an off-white solid. MS (ESI) m/z 427, 429 [M, M+2]$^+$.

9-(3-(Aminocyclobutyl)-N8-(3-chlorophenyl)-N2-(4-methyltetrahydro-2H-pyran-4-yl)-9H-purine-2,8-diamin. To a stirred solution of tert-butyl (3-(8-((3-chlorophenyl) amino)-2-((4-methyltetrahydro-2H-pyran-4-yl)amino)-9H-purin-9-yl)cyclobutyl)carbamate (0.11 g, 0.5 mmol) in DCM (10 mL) was added HCl in dioxane (2 mL) at 0° C. The reaction mixture was stirred at ambient temperature for 2 h. Completion of the reaction was confirmed by UPLC. The product was purified via standard methods to afford 9-(3-(aminocyclobutyl)-N8-(3-chlorophenyl)-N2-(4-methyltetrahydro-2H-pyran-4-yl)-9H-purine-2,8-diamine (10 mg, 12%). MS (ESI) m/z 428.2, 429.2 [M, M+1]+. $^1$H NMR (400 MHz, CD$_3$OD): δ 8.26 (s, 1H), 7.63 (s, 1H), 7.29-7.39 (m, 2H), 7.03 (dd, J=1.6 Hz & 8.8 Hz, 1H),5.21-5.25 (m, 1H), 4.10-4.20 (m, 1H), 3.73-3.84 (m, 4H), 3.46-3.51 (m, 2H), 2.42-2.55 (m, 4H), 1.73-1.80 (m, 2H) 1.59 (s, 3H).

Example 31: 9-((1S, 4S)-4-(Aminomethyl)cyclohexyl)-N8-(3-chloro-5-(trifluoromethyl)phenyl)-N2-(4-methyltetrahydro-2H-pyran-4-yl)-9H-purine-2,8-diamine

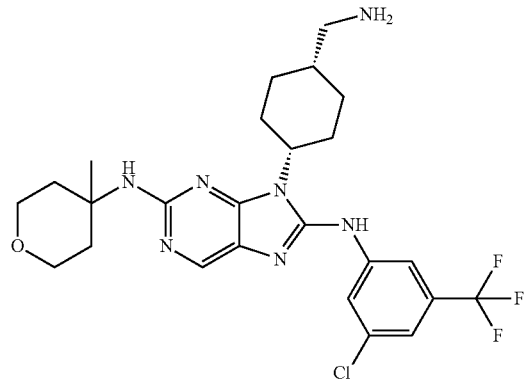 [SMILES: CC1(Nc2ncc3nc(Nc4cc(Cl)cc(C(F)(F)F)c4)n([C@H]4CC[C@@H](CN)CC4)c3n2)CCOCC1]

(1S, 4S)-4-((2-((4-Methyltetrahydro-2H-pyran-4-yl)amino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (5 g, 20 mmol) in DMF (50 mL) was added sodium carbonate (5.3 g, 60 mmol) portionwise followed by 4-methyltetrahydro-2H-pyran-4-amine (3 g, 20 mmol) at ambient temperature. The reaction mixture was stirred at ambient temperature for 16 h. Completion of the reaction was confirmed by UPLC. The product was isolated via standard purification methods to afford (1S, 4S)-4-((2-((4-methyltetrahydro-2H-pyran-4-yl)amino)-5-nitropyrimidin-4-yl)amino)cyclohexane-1-carboxamide (3.2 g, 50%) as a yellow solid. MS (ESI) m/z 379 [M+1]$^+$.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl)amino)cyclohexane-1-carboxamide (3.2 g, 8 mmol) in ethanol:water (60 mL, 10:1) was added iron powder (8.4 g, 80 mmol) and ammonium chloride (0.5 g, 8 mmol) at ambient temperature. The reaction mixture was heated to 85° C. for 16 h. Completion of the reaction was confirmed by UPLC. The resulting mixture was filtered through a bed of celite, washed with ethyl acetate and concentrated to afford (1S, 4S)-4-((5-amino-2-((4-methyltetrahydro-2H-pyran-4-yl)amino)pyrimidin-4-yl)amino)cyclohexane-1-carboxamide (2.8 g, 90%) as a violet solid. MS (ESI) m/z 349 [M+1]+.

(1S, 4S)-4-(8-((3-Chloro-5-(trifluoromethyl)phenyl)amino)-2-((4-methyltetrahydro-2H-pyran-4-yl)amino)-9H-purin-9-yl)cyclohexane-1-carboxamide. To a stirred solution of (1S, 4S)-4-((5-Amino-2-((4-methyltetrahydro-2H-pyran-4-yl)amino)pyrimidin-4-yl)amino)cyclohexane-1-carboxamide (0.6 g, 2 mmol) in THF:DMF (1:1; 20 mL) was added 1-ethyl-3-(3-dimethylaminopropyl)carbodiimide (0.6 g, 3 mmol) and 1-chloro-3-isothiocyanato-5-(trifluoromethyl)benzene (0.5 g, 2 mmol) at ambient temperature. The reaction mixture was heated to 60° C. for 4 h. Completion of the reaction was confirmed by UPLC. The product was isolated and purified via standard purification methods to afford (1S, 4S)-4-(8-((3-chloro-5-(trifluoromethyl)phenyl)amino)-2-((4-methyltetrahydro-2H-pyran-4-yl)amino)-9H-purin-9-yl)cyclohexane-1-carboxamide (0.4 g, 42%) as pale yellow solid. MS (ESI) m/z 552, 553 [M, M+1]+.

9-((1S, 4S)-4-(Aminomethyl)cyclohexyl)-N8-(3-chloro-5-(trifluoromethyl)phenyl)-N2-(4-methyltetrahydro-2H-pyran-4-yl)-9H-purine-2, 8-diamine. To a stirred solution of (1S, 4S)-4-(8-((3-chloro-5- (trifluoromethyl)phenyl)amino)-2-((4-methyltetrahydro-2H-pyran-4-yl)amino)-9H-purin-9-yl)cyclohexane-1-carboxamide (0.3 g, 1 mmol) in THF (3 mL) was added lithium aluminum hydride in THF (1.6 M; 5 mL) at 0° C. The reaction mixture was stirred at ambient temperature for 3 h. Completion of the reaction was confirmed by UPLC. The product was purified via standard methods to afford 9-((1S, 4S)-4-(aminomethyl)cyclohexyl)-N8-(3-chloro-5-(trifluoromethyl)phenyl)-N2-(4-methyltetrahydro-2H-pyran-4-yl)-9H-purine-2,8-diamine (0.05 g, 15%). MS (ESI) m/z 538.2, 539.2 [M+, M+1]+. 1H NMR (400 MHz, CD3OD): δ 8.28 (s, 1H), 8.07 (s, 1H), 7.89 (s, 1H), 7.31 (s, 1H), 4.33-4.39 (m, 1H), 3.76-3.82 (m, 4H), 3.05 (d, J=7.2 Hz, 2H), 2.65-2.74 (m, 2H), 2.38-2.41 (m, 2H), 1.98-2.02 (m, 3H), 1.75-1.91 (m, 6H), 1.62 (s, 3H).

Example 32: 9-((1S, 4S)-4-(Aminomethyl)cyclohexyl)-N2-(4-methyltetrahydro-2H-pyran-4-yl)-N8-(3-(trifluoromethoxy)phenyl)-9H-purine-2,8-diamine

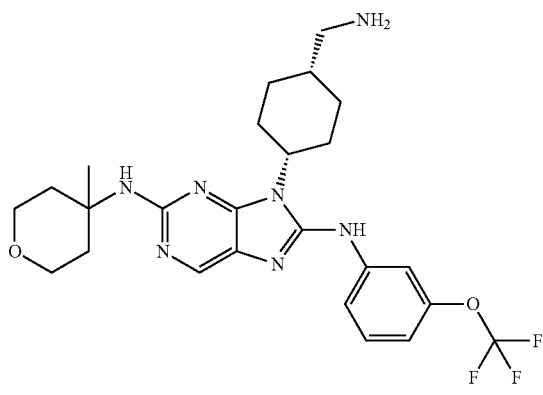 [SMILES: CC1(Nc2ncc3nc(Nc4cccc(OC(F)(F)F)c4)n([C@H]4CC[C@@H](CN)CC4)c3n2)CCOCC1]

(1S, 4S)-4-((2-((4-Methyltetrahydro-2H-pyran-4-yl)amino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (5 g, 20 mmol) in DMF (50 mL) was added sodium carbonate (5.3 g, 50 mmol) portionwise followed by 4-methyltetrahydro-2H-pyran-4-amine (3 g, 20 mmol) at ambient temperature. The reaction mixture was stirred at ambient temperature for 16 h. Completion of the reaction was confirmed by UPLC. The product was isolated via standard purification method to afford (1S, 4S)-4-((2-((4-methyltetrahydro-2H-pyran-4-yl)amino)-5-nitropyrimidin-4-yl)amino)cyclohexane-1-carboxamide (3.2 g, 50%) as a yellow solid. MS (ESI) m/z 379 [M+1]+.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl)amino)cyclohexane-1-carboxamide (3.2 g, 8 mmol) in ethanol:water (70 mL, 10:1) was added iron powder (8.4 g, 80 mmol) and ammonium chloride (0.5 g, 8 mmol) at ambient temperature. The reaction mixture was heated to 85° C. for 16 h. Completion of the reaction was confirmed by UPLC. The resulting reaction mixture was filtered through a bed of celite, washed with ethyl acetate and concentrated to afford (1S, 4S)-4-((5-amino-2-((4-methyltetrahydro-2H-pyran-4-yl)amino)pyrimidin-4-yl)amino)cyclohexane-1-carboxamide (2.8 g, 90%) as a violet solid. MS (ESI) m/z 349 [M+1]+.

(1S, 4S)-4-(2-((4-Methyltetrahydro-2H-pyran-4-yl)amino)-8-((3-(trifluoromethoxy)phenyl)amino)-9H-purin-9-yl)cyclohexane-1-carboxamide. To a stirred solution of (1S, 4S)-4-((5-amino-2-((4-methyltetrahydro-2H-pyran-4-yl)amino)pyrimidin-4-yl)amino)cyclohexane-1-carboxamide (0.6 g, 2 mmol) in THF:DMF (20 mL, 1:1) was added 1-ethyl-3-(3-dimethylaminopropyl)carbodiimide (0.6 g, 3 mmol) and 1-isothiocyanato-3-(trifluoromethoxy)-benzene (0.4 g, 2 mmol) at ambient temperature. The reaction mixture was heated to 60° C. for 4 h. Completion of the reaction was confirmed by UPLC. The product was isolated and purified via standard purification methods to afford (1S, 4S)-4-(2-((4-methyltetrahydro-2H-pyran-4-yl)amino)-8-((3-trifluoromethoxy)phenyl)amino)-9H-purin-9-yl)cyclohexane-1-carboxamide (0.4 g, 43%) as pale yellow solid. MS (ESI) m/z 534 [M+1]+.

9-((1S, 4S)-4-(Aminomethyl)cyclohexyl)-N2-(4-methyltetrahydro-2H-pyran-4-yl)-N8-(3-(trifluoromethoxy)phenyl)-9H-purine-2,8-diamine. To a stirred solution of (1S, 4S)-4-(2-((4-methyltetrahydro-2H-pyran-4-yl)amino)-8-((3-(trifluoromethoxy)phenyl)amino)-9H-purin-9-yl)cyclohexane-1-carboxamide (0.27 g, 1 mmol) in THF (3 mL) was added lithium aluminum hydride in THF (1.6 M; 5 mL) at 0° C. The reaction mixture was heated to 50° C. for 3 h. Completion of the reaction was confirmed by UPLC. The product was purified via standard methods to afford 9-((1S, 4S)-4-(aminomethyl)cyclohexyl)-N8-(5-chloropyridin-3-yl)-N2-(4-methyltetrahydro-2H-pyran-4-yl)-9H-purine-2,8-diamine (0.09 g, 23%). MS (ESI) m/z 520.2 [M+1]+. 1H NMR (400 MHz, CD3OD): δ 8.22 (s, 1H), 7.62 (s, 1H), 7.58 (dd, J=1.4 Hz & 8.2 Hz, 1H),7.40-7.44 (m, 1H), 6.93-6.95 (m, 1H), 4.31-4.39 (m, 1H), 3.77-3.79 (m, 4H), 2.97 (d, J=7.5 Hz, 2H), 2.65-2.74 (m, 2H), 2.34-2.38 (m, 2H), 1.98-2.01 (m, 2H), 1.85-1.87 (m, 7H), 1.62 (s, 3H).

Example 33: 9-((1S, 4S)-4-(Aminomethyl)cyclohexyl)-N2-(4-methyltetrahydro-2H-pyran-4-yl)-N8-(4-(trifluoromethoxy)phenyl)-9H-purine-2,8-diamine

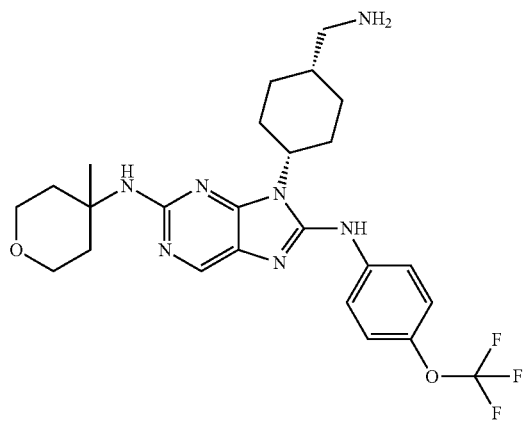 [SMILES: CC1(Nc2ncc3nc(Nc4ccc(OC(F)(F)F)cc4)n([C@H]4CC[C@@H](CN)CC4)c3n2)CCOCC1]

(1S, 4S)-4-((2-((4-Methyltetrahydro-2H-pyran-4-yl)amino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (5 g, 20 mmol) in DMF (50 mL) was added sodium bicarbonate (5.3 g, 50 mmol) portionwise followed by 4-methyltetrahydro-2H-pyran-4-amine (3 g, 20 mmol) at ambient temperature. The reaction mixture was stirred for 16 h. Completion of the reaction was confirmed by UPLC. The product was isolated to afford (1S, 4S)-4-((2-((4-methyltetrahydro-2H-pyran-4-yl)amino)-5-nitropyrimidin-4-yl)amino)cyclohexane-1-carboxamide (3.2 g, 50%) as a yellow solid. MS (ESI) m/z 379 [M+1]+.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl)amino)cyclohexane-1-carboxamide (3.2 g, 8 mmol) in ethanol:water (66 mL, 10:1) was added iron powder (8.4 g, 80 mmol) and ammonium chloride (0.5 g, 8 mmol) at ambient temperature. The reaction mixture was heated to 85° C. for 16 h. Completion of the reaction was confirmed by UPLC. The resulting reaction mixture was filtered through a bed of celite, washed with ethyl acetate and concentrated to afford (1S, 4S)-4-((5-amino-2-((4-methyltetrahydro-2H-pyran-4-yl)amino)pyrimidin-4-yl)amino)cyclohexane-1-carboxamide (2.8 g, 90%) as a violet solid. MS (ESI) m/z 349 [M+1]+.

(1S, 4S)-4-(2-((4-Methyltetrahydro-2H-pyran-4-yl)amino)-8-((4-(trifluoromethoxy)phenyl)amino)-9H-purin-9-yl)cyclohexane-1-carboxamide. To a stirred solution of (1S, 4S)-4-((5-amino-2-((4-methyltetrahydro-2H-pyran-4-yl)amino)pyrimidin-4-yl)amino)cyclohexane-1-carboxamide (0.6 g, 2 mmol) in THF:DMF (20 mL, 1:1) was added 1-ethyl-3-(3-dimethylamino propyl)carbodiimide (0.7 g, 3 mmol) and 1-isothiocyanato-4-(trifluoromethoxy)benzene (0.5 g, 2 mmol) at ambient temperature. The reaction mixture was heated to 50° C. for 4 h. Completion of the reaction was confirmed by UPLC. The product was isolated and purified via standard methods to afford (1S, 4S)-4-(2-((4-methyltetrahydro-2H-pyran-4-yl)amino)-8-((4-(trifluoromethoxy)phenyl)amino)-9H-purin-9-yl)cyclohexane-1-carboxamide (0.5 g, 54%) as white solid. MS (ESI) m/z 534 [M+1]+.

9-((1S, 4S)-4-(Aminomethyl)cyclohexyl)-N2-(4-methyltetrahydro-2H-pyran-4-yl)-N8-(4-(trifluoromethoxy)phenyl)-9H-purine-2,8-diamine. To a stirred solution of (1S, 4S)-4-(2-((4-methyltetrahydro-2H-pyran-4-yl)amino)-8-((4-(trifluoromethoxy)phenyl)amino)-9H-purin-9-yl)cyclohexane-1-carboxamide (400 mg, 1 mmol) in THF (3 mL) was added lithium aluminum hydride in THF (1.6 M; 6 mL) at 0° C. The reaction mixture was stirred at ambient temperature for 2 h. Completion of the reaction was confirmed by UPLC. The product was purified via standard methods to afford 9-((1S, 4S)-4-(aminomethyl)cyclohexyl)-N2-(4-methyltetrahydro-2H-pyran-4-yl)-N8-(4-(trifluoromethoxy)phenyl)-9H-purine-2,8-diamine (0.08 g, 20%). MS (ESI) m/z 521.2 [M+1]+. 1H NMR (400 MHz, CD3OD): δ 8.17 (s, 1H), 7.65 (d, J=8 Hz, 2H), 7.27 (d, J=8 Hz, 2H), 4.31-4.38 (m, 1H), 3.77-3.82 (m, 4H), 2.97 (d, J=7.2 Hz, 2H), 2.68-2.74 (m, 2H), 2.34-2.38 (m, 2H), 1.98-2.02 (m, 2H), 1.73-1.91 (m, 7H), 1.62 (s, 3H).

Example 34: N8-(3-Chlorophenyl)-9-((1S, 4S)-4-((dimethylamino)methyl)cyclohexyl)-N2-(4-methyltetrahydro-2H-pyran-4-yl)-9H-purine-2,8-diamine

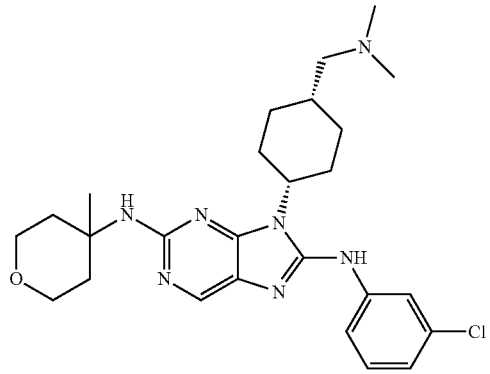 [SMILES: CN(C)C[C@H]1CC[C@@H](n2c(Nc3cccc(Cl)c3)nc3cnc(NC4(C)CCOCC4)nc32)CC1]

tert-Butyl ((1S, 4S)-4-(dimethylcarbamoyl)cyclohexyl)carbamate. To a solution of (1S, 4S)-4-((tert-butoxycarbonyl)amino)cyclohexane-1-carboxylic acid (2 g, 8.2 mmol) in dry DCM (30 mL) was added 1-ethyl-3-(3-dimethylaminopropyl)carbodiimide (1.6 g, 16 mmol), HOBt (1.1 g, 16 mmol), DIPEA (2.12 g, 33 mmol) and dimethyl amine (1.35 g, 33 mmol, 2.4M solution in THF) at 0° C. and stirred for 16 h at ambient temperature. Completion of the reaction was confirmed by TLC. The product was isolated via standard purification methods to afford tert-butyl ((1S, 4S)-4-(dimethylcarbamoyl)cyclohexyl)carbamate (2 g, 90%) as gummy solid. GCMS m/z 270 [M]+.

(1S, 4S)-4-Amino-N, N-dimethylcyclohexane-1-carboxamide. To a stirred solution of tert-butyl ((1S, 4S)-4-(dimethylcarbamoyl)cyclohexyl)carbamate (2 g, 8 mmol) in ethanol (10 mL) was added dropwise HCl in 1, 4-dioxane in (4.5 M, 5 mL) at 0° C. The reaction mixture was stirred at ambient temperature for 4 h. Completion of the reaction was confirmed by TLC. The product was isolated and purified via standard purification methods to afford (1S, 4S)-4-amino-N,N-dimethylcyclohexane-1-carboxamide (1.2 g, 80%) as white solid. GCMS m/z 170 [M]+.

(1S,4S)-4-((2-Chloro-5-nitropyrimidin-4-yl)amino)-N,N-dimethylcyclohexane-1-carboxamide. To a solution of (1S, 4S)-4-amino-N, N-dimethylcyclohexane-1-carboxamide (1.9 g, 10 mmol) in IPA was added 2,4-dichloro-5-nitropyrimidine (1.9 g, 10 mmol) and DIPEA (3.7 g, 30 mmol) at ambient temperature. The reaction was stirred for 2 h at 50° C. Completion of the reaction was confirmed by UPLC. The product was isolated via standard purification methods to afford (1S, 4S)-4-((2-chloro-5-nitropyrimidin-4-yl)amino)-N, N-dimethylcyclohexane-1-carboxamide (1 g, 30%). MS (ESI) m/z 327, 328 [M, M+1]$^+$.

(1S,4S)—N,N-Dimethyl-4-((2-((4-Methyltetrahydro-2H-pyran-4-yl)amino)-5-nitropyrimidin-4-yl)amino)cyclohexane-1-carboxamide. To a stirred solution of (1S, 4S)-4-((2-chloro-5-nitropyrimidin-4-yl)amino)-N,N-dimethylcyclohexane-1-carboxamide (0.28 g, 2 mmol) in DMF (10 mL) was added 4-methyl tetrahydro-2H-pyran-4-amine (0.5 g, 2 mmol), sodium carbonate (0.5 g, 5 mmol). The reaction mass was stirred at ambient temperature for 16 h. Completion of the reaction was confirmed by UPLC. The product was isolated via standard purification methods to afford (1S, 4S)—N,N-dimethyl-4-((2-((4-methyltetrahydro-2H-pyran-4-yl)amino)-5-nitropyrimidin-4-yl)amino)cyclohexane-1-carboxamide (0.23 g, 37%) as a pale brown solid MS (ESI) m/z 407 [M+1]$^+$.

(1S, 4S)-4-((5-Amino-2-((4-methyltetrahydro-2H-pyran-4-yl)amino)pyrimidin-4-yl) amino)-N,N-dimethylcyclohexane-1-carboxamide. To a stirred solution of (1S, 4S)—N,N-dimethyl-4-((2-((4-methyltetrahydro-2H-pyran-4-yl) amino)-5-nitropyrimidin-4-yl)amino) cyclohexane-1-carboxamide (0.23 g, 1 mmol) in ethanol (10 mL) was added palladium on carbon (30 mg, 10% W/M) under argon atmosphere. Reaction mixture was stirred at ambient temperature under atmospheric hydrogen. Completion of the reaction was confirmed by UPLC. The product was isolated by standard purification methods to afford (1S, 4S)-4-((5-amino-2-((4-methyltetrahydro-2H-pyran-4-yl)amino)pyrimidin-4-yl)amino)-N,N-dimethylcyclohexane-1-carboxamide (0.2 g, 90%) as violet solid MS (ESI) m/z 377 [M+1]$^+$.

(1S,4S)-4-(8-((3-Chlorophenyl)amino)-2-((4-methyltetrahydro-2H-pyran-4-yl)amino)-9H-purin-9-yl)-N,N-dimethylcyclohexane-1-carboxamide. A solution of (1S, 4S)-4-((5-amino-2-(4-methyltetrahydro-2H-pyran-4-yl)pyrimidin-4-yl)amino)-N,N-dimethylcyclohexane-1-carboxamide (0.35 g, 1 mmol), 1-ethyl-3-(3-dimethylaminopropyl)carbodiimide (0.35 g, 2 mmol) and 1-chloro-3-isothiocyanatobenzene (0.19 g, 1.2 mmol) in THF (5 mL) was mixed at ambient temperature. The reaction was heated to 50° C. for 4 h. Completion of the reaction was confirmed by UPLC. The product was isolated by standard purification methods to afford (1S, 4S)-4-(8-((3-chlorophenyl)amino)-2-((4-methyltetrahydro-2H-pyran-4-yl)amino)-9H-purin-9-yl)-N, N-dimethylcyclohexane-1-carboxamide (0.2 g, 42%) as an off-white solid MS (ESI) m/z 511, 512 [M, M+1]$^+$.

N8-(3-Chlorophenyl)-9-((1S, 4S)-4-((dimethylamino)methyl)cyclohexyl)-N2-(4-methyl tetrahydro-2H-pyran-4-yl)-9H-purine-2,8-diamine. To a stirred solution of (1S, 4S)-4-(8-((3-chlorophenyl)amino)-2-((4-methyltetrahydro-2H-pyran-4-yl)amino)-9H-purin-9-yl)-N,N-dimethylcyclohexane-1-carboxamide (0.17 g, 0.33 mmol) in THF (3 mL) was added lithium aluminium hydride in THF (1.6 M; 5 mL) at 0° C. The reaction was heated at 50° C. for 1 h. Completion of the reaction was confirmed by TLC. The reaction mixture was quenched with 10% NaOH solution and water (10 mL, 1:1) and extracted with ethyl acetate. The product was purified by standard methods to afford N8-(3-chlorophenyl)-9-((1S, 4S)-4-((dimethylamino)methyl)cyclohexyl)-N2-(4-methyltetrahydro-2H-pyran-4-yl)-9H-purine-2,8-diamine (0.060 g, 33%). MS (ESI) m/z 498.4, 499.4 [M$^+$, M+1]$^+$. $^1$H NMR (400 MHz, CD$_3$OD): δ 8.34 (brs, 1H, NH proton), 8.21 (s, 1H), 7.63-7.64 (m, 1H), 7.40-7.42 (m, 1H), 7.27-7.31 (m, 1H), 7.02-7.04 (m, 1H), 4.29-4.35 (m, 1H), 3.72-3.82 (m, 4H), 3.13 (d, J=6.4 Hz, 2H), 2.79 (s, 6H), 2.57-2.67 (m, 2H), 2.38-2.41 (m, 2H), 2.23 (brs, 1H), 1.75-1.97 (m, 8H), 1.00 (s, 3H).

Example 35: 9-((1R, 4R)-4-(Aminomethyl)cyclohexyl)-N8-(3-chlorophenyl)-N2-(4-methyltetrahydro-2H-pyran-4-yl)-9H-purine-2,8-diamine

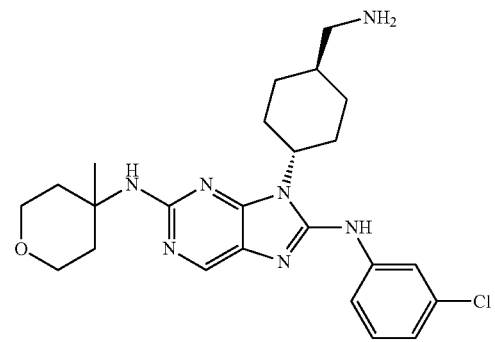 [SMILES: CC1(Nc2ncc3nc(Nc4cccc(Cl)c4)n([C@H]4CC[C@H](CN)CC4)c3n2)CCOCC1]

(1R, 4R)-4-((tert-Butoxycarbonyl)amino)cyclohexane-1-carboxylic acid. To a solution of (1R, 4R)-4-aminocyclohexane-1-carboxylic acid (2 g, 13 mmol) in N, N-dimethyl formamide (10 mL) was added Boc anhydride (5 g, 20 mmol) and triethylamine (4.2 g, 13 mmol). Then, the resulting reaction mixture was stirred at ambient temperature for 18 h. Completion of the reaction was confirmed by GCMS. The product was isolated to afford (1R, 4R)-4-((tert-butoxycarbonyl)amino)cyclohexane-1-carboxylic acid (2.5 g, 95%) as a pale yellow solid. GCMS m/z 243 [M]$^+$.

tert-Butyl((1R, 4R)-4-carbamoylcyclohexyl)carbamate. To a solution of (1R, 4R)-4-((tert-butoxycarbonyl)amino) cyclohexane-1-carboxylic acid (2.5 g, 10 mmol) in dry THF (10 mL) was added ethyl chloroformate (1.6 g, 15 mmol) and triethyl amine (3.1 g, 30 mmol) at 0° C. and the reaction was stirred at ambient temperature for 3 h. Completion of the reaction was confirmed by TLC. The reaction was quenched with ammonia in THF (10 M solution). The product was isolated via standard methods to afford tert-butyl((1R, 4R)-4-carbamoylcyclohexyl)carbamate (1.4 g, 50%) as white solid. GCMS m/z 242 [M]$^+$.

(1R, 4R)-4-Aminocyclohexane-1-carboxamide. To a stirred solution of tert-butyl ((1R, 4R)-4-carbamoylcyclohexyl)carbamate (1.4 g, 0.88 mmol) in ethanol (10 mL) was added dropwise HCl in 1, 4-dioxane (4.5 M, 5 mL) at 0° C. The reaction mixture was stirred for 4 h. Completion of the reaction was confirmed by TLC. The product was isolated and purified via standard methods to afford (1R, 4R)-4-aminocyclohexane-1-carboxamidehydrochloride (0.8 g, 96%) as white solid. GCMS m/z 142 [M]$^+$.

(1R, 4R)-4-((2-Chloro-5-nitropyrimidin-4-yl)amino)cyclohexane-1-carboxamide. To a solution of (1R, 4R)-4-aminocyclohexane-1-carboxamidehydrochloride (0.8 g, 4 mmol) in IPA (20 mL) was added 2,4-dichloro-5-nitropyrimidine (1 g, 4 mmol) and DIPEA (1.7 g, 14 mmol) at ambient temperature. Reaction mixture temperature was raised to 50° C. and stirred for 2 h. Completion of the reaction was confirmed by UPLC. The product was isolated via standard purification methods to afford (1R, 4R)-4-((2-chloro-5-nitropyrimidin-4-yl)amino)cyclohexane-1-carboxamide (0.8 g, 59%). MS (ESI) m/z 299, 300 [M, M+1]$^+$.

(1R, 4R)-4-((2-((4-Methyltetrahydro-2H-pyran-4-yl)amino)-5-nitropyrimidin-4-yl)amino) cyclohexane-1-carboxamide. To a stirred solution of (1R, 4R)-4-((2-chloro-5-nitropyrimidin-4-yl)amino)cyclohexane-1-carboxamide (0.6 g, 2 mmol) in DMF (10 mL) was added 4-methyltetrahydro-2H-pyran-4-amine (0.3 g, 2 mmol) and sodium carbonate (0.6 g, 5 mmol). The reaction mixture was stirred at ambient temperature for 16 h. Completion of the reaction was confirmed by UPLC. The product was isolated via standard purification methods to afford (1R, 4R)-4-((2-((4-methyltetrahydro-2H-pyran-4-yl)amino)-5-nitropyrimidin-4-yl)amino)cyclohexane-1-carboxamide (0.25 g, 33%) as pale yellow solid. MS (ESI) m/z 378, 379 [M, M+1]$^+$.

(1R, 4R)-4-((5-Amino-2-((4-methyltetrahydro-2H-pyran-4-yl)amino)pyrimidin-4-yl)amino) cyclohexane-1-carboxamide. To a stirred solution of (1R, 4R)-4-((2-((4-methyltetrahydro-2H-pyran-4-yl)amino)-5-nitropyrimidin-4-yl)amino)cyclohexane-1-carboxamide (0.25 g, 1 mmol) in ethanol (10 mL) was added palladium on carbon (0.003 g, 10% w/w) under argon atmosphere. The reaction mixture was stirred under atmospheric hydrogen pressure at ambient temperature for 16 h. Completion of the reaction was confirmed by TLC. The product was isolated by standard purification method to afford (1R, 4R)-4-((5-amino-2-((4-methyltetrahydro-2H-pyran-4-yl)amino)pyrimidin-4-yl)amino)cyclohexane-1-carboxamide (0.2 g, 90%) as violet solid. MS (ESI) m/z 349 [M+1]$^+$.

(1R, 4R)-4-(8-((3-Chlorophenyl)amino)-2-((4-methyltetrahydro-2H-pyran-4-yl)amino)-9H-purin-9-yl)cyclohexane-1-carboxamide. To a stirred solution of (1R, 4R)-4-((5-amino-2-((4-methyltetrahydro-2H-pyran-4-yl)amino)pyrimidin-4-yl)amino)cyclohexane-1-carboxamide (0.35 g, 1 mmol) and 1-chloro-3-isothiocyanatobenzene (0.2 g, 1.2 mmol) was added 1-ethyl-3-(3-dimethylaminopropyl) carbodiimide (0.39 g, 2 mmol) in THF (5 mL) at ambient temperature. The reaction was heated to 50° C. for 4 h. Completion of the reaction was confirmed by UPLC. The product was isolated by standard purification methods to afford (1R, 4R)-4-(8-((3-chlorophenyl)amino)-2-((4-methyltetrahydro-2H-pyran-4-yl)amino)-9H-purin-9-yl)cyclohexane-1-carboxamide (0.25 g, 51%) as an off-white solid. MS (ESI) m/z 484, 485 [M, M+1]$^+$.

9-((1R, 4R)-4-(Aminomethyl)cyclohexyl)-N8-(3-chlorophenyl)-N2-(4-methyltetrahydro-2H-pyran-4-yl)-9H-purine-2,8-diamine. To a stirred solution (1R, 4R)-4-(8-((3-chlorophenyl)amino)-2-((4-methyltetrahydro-2H-pyran-4-yl)amino)-9H-purin-9-yl)cyclohexane-1-carboxamide (0.25 g, 0.5 mmol) in THF (3 mL) was added lithium aluminum hydride in THF (1.6 M, 5 mL) at 0° C. and the reaction was heated at 50° C. for 1 h. Completion of the reaction was confirmed by TLC. The product was purified by standard methods to afford 9-((1R, 4R)-4-(aminomethyl)cyclohexyl)-N8-(3-chlorophenyl)-N2-(4-methyltetrahydro-2H-pyran-4-yl)-9H-purine-2, 8-diamine (0.05 g, 21%) as an off-white solid. MS (ESI) m/z 470.2, 471.2 [M, M+1]$^+$. $^1$HNMR (400 MHz, CD$_3$OD): δ 8.25 (m, 1H), 7.90 (s, 1H), 7.64 (d, J=8 Hz, 1H), 7.29-7.33 (m, 1H), 6.97-6.99 (dd, J=1.6 Hz, 8 Hz, 1H), 5.86 (s, 1H) 4.34-4.40 (m, 1H), 3.57-3.70 (m, 4H), 2.49-2.66 (m, 4H), 2.27-2.32 (m, 2H), 1.92-1.95 (m, 2H), 1.83-1.86 (m, 2H), 1.64-1.71 (m, 2H), 1.49 (s, 3H), 1.26-1.40 (m, 1H), 1.12-1.18 (m, 2H).

Example 36: N-((1S, 4S)-4-(8-((3-Chlorophenyl)amino)-2-((4-methyltetrahydro-2H-pyran-4-yl)amino)-9H-purin-9-yl)cyclohexyl)acetamide

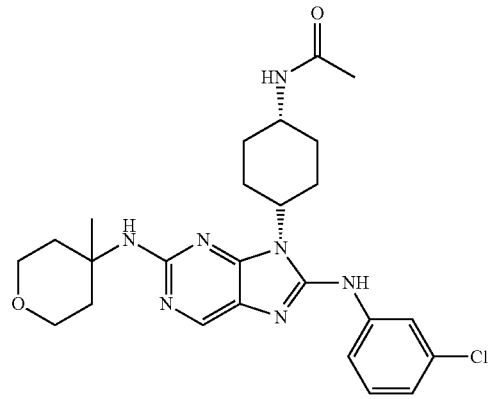

N-((1S, 4S)-4-(8-((3-Chlorophenyl)amino)-2-((4-methyltetrahydro-2H-pyran-4-yl)amino)-9H-purin-9-yl)cyclohexyl)acetamide. To a solution of 9-((1S, 4S)-4-aminocyclohexyl)-N8-(3-chlorophenyl)-N2-(4-methyltetrahydro-2H-pyran-4-yl)-9H-purine-2,8-diamine (0.2 g, 0.43 mmol) in dry chloroform (10 mL) was added acetic anhydride (0.053 g, 0.52 mmol) at 0° C. under nitrogen. The reaction mixture was stirred at ambient temperature for 3 h. Completion of the reaction was confirmed by TLC. The product was purified via standard methods to afford N-((1S, 4S)-4-(8-((3-chlorophenyl)amino)-2-((4-methyltetrahydro-2H-pyran-4-yl)amino)-9H-purin-9-yl)cyclohexyl)acetamide (0.04 g, 74%). MS (ESI) m/z 498.2, 499.2 [M, M+1]$^+$. $^1$H NMR (400 MHz, CD$_3$OD): δ 8.20 (s, 1H), 7.66 (s, 1H), 7.43 (dd, J=1.6 Hz, 8.4 Hz, 1H), 7.27-7.31 (m, 1H), 7.02-7.05 (m, 1H), 4.30-4.36 (m, 1H), 4.01 (brs, 1H), 3.72-3.83 (m, 4H), 2.67-2.77 (m, 2H), 2.38-2.41 (m, 2H), 2.12-2.16 (m, 2H), 2.05 (s, 3H), 1.72-1.80 (m, 6H), 1.59 (s, 3H).

Example 37: ((1R, 4R)-4-(8-((3-Chlorophenyl)amino)-2-((4-methyltetrahydro-2H-pyran-4-yl)amino)-9H-purin-9-yl)cyclohexyl)methanol

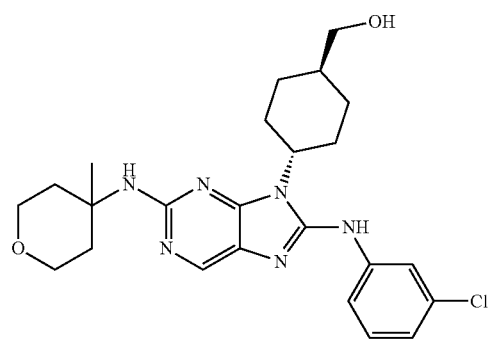 [SMILES: CC1(Nc2ncc3nc(Nc4cccc(Cl)c4)n([C@H]4CC[C@H](CO)CC4)c3n2)CCOCC1]

((1R, 4R)-4-((2-Chloro-5-nitropyrimidin-4-yl)amino)cyclohexyl)methanol. To a stirred solution of 2,4-dichloro-5-nitropyrimidine (0.6 g, 3 mmol) in THF (10 mL) was added DIPEA (0.4 g, 3 mmol) dropwise followed by ((1R, 4R)-4-aminocyclohexyl)methanol (0.4 g, 3 mmol) at ambient temperature. The reaction mixture was stirred at ambient temperature for 4 h. Completion of the reaction was confirmed by UPLC. The product was isolated to afford ((1R, 4R)-4-((2-chloro-5-nitropyrimidin-4-yl)amino)cyclohexyl)methanol (0.3 g, 33%) as a yellow solid. MS (ESI) m/z 287 [M+1]⁺.

((1R, 4R)-4-((2-((4-Methyltetrahydro-2H-pyran-4-yl)amino)-5-nitropyrimidin-4-yl)amino)cyclohexyl)methanol. To a stirred solution of ((1R, 4R)-4-((2-chloro-5-nitropyrimidin-4-yl)amino)cyclohexyl)methanol (0.3 g, 1 mmol) in DMF (10 mL) was added sodium carbonate (0.2 g, 2 mmol) portionwise followed by 4-methyltetrahydro-2H-pyran-4-aminehydrochloride (0.1 g, 1 mmol) at ambient temperature. The reaction mixture was stirred for 4 h at ambient temperature. Completion of the reaction was confirmed by UPLC. The product was isolated to afford ((1R, 4R)-4-((2-((4-methyltetrahydro-2H-pyran-4-yl)amino)-5-nitropyrimidin-4-yl)amino)cyclohexyl) methanol (0.25 g, 64%) as a yellow solid. MS (ESI) m/z 366 [M+1]⁺.

((1R, 4R)-4-((5-Amino-2-((4-methyltetrahydro-2H-pyran-4-yl)amino)pyrimidin-4-yl)amino)cyclohexyl)methanol. To a stirred solution of ((1R, 4R)-4-((2-((4-methyltetrahydro-2H-pyran-4-yl) amino)-5-nitropyrimidin-4-yl) amino)cyclohexyl)methanol (0.25 g, 1 mmol) in ethanol:water (10 mL, 2:2) was added iron powder (0.4 g, 7 mmol) portionwise followed by ammonium chloride (0.04 g, 1 mmol) at ambient temperature. The reaction mixture was heated to 80° C. for 4 h. Completion of the reaction was confirmed by UPLC. The product was isolated and purified via standard methods to afford ((1R, 4R)-4-((5-amino-2-((4-methyltetrahydro-2H-pyran-4-yl)amino)pyrimidin-4-yl) amino)cyclohexyl)methanol (0.2 g) as an off-white solid. MS (ESI) m/z 336 [M+1].

((1R, 4R)-4-(8-((3-Chlorophenyl)amino)-2-((4-methyltetrahydro-2H-pyran-4-yl)amino)-9H-purin-9-yl)cyclohexyl)methanol. To a stirred solution of ((1R, 4R)-4-((5-amino-2-((4-methyltetrahydro-2H-pyran-4-yl)amino) pyrimidin-4-yl)amino)cyclohexyl)methanol (0.25 g, 1 mmol) in THF (10 mL) was added to 1-ethyl-3-(3-dimethylaminopropyl)carbodiimide (0.2 g, 1 mmol) and 1-isothiocyanato-3-chlorobenzene (0.1 g, 1 mmol) at ambient temperature. The reaction mixture was heated to 60° C. for 4 h. Completion of the reaction was confirmed by UPLC. The product was via standard methods to afford ((1R, 4R)-4-(8-((3-chlorophenyl)amino)-2-((4-methyltetrahydro-2H-pyran-4-yl)amino)-9H-purin-9-yl)cyclohexyl)methanol (0.06 g, 40%). MS (ESI) m/z 471 [M+1]⁺. ¹H NMR (400 MHz, CD₃OD): δ 8.20 (s, 1H), 7.71 (s, 1H), 7.45 (d, J=8.0 Hz, 1H), 7.28-7.32 (m, 1H), 7.03 (d, J=8.0 Hz, 1H), 4.30-4.36 (m, 1H), 3.73-3.81 (m, 4H), 3.45-3.47 (m, 2H), 2.64-2.73 (m, 2H), 2.35-2.39 (m, 2H), 1.94-2.04 (m, 4H), 1.74-1.81 (m, 2H), 1.61-1.62 (m, 1H), 1.57 (s, 3H), 1.19-1.23 (m, 2H).

Example 38: 9-((1S, 4S)-4-Aminocyclohexyl)-N8-(3-chlorophenyl)-N2-(4-methyltetrahydro-2H-pyran-4-yl)-9H-purine-2,8-diamine

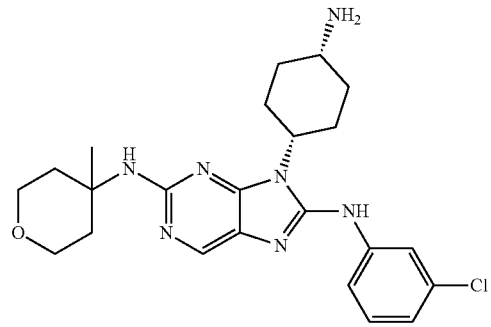 [SMILES: CC1(Nc2ncc3nc(Nc4cccc(Cl)c4)n([C@H]4CC[C@@H](N)CC4)c3n2)CCOCC1]

tert-Butyl ((1S, 4S)-4-((2-chloro-5-nitropyrimidin-4-yl) amino)cyclohexyl)carbamate. To a stirred solution of 2,4-dichloro-5-nitropyrimidine (1 g, 5 mmol) in IPA (10 mL) was added tert-butyl ((S, 4S)-4-aminocyclohexyl)carbamate (1.3 g, 6 mmol) and DIPEA (2 g, 15 mmol) at 0° C. The reaction mixture was stirred for 1 h. Completion of the reaction was confirmed by UPLC. The product was isolated and triturated with petroleum ether to afford tert-butyl ((1S, 4S)-4-((2-chloro-5-nitropyrimidin-4-yl)amino)cyclohexyl) carbamate (1 g, 52%) as a yellow solid. MS (ESI) m/z 371, 372 [M, M+1]⁺.

tert-Butyl ((1S, 4S)-4-((2-((4-methyltetrahydro-2H-pyran-4-yl)amino)-5-nitropyrimidin-4-yl)amino)cyclohexyl)carbamate. To a stirred solution tert-butyl-((1S, 4S)-4-((2-chloro-5-nitropyrimidin-4-yl)amino)cyclohexyl) carbamate (1 g, 3 mmol) in DMF (20 mL) was added 4-methyltetrahydro-2H-pyran-4-amine (0.5 g, 3 mmol) and sodium carbonate (0.7 g, 8 mmol) under inert atmosphere at ambient temperature. The reaction mixture was stirred for 16 h. Completion of the reaction was confirmed by UPLC. The product was isolated and purified via standard methods to afford tert-butyl((1S, 4S)-4-((2-((4-methyltetrahydro-2H-pyran-4-yl)amino)-5-nitropyrimidin-4-yl)amino)cyclohexyl)carbamate (1 g, 81%) as a yellow solid. MS (ESI) m/z 451 [M+1]⁺.

tert-Butyl ((1S, 4S)-4-((5-Amino-2-((4-methyltetrahydro-2H-pyran-4-yl)amino)pyrimidin-4-yl)amino)cyclohexyl) carbamate. To a stirred solution tert-butyl ((1S, 4S)-4-((2-((4-methyltetrahydro-2H-pyran-4-yl)amino)-5-nitropyrimidin-4-yl)amino)cyclohexyl)carbamate (1 g, 2 mmol) in ethanol:water (30 mL, 10:1) was added iron powder (1.2 g, 20 mmol) and ammonium chloride (0.14 g, 2 mmol) at ambient temperature. The reaction mixture was heated to 85° C. and maintained for 12 h. Completion of the reaction was confirmed by UPLC. The product was isolated via standard methods to afford tert-butyl ((1S, 4S)-4-((5-amino-2-((4-methyltetrahydro-2H-pyran-4-yl)amino)pyrimidin-4-yl)amino)cyclohexyl)carbamate (0.9 g, 95%) as a brown solid. MS (ESI) m/z 421 [M+1]⁺.

tert-Butyl-((1S, 4S)-4-(8-((3-chlorophenyl)amino)-2-((4-methyltetrahydro-2H-pyran-4-yl)amino)-9H-purin-9-yl)cyclohexyl)carbamate. To a stirred solution of tert-butyl ((1S, 4S)-4-((5-amino-2-((4-methyltetrahydro-2H-pyran-4-yl) amino)pyrimidin-4-yl)amino)cyclohexyl) carbamate (0.9 g, 2 mmol) and 1-chloro-3-isothiocyanatobenzene (0.5 g, 2.5 mmol) in THF was added EDCI (0.8 g, 4 mmol) at ambient temperature. The reaction mixture was heated to 60° C. for 4 h. Completion of the reaction was confirmed by UPLC. The product was isolated and purified via standard methods to afford tert-butyl((1S, 4S)-4-(8-((3-chlorophenyl)amino)-2-((4-methyltetrahydro-2H-pyran-4-yl)amino)-9H-purin-9-yl)cyclohexyl)carbamate (0.45 g, 38%) as a yellow solid. MS (ESI) m/z 556, 557 [M, M+1]+.

9-((1S, 4S)-4-Aminocyclohexyl)-N8-(3-chlorophenyl)-N2-(4-methyltetrahydro-2H-pyran-4-yl)-9H-purine-2,8-diamine. To a stirred solution of tert-butyl-((1S, 4S)-4-(8-((3-chloro phenyl)amino)-2-((4-methyltetrahydro-2H-pyran-4-yl)amino)-9H-purin-9-yl)cyclohexyl) carbamate (0.3 g, 0.13 mmol) in ethanol (10 mL) was added HCl in 1, 4-dioxane (4.5 M, 5 mL) dropwise at 0° C. The reaction was stirred at ambient temperate for 4 h. Completion of the reaction was confirmed by TLC. The product was purified via standard methods to afford 9-((1S, 4S)-4-aminocyclohexyl)-N8-(3-chlorophenyl)-N2-(4-methyltetrahydro-2H-pyran-4-yl)-9H-purine-2,8-diamine (0.1 g, 30%). MS (ESI) m/z 456.2, 457.2 [M, M+1]+. $^1$HNMR (400 MHz, CD$_3$OD): δ 8.21 (s, 1H), 7.71 (s, 1H), 7.45 (d, J=8 Hz, 1H), 7.29-7.33 (m, 1H), 7.04 (dd, J=1.2 Hz & 8 Hz, 1H),4.35-4.44 (m, 1H), 3.72-3.81 (m, 5H), 2.77-2.81 (m, 2H), 2.45-2.48 (m, 2H), 1.90-2.04 (m, 4H), 1.70-1.83 (m, 4H) 1.57 (s, 3H).

Example 39: 9-((1S, 4S)-4-(Aminomethyl)cyclohexyl)-N2-(4-methyltetrahydro-2H-pyran-4-yl)-N8-(3-(trifluoromethyl)phenyl)-9H-purine-2,8-diamine

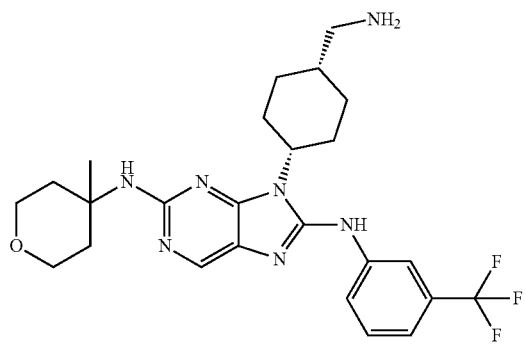 [SMILES: CC1(Nc2ncc3nc(Nc4cccc(C(F)(F)F)c4)n([C@H]4CC[C@@H](CN)CC4)c3n2)CCOCC1]

(1S, 4S)-4-((2-((4-Methyltetrahydro-2H-pyran-4-yl) amino)-5-nitropyrimidin-4-yl)amino) cyclohexane-1-carboxamide. To a stirred solution of (1S, 4S)-4-((2-chloro-5-nitro pyrimidine-4-yl)amino)cyclohexane-1-carboxamide (2.0 g, 6 mmol) in DMF (10 mL) was added sodium carbonate (1.9 g, 18 mmol) portionwise followed by 4-methyltetrahydro-2H-pyran-4-amine hydrochloride (1.2 g, 8 mmol) at ambient temperature. The reaction mixture was stirred for 4 h at ambient temperature. Completion of the reaction was confirmed by UPLC. The product was isolated to afford (1S, 4S)-4-((2-((4-methyltetrahydro-2H-pyran-4-yl)amino)-5-nitropyrimidin-4-yl)amino)cyclohexane-1-carboxamide (1.5 g, 66%) as a yellow solid. MS (ESI) m/z 379 [M+1]+.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl) amino)cyclohexane-1-carboxamide (0.7 g, 2 mmol) in ethanol (10 mL) was added palladium on charcoal (0.07 g, 10% w/m) portionwise under argon atmosphere. The reaction was stirred at ambient temperature under atmospheric hydrogen. Completion of the reaction was confirmed by UPLC. The resulting reaction mixture was filtered through a bed of celite, washed with ethyl acetate and concentrated to afford (1S, 4S)-4-((5-amino-2-((4-methyltetrahydro-2H-pyran-4-yl)amino)pyrimidin-4-yl)amino)cyclohexane-1-carboxamide (0.5 g, 71%) as a yellow solid. MS (ESI) m/z 349 [M+1]+.

(1S, 4S)-4-(2-((4-Methyltetrahydro-2H-pyran-4-yl) amino)-8-((3-(trifluoromethyl)phenyl) amino)-9H-purin-9-yl)cyclohexane-1-carboxamide. To a stirred solution of (1S, 4S)-4-((5-amino-2-((4-methyltetrahydro-2H-pyran-4-yl) amino)pyrimidin-4-yl)amino)cyclohexane-1-carboxamide (0.5 g, 1 mmol) in THF (10 mL) was added 1-ethyl-3-(3-dimethylaminopropyl)carbodiimide (0.6 g, 3 mmol) and 1-isothiocyanato-3-(trifluoromethyl)benzene (0.25 g, 2 mmol) at ambient temperature. The reaction mixture was heated to 60° C. for 4 h. Completion of the reaction was confirmed by UPLC. The product was isolated and purified via standard methods to afford (1S, 4S)-4-(2-((4-methyltetrahydro-2H-pyran-4-yl)amino)-8-((3-(trifluoromethyl)phenyl)amino)-9H-purin-9-yl)cyclohexane-1-carboxamide (0.3 g, 42%) as an off-white solid. MS (ESI) m/z 517 [M+1]+.

9-((1S, 4S)-4-(Aminomethyl)cyclohexyl)-N2-(4-methyltetrahydro-2H-pyran-4-yl)-N8-(3-(trifluoromethyl)phenyl)-9H-purine-2,8-diamine. To a stirred solution of (1S, 4S)-4-(2-((4-methyltetrahydro-2H-pyran-4-yl)amino)-8-((3-(trifluoromethyl)phenyl)amino)-9H-purin-9-yl) cyclohexane-1-carboxamide (0.25 g, 1 mmol) in diethylether (3 mL) was added lithium aluminum hydride in THF (1.6 M; 5 mL) at 0° C. The reaction mixture was stirred at ambient temperature for 4 h. Completion of the reaction was confirmed by UPLC. The product was purified via standard methods to afford 9-((1S, 4S)-4-(amino methyl) cyclohexyl)-N2-(4-methyltetrahydro-2H-pyran-4-yl)-N8-(3-(trifluoromethyl)phenyl)-9H-purine-2,8-diamine (0.06 g, 26%). MS (ESI) m/z 504 [M+1]+. $^1$H NMR (400 MHz, CD$_3$OD): δ 8.60 (s, 1H), 8.24 (s, 1H), 7.96 (brs, 1H), 7.85 (d, J=8.0 Hz, 1H), 7.51-7.55 (m, 1H), 7.33 (d, J=8.0 Hz, 1H), 4.38-4.42 (m, 1H), 3.75-3.85 (m, 4H), 3.24 (d, J=7.6 Hz, 2H), 2.65-2.71 (m, 2H), 2.45-2.49 (m, 2H), 2.11-2.14 (m, 1H), 1.98-2.0 (m, 2H), 1.72-1.94 (m, 6H), 1.61 (s, 3H).

Example 40: 9-((1S, 4S)-4-Aminocyclohexyl)-N2-(tert-butyl)-N8-(3-(trifluoromethyl) phenyl)-9H-purine-2,8-diamine

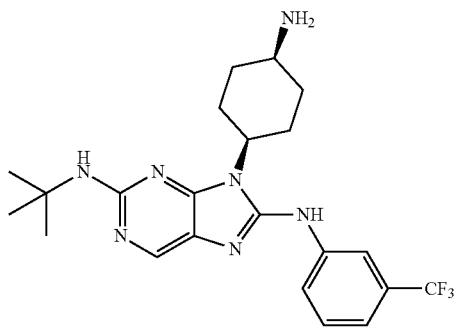 [SMILES: CC(C)(C)Nc1ncc2nc(Nc3cccc(C(F)(F)F)c3)n([C@H]3CC[C@@H](N)CC3)c2n1]

tert-Butyl ((1S, 4S)-4-((2-chloro-5-nitropyrimidin-4-yl) amino)cyclohexyl)carbamate. To a stirred solution of 2, 4-dichloro-5-nitropyrimidine (0.8 g, 4 mmol) and DIPEA (2 mL, 12 mmol) in IPA (10 mL) was added portionwise tert-butyl ((1S, 4S)-4-aminocyclohexyl) carbamate (0.8 g, 4 mmol) at 0° C. under nitrogen. The reaction mixture was slowly warmed to ambient temperature and stirred for 1 h. Completion of the reaction was confirmed by UPLC. The product was isolated to afford tert-butyl ((1S, 4S)-4-((2-chloro-5-nitropyrimidin-4-yl) aminocyclohexyl)carbamate (1 g) as yellow solid. MS (ESI) m/z 372, 373 [M, M+1]+.

tert-Butyl ((1S, 4S)-4-((2-(tert-butylamino)-5-nitropyrimidin-4-yl)amino)cyclohexyl) carbamate. To a stirred solution of tert-butyl ((1S, 4S)-4-((2-chloro-5-nitropyrimidin-4-yl)amino)cyclohexyl)carbamate (1 g, 3 mmol) in DMF (12 mL) was added tert butylamine (0.5 g, 7 mmol) and sodium bicarbonate (0.4 g, 5 mmol) at ambient temperature. The reaction mixture was heated to 60° C. for 4 h. The product was isolated and purified via standard methods to afford tert-butyl ((1S, 4S)-4-((2-(tert-butylamino)-5-nitropyrimidin-4-yl)amino)cyclohexyl)carbamate (0.9 g, 65%) as yellow solid. MS (ESI) m/z 409 [M+1]+.

tert-Butyl ((1S, 4S)-4-((5-amino-2-(tert-butylamino)pyrimidin-4-yl)amino)cyclohexyl) carbamate. To a stirred solution of tert-butyl ((1S, 4S)-4-((2-(tert-butylamino)-5-nitropyrimidin-4-yl)amino)cyclohexyl)carbamate (0.9 g, 2 mmol) in ethanol:water (15 mL, 3:1) was added iron powder (1 g, 22 mmol) and ammonium chloride (0.1 g, 2 mmol) at ambient temperature. The reaction mixture was heated to 85° C. for 2 h. Completion of the reaction was confirmed by UPLC. The resulting reaction mixture was filtered through a bed of celite, washed with ethyl acetate and concentrated to tert-butyl ((1S, 4S)-4-((5-amino-2-(tert-butylamino)pyrimidin-4-yl) amino)cyclohexyl)carbamate (0.8 g, 90%) as a brown solid. MS (ESI) m/z 379 [M+1]+.

tert-Butyl ((1S, 4S)-4-(2-(tert-butylamino)-8-((3-(trifluoromethyl)phenyl)amino)-9H-purin-9-yl)cyclohexyl)carbamate. To a stirred solution of tert-butyl ((1S, 4S)-4-((5-amino-2-(tert-butylamino)pyrimidin-4-yl)amino) cyclohexyl)carbamate (0.7 g, 2 mmol) and 1-isothiocyanato-3-(trifluoromethyl)benzene (0.4 g, 2 mmol) in THF was added EDCI (0.71 g, 4 mmol) at ambient temperature. The reaction mixture was heated to 60° C. for 4 h. Completion of the reaction was confirmed by UPLC. The product was isolated and purified via standard methods to afford tert-butyl ((1S, 4S)-4-(2-(tert-butylamino)-8-((3-(trifluoromethyl)phenyl)amino)-9H-purin-9-yl)cyclohexyl)carbamate (0.35 g, 35%) as an off-white solid. MS (ESI) m/z 548 [M+1]+.

9-((1S, 4S)-4-Aminocyclohexyl)-N2-(tert-butyl)-N8-(3-(trifluoromethyl)phenyl)-9H-purine-2,8-diamine. To a stirred solution of tert-butyl ((1S, 4S)-4-(2-(tert-butylamino)-8-((3-(trifluoromethyl)phenyl)amino)-9H-purin-9-yl)cyclohexyl)carbamate (0.35 g, 0.64 mmol) in methanol (10 mL) was added HCl in dioxane (5 mL) at 0° C. The reaction mixture was stirred ambient temperature for 16 h. Completion of the reaction was confirmed by UPLC. The product was purified via standard methods to afford 9-((1S, 4S)-4-aminocyclohexyl)-N2-(tert-butyl)-N8-(3-(trifluoromethyl)phenyl)-9H-purine-2,8-diamine (0.28 g, 98%). MS (ESI) m/z 448 [M+1]+. 1H NMR (400 MHz, CD3OD): δ 8.21 (s, 1H), 7.95 (s, 1H), 7.86 (d, J=8.1 Hz, 1H), 7.52-7.56 (m, 1H), 7.33 (d, J=7.7 Hz, 1H), 4.40-4.46 (m, 1H), 3.37 (brs, 1H), 2.82-2.86 (m, 2H), 1.97-2.02 (m, 4H), 1.83-1.86 (m, 2H), 1.53 (s, 9H).

Example 41: 9-((1R, 4R)-4-Aminocyclohexyl)-N2-(tert-butyl)-N8-(3-(trifluoromethyl) phenyl)-9H-purine-2,8-diamine

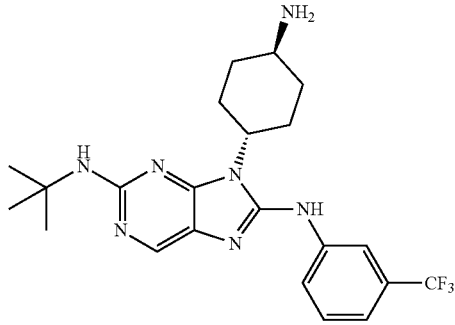 [SMILES: CC(C)(C)Nc1ncc2nc(Nc3cccc(C(F)(F)F)c3)n([C@H]3CC[C@H](N)CC3)c2n1]

tert-Butyl ((1R, 4R)-4-((2-(tert-butylamino)-5-nitropyrimidin-4-yl)amino)cyclohexyl) carbamate. To a stirred solution of tert-butyl ((1R, 4R)-4-((2-chloro-5-nitropyrimidin-4-yl) amino)cyclohexyl)carbamate (1 g, 2.7 mmol) in DMF (10 mL) was added tert-butylamine (0.39 g, 5.4 mmol) and sodium bicarbonate (0.34 g, 4 mmol) at ambient temperature. The reaction mixture was heated to 60° C. for 4 h. Completion of the reaction was confirmed by UPLC. The product was isolated and purified via standard methods to afford tert-butyl ((1R, 4R)-4-((2-(tert-butylamino)-5-nitropyrimidin-4-yl)amino)cyclohexyl)carbamate (0.6 g, 55%) as yellow solid. MS (ESI) m/z 409 [M+1]+.

tert-Butyl ((1R, 4R)-4-((5-amino-2-(tert-butylamino)pyrimidin-4-yl)amino)cyclohexyl) carbamate. To a stirred solution of tert-butyl ((1R, 4R)-4-((2-(tert-butylamino)-5-nitropyrimidin-4-yl) amino)cyclohexyl)carbamate (0.6 g, 1.47 mmol) in ethanol:water (10 mL, 3:1) was added iron powder (0.83 g, 15 mmol) and ammonium chloride (0.08 g, 1.47 mmol) at ambient temperature. The reaction mixture was heated to 85° C. for 2 h. Completion of the reaction was confirmed by UPLC. The resulting reaction mixture was filtered through bed of celite, washed with ethyl acetate and concentrated to afford tert-butyl ((1R, 4R)-4-((5-amino-2-(tert-butylamino)pyrimidin-4-yl)amino)cyclohexyl)carbamate (0.6 g, 99%) as a brown solid. MS (ESI) m/z 379 [M+1]+.

tert-Butyl ((1R, 4R)-4-(2-(tert-butylamino)-8-((3-(trifluoromethyl)phenyl)amino)-9H-purin-9-yl)cyclohexyl)carbamate. To a stirred solution of tert-butyl ((1R, 4R)-4-((5-amino-2-(tert-butylamino)pyrimidin-4-yl)amino) cyclohexyl)carbamate (0.6 g, 1.5 mmol) and 1-isothiocyanato-3-(trifluoromethyl)benzene (0.3 g, 1.5 mmol) in THF was added EDCI (0.6 g, 3 mmol) at ambient temperature. The reaction mixture was heated to 60° C. for 4 h. Completion of the reaction was confirmed by UPLC. The product was isolated and purified via standard methods to afford tert-butyl ((1R, 4R)-4-(2-(tert-butylamino)-8-((3-(trifluoromethyl)phenyl) amino)-9H-purin-9-yl)cyclohexyl) carbamate (0.4 g, 50%) as an off-white solid. MS (ESI) m/z 546 [M−1]+.

9-((1R, 4R)-4-Aminocyclohexyl)-N2-(tert-butyl)-N8-(3-(trifluoromethyl)phenyl)-9H-purine-2,8-diamine. To a stirred solution of tert-butyl ((1R, 4R)-4-(2-(tert-butylamino)-8-((3-(trifluoromethyl) phenyl)amino)-9H-purin-9-yl)cyclohexyl)carbamate (0.4 g, 0.7 mmol) in methanol (10 mL) was added HCl in dioxane (5 mL) at 0° C. The reaction mixture was stirred at ambient temperature for 16 h. Completion of the reaction was confirmed by UPLC. The product was purified via standard methods to afford 9-((1R, 4R)-4-aminocyclohexyl)-N2-(tert-butyl)-N8-(3-(trifluoromethyl)phenyl)-9H-purine-2,8-diamine (120 mg, 37%). MS (ESI) m/z 448 [M+1]+. $^1$H NMR (400 MHz, CD$_3$OD): δ 8.18 (s, 1H), 7.96 (s, 1H), 7.86 (d, J=8.1 Hz, 1H), 7.51-7.55 (m, 1H), 7.32 (d, J=7.8 Hz, 1H), 4.35-4.42 (m, 1H), 2.77-2.91 (m, 3H), 2.07-2.10 (m, 2H), 1.93-1.96 (m, 2H), 1.52 (s, 9H), 1.36-1.42 (m, 2H).

Example 42: 9-((1S, 4S)-4-(Aminomethyl)cyclohexyl)-N2-(4-methyltetrahydro-2H-pyran-4-yl)-N8-(4-(trifluoromethyl)phenyl)-9H-purine-2, 8-diamine

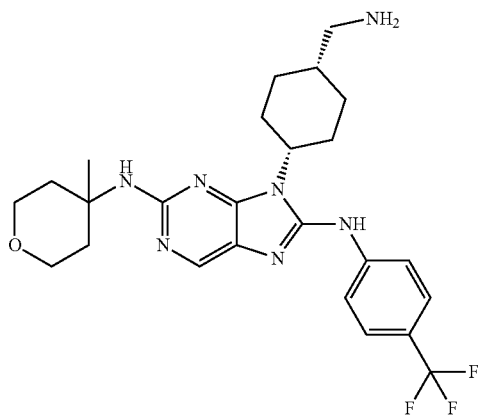 [SMILES: CC1(Nc2ncc3nc(Nc4ccc(C(F)(F)F)cc4)n([C@H]4CC[C@@H](CN)CC4)c3n2)CCOCC1]

(1S, 4S)-4-((2-((4-Methyltetrahydro-2H-pyran-4-yl)amino)-5-nitropyrimidin-4-yl)amino) cyclohexane-1-carboxamide. To a stirred solution of (1S, 4S)-4-((2-chloro-5-nitro pyrimidine-4-yl)amino)cyclohexane-1-carboxamide (2.0 g, 6 mmol) in DMF (10 mL) was added sodium carbonate (1.9 g, 18 mmol) portionwise followed by 4-methyltetrahydro-2H-pyran-4-aminehydrochloride (1.2 g, 8 mmol) at ambient temperature. The reaction mixture was stirred at ambient temperature for 4 h. Completion of the reaction was confirmed by UPLC. The product was isolated to afford (1S, 4S)-4-((2-((4-methyltetrahydro-2H-pyran-4-yl)amino)-5-nitropyrimidin-4-yl)amino) cyclohexane-1-carboxamide (1.5 g, 66%) as a yellow solid. MS (ESI) m/z 379 [M+1]+.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl) amino)cyclohexane-1-carboxamide (0.7 g, 2 mmol) in ethanol (10 mL) was added palladium on charcoal (0.07 g, 10% W/M) portionwise under argon atmosphere. The reaction was stirred at ambient temperature under atmospheric hydrogen atmosphere. Completion of the reaction was confirmed by UPLC. The resulting reaction mixture was filtered through a bed of celite, washed with ethyl acetate and concentrated to afford (1S, 4S)-4-((5-amino-2-((4-methyltetrahydro-2H-pyran-4-yl)amino)pyrimidin-4-yl)amino)cyclohexane-1-carboxamide (0.5 g, 71%) as a yellow solid. MS (ESI) m/z 349 [M+1]+.

(1S, 4S)-4-(2-((4-Methyltetrahydro-2H-pyran-4-yl)amino)-8-((4-(trifluoromethyl)phenyl) amino)-9H-purin-9-yl)cyclohexane-1-carboxamide. To a stirred solution of (1S, 4S)-4-((5-amino-2-((4-methyltetrahydro-2H-pyran-4-yl)amino)pyrimidin-4-yl)amino)cyclohexane-1-carboxamide (0.5 g, 1 mmol) in THF (10 mL) was added 1-ethyl-3-(3-dimethylaminopropyl)carbodiimide (0.6 g, 3 mmol) and 1-isothiocyanato-3-(trifluoromethyl)benzene (0.25 g, 2 mmol) at ambient temperature. The reaction mixture was heated to 60° C. for 4 h. Completion of the reaction was confirmed by UPLC. The product was isolated and purified via standard methods to afford (1S, 4S)-4-(2-((4-methyltetrahydro-2H-pyran-4-yl)amino)-8-((4-(trifluoromethyl)phenyl)amino)-9H-purin-9-yl)cyclohexane-1-carboxamide (0.3 g, 42%) as an off-white solid. MS (ESI) m/z 517 [M+1]+.

(1S, 4S)-4-(2-((4-Methyltetrahydro-2H-pyran-4-yl)amino)-8-((4-(trifluoromethyl)phenyl) amino)-9H-purin-9-yl)cyclohexane-1-carbonitrile. To a stirred solution of (1S, 4S)-4-(2-((4-methyltetrahydro-2H-pyran-4-yl)amino)-8-((4-(trifluoromethyl)phenyl)amino)-9H-purin-9-yl) cyclohexane-1-carboxamide (0.25 g, 1 mmol) in pyridine (5 mL) was added phosphorus oxychloride (0.5 ml) dropwise at 0° C. The reaction mixture was stirred at ambient temperature for 4 h. Completion of the reaction was confirmed by UPLC. The product was isolated and purified via standard methods to afford (1S, 4S)-4-(2-((4-methyltetrahydro-2H-pyran-4-yl)amino)-8-((4-(trifluoromethyl)phenyl)amino)-9H-purin-9-yl)cyclohexane-1-carbonitrile (0.2 g, 74%) as off-white solid. MS (ESI) m/z 499 [M+1]+.

9-((1S, 4S)-4-(Aminomethyl)cyclohexyl)-N2-(4-methyltetrahydro-2H-pyran-4-yl)-N8-(4-(trifluoromethyl)phenyl)-9H-purine-2,8-diamine. To a stirred solution of (1S, 4S)-4-(2-((4-methyltetrahydro-2H-pyran-4-yl)amino)-8-((4-(trifluoromethyl)phenyl)amino)-9H-purin-9-yl) cyclohexane-1-carboxamide (0.3 g, 1 mmol) in diethylether (3 mL) was added lithium aluminum hydride in THF (1.6 M; 2 mL) at 0° C. The reaction mixture was stirred at ambient temperature for 4 h. Completion of the reaction was confirmed by UPLC. The product was purified via standard methods to afford 9-((1S, 4S)-4-(aminomethyl)cyclohexyl)-N2-(4-methyltetrahydro-2H-pyran-4-yl)-N8-(4-(trifluoromethyl)phenyl)-9H-purine-2,8-diamine (0.04 g, 15%). MS (ESI) m/z 504 [M+1]+. $^1$H NMR (400 MHz, CD$_3$OD): δ 8.25 (s, 1H), 7.75 (d, J=8.4 Hz, 2H), 7.63 (d, J=8.4 Hz, 2H), 4.38-4.44 (m, 1H), 3.75-3.85 (m, 4H), 3.22 (d, J=7.6 Hz, 2H), 2.68-2.71 (m, 2H), 2.45-2.48 (m, 2H), 2.11-2.14 (m, 1H), 1.98-2.00 (brs, 2H), 1.90-1.95 (m, 4H), 1.76-1.84 (m, 4H), 1.61 (s, 3H).

Example 43: 9-(4-(Aminomethyl)phenyl)-N8-(3-chlorophenyl)-N2-(4-methyltetrahydro-2H-pyran-4-yl)-9H-purine-2,8-diamine

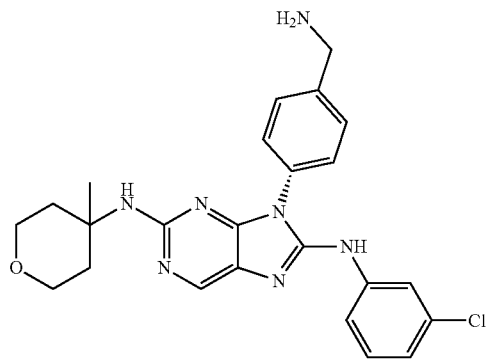

tert-Butyl(4-((2-chloro-5-nitropyrimidin-4-yl)amino)benzyl)carbamate. To a stirred solution of 2, 4-dichloro-5-nitropyrimidine (0.5 g, 2 mmol) and DIPEA (1.34 mL, 8 mmol) in dioxane (20 mL) was added tert-butyl(4-aminobenzyl)carbamate (0.63 g, 3 mmol) portionwise at 0° C. under nitrogen. The reaction mixture was slowly warmed to ambient temperature and stirred for 1 h. Completion of the reaction was confirmed by UPLC. The product was isolated to afford tert-butyl (4-((2-chloro-5-nitropyrimidin-4-yl)amino)benzyl)carbamate (0.9 g, 91%) as yellow solid. MS (ESI) m/z 380 [M+2]+.

tert-Butyl(4-((2-((4-methyltetrahydro-2H-pyran-4-yl)amino)-5-nitropyrimidin-4-yl)amino)benzyl)carbamate. To a stirred solution of tert-butyl (4-((2-chloro-5-nitropyrimidin-4-yl)amino)benzyl)carbamate (0.9 g, 2 mmol) in DMF (10 mL) was added 4-methyltetrahydro-2H-pyran-4-amine (0.3 g, 2 mmol) and sodium bicarbonate (0.9 g, 11 mmol) at ambient temperature. The reaction mixture was stirred for 5 h. Completion of the reaction was confirmed by UPLC. The product was isolated and triturated with petroleum ether to afford tert-butyl (4-((2-((4-methyltetrahydro-2H-pyran-4-yl)amino)-5-nitropyrimidin-4-yl)amino)benzyl)carbamate (0.95 g, 90%) as yellow solid. MS (ESI) m/z 459 [M+1]+.

tert-Butyl (4-((5-amino-2-((4-methyltetrahydro-2H-pyran-4-yl)amino)pyrimidin-4-yl)amino)benzyl)carbamate. To a stirred solution of tert-butyl (4-((2-((4-methyltetrahydro-2H-pyran-4-yl)amino)-5-nitropyrimidin-4-yl)amino)benzyl)carbamate (0.95 g, 2 mmol) in ethanol:water (50 mL, 3:1) was added iron powder (1.2 g, 20 mmol) and ammonium chloride (0.1 g, 2 mmol) at ambient temperature. The reaction mixture was heated to 85° C. for 6 h. Completion of the reaction was confirmed by UPLC. The resulting reaction mixture was filtered through a bed of celite, washed with ethyl acetate and concentrated to afford tert-butyl(4-((5-amino-2-((4-methyltetrahydro-2H-pyran-4-yl)amino)pyrimidin-4-yl)amino)benzyl)carbamate (0.92 g) as a brown solid. MS (ESI) m/z 430 [M+2]+.

tert-Butyl (4-(8-((3-chlorophenyl)amino)-2-((4-methyltetrahydro-2H-pyran-4-yl)amino)-9H-purin-9-yl)benzyl)carbamate. To a stirred solution of tert-butyl(4-((5-amino-2-((4-methyltetrahydro-2H-pyran-4-yl)amino)pyrimidin-4-yl)amino)benzyl)carbamate (0.95 g, 2 mmol) and 1-chloro-3-isothiocyanatobenzene (0.41 g, 2 mmol) in THF was added EDCI (0.85 g, 4 mmol) at ambient temperature. The reaction mixture was heated to 60° C. for 4 h. Completion of the reaction was confirmed by UPLC. The product was isolated and purified via standard methods to afford tert-butyl (4-(8-((3-chlorophenyl) amino)-2-((4-methyltetrahydro-2H-pyran-4-yl)amino)-9H-purin-9-yl)benzyl)carbamate (0.5 g, 42%) as an off-white solid. MS (ESI) m/z 564, 566 [M, M+2]+.

9-(4-(Aminomethyl)phenyl)-N8-(3-chlorophenyl)-N2-(4-methyltetrahydro-2H-pyran-4-yl)-9H-purine-2,8-diamine. To a stirred solution of tert-butyl (4-(8-((3-chlorophenyl)amino)-2-((4-methyltetrahydro-2H-pyran-4-yl)amino)-9H-purin-9yl)benzyl)carbamate (0.180 g, 0.32 mmol) in DCM (20 mL) was added HCl in dioxane (5 mL) at 0° C. The reaction mixture was stirred at ambient temperature for 4 h. Completion of the reaction was confirmed by UPLC. The product was purified via standard methods to afford 9-(4-(aminomethyl)phenyl)-N8-(3-chlorophenyl)-N2-(4-methyltetrahydro-2H-pyran-4-yl)-9H-purine-2,8-diamine (120 mg, 81%). MS (ESI) m/z 464.2, 465.2 [M, M+1]+. 1H NMR (400 MHz, CD3OD): δ8.31 (s, 1H), 7.75 (s, 1H), 7.70 (d, J=8.4 Hz, 2H), 7.62 (d, J=8.4 Hz, 2H), 7.44 (d, J=7.6 Hz, 1H), 7.26-7.30 (m, 1H), 7.03 (d, J=8.0 Hz, 1H), 4.15 (s, 2H), 3.64-3.72 (m, 4H), 1.93-2.23 (m, 2H), 1.58-1.65 (m, 2H), 1.40 (s, 3H).

Example 44: N8-(3-Chlorophenyl)-9-((1S, 4S)-4-((methylamino) methyl) cyclohexyl)-N2-(4-methyltetrahydro-2H-pyran-4-yl)-9H-purine-2,8-diamine

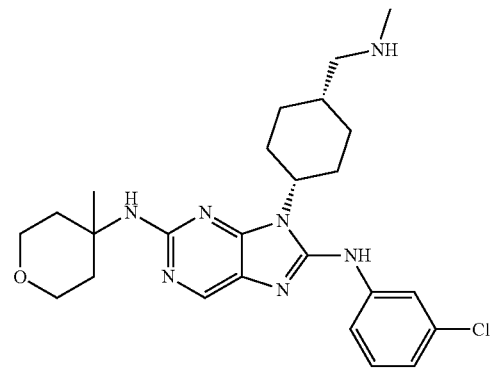 [SMILES: CNC[C@H]1CC[C@@H](n2c(Nc3cccc(Cl)c3)nc3cnc(NC4(C)CCOCC4)nc32)CC1]

tert-Butyl (((1S, 4S)-4-(8-((3-chlorophenyl)amino)-2-((4-methyltetrahydro-2H-pyran-4-yl)amino)-9H-purin-9-yl)cyclohexyl)methyl)carbamate. To a solution of 9-((1S, 4S)-4-(aminomethyl)cyclohexyl)-N8-(3-chlorophenyl)-N2-(4-methyltetrahydro-2H-pyran-4-yl)-9H-purine-2,8-diamine (0.5 g, 1.06 mmol) in dry chloroform (10 mL) was added di-tert-butyldicarbonate (0.25 g, 1.17 mmol) at 0° C. and the reaction was stirred for 3 h. Completion of the reaction was confirmed by UPLC. The product was isolated to afford tert butyl (((1S, 4S)-4-(8-((3-chlorophenyl)amino)-2-((4-methyltetrahydro-2H-pyran-4-yl)amino)-9H-purin-9-yl)cyclohexyl)methyl)carbamate (0.5 g, 83%) as white solid. MS (ESI) m/z 570, 571 [M, M+1]+.

N8-(3-Chlorophenyl)-9-((1S, 4S)-4-((methylamino) methyl)cyclohexyl)-N2-(4-methyltetrahydro-2H-pyran-4-yl)-9H-purine-2, 8-diamine. To a stirred solution of tertbutyl (((1S, 4S)-4-(8-((3-chlorophenyl)amino)-2-((4-methyltetrahydro-2H-pyran-4-yl)amino)-9H-purin-9-yl)cyclohexyl)methyl)carbamate (0.5 g, 0.88 mmol) in THF (10 mL) was added dropwise lithium aluminum hydride in THF (1.6 M, 5 mL) at 0° C. and heated at 50° C. for 8 h. Completion of the reaction was confirmed by UPLC. The product was purified via standard methods to afford N8-(3-chlorophenyl)-9-((1S, 4S)-4-((methylamino)methyl)cyclohexyl)-N2-(4-methyltetrahydro-2H-pyran-4-yl)-9H-purine-2, 8-diamine (24 mg, 6%). MS (ESI) m/z 484, 485 [M, M+1]+. 1H NMR (400 MHz, CD3OD): δ 8.20 (s, 1H), 7.92 (s, 1H), 7.59 (d, J=8.4 Hz, 1H), 7.36-7.40 (m, 1H), 7.17 (d, J=8.4 Hz, 1H), 4.48-4.54 (m, 1H), 3.80-3.83 (m, 4H), 3.28 (d, J=6.8 Hz, 2H), 2.82 (s, 3H), 2.47-2.59 (m, 4H), 2.26 (brs, 1H), 1.93-2.00 (m, 6H), 1.77-1.84 (m, 2H), 1.67 (s, 3H).

Example 45: 9-((1S, 4S)-4-(Aminomethyl)cyclohexyl)-N2-(tert-butyl)-N8-(4-(trifluoromethyl)phenyl)-9H-purine-2,8-diamine

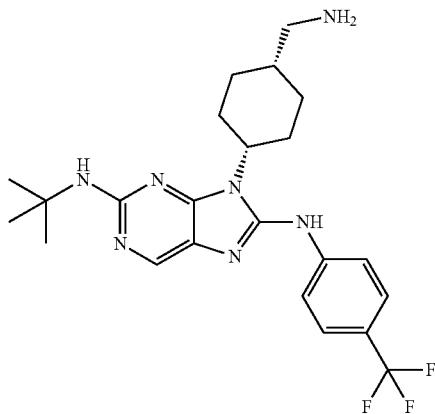 [SMILES: CC(C)(C)Nc1ncc2nc(Nc3ccc(C(F)(F)F)cc3)n([C@H]3CC[C@@H](CN)CC3)c2n1]

(1S, 4S)-4-((2-(tert-Butylamino)-5-nitropyrimidin-4-yl)amino)cyclohexane-1-carboxamide. To a stirred solution of (1S, 4S)-4-((2-chloro-5-nitropyrimidin-4-yl)amino)cyclohexane-1-carboxamide (1 g, 3.3 mmol) in DMF (10 mL) was added tert-butylamine (0.3 g, 4 mmol) and sodium bicarbonate (0.84 g, 10 mmol) at ambient temperature. The reaction mixture was heated to 60° C. for 4 h. Completion of the reaction was confirmed by UPLC. The product was isolated and triturated with petroleum ether to afford (1S, 4S)-4-((2-(tert-butylamino)-5-nitropyrimidin-4-yl)amino)cyclohexane-1-carboxamide (0.7 g, 63%) as a yellow solid. MS (ESI) m/z 337 [M+1]$^+$.

(1S, 4S)-4-((5-Amino-2-(tert-butylamino)pyrimidin-4-yl)amino)cyclohexane-1-carboxamide. To a stirred solution (1S, 4S)-4-((2-(tert-butylamino)-5-nitropyrimidin-4-yl)amino)cyclohexane-1-carboxamide (0.7 g, 2 mmol) in ethanol (24 mL) was added palladium on carbon (0.1 g, W/W) under inert atmosphere at ambient temperature. The reaction mixture was stirred under atmospheric hydrogen at ambient temperature. Completion of the reaction was confirmed by UPLC. The product was isolated via standard methods to afford (1S, 4S)-4-((5-amino-2-(tert-butylamino)pyrimidin-4-yl)amino)cyclohexane-1-carboxamide (0.6 g, 90%) as a brown solid. MS (ESI) m/z 307 [M+1]$^+$.

(1S, 4S)-4-(2-(tert-Butylamino)-8-((4-(trifluoromethyl)phenyl)amino)-7,8-dihydro-9H-purin-9-yl)cyclohexane-1-carboxamide. To a stirred solution of (1S, 4S)-4-((5-amino-2-(tert-butylamino)pyrimidin-4-yl)amino)cyclohexane-1-carboxamide (0.6 g, 2 mmol) and 1-isothiocyanato-4-(trifluoromethyl)benzene (0.5 g, 2 mmol) in THF (15 mL) was added EDCI (0.75 g, 4 mmol) at ambient temperature. The reaction mixture was heated to 60° C. for 4 h. Completion of the reaction was confirmed by UPLC. The product was isolated and purified via standard methods to afford (1S, 4S)-4-(2-(tert-butylamino)-8-((4-(trifluoromethyl)phenyl)amino)-7,8-dihydro-9H-purin-9-yl)cyclohexane-1-carboxamide (0.45 g, 48%) as a yellow solid. MS (ESI) m/z 476 [M+1]$^+$.

(1S, 4S)-4-(2-(tert-Butylamino)-8-((4-(trifluoromethyl)phenyl)amino)-9H-purin-9-yl)cyclohexane-1-carbonitrile. To a stirred solution of (1S, 4S)-4-(2-(tert-butylamino)-8-((4-(trifluoromethyl)phenyl)amino)-9H-purin-9-yl)cyclohexane-1-carboxamide (0.5 g, 1 mmol) in pyridine (5 mL) was added imidazole (0.2 g, 3 mmol) at 0° C. followed by dropwise addition of phosphorous oxychloride (0.5 mL). The reaction mixture was stirred at ambient temperature for 4 h. Completion of the reaction was confirmed by UPLC. The product was isolated and purified via standard methods to afford (1S, 4S)-4-(2-(tert-butylamino)-8-((4-(trifluoromethyl)phenyl)amino)-9H-purin-9-yl)cyclohexane-1-carbonitrile (0.25 g, 52%) as an off-white solid. MS (ESI) m/z 458 [M+1]$^+$.

9-((1S, 4S)-4-(Aminomethyl)cyclohexyl)-N2-(tert-butyl)-N8-(4-(trifluoromethyl)phenyl)-9H-purine-2, 8-diamine. To a stirred solution of (1S, 4S)-4-(2-(tert-butylamino)-8-((4-(trifluoromethyl)phenyl)amino)-9H-purin-9-yl)cyclohexane-1-carbonitrile (0.25 g, 1 mmol) in THF (10 mL) was added lithium aluminium hydride (1.6 M in THF, 5 mL) dropwise at 0° C. The reaction mixture stirred at ambient temperature for 3 h. Completion of the reaction was confirmed by UPLC. The product was purified via standard methods to afford 9-((1S, 4 S)-4-(aminomethyl)cyclohexyl)-N2-(tert-butyl)-N8-(4-(trifluoromethyl)phenyl)-9H-purine-2,8-diamine (0.045 g, 18%). MS (ESI) m/z 462 [M+1]$^+$. $^1$H NMR (400 MHz, CD$_3$OD): δ 8.20 (s, 1H), 7.73 (d, J=8.4 Hz, 2H), 7.61 (d, J=8.4 Hz, 2H), 4.34-4.40 (m, 1H), 3.04-3.06 (m, 2H), 2.71-2.80 (m, 2H), 1.91-2.01 (m, 4H), 1.75-1.85 (m, 3H), 1.55 (s, 9H).

Example 46: 9-((1S, 4S)-4-((Dimethylamino)methyl)cyclohexyl)-N2-(4-methyltetrahydro-2H-pyran-4-yl)-N8-(3-(trifluoromethyl)phenyl)-9H-purine-2,8-diamine

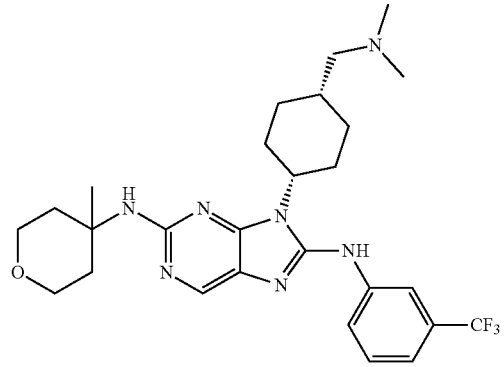 [SMILES: CN(C)C[C@H]1CC[C@@H](n2c(Nc3cccc(C(F)(F)F)c3)nc3cnc(NC4(C)CCOCC4)nc32)CC1]

tert-Butyl ((1S, 4S)-4-(dimethylcarbamoyl)cyclohexyl)carbamate. To a solution of (1S, 4S)-4-((tert-butoxycarbonyl)amino)cyclohexane-1-carboxylic acid (2 g, 8.2 mmol) in dry DCM (30 mL) was added 1-ethyl-3-(3-dimethylaminopropyl)carbodiimide (1.6 g, 16 mmol), HOBt (1.1 g, 16 mmol), DIPEA (2.12 g, 33 mmol) and dimethyl amine (1.35 g, 33 mmol, 2.4M solution in THF) at 0° C. The reaction mixture was stirred at ambient temperature for 16 h. Completion of the reaction was confirmed by TLC. The product was isolated via standard purification methods to afford tert-butyl ((1S, 4S)-4-(dimethylcarbamoyl)cyclohexyl)carbamate (2 g, 90%) as gummy solid. GCMS m/z 270 [M]$^+$.

(1S, 4S)-4-Amino-N, N-dimethylcyclohexane-1-carboxamide. To a stirred solution of tert-butyl ((1S, 4S)-4-(dimethylcarbamoyl)cyclohexyl)carbamate (2 g, 8 mmol) in ethanol (10 mL) was added dropwise to HCl in 1, 4-dioxane (4.5 M, 5 mL) at 0° C. The reaction mixture was stirred at ambient temperature for 4 h. Completion of the reaction was confirmed by TLC. The product was isolated and purified via standard purification methods to afford (1S, 4S)-4-amino-N,N-dimethylcyclohexane-1-carboxamide (1.2 g, 80%) as white solid. GCMS m/z 170 [M]⁺.

(1S, 4S)-4-((2-Chloro-5-nitropyrimidin-4-yl)amino)-N,N-dimethylcyclohexane-1-carboxamide. To a stirred solution of (1S, 4S)-4-amino-N, N-dimethylcyclohexane-1-carboxamide (1.9 g, 10 mmol) in IPA (30 mL) was added 2,4-dichloro-5-nitropyrimidine (1.9 g, 10 mmol) and DIPEA (3.7 g, 30 mmol) at ambient temperature. The reaction mixture temperature was raised to 50° C. and maintained for 2 h. Completion of the reaction was confirmed by UPLC. The product was isolated via standard purification methods to afford (1S, 4S)-4-((2-chloro-5-nitropyrimidin-4-yl)amino)-N, N-dimethylcyclohexane-1-carboxamide (1 g, 30%). MS (ESI) m/z 327, 328 [M, M+1]⁺.

(1S, 4S)—N,N-Dimethyl-4-((2-((4-Methyltetrahydro-2H-pyran-4-yl)amino)-5-nitropyrimidin-4-yl)amino)cyclohexane-1-carboxamide. To a stirred solution of (1S, 4S)-4-((2-chloro-5-nitropyrimidin-4-yl)amino)-N,N-dimethylcyclohexane-1-carboxamide (0.28 g, 2 mmol) in DMF (10 mL) was added 4-methyl tetrahydro-2H-pyran-4-amine (0.5 g, 2 mmol), sodium carbonate (0.5 g, 5 mmol). The reaction was stirred at ambient temperature for 16 h. Completion of the reaction was confirmed by UPLC. The product was isolated via standard purification method to afford (1S, 4S)—N,N-dimethyl-4-((2-((4-methyltetrahydro-2H-pyran-4-yl)amino)-5-nitropyrimidin-4-yl)amino)cyclohexane-1-carboxamide (0.23 g, 37%) as a pale brown solid MS (ESI) m/z 407 [M+1]⁺.

(1S, 4S)-4-((5-Amino-2-((4-methyltetrahydro-2H-pyran-4-yl)amino)pyrimidin-4-yl) amino)-N,N-dimethylcyclohexane-1-carboxamide. To a stirred solution of (1S, 4S)—N,N-dimethyl-4-((2-((4-methyltetrahydro-2H-pyran-4-yl)amino)-5-nitropyrimidin-4-yl)amino) cyclohexane-1-carboxamide (0.23 g, 1 mmol) in ethanol (10 mL) was added palladium on carbon (30 mg, 10% W/M) under argon atmosphere. The reaction mixture was stirred at ambient temperature under atmospheric hydrogen. Completion of the reaction was confirmed by UPLC. The product was isolated by standard purification methods to afford (1S, 4S)-4-((5-amino-2-((4-methyltetrahydro-2H-pyran-4-yl)amino)pyrimidin-4-yl)amino)-N,N-dimethylcyclohexane-1-carboxamide (0.2 g, 90%) as violet solid MS (ESI) m/z 377 [M+1]⁺.

(1S, 4S)—N, N-Dimethyl-4-(2-((4-methyltetrahydro-2H-pyran-4-yl)amino)-8-((3-(trifluoromethyl)phenyl)amino)-9H-purin-9-yl)cyclohexane-1-carboxamide. A solution of (1S, 4S)-4-((5-amino-2-(4-methyltetrahydro-2H-pyran-4-yl)pyrimidin-4-yl)amino)-N,N-dimethylcyclohexane-1-carboxamide (0.5 g, 1.3 mmol), 1-ethyl-3-(3-dimethylaminopropyl)carbodiimide (0.5 g, 2.6 mmol) and 1-isothiocyanato-3-(trifluoromethyl)benzene (0.3 g, 1.6 mmol) in THF (5 mL) were mixed at ambient temperature. The reaction was heated to 50° C. for 4 h. Completion of the reaction was confirmed by UPLC. The product was isolated by standard purification methods to afford (1S, 4S)—N,N-dimethyl-4-(2-((4-methyltetrahydro-2H-pyran-4-yl)amino)-8-((3-(trifluoromethyl)phenyl)amino)-9H-purin-9-yl)cyclohexane-1-carboxamide (0.35 g, 48%) as an off-white solid MS (ESI) m/z 545, 546 [M, M+1]⁺.

9-((1S, 4S)-4-((Dimethylamino)methyl)cyclohexyl)-N2-(4-methyltetrahydro-2H-pyran-4-yl)-N8-(3-(trifluoromethyl)phenyl)-9H-purine-2,8-diamine. To a stirred solution (1S, 4S)—N,N-dimethyl-4-(2-((4-methyltetrahydro-2H-pyran-4-yl)amino)-8-((3-(trifluoromethyl)phenyl)amino)-9H-purin-9-yl)cyclohexane-1-carboxamide (0.35 g, 0.64 mmol) in THF (3 mL) was added lithium aluminium hydride in THF (1.6 M; 4 mL) at 0° C. The reaction was stirred at ambient temperature for 1 h. Completion of the reaction was confirmed by TLC. The reaction mixture was quenched with 10% NaOH solution and water (10 mL, 1:1) and extracted with ethyl acetate. The product was isolated by standard methods to afford 9-((1S, 4S)-4-((dimethylamino)methyl)cyclohexyl)-N2-(4-methyltetrahydro-2H-pyran-4-yl)-N8-(3-(trifluoromethyl)phenyl)-9H-purine-2,8-diamine (0.060 g, 33%). MS (ESI) m/z 532.4, 533.4 [M, M+1]⁺. ¹H NMR (400 MHz, DMSO-d₆): δ 9.22 (s, 1H), 8.31 (s, 1H, NH proton), 8.15 (s, 1H), 8.10 (d, J=8.3 Hz, 1H), 7.54-7.58 (m, 1H), 7.30 (d, J=7.0 Hz, 1H), 6.35 (s, 1H), 4.32-4.38 (m, 1H), 3.57-3.70 (m, 4H), 2.34-2.37 (m, 2H), 2.26-2.30 (m, 2H), 2.19 (s, 6H), 2.00-2.15 (m, 1H), 1.85 (brs, 1H), 1.83-1.86 (m, 2H), 1.62-1.70 (m, 7H), 1.50 (s, 3H).

Example 47: 9-((1S, 4S)-4-((Methylamino)methyl)cyclohexyl)-N2-(4-methyltetrahydro-2H-pyran-4-yl)-N8-(3-(trifluoromethyl)phenyl)-9H-purine-2,8-diamine

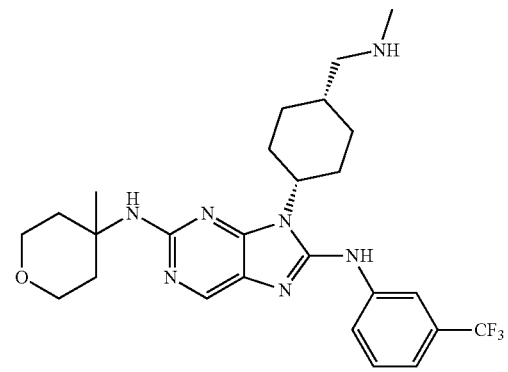 [SMILES: CNC[C@H]1CC[C@@H](n2c(Nc3cccc(C(F)(F)F)c3)nc3cnc(NC4(C)CCOCC4)nc32)CC1]

tert-Butyl(((1S, 4S)-4-(2-((4-methyltetrahydro-2H-pyran-4-yl)amino)-8-((3-(trifluoromethylphenyl)amino)-9H-purin-9-yl)cyclohexyl)methyl)carbamate. To a solution of 9-((1S, 4 S)-4-(aminomethyl)cyclohexyl)-N2-(4-methyltetrahydro-2H-pyran-4-yl)-N8-(3-(trifluoromethyl)phenyl)-9H-purine-2,8-diamine (0.5 g, 0.99 mmol) in dry chloroform (10 mL) was added di-tert-butyldicarbonate (0.22 g, 0.99 mmol) at 0° C. and the reaction was stirred for 3 h. Completion of the reaction was confirmed by TLC. The product was isolated to afford tert-butyl(((1S, 4S)-4-(2-((4-methyltetrahydro-2H-pyran-4-yl)amino)-8-((3-(trifluoromethyl)phenyl)amino)-9H-purin-9-yl)cyclohexyl)methyl)carbamate (0.4 g, 67%) as a white solid. MS (ESI) m/z 604.2, 605.2 [M, M+1]⁺.

9-((1S, 4S)-4-((Methylamino)methyl)cyclohexyl)-N2-(4-methyltetrahydro-2H-pyran-4-yl)-N8-(3-(trifluoromethyl)phenyl)-9H-purine-2,8-diamine. To a stirred solution of tert-butyl (((1S, 4S)-4-(2-((4-methyltetrahydro-2H-pyran-4-yl)amino)-8-((3-(trifluoromethyl)phenyl)amino)-9H-purin-9-yl) cyclohexyl)methyl)carbamate (0.4 g, 0.66 mmol) in diethyl ether (10 mL) was added dropwise LiAlH4 in THF (2 M; 4 mL) at 0° C. The reaction mixture was stirred at ambient temperature for 12 h. Completion of the reaction was confirmed by TLC. The product was purified via standard methods to afford 9-((1S, 4S)-4-((methylamino)methyl)cyclohexyl)-N2-(4-methyltetrahydro-2H-pyran-4-yl)-N8-(3-(trifluoromethyl)phenyl)-9H-purine-2,8-diamine (0.025 g; 7%). MS (ESI) m/z 518.4, [M+1]⁺. ¹HNMR (400 MHz, CD₃OD): δ 8.23 (s, 1H), 7.95 (s, 1H), 7.85 (d, J=8.5

Hz, 1H), 7.51-7.55 (m, 1H), 7.3 (d, J=7.3 Hz, 1H), 4.36 (brs, 1H), 3.77-3.78 (m, 4H), 2.95-2.96 (m, 1H), 2.68-2.71 (m, 2H), 2.56 (brs, 2H), 2.34-2.38 (m, 2H), 1.96-2.03 (m, 4H), 1.76-1.83 (m, 7H), 1.63 (s, 3H).

Example 48: 9-((1S, 4S)-4-(Aminomethyl)cyclohexyl)-N2-(tert-pentyl)-N8-(4(trifluoromethyl)phenyl)-9H-purine-2,8-diamine

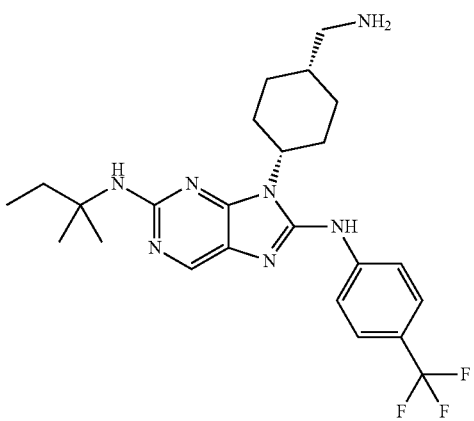 [SMILES: CCC(C)(C)Nc1ncc2nc(Nc3ccc(C(F)(F)F)cc3)n([C@H]3CC[C@@H](CN)CC3)c2n1]

(1S, 4S)-4-((5-Nitro-2-(tert-pentylamino)pyrimidin-4-yl)amino)cyclohexane-1-carboxamide. To a stirred solution of (1S, 4S)-4-((2-chloro-5-nitropyrimidin-4-yl)amino)cyclohexane-1-carboxamide (0.6 g, 2 mmol) in DMF (10 mL) was added sodium bicarbonate (0.17 g, 2 mmol) portionwise followed by 2-methylbutane-2-amine (0.22 g, 2 mmol) at ambient temperature. The reaction mixture was heated to 60° C. for 16 h. Completion of the reaction was confirmed by UPLC. The product was isolated to afford (1S, 4S)-4-((5-nitro-2-(tert-pentylamino)pyrimidin-4-yl) amino) cyclohexane-1-carboxamide (0.6 g, 83%) as a yellow solid. MS (ESI) m/z 351 [M+1]$^+$.

(1S, 4S)-4-8-((3-Chlorophenyl)amino-2-(tert-pentylamino)-9H-purin-9-yl)cyclohexane-1-carboxamide. To a stirred solution of (1S, 4S)-4-((5-nitro-2-(tert-pentylamino) pyrimidin-4-yl) amino)cyclohexane-1-carboxamide (0.5 g, 2 mmol) in ethanol (10 mL) was added portionwise palladium on charcoal (0.06 g, 10% W/M) under an argon atmosphere. The reaction was stirred at ambient temperature under atmospheric hydrogen. Completion of the reaction was confirmed by UPLC. The mixture was filtered through a bed of celite, washed with ethyl acetate and concentrated to afford (1S, 4S)-4-8-((3-chlorophenyl)amino-2-(tert-pentylamino)-9H-purin-9-yl) cyclohexane-1-carboxamide (0.4 g, 90%) as a yellow solid. MS (ESI) m/z 321 [M+1]$^+$.

(1S, 4S)-4-(2-(tert-Pentylamino)-8-((4-(trifluoromethyl)phenyl)amino)-9H-purin-9-yl)cyclohexane-1-carboxamide. To a stirred solution of (1S, 4S)-4-((5-amino-2-(tert-pentylamino) pyrimidin-4-yl)amino)cyclohexane-1-carboxamide (0.5 g, 2 mmol) in THF (10 mL) was added 1-ethyl-3-(3-dimethylaminopropyl)carbodiimide (0.6 g, 3 mmol) and 1-isothiocyanato-4-(trifluoromethyl)benzene (0.3 g, 2 mmol) at ambient temperature. The reaction mixture was heated to 60° C. for 4 h. Completion of the reaction was confirmed by UPLC. The product was isolated and purified via standard methods to afford (1S, 4S)-4-(2-(tert-pentylamino)-8-((4-(trifluoromethyl)phenyl)amino)-9H-purin-9-yl) cyclohexane-1-carboxamide (0.45 g, 58%) as colorless solid. MS (ESI) m/z 490 [M+1]$^+$.

(1S, 4S)-4-(2-(tert-Pentylamino)-8-((4-(trifluoromethyl)phenyl)amino)-9H-purin-9-yl)cyclohexane-1-carbonitrile. To a stirred solution of (1S, 4S)-4-(2-(tert-pentylamino)-8-((4-(trifluoromethyl)phenyl)amino)-9H-purin-9-yl) cyclohexane-1-carboxamide (0.25 g, 1 mmol) in pyridine (5 mL) was added portionwise phosphorus oxychloride (0.5 ml) at 0° C. temperature. The reaction mixture was stirred for 4 h. Completion of the reaction was confirmed by UPLC. The product was isolated and purified via standard methods to afford (1S, 4S)-4-(2-(tert-pentylamino)-8-((4-(trifluoromethyl)phenyl)amino)-9H-purin-9-yl)cyclohexane-1-carbonitrile (0.2 g, 74%) as colorless solid. MS (ESI) m/z 472 [M+1]$^+$.

9-((1S, 4S)-4-(Aminomethyl)cyclohexyl)-N2-(tert-pentyl)-N8-(4-(trifluoromethyl)phenyl)-9H-purine-2,8-diamine. To a stirred solution of (1S, 4S)-4-(2-(tert-pentylamino)-8-((4-(trifluoromethyl)phenyl)amino)-9H-purin-9-yl)cyclohexane-1-carbonitrile (0.2 g, 1 mmol) in diethyl ether (3 mL) was added lithium aluminum hydride in THF (1.6 M; 2 mL) at 0° C. The reaction mixture was stirred at ambient temperature for 4 h. Completion of the reaction was confirmed by UPLC. The product was purified via standard methods to afford 9-((1S, 4S)-4-(aminomethy)cyclohexyl)-N2-(tert-pentyl)-N8-(4-(trifluoromethyl)phenyl)-9H-purine-2,8-diamine (0.03 g. 17%). MS (ESI) m/z 476 [M+1]$^+$. $^1$H NMR (400 MHz, CD$_3$OD): δ 8.2 (s, 1H), 7.74 (d, J=8.4 Hz, 2H), 7.62 (d, J=8.4 Hz, 2H), 4.33-4.40 (m, 1H), 3.01 (d, J=7.2 Hz, 2H), 2.69-2.78 (m, 2H), 1.98-2.03 (m, 4H), 1.74-1.89 (m, 5H), 1.50 (s, 6H), 0.93 (t, J=7.2 Hz, 3H).

Example 49: 4-(2-((4-Methyltetrahydro-2H-pyran-4-yl)amino)-8-((3-(trifluoromethyl)phenyl)amino)-9H-purin-9-yl)cyclohexane-1-carbonitrile

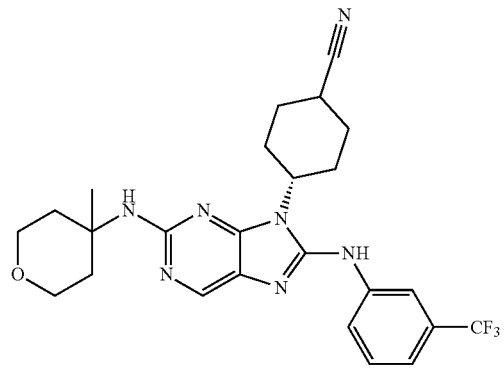

(1S, 4S)-4-((2-((4-Methyltetrahydro-2H-pyran-4-yl)amino)-5-nitropyrimidin-4-yl)amino)cyclohexane-1-carboxamide. To the stirred solution of (1S, 4S)-4-((2-chloro-5-nitropyrimidin-4-yl)amino)cyclohexane-1-carboxamide (3.0 g, 9.24 mmol) in DMF (20 mL) was added 4-methyltetrahydro-2H-pyran-4-amine (2.10 g, 13.86 mmol) and sodium bicarbonate (3.0 g, 28 mmol) at ambient temperature and the mixture was heated to 60° C. for 16 h. Completion of the reaction was confirmed by TLC. The product was isolated to afford (1S, 4S)-4-((2-((4-methyltetrahydro-2H-pyran-4-yl)amino)-5-nitropyrimidin-4-yl)amino)cyclohexane-1-carboxamide (1.5 g, 43%) as off-white solid. MS (ESI) m/z 379, 380 [M, M+1]$^+$.

(1S, 4S)-4-((5-Amino-2-((4-methyltetrahydro-2H-pyran-4-yl)amino)pyrimidin-4-yl)amino)cyclohexane-1-carboxamide. To a stirred solution of (1S, 4S)-4-((2-((4-methyltetrahydro-2H-pyran-4-yl)amino)-5-nitropyrimidin-4-yl)amino)cyclohexane-1-carboxamide (0.6 g, 1.59 mmol) in methanol (10 mL) was added palladium on carbon (0.15 g) under inert atmosphere at ambient temperature. The reaction mixture was stirred under atmospheric hydrogen at ambient temperature. Completion of the reaction was confirmed by UPLC. The resulting reaction mixture was filtered through bed of celite, washed with methanol and concentrated to afford (1S, 4S)-4-((5-amino-2-((1-methylcyclopentyl)amino)pyrimidin-4-yl) amino)cyclohexane-1-carboxamide (0.5 g) as brown gummy solid. MS (ESI) m/z 349 [M]$^+$.

(1S, 4S)-4-(8-((3-Chlorophenyl)amino)-2-((1-methylcyclopentyl)amino)-9H-purin-9-yl) cyclohexane-1-carboxamide. To a stirred solution of (1S, 4S)-4-((5-amino-2-((1-methylcyclopentyl)amino)pyrimidin-4-yl)amino) cyclohexane-1-carboxamide (0.5 g, 1.44 mmol) and 1-isothiocyanato-3-(trifluoromethyl)benzene (0.35 g, 1.72 mmol) in THF was added EDCI (0.82 g, 4.31 mmol) at ambient temperature. The reaction mixture was heated to 60° C. for 4 h. Completion of the reaction was confirmed by UPLC. The product was isolated and purified via standard methods to afford (1S, 4S)-4-(8-((3-chlorophenyl)amino)-2-((1-methylcyclopentyl) amino)-9H-purin-9-yl) cyclohexane-1-carboxamide (0.3 g, 41%) as off-white solid. MS (ESI) m/z 519 [M+1]$^+$.

4-(2-((4-Methyltetrahydro-2H-pyran-4-yl)amino)-8-((3-(trifluoromethyl)phenyl) amino)-9H-purin-9-yl)cyclohexane-1-carbonitrile. To a stirred solution (1S, 4S)-4-(8-((3-chlorophenyl)amino)-2-((1-methylcyclopentyl)amino)-9H-purin-9-yl)cyclohexane-1-carboxamide (0.24 g, 0.51 mmol) in pyridine (2 mL) was added imidazole (0.03 g, 0.46) at 0° C. POCl$_3$ (0.5 mL) was added dropwise at room temperature. The reaction mixture was stirred at ambient temperature for 2 h. Completion of the reaction was confirmed by TLC. The product was purified via standard methods to afford 4-(2-((4-methyltetrahydro-2H-pyran-4-yl) amino)-8-((3-(trifluoromethyl)phenyl)amino)-9H-purin-9-yl)cyclohexane-1-carbonitrile (0.15 g, 78%). MS (ESI) m/z 500, 501 [M, M+1]+. $^1$H NMR (400 MHz, CD$_3$OD): δ 8.22 (s, 1H), 8.08 (s, 1H), 7.92 (d, 1H, J=8 Hz), 7.54-7.58 (m, 1H), 7.38 (d, 1H, J=8 Hz), 4.40-4.46 (m, 1H), 3.74-3.77 (m, 4H), 3.23 (brs, 1H), 2.80-2.89 (m, 2H), 2.21-2.24 (m, 4H), 1.88-2.03 (m, 6H), 1.66 (s, 3H).

In Vitro Parasite Growth Assays

In Vitro Alamar Blue 72 Hrs Drug Sensitivity Assay for T. Congolense. Compounds were tested in vitro for chemotherapeutic efficacy against the IL3000 T. congolense (drug sensitive) strain using an Alamar Blue assay. Test compounds were prepared as 10 mg/mL DMSO stocks for each assay run. Compounds were assayed in at least three separate, independent test runs and an 11-point dilution curve was used to determine the IC$_{50}$ values. Bloodstream form trypanosomes were supported in HMI media containing 20% bovine serum and were incubated with test compounds for 69 hrs at 34° C. in a humidified atmosphere containing 5% CO$_2$. Thereafter, 10 μL of Resazurin dye (12.5 mg in 100 mL of phosphate buffered saline, Sigma-Aldrich, Buchs, Switzerland) were added for an additional 3 hrs. Plates were then read using a fluorescent plate reader (Spectramax, Gemini XS, Bucher Biotec, Basel, Switzerland) using an excitation wavelength of 536 nm and an emission wavelength of 588 nm. Data points were averaged to generate sigmoidal dose-response curves and IC$_{50}$ values were determined using Softmax Pro 5.2 software.

Ex vivo Alamar Blue48 hrs drug sensitivity assay for T. vivax. Compounds were tested ex vivo for chemotherapeutic efficacy against the STIB 719/ILRAD 560 T. vivax (drug sensitive) strain, using an Alamar Blue assay. Test compounds were prepared as 10 mg/mL DMSO stocks for each assay run. Compounds were assayed in at least three separate, independent test runs and an 11-point dilution curve was used to determine the IC$_{50}$ values. Bloodstream form trypanosomes were propagated and harvested from a highly parasitaemic mouse (via cardiac puncture) and were incubated with test compounds for 45 hrs at 37° C. in a humidified atmosphere containing 5% CO$_2$, supported in HMI media containing 20% bovine serum. Thereafter, 10 μL of Resazurin dye (12.5 mg in 100 mL of phosphate buffered saline, Sigma-Aldrich, Buchs, Switzerland) were added for an additional 3 hrs. Plates were then read using a fluorescent plate reader (Spectramax, Gemini XS, Bucher Biotec, Basel, Switzerland) using an excitation wavelength of 536 nm and an emission wavelength of 588 nm. Data points were averaged to generate sigmoidal dose-response curves and IC$_{50}$ values were determined using Softmax Pro 5.2 software.

In vitro Alamar Blue 72 hrs drug sensitivity assay for T. evansi. Compounds were tested in vitro for chemotherapeutic efficacy against the STIB 806 K T. evansi (drug sensitive) strain, using an Alamar Blue assay. Test compounds were prepared as 10 mg/mL DMSO stocks for each assay run. Compounds were assayed in at least three separate, independent test runs and an 11-point dilution curve was used to determine the IC$_{50}$ values. Bloodstream form trypanosomes were incubated with test compounds for 69 hrs at 37° C. in a humidified atmosphere containing 5% CO$_2$, supported in HMI media containing 15% horse serum. Thereafter, 10 μL of Resazurin dye (12.5 mg in 100 mL of phosphate buffered saline, Sigma-Aldrich, Buchs, Switzerland) were added for an additional 3 hrs. Plates were then read using a fluorescent plate reader (Spectramax, Gemini XS, Bucher Biotec, Basel, Switzerland) using an excitation wavelength of 536 nm and an emission wavelength of 588 nm. Data points were averaged to generate sigmoidal dose-response curves and IC$_{50}$ values were determined using Softmax Pro 5.2 software.

In Vitro Alamar Blue 72 Hrs Drug Cytotoxicity Assay. Compounds were tested in vitro for cytotoxicity against the rat myoblast (L6) cell line, using an Alamar Blue assay. Test compounds were prepared as 10 mg/mL DMSO stocks for each assay run. Compounds were assayed in at least three separate, independent test runs and an 11-point dilution curve was used to determine the IC$_{50}$ values. The L6 cells were seeded and allowed to attach to the plates overnight, before the compounds were applied. The L6 cells were incubated with test compounds for 69 hrs at 37° C. in a humidified atmosphere containing 5% CO$_2$, supported in RPMI media containing 10% fetal calf serum. Thereafter, 10 μL of Resazurin dye (12.5 mg in 100 mL of phosphate buffered saline, Sigma-Aldrich, Buchs, Switzerland) were added for an additional 3 hrs. Plates were then read using a fluorescent plate reader (Spectramax, Gemini XS, Bucher Biotec, Basel, Switzerland) using an excitation wavelength of 536 nm and an emission wavelength of 588 nm. Data points were averaged to generate sigmoidal dose-response curves and IC$_{50}$ values were determined using Softmax Pro 5.2 software.

Activity Table

Each of the compounds in Table 1 and Table 2 was tested in at least one of the in vitro parasite growth assays and was found to have activity therein, with all of the Aminopurine Compounds of Formula (I) having an IC$_{50}$ below or at 0.5 µM in the assay, with some compounds having an IC$_{50}$ between 0.5 µM and 0.35 µM (activity level A), some an IC$_{50}$ between 0.15 µM and 0.35 µM (activity level B), and some an IC$_{50}$ below 0.15 µM (activity level C).

TABLE 1

| Cpd #A- | Structure | Name | MH+ | T. congo Act. | T. vivax Act. | T. evansi Act. |
|---|---|---|---|---|---|---|
| 1 | 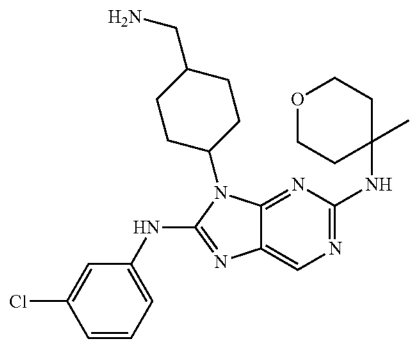 [SMILES: CC1(Nc2ncc3nc(Nc4cccc(Cl)c4)n(C4CCC(CN)CC4)c3n2)CCOCC1] | 9-((1s,4s)-4-(aminomethyl)cyclohexyl)-N8-(3-chlorophenyl)-N2-(4-methyltetrahydro-2H-pyran-4-yl)-9H-purine-2,8-diamine | 471.2 | C | C | C |
| 2 | 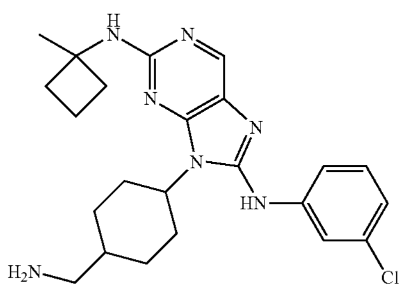 [SMILES: CC1(Nc2ncc3nc(Nc4cccc(Cl)c4)n(C4CCC(CN)CC4)c3n2)CCC1] | 9-((1s,4s)-4-(aminomethyl)cyclohexyl)-N8-(3-chlorophenyl)-N2-(1-methylcyclobutyl)-9H-purine-2,8-diamine | 440.2 | C | C | |
| 3 | 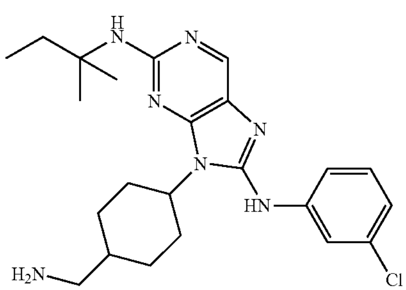 [SMILES: CCC(C)(C)Nc1ncc2nc(Nc3cccc(Cl)c3)n(C3CCC(CN)CC3)c2n1] | 9-((1s,4s)-4-(aminomethyl)cyclohexyl)-N8-(3-chlorophenyl)-N2-tert-pentyl-9H-purine-2,8-diamine | 442.2 | C | C | |
| 4 | 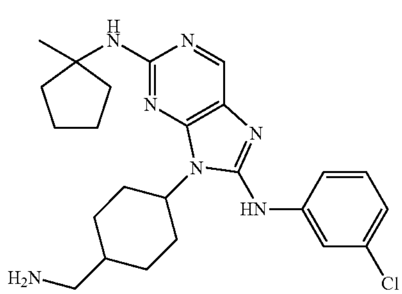 [SMILES: CC1(Nc2ncc3nc(Nc4cccc(Cl)c4)n(C4CCC(CN)CC4)c3n2)CCCC1] | 9-((1s,4s)-4-(aminomethyl)cyclohexyl)-N8-(3-chlorophenyl)-N2-(1-methylcyclopentyl)-9H-purine-2,8-diamine | 454.2 | C | C | C |

TABLE 1-continued

| Cpd #A- | Structure | Name | MH+ | T. congo Act. | T. vivax Act. | T. evansi Act. |
|---|---|---|---|---|---|---|
| 5 | 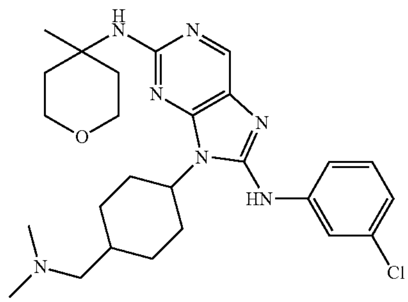 [SMILES: CN(C)CC1CCC(n2c(Nc3cccc(Cl)c3)nc3cnc(NC4(C)CCOCC4)nc32)CC1] | N8-(3-chlorophenyl)-9-((1s,4s)-4-((dimethylamino)methyl)cyclohexyl)-N2-(4-methyltetrahydro-2H-pyran-4-yl)-9H-purine-2,8-diamine | 498.4 | C | C | C |
| 6 | 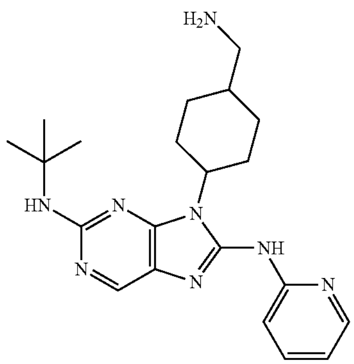 [SMILES: CC(C)(C)Nc1ncc2nc(Nc3ccccn3)n(C3CCC(CN)CC3)c2n1] | 9-((1s,4s)-4-(aminomethyl)cyclohexyl)-N2-tert-butyl-N8-(pyridin-2-yl)-9H-purine-2,8-diamine | 395.2 | A | C | |
| 7 | 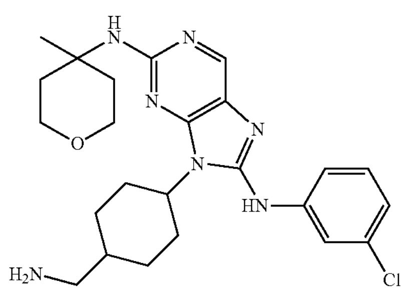 [SMILES: CC1(Nc2ncc3nc(Nc4cccc(Cl)c4)n(C4CCC(CN)CC4)c3n2)CCOCC1] | 9-((1r,4r)-4-(aminomethyl)cyclohexyl)-N8-(3-chlorophenyl)-N2-(4-methyltetrahydro-2H-pyran-4-yl)-9H-purine-2,8-diamine | 470.2 | C | C | C |
| 8 | 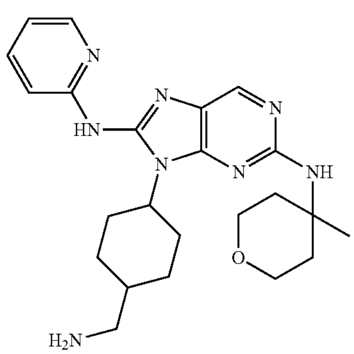 [SMILES: CC1(Nc2ncc3nc(Nc4ccccn4)n(C4CCC(CN)CC4)c3n2)CCOCC1] | 9-((1s,4s)-4-(aminomethyl)cyclohexyl)-N2-(4-methyltetrahydro-2H-pyran-4-yl)-N8-(pyridin-2-yl)-9H-purine-2,8-diamine | 437.2 | A | B | |

TABLE 1-continued

| Cpd #A- | Structure | Name | MH+ | T. congo Act. | T. vivax Act. | T. evansi Act. |
|---|---|---|---|---|---|---|
| 9 | 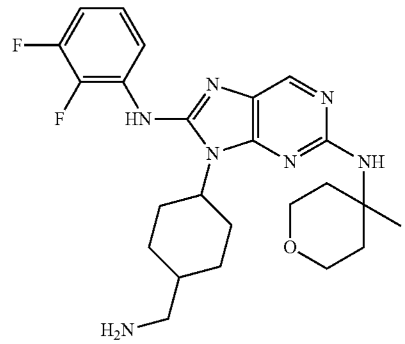 [SMILES: CC1(Nc2ncc3nc(Nc4cccc(F)c4F)n(C4CCC(CN)CC4)c3n2)CCOCC1] | 9-((1s,4s)-4-(aminomethyl)cyclohexyl)-N8-(2,3-difluorophenyl)-N2-(4-methyltetrahydro-2H-pyran-4-yl)-9H-purine-2,8-diamine | 472.2 | C | C | |
| 10 | 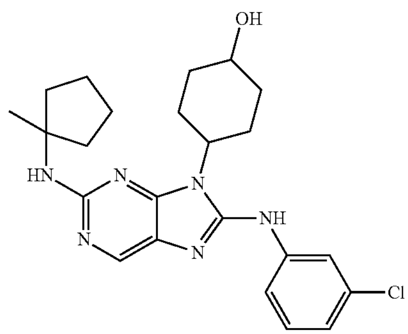 [SMILES: CC1(Nc2ncc3nc(Nc4cccc(Cl)c4)n(C4CCC(O)CC4)c3n2)CCCC1] | (1s,4s)-4-(8-(3-chlorophenylamino)-2-(1-methylcyclopentylamino)-9H-purin-9-yl)cyclohexanol | 441.2 | A | A | |
| 11 | 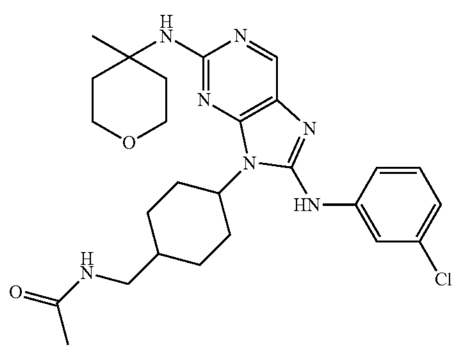 [SMILES: CC(=O)NCC1CCC(n2c(Nc3cccc(Cl)c3)nc3cnc(NC4(C)CCOCC4)nc32)CC1] | N-(((1s,4s)-4-(8-(3-chlorophenylamino)-2-(4-methyltetrahydro-2H-pyran-4-ylamino)-9H-purin-9-yl)cyclohexyl)methyl)acetamide | 512.2 | A | C | A |
| 12 | 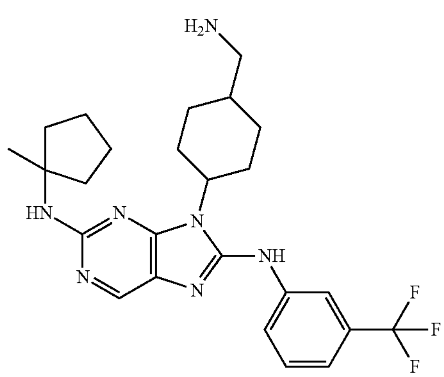 [SMILES: CC1(Nc2ncc3nc(Nc4cccc(C(F)(F)F)c4)n(C4CCC(CN)CC4)c3n2)CCCC1] | 9-((1s,4s)-4-(aminomethyl)cyclohexyl)-N2-(1-methylcyclopentyl)-N8-(3-(trifluoromethyl)phenyl)-9H-purine-2,8-diamine | 488.2 | A | B | |

TABLE 1-continued

| Cpd #A- | Structure | Name | MH+ | T. congo Act. | T. vivax Act. | T. evansi Act. |
|---|---|---|---|---|---|---|
| 13 | 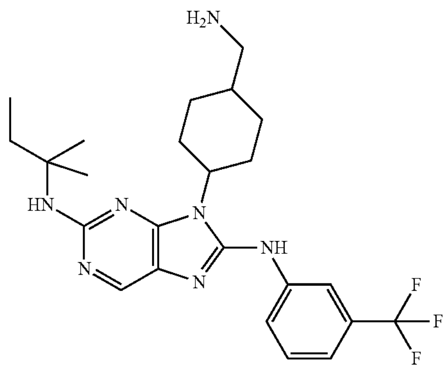 [SMILES: CCC(C)(C)Nc1ncc2nc(Nc3cccc(C(F)(F)F)c3)n(C3CCC(CN)CC3)c2n1] | 9-((1s,4s)-4-(aminomethyl)cyclo-hexyl)-N2-tert-pentyl-N8-(3-(trifluoromethyl)phenyl)-9H-purine-2,8-diamine | 476.4 | C | C | C |
| 14 | 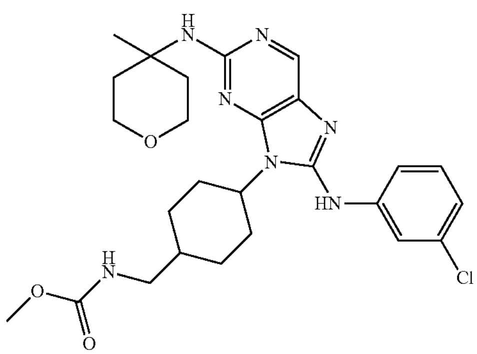 [SMILES: COC(=O)NCC1CCC(n2c(Nc3cccc(Cl)c3)nc3cnc(NC4(C)CCOCC4)nc32)CC1] | methyl ((1s,4s)-4-(8-(3-chlorophenylamino)-2-(4-methyltetrahydro-2H-pyran-4-ylamino)-9H-purin-9-yl)cyclohexyl)methylcarbamate | 528.2 | B | A | |
| 15 | 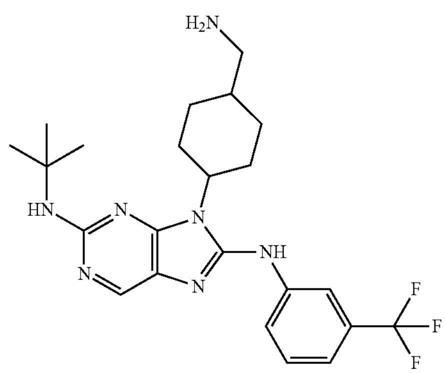 [SMILES: CC(C)(C)Nc1ncc2nc(Nc3cccc(C(F)(F)F)c3)n(C3CCC(CN)CC3)c2n1] | 9-((1s,4s)-4-(aminomethyl)cyclo-hexyl)-N2-tert-butyl-N8-(3-(trifluoromethyl)phenyl)-9H-purine-2,8-diamine | 462.2 | C | C | |
| 16 | 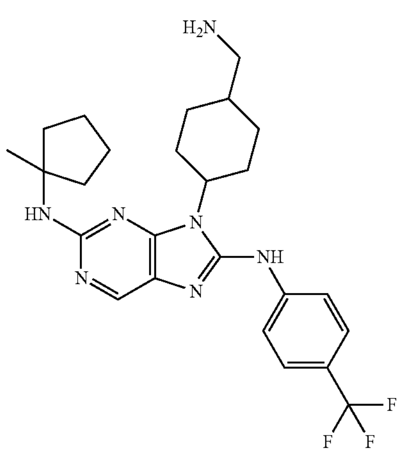 [SMILES: CC1(Nc2ncc3nc(Nc4ccc(C(F)(F)F)cc4)n(C4CCC(CN)CC4)c3n2)CCCC1] | 9-((1s,4s)-4-(aminomethyl)cyclo-hexyl)-N2-(1-methylcyclopentyl)-N8-(4-(trifluoromethyl)phenyl)-9H-purine-2,8-diamine | 489.4 | A | A | |

TABLE 1-continued

| Cpd #A- | Structure | Name | MH+ | T. congo Act. | T. vivax Act. | T. evansi Act. |
|---|---|---|---|---|---|---|
| 17 | 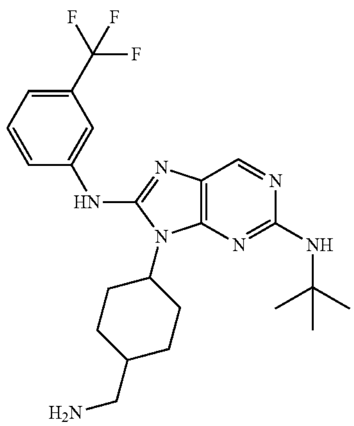 [SMILES: CC(C)(C)Nc1ncc2nc(Nc3cccc(C(F)(F)F)c3)n(C3CCC(CN)CC3)c2n1] | 9-((1r,4r)-4-(aminomethyl)cyclohexyl)-N2-tert-butyl-N8-(3-(trifluoromethyl)phenyl)-9H-purine-2,8-diamine | 462.2 | C | C | |
| 18 | 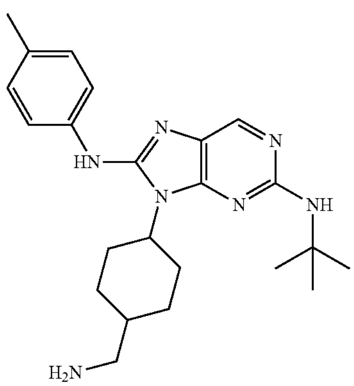 [SMILES: Cc1ccc(Nc2nc3cnc(NC(C)(C)C)nc3n2C2CCC(CN)CC2)cc1] | 9-((1r,4r)-4-(aminomethyl)cyclohexyl)-N2-tert-butyl-N8-p-tolyl-9H-purine-2,8-diamine | 408.4 | A | B | |
| 19 | 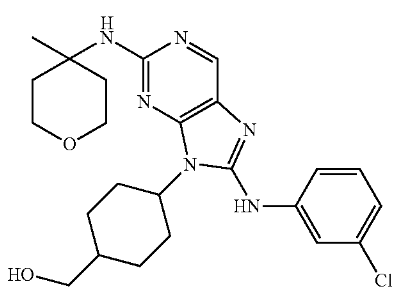 [SMILES: CC1(Nc2ncc3nc(Nc4cccc(Cl)c4)n(C4CCC(CO)CC4)c3n2)CCOCC1] | ((1s,4s)-4-(8-(3-chlorophenylamino)-2-(4-methyltetrahydro-2H-pyran-4-ylamino)-9H-purin-9-yl)cyclohexyl)methanol | 471.2 | A | B | |
| 20 | 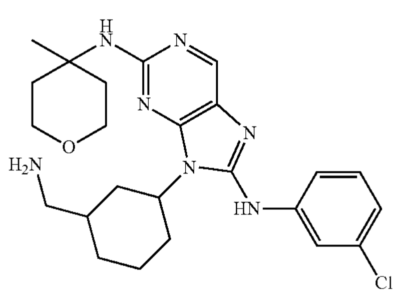 [SMILES: CC1(Nc2ncc3nc(Nc4cccc(Cl)c4)n(C4CCCC(CN)C4)c3n2)CCOCC1] | 9-((1R,3S)-3-(aminomethyl)cyclohexyl)-N8-(3-chlorophenyl)-N2-(4-methyltetrahydro-2H-pyran-4-yl)-9H-purine-2,8-diamine | 470 | A | C | |

TABLE 1-continued

| Cpd #A- | Name | MH+ | T. congo Act. | T. vivax Act. | T. evansi Act. |
|---|---|---|---|---|---|
| 21 | N8-(3-chlorophenyl)-9-((1s,4s)-4-((methylamino)methyl)cyclohexyl)-N2-(4-methyltetrahydro-2H-pyran-4-yl)-9H-purine-2,8-diamine | 484 | C | C | |
| 22 | 9-((1s,4s)-4-(aminomethyl)cyclohexyl)-N2-tert-butyl-N8-(4-(trifluoromethyl)phenyl)-9H-purine-2,8-diamine | 462 | B | A | |
| 23 | 9-((1s,4s)-4-(aminomethyl)cyclohexyl)-N2-tert-pentyl-N8-(4-(trifluoromethyl)phenyl)-9H-purine-2,8-diamine | 476 | A | A | |
| 24 | (1s,4s)-4-(2-(4-methyltetrahydro-2H-pyran-4-ylamino)-8-(3-(trifluoromethyl)phenylamino)-9H-purin-9-yl)cyclohexanecarbonitrile | 500 | B | B | |

TABLE 1-continued

| Cpd #A- | Structure | Name | MH+ | T. congo Act. | T. vivax Act. | T. evansi Act. |
|---|---|---|---|---|---|---|
| 25 | 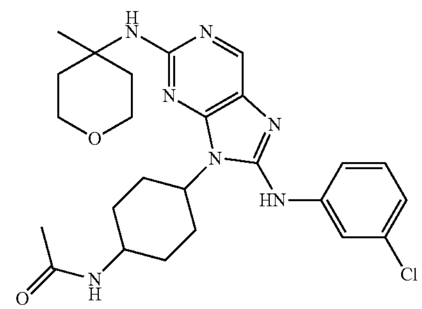 [SMILES: CC(=O)NC1CCC(n2c(Nc3cccc(Cl)c3)nc3cnc(NC4(C)CCOCC4)nc32)CC1] | N-((1s,4s)-4-(8-(3-chlorophenylamino)-2-(4-methyltetrahydro-2H-pyran-4-ylamino)-9H-purin-9-yl)cyclohexyl)acetamide | 498.2 | A | C | |
| 26 | 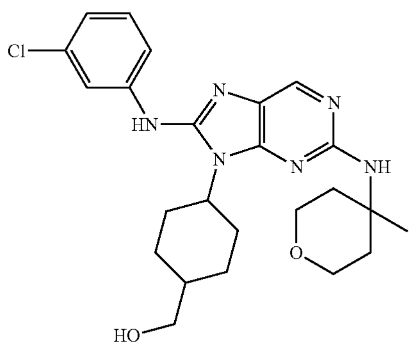 [SMILES: CC1(Nc2ncc3nc(Nc4cccc(Cl)c4)n(C4CCC(CO)CC4)c3n2)CCOCC1] | ((1r,4r)-4-(8-(3-chlorophenylamino)-2-(4-methyltetrahydro-2H-pyran-4-ylamino)-9H-purin-9-yl)cyclohexyl)methanol | 471.2 | B | C | |
| 27 | 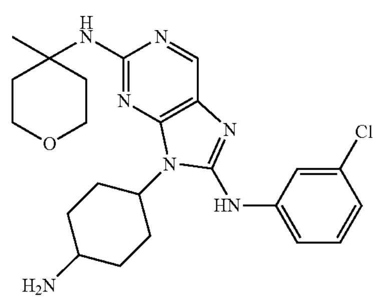 [SMILES: CC1(Nc2ncc3nc(Nc4cccc(Cl)c4)n(C4CCC(N)CC4)c3n2)CCOCC1] | 9-((1s,4s)-4-aminocyclohexyl)-N8-(3-chlorophenyl)-N2-(4-methyltetrahydro-2H-pyran-4-yl)-9H-purine-2,8-diamine | 456.2 | C | C | |
| 28 | 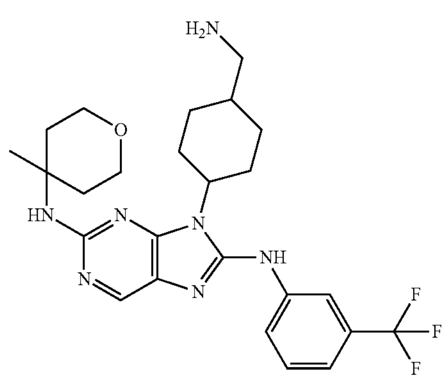 | 9-((1s,4s)-4-(aminomethyl)cyclohexyl)-N2-(4-methyltetrahydro-2H-pyran-4-yl)-N8-(3-(trifluoromethyl)phenyl)-9H-purine-2,8-diamine | 504.2 | C | C | C |

TABLE 1-continued

| Cpd #A- | Structure | Name | MH+ | T. congo Act. | T. vivax Act. | T. evansi Act. |
|---|---|---|---|---|---|---|
| 29 | 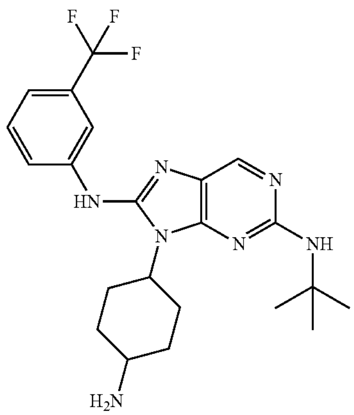 [SMILES: CC(C)(C)Nc1ncc2nc(Nc3cccc(C(F)(F)F)c3)n(C3CCC(N)CC3)c2n1] | 9-((1s,4s)-4-aminocyclohexyl)-N2-tert-butyl-N8-(3-(trifluoromethyl)phenyl)-9H-purine-2,8-diamine | 448.2 | C | C | |
| 30 | 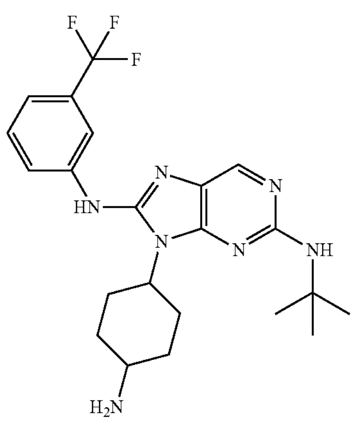 [SMILES: CC(C)(C)Nc1ncc2nc(Nc3cccc(C(F)(F)F)c3)n(C3CCC(N)CC3)c2n1] | 9-((1r,4r)-4-aminocyclohexyl)-N2-tert-butyl-N8-(3-(trifluoromethyl)phenyl)-9H-purine-2,8-diamine | 448.2 | C | C | |
| 31 | 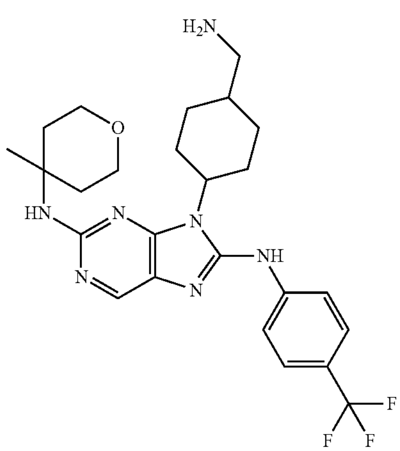 [SMILES: CC1(Nc2ncc3nc(Nc4ccc(C(F)(F)F)cc4)n(C4CCC(CN)CC4)c3n2)CCOCC1] | 9-((1s,4s)-4-(aminomethyl)cyclohexyl)-N2-(4-methyltetrahydro-2H-pyran-4-yl)-N8-(4-(trifluoromethyl)phenyl)-9H-purine-2,8-diamine | 504.2 | B | C | |

TABLE 1-continued

| Cpd #A- | Structure | Name | MH+ | T. congo Act. | T. vivax Act. | T. evansi Act. |
|---|---|---|---|---|---|---|
| 32 | 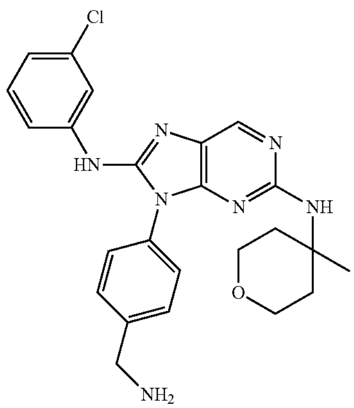 [SMILES: CC1(Nc2ncc3nc(Nc4cccc(Cl)c4)n(-c4ccc(CN)cc4)c3n2)CCOCC1] | 9-(4-(aminomethyl)phenyl)-N8-(3-chlorophenyl)-N2-(4-methyltetrahydro-2H-pyran-4-yl)-9H-purine-2,8-diamine | 464.2 | B | C | |
| 33 | 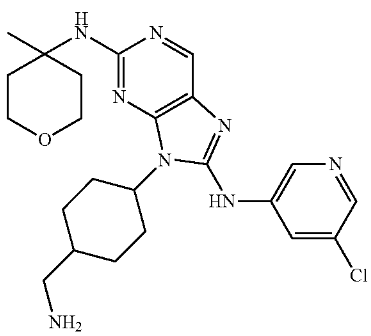 [SMILES: CC1(Nc2ncc3nc(Nc4cncc(Cl)c4)n(C4CCC(CN)CC4)c3n2)CCOCC1] | 9-((1s,4s)-4-(aminomethyl)cyclohexyl)-N8-(5-chloropyridin-3-yl)-N2-(4-methyltetrahydro-2H-pyran-4-yl)-9H-purine-2,8-diamine | 471.2 | B | C | |
| 34 | 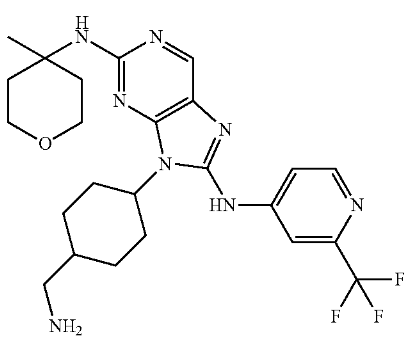 [SMILES: CC1(Nc2ncc3nc(Nc4ccnc(C(F)(F)F)c4)n(C4CCC(CN)CC4)c3n2)CCOCC1] | 9-((1s,4s)-4-(aminomethyl)cyclohexyl)-N2-(4-methyltetrahydro-2H-pyran-4-yl)-N8-(2-(trifluoromethyl)pyridin-4-yl)-9H-purine-2,8-diamine | 505.2 | C | C | C |
| 35 | 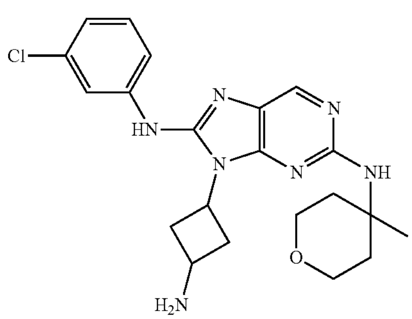 [SMILES: CC1(Nc2ncc3nc(Nc4cccc(Cl)c4)n(C4CC(N)C4)c3n2)CCOCC1] | 9-(3-aminocyclobutyl)-N8-(3-chlorophenyl)-N2-(4-methyltetrahydro-2H-pyran-4-yl)-9H-purine-2,8-diamine | 428.2 | C | C | |

TABLE 1-continued

| Cpd #A- | Structure | Name | MH+ | T. congo Act. | T. vivax Act. | T. evansi Act. |
|---|---|---|---|---|---|---|
| 36 | 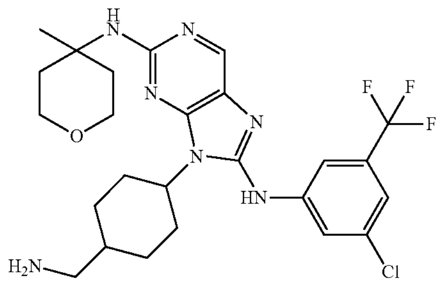 [SMILES: CC1(Nc2ncc3nc(Nc4cc(Cl)cc(C(F)(F)F)c4)n(C4CCC(CN)CC4)c3n2)CCOCC1] | 9-((1s,4s)-4-(aminomethyl)cyclo-hexyl)-N8-(3-chloro-5-(trifluoromethyl)phenyl)-N2-(4-methyltetrahydro-2H-pyran-4-yl)-9H-purine-2,8-diamine | 538.2 | C | C | B |
| 37 | 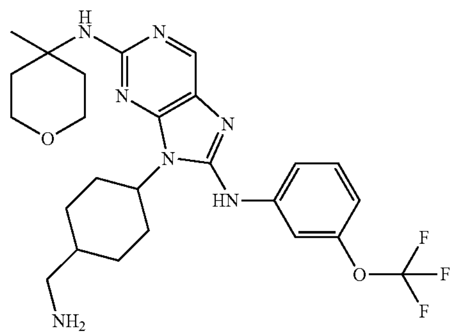 [SMILES: CC1(Nc2ncc3nc(Nc4cccc(OC(F)(F)F)c4)n(C4CCC(CN)CC4)c3n2)CCOCC1] | 9-((1s,4s)-4-(aminomethyl)cyclo-hexyl)-N2-(4-methyltetrahydro-2H-pyran-4-yl)-N8-(3-(trifluoromethoxy)phenyl)-9H-purine-2,8-diamine | 520.2 | C | C | C |
| 38 | 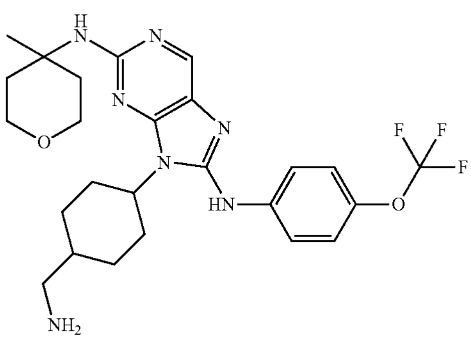 [SMILES: CC1(Nc2ncc3nc(Nc4ccc(OC(F)(F)F)cc4)n(C4CCC(CN)CC4)c3n2)CCOCC1] | 9-((1s,4s)-4-(aminomethyl)cyclo-hexyl)-N2-(4-methyltetrahdro-2H-pyran-4-yl)-N8-(4-(trifluoromethoxy)phenyl)-9H-purine-2,8-diamine | 520.2 | C | C | B |
| 39 | 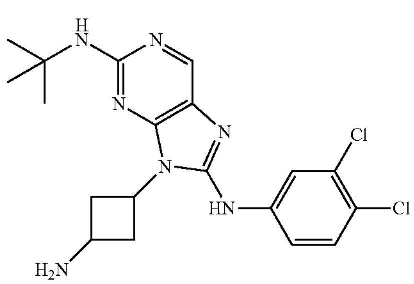 [SMILES: CC(C)(C)Nc1ncc2nc(Nc3ccc(Cl)c(Cl)c3)n(C3CC(N)C3)c2n1] | 9-(3-aminocyclobutyl)-N2-tert-butyl-N8-(3,4-dichlorophenyl)-9H-purine-2,8-diamine | 420.2 | A | B | |

TABLE 1-continued

| Cpd #A- | Structure | Name | MH+ | T. congo Act. | T. vivax Act. | T. evansi Act. |
|---|---|---|---|---|---|---|
| 40 | 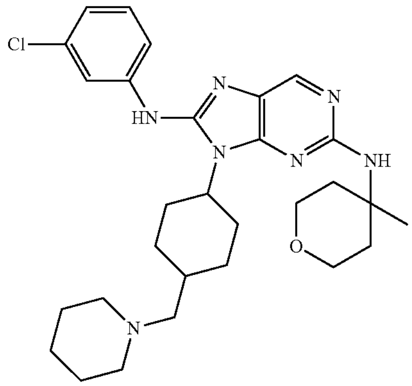 [SMILES: CC1(Nc2ncc3nc(Nc4cccc(Cl)c4)n(C4CCC(CN5CCCCC5)CC4)c3n2)CCOCC1] | N8-(3-chlorophenyl)-N2-(4-methyltetrahydro-2H-pyran-4-yl)-9-((1s,4s)-4-(piperidin-1-ylmethyl)cyclohexyl)-9H-purine-2,8-diamine | 538.2 | C | C | C |
| 41 | 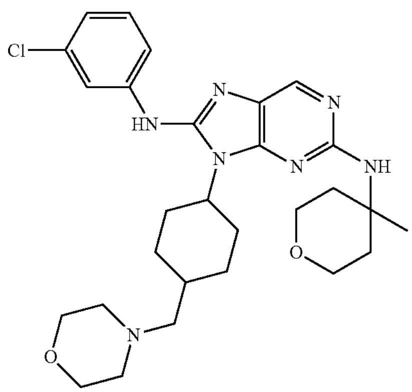 [SMILES: CC1(Nc2ncc3nc(Nc4cccc(Cl)c4)n(C4CCC(CN5CCOCC5)CC4)c3n2)CCOCC1] | N8-(3-chlorophenyl)-N2-(4-methyltetrahydro-2H-pyran-4-yl)-9-((1s,4s)-4-(morpholinomethyl)cyclohexyl)-9H-purine-2,8-diamine | 540.2 | C | A | |
| 42 | 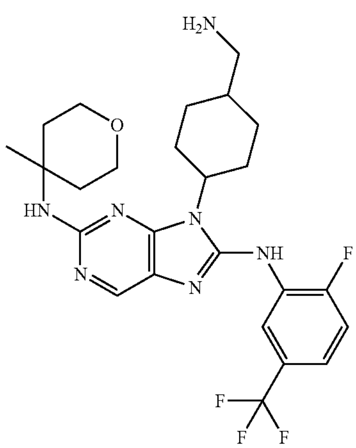 [SMILES: CC1(Nc2ncc3nc(Nc4cc(C(F)(F)F)ccc4F)n(C4CCC(CN)CC4)c3n2)CCOCC1] | 9-((1s,4s)-4-(aminomethyl)cyclohexyl)-N8-(2-fluoro-5-(trifluoromethyl)phenyl)-N2-(4-methyltetrahydro-2H-pyran-4-yl)-9H-purine-2,8-diamine | 522.2 | C | C | |

TABLE 1-continued

| Cpd #A- | Structure | Name | MH+ | T. congo Act. | T. vivax Act. | T. evansi Act. |
|---|---|---|---|---|---|---|
| 43 | 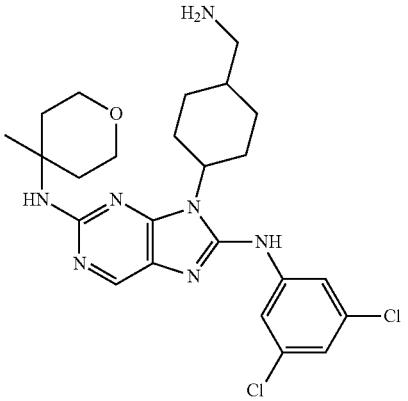 [SMILES: CC1(Nc2ncc3nc(Nc4cc(Cl)cc(Cl)c4)n(C4CCC(CN)CC4)c3n2)CCOCC1] | 9-((1s,4s)-4-(aminomethyl)cyclo-hexyl)-N8-(3,5-dichlorophenyl)-N2-(4-methyltetrahydro-2H-pyran-4-yl)-9H-purine-2,8-diamine | 504.2 | C | C | C |
| 44 | 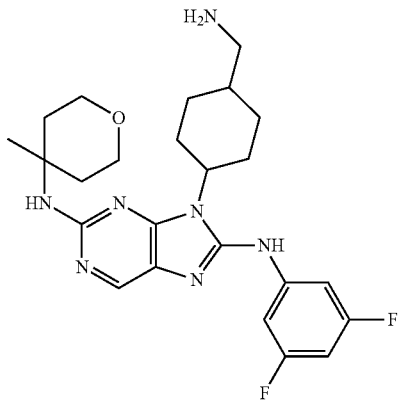 [SMILES: CC1(Nc2ncc3nc(Nc4cc(F)cc(F)c4)n(C4CCC(CN)CC4)c3n2)CCOCC1] | 9-((1s,4s)-4-(aminomethyl)cyclo-hexyl)-N8-(3,5-difluorophenyl)-N2-(4-methyltetrahydro-2H-pyran-4-yl)-9H-purine-2,8-diamine | 472.2 | C | C | C |
| 45 | 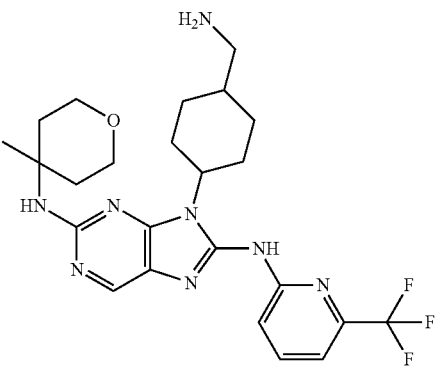 [SMILES: CC1(Nc2ncc3nc(Nc4cccc(C(F)(F)F)n4)n(C4CCC(CN)CC4)c3n2)CCOCC1] | 9-((1s,4s)-4-(aminomethyl)cyclo-hexyl)-N2-(4-methyltetrahydro-2H-pyran-4-yl)-N8-(6-(trifluoromethyl)pyridin-2-yl)-9H-purine-2,8-diamine | 503.2 (M − H); 505.2 | B | B | |
| 46 | 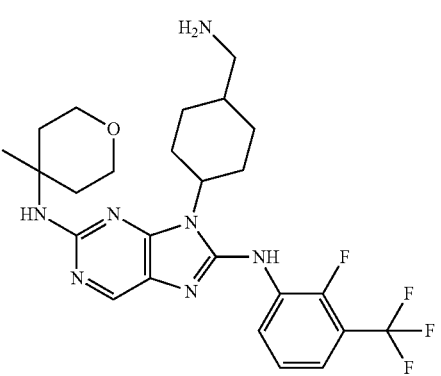 [SMILES: CC1(Nc2ncc3nc(Nc4cccc(C(F)(F)F)c4F)n(C4CCC(CN)CC4)c3n2)CCOCC1] | 9-((1s,4s)-4-(aminomethyl)cyclo-hexyl)-N8-(2-fluoro-3-(trifluoromethyl)phenyl)-N2-(4-methyltetrahydro-2H-pyran-4-yl)-9H-purine-2,8-diamine | 522.2 | C | C | C |

TABLE 1-continued

| Cpd #A- | Structure | Name | MH+ | T. congo Act. | T. vivax Act. | T. evansi Act. |
|---|---|---|---|---|---|---|
| 47 | 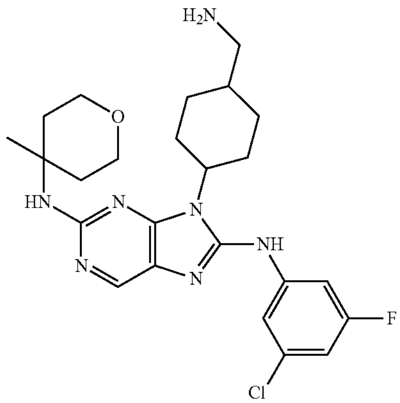 [SMILES: CC1(Nc2ncc3nc(Nc4cc(F)cc(Cl)c4)n(C4CCC(CN)CC4)c3n2)CCOCC1] | 9-((1s,4s)-4-(aminomethyl)cyclo-hexyl)-N8-(3-chloro-5-fluorophenyl)-N2-(4-methyltetrahydro-2H-pyran-4-yl)-9H-purine-2,8-diamine | 488.2 | C | C | C |
| 48 | 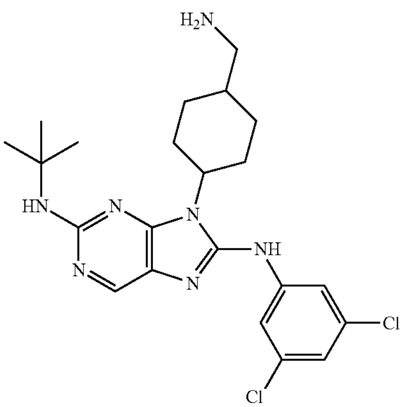 [SMILES: CC(C)(C)Nc1ncc2nc(Nc3cc(Cl)cc(Cl)c3)n(C3CCC(CN)CC3)c2n1] | 9-((1s,4s)-4-(aminomethyl)cyclo-hexyl)-N2-tert-butyl-N8-(3,5-dichlorophenyl)-9H-purine-2,8-diamine | 462.2 | B | A | |
| 49 | 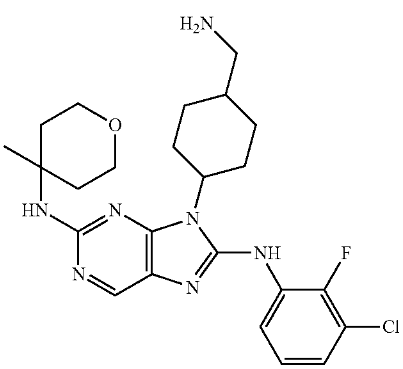 [SMILES: CC1(Nc2ncc3nc(Nc4cccc(Cl)c4F)n(C4CCC(CN)CC4)c3n2)CCOCC1] | 9-((1s,4s)-4-(aminomethyl)cyclo-hexyl)-N8-(3-chloro-2-fluorophenyl)-N2-(4-methyltetrahydro-2H-pyran-4-yl)-9H-purine-2,8-diamine | 488.2 | C | C | C |
| 50 | 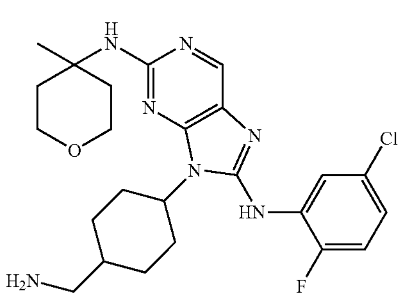 [SMILES: CC1(Nc2ncc3nc(Nc4cc(Cl)ccc4F)n(C4CCC(CN)CC4)c3n2)CCOCC1] | 9-((1s,4s)-4-(aminomethyl)cyclo-hexyl)-N8-(5-chloro-2-fluorophenyl)-N2-(4-methyltetrahydro-2H-pyran-4-yl)-9H-purine-2,8-diamine | 488.2 | C | | C |

TABLE 1-continued

| Cpd #A- | Structure | Name | MH+ | T. congo Act. | T. vivax Act. | T. evansi Act. |
|---|---|---|---|---|---|---|
| 51 | 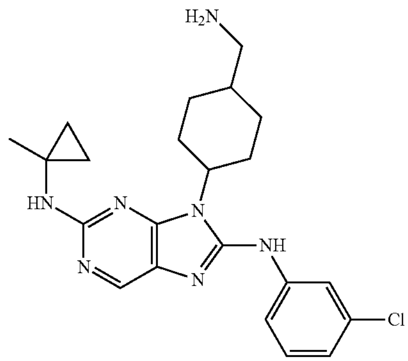 [SMILES: CC1(Nc2ncc3nc(Nc4cccc(Cl)c4)n(C4CCC(CN)CC4)c3n2)CC1] | 9-((1s,4s)-4-(aminomethyl)cyclo-hexyl)-N8-(3-chlorophenyl)-N2-(1-methylcyclopropyl)-9H-purine-2,8-diamine | 426.2 | C | C | |
| 52 | 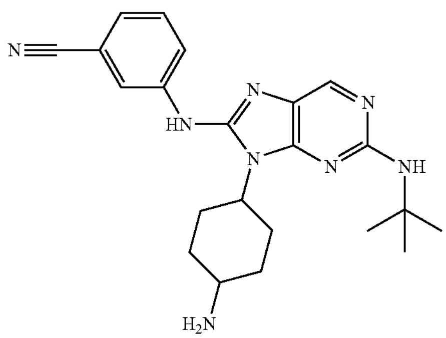 [SMILES: CC(C)(C)Nc1ncc2nc(Nc3cccc(C#N)c3)n(C3CCC(N)CC3)c2n1] | 3-(9-((1r,4r)-4-aminocyclohexyl)-2-(tert-butylamino)-9H-purin-8-ylamino)benzonitrile | 405.4 | A | C | |
| 53 | 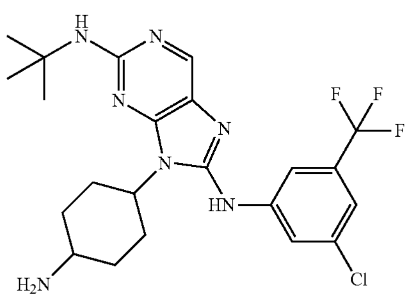 [SMILES: CC(C)(C)Nc1ncc2nc(Nc3cc(Cl)cc(C(F)(F)F)c3)n(C3CCC(N)CC3)c2n1] | 9-((1r,4r)-4-aminocyclohexyl)-N2-tert-butyl-N8-(3-chloro-5-(trifluoromethyl)phenyl)-9H-purine-2,8-diamine | 482.2 | B | B | |
| 54 | 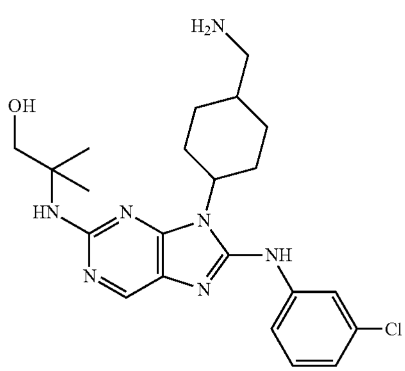 [SMILES: CC(C)(CO)Nc1ncc2nc(Nc3cccc(Cl)c3)n(C3CCC(CN)CC3)c2n1] | 2-(9-((1s,4s)-4-(aminomethyl)cyclo-hexyl)-8-(3-chlorophenylamino)-9H-purin-2-ylamino)-2-methylpropan-1-ol | 444.2 | B | C | |

TABLE 1-continued

| Cpd #A- | Structure | Name | MH+ | T. congo Act. | T. vivax Act. | T. evansi Act. |
|---|---|---|---|---|---|---|
| 55 | 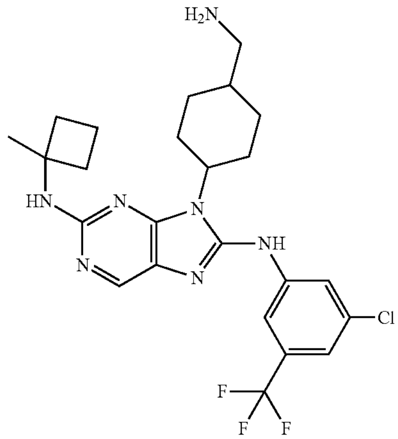 [SMILES: CC1(Nc2ncc3nc(Nc4cc(Cl)cc(C(F)(F)F)c4)n(C4CCC(CN)CC4)c3n2)CCC1] | 9-((1s,4s)-4-(aminomethyl)cyclohexyl)-N8-(3-chloro-5-(trifluoromethyl)phenyl)-N2-(1-methylcyclobutyl)-9H-purine-2,8-diamine | 508.2 | B | A | |
| 56 | 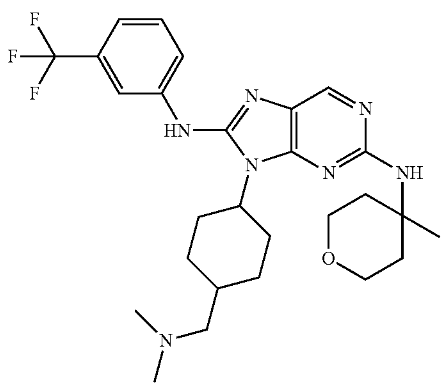 [SMILES: CN(C)CC1CCC(n2c(Nc3cccc(C(F)(F)F)c3)nc3cnc(NC4(C)CCOCC4)nc32)CC1] | 9-((1s,4s)-4-((dimethylamino)methyl)cyclohexyl)-N2-(4-methyltetrahydro-2H-pyran-4-yl)-N8-(3-(trifluoromethyl)phenyl)-9H-purine-2,8-diamine | 532.4 | C | | C |
| 57 | 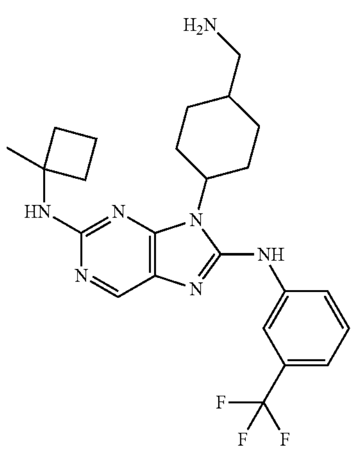 [SMILES: CC1(Nc2ncc3nc(Nc4cccc(C(F)(F)F)c4)n(C4CCC(CN)CC4)c3n2)CCC1] | 9-((1s,4s)-4-(aminomethyl)cyclohexyl)-N2-(1-methylcyclobutyl)-N8-(3-(trifluoromethyl)phenyl)-9H-purine-2,8-diamine | 473.2 | C | | |

TABLE 1-continued

| Cpd #A- | Structure | Name | MH+ | T. congo Act. | T. vivax Act. | T. evansi Act. |
|---|---|---|---|---|---|---|
| 58 | 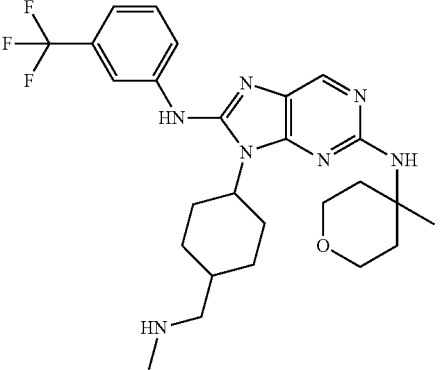 [SMILES: CNCC1CCC(n2c(Nc3cccc(C(F)(F)F)c3)nc3cnc(NC4(C)CCOCC4)nc32)CC1] | 9-((1s,4s)-4-((methylamino)methyl)cyclohexyl)-N2-(4-methyltetrahydro-2H-pyran-4-yl)-N8-(3-(trifluoromethyl)phenyl)-9H-purine-2,8-diamine | 518.4 | C | C | |
| 59 | 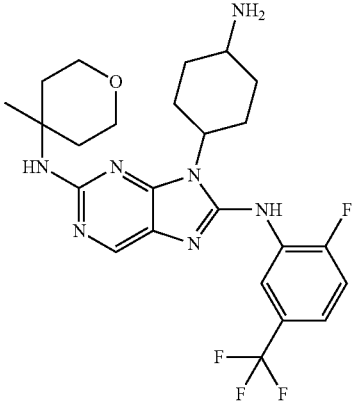 [SMILES: CC1(Nc2ncc3nc(Nc4cc(C(F)(F)F)ccc4F)n(C4CCC(N)CC4)c3n2)CCOCC1] | 9-(4-aminocyclohexyl)-N8-(2-fluoro-5-(trifluoromethyl)phenyl)-N2-(4-methyltetrahydro-2H-pyran-4-yl)-9H-purine-2,8-diamine | 508.2 | B | C | |
| 60 | 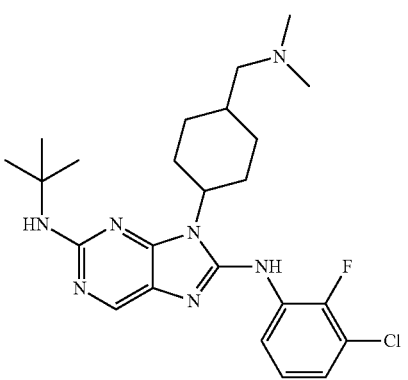 [SMILES: CN(C)CC1CCC(n2c(Nc3cccc(Cl)c3F)nc3cnc(NC(C)(C)C)nc32)CC1] | N2-tert-butyl-N8-(3-chloro-2-fluorophenyl)-9-((1s,4s)-4-((dimethylamino)methyl)cyclohexyl)-9H-purine-2,8-diamine | 475.2 | C | C | |

TABLE 1-continued

| Cpd #A- | Structure | Name | MH+ | T. congo Act. | T. vivax Act. | T. evansi Act. |
|---|---|---|---|---|---|---|
| 61 | 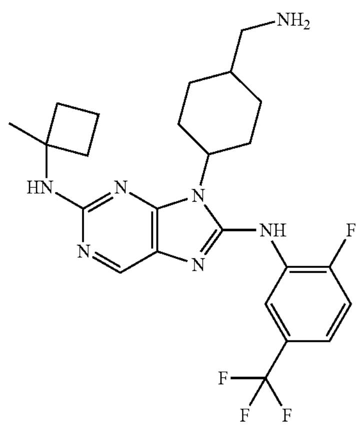 [SMILES: CC1(Nc2ncc3nc(Nc4cc(C(F)(F)F)ccc4F)n(C4CCC(CN)CC4)c3n2)CCC1] | 9-((1s,4s)-4-(aminomethyl)cyclohexyl)-N8-(2-fluoro-5-(trifluoromethyl)phenyl)-N2-(1-methylcyclobutyl)-9H-purine-2,8-diamine | 492.2 | B | C | |

TABLE 2

| Cpd #B- | Structure | Name | MH+ | T. congo Act. | T. vivax Act. | T. evansi Act. |
|---|---|---|---|---|---|---|
| 1 | 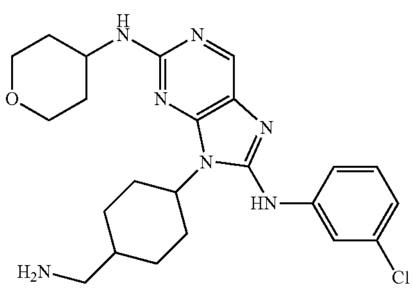 [SMILES: NCC1CCC(n2c(Nc3cccc(Cl)c3)nc3cnc(NC4CCOCC4)nc32)CC1] | 9-((1s,4s)-4-(aminomethyl)cyclohexyl)-N8-(3-chlorophenyl)-N2-(tetrahydro-2H-pyran-4-yl)-9H-purine-2,8-diamine | 456.2 | B | A | |
| 2 | 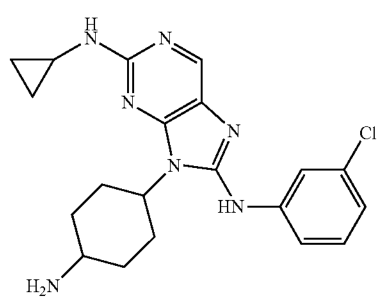 [SMILES: NC1CCC(n2c(Nc3cccc(Cl)c3)nc3cnc(NC4CC4)nc32)CC1] | 9-((1r,4r)-4-aminocyclohexyl)-N8-(3-chlorophenyl)-N2-cyclopropyl-9H-purine-2,8-diamine | 368.2 | A | C | |
| 3 | 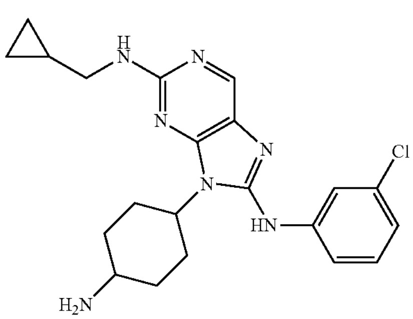 [SMILES: NC1CCC(n2c(Nc3cccc(Cl)c3)nc3cnc(NCC4CC4)nc32)CC1] | 9-((1r,4r)-4-aminocyclohexyl)-N8-(3-chlorophenyl)-N2-(cyclopropylmethyl)-9H-purine-2,8-diamine | 412.2 | A | A | |

TABLE 2-continued

| Cpd #B- | Structure | Name | MH+ | T. congo Act. | T. vivax Act. | T. evansi Act. |
|---|---|---|---|---|---|---|
| 4 | 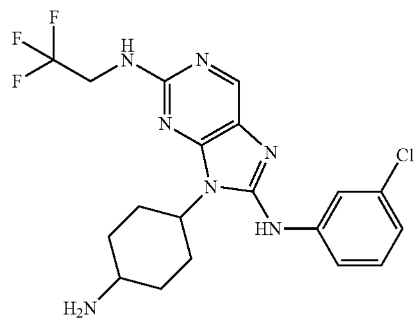 [SMILES: NC1CCC(n2c(Nc3cccc(Cl)c3)nc3cnc(NCC(F)(F)F)nc32)CC1] | 9-((1r,4r)-4-aminocyclohexyl)-N8-(3-chlorophenyl)-N2-(2,2,2-trifluoroethyl)-9H-purine-2,8-diamine | 440.2 | A | C | |
| 5 | 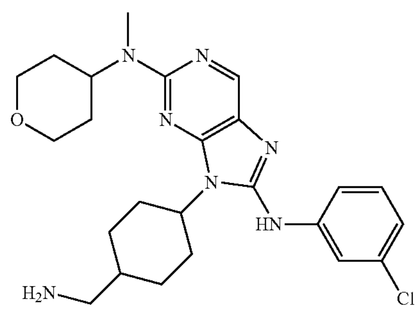 [SMILES: CN(c1ncc2nc(Nc3cccc(Cl)c3)n(C3CCC(CN)CC3)c2n1)C1CCOCC1] | 9-((1s,4s)-4-(aminomethyl)cyclohexyl)-N8-(3-chlorophenyl)-N2-methyl-N2-(tetrahydro-2H-pyran-4-yl)-9H-purine-2,8-diamine | 470 | A | C | |
| 6 | 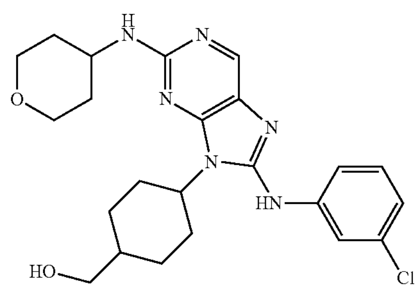 [SMILES: OCC1CCC(n2c(Nc3cccc(Cl)c3)nc3cnc(NC4CCOCC4)nc32)CC1] | ((1s,4s)-4-(8-(3-chlorophenylamino)-2-(tetrahydro-2H-pyran-4-ylamino)-9H-purin-9-yl)cyclohexyl)methanol | 457 | A | A | |
| 7 | 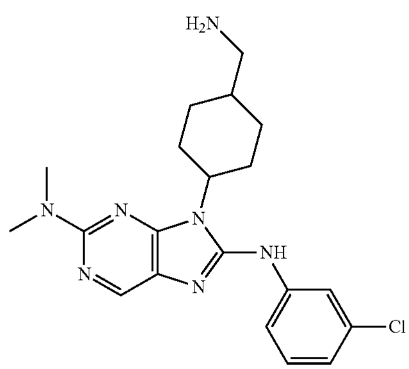 [SMILES: CN(C)c1ncc2nc(Nc3cccc(Cl)c3)n(C3CCC(CN)CC3)c2n1] | 9-((1s,4s)-4-(aminomethyl)cyclohexyl)-N8-(3-chlorophenyl)-N2,N2-dimethyl-9H-purine-2,8-diamine | 400.2 | A | C | |
| 8 | 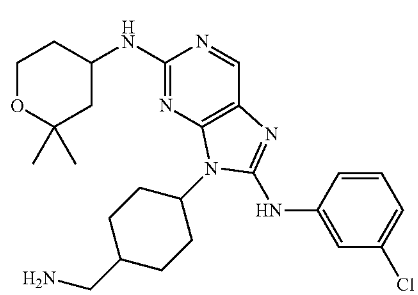 [SMILES: CC1(C)CC(Nc2ncc3nc(Nc4cccc(Cl)c4)n(C4CCC(CN)CC4)c3n2)CCO1] | 9-((1s,4s)-4-(aminomethyl)cyclohexyl)-N8-(3-chlorophenyl)-N2-(2,2-dimethyltetrahydro-2H-pyran-4-yl)-9H-purine-2,8-diamine | 484.2 | B | C | |

TABLE 2-continued

| Cpd #B- | Structure | Name | MH+ | T. congo Act. | T. vivax Act. | T. evansi Act. |
|---|---|---|---|---|---|---|
| 9 | 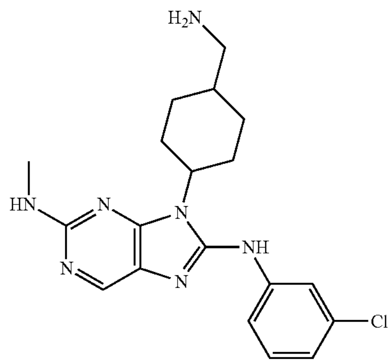 [SMILES: CNc1ncc2nc(Nc3cccc(Cl)c3)n(C3CCC(CN)CC3)c2n1] | 9-((1s,4s)-4-(aminomethyl)cyclohexyl)-N8-(3-chlorophenyl)-N2-methyl-9H-purine-2,8-diamine | 386.2 | A | C | |
| 10 | 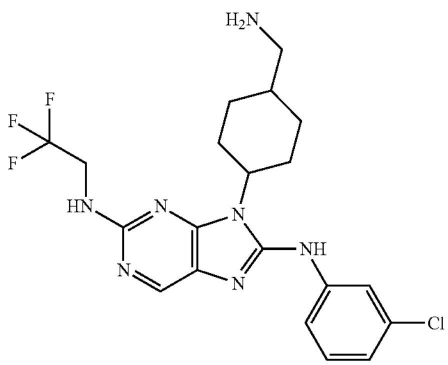 [SMILES: NCC1CCC(n2c(Nc3cccc(Cl)c3)nc3cnc(NCC(F)(F)F)nc32)CC1] | 9-((1s,4s)-4-(aminomethyl)cyclohexyl)-N8-(3-chlorophenyl)-N2-(2,2,2-trifluoroethyl)-9H-purine-2,8-diamine | 454.2 | A | C | |
| 11 | 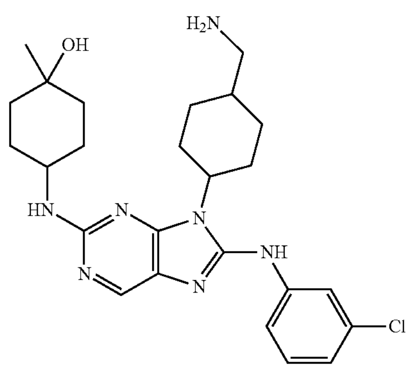 [SMILES: CC1(O)CCC(Nc2ncc3nc(Nc4cccc(Cl)c4)n(C4CCC(CN)CC4)c3n2)CC1] | 4-(9-((1s,4s)-4-(aminomethyl)cyclohexyl)-8-(3-chlorophenylamino)-9H-purin-2-ylamino)-1-methylcyclohexanol | 484.4 | A | C | |
| 12 | 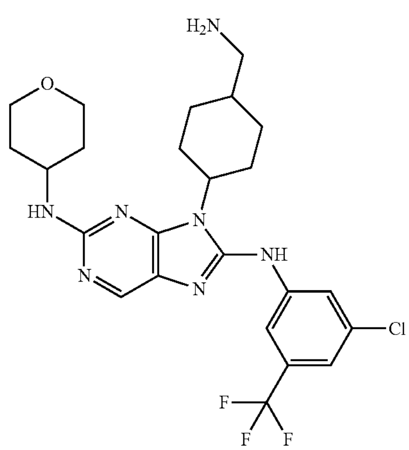 [SMILES: NCC1CCC(n2c(Nc3cc(Cl)cc(C(F)(F)F)c3)nc3cnc(NC4CCOCC4)nc32)CC1] | 9-((1s,4s)-4-(aminomethyl)cyclohexyl)-N8-(3-chloro-5-(trifluoromethyl)phenyl)-N2-(tetrahydro-2H-pyran-4-yl)-9H-purine-2,8-diamine | 524.2 | A | A | |

TABLE 2-continued

| Cpd #B- | Structure | Name | MH+ | T. congo Act. | T. vivax Act. | T. evansi Act. |
|---|---|---|---|---|---|---|
| 13 | 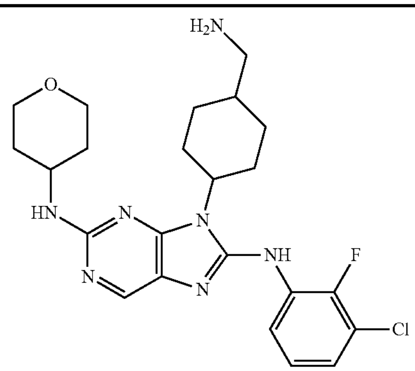 | 9-((1s,4s)-4-(aminomethyl)cyclohexyl)-N8-(3-chloro-2-fluorophenyl)-N2-(tetrahydro-2H-pyran-4-yl)-9H-purine-2,8-diamine | 474.2 | C | | |
| 14 | 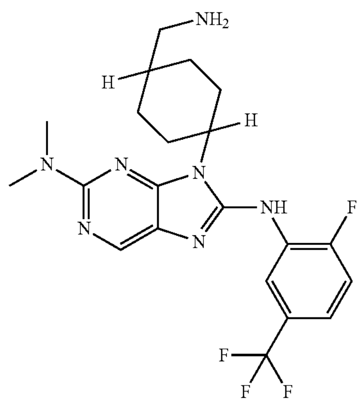 [SMILES: CN(C)c1ncc2nc(Nc3cc(C(F)(F)F)ccc3F)n(C3CCC(CN)CC3)c2n1] | 9-((1s,4s)-4-(aminomethyl)cyclohexyl)-N8-(2-fluoro-5-(trifluoromethyl)phenyl)-N2,N2-dimethyl-9H-purine-2,8-diamine | 452.2 | A | C | |
| 15 | 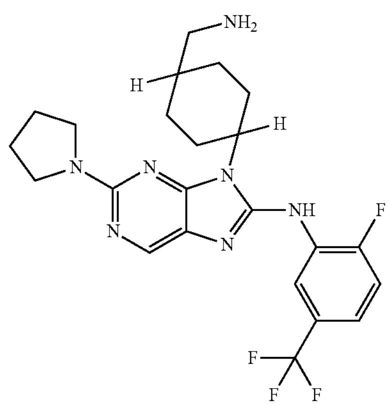 [SMILES: NCC1CCC(n2c(Nc3cc(C(F)(F)F)ccc3F)nc3cnc(N4CCCC4)nc32)CC1] | 9-((1s,4s)-4-(aminomethyl)cyclohexyl)-N-(2-fluoro-5-(trifluoromethyl)phenyl)-2-(pyrrolidin-1-yl)-9H-purin-8-amine | 478.2 | B | C | |
| 16 | 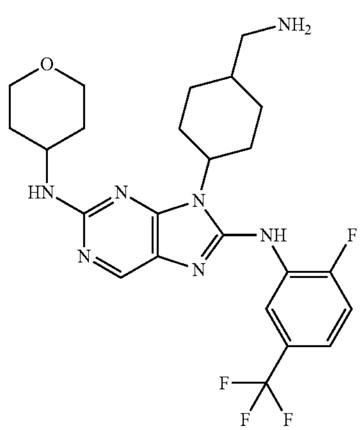 [SMILES: NCC1CCC(n2c(Nc3cc(C(F)(F)F)ccc3F)nc3cnc(NC4CCOCC4)nc32)CC1] | 9-((1s,4s)-4-(aminomethyl)cyclohexyl)-N8-(2-fluoro-5-(trifluoromethyl)phenyl)-N2-(tetrahydro-2H-pyran-4-yl)-9H-purine-2,8-diamine | 508.2 | A | C | |

TABLE 2-continued

| Cpd #B- | Structure | Name | MH+ | T. congo Act. | T. vivax Act. | T. evansi Act. |
|---|---|---|---|---|---|---|
| 17 | 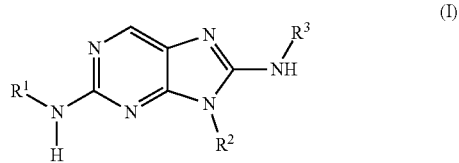 | 9-((1s,4s)-4-(aminomethyl)cyclohexyl)-N8-(5-chloro-2-fluorophenyl)-N2-(tetrahydro-2H-pyran-4-yl)-9H-purine-2,8-diamine | 475.2 | C | C | |

A number of references have been cited, the disclosures of which are incorporated herein by reference in their entirety.

What is claimed is:

1. A method for the treatment of trypanosomosis, trypanosomiasis, or leishmaniasis, the method comprising administering to a subject having trypanosomosis, trypanosomiasis, or leishmaniasis an effective amount of a compound of formula (I):

(I)

or a pharmaceutically acceptable salt, tautomer, isotopologue, or stereoisomer thereof, wherein:
$R^1$ is $CR^{1a}R^{1b}R^{1c}$, wherein each of $R^{1a}$, $R^{1b}$ and $R^{1c}$ is independently $(C_{1-4})$alkyl, or $(C_{1-4})$alkyl(OR); or $R^{1a}$ and $R^{1b}$ and the carbon to which they are attached form a 3-6 membered cycloalkyl or 3-6 membered heterocyclyl, and $R^{1c}$ is $(C_{1-4})$alkyl;
$R^2$ is cycloalkyl or aryl, substituted with at least one $NR_2$, OR, CN, NRC(O)R, $CH_2OR$, $CH_2NR_2$, $CH_2NRCOR$, $CH_2NRCOOR'$, or heterocyclylalkyl;
$R^3$ is phenyl or pyridyl, optionally substituted with at least one halogen, CN, $(C_{1-2})$alkyl, or $O(C_{1-2})$alkyl, wherein the alkyl is optionally fluorinated;
R is H or $(C_{1-4})$ alkyl; and
R' is $(C_{1-4})$alkyl.

2. The method of claim 1, wherein $R^1$ is $CR^{1a}R^{1b}R^{1c}$, wherein each of $R^{1a}$, $R^{1b}$ and $R^{1c}$ is independently $(C_{1-2})$alkyl.

3. The method of claim 1, wherein $R^1$ is t-butyl, $C(CH_3)_2CH_2CH_3$, or $C(CH_3)_2CH_2OH$.

4. The method of claim 1, wherein $R^1$ is $CR^{1a}R^{1b}R^{1c}$, and wherein $R^{1a}$ and $R^{1b}$ and the carbon to which they are attached form a 3-6 membered cycloalkyl or 3-6 membered heterocyclyl, and $R^{1c}$ is $(C_{1-4})$alkyl.

5. The method of claim 4, wherein $R^{1a}$ and $R^{1b}$ and the carbon to which they are attached form a cyclopropyl, cyclobutyl, cyclohexyl, or tetrahydropyranyl.

6. The method of claim 4, wherein $R^{1c}$ is $CH_3$.

7. The method of claim 1, wherein $R^1$ is 1-methylcyclopropyl, 1-methylcyclobutyl, 1-methylcyclpentyl or 1-methyl-tetrahydropyranyl.

8. The method of claim 1, wherein $R^2$ is $(C_{3-7})$cycloalkyl, substituted with at least one $NR_2$, OR, CN, NRC(O)R, $CH_2OR$, $CH_2NR_2$, $CH_2NRC(O)R$, $CH_2NRC(O)OR'$ or heterocyclylalkyl.

9. The method of claim 8, wherein $R^2$ is cyclobutyl, cyclopentyl, or cyclohexyl.

10. The method of claim 8, wherein $R^2$ is substituted with at least one $NH_2$, $NHCH_3$, $N(CH_3)_2$, OH, $OCH_3$, CN, $NHC(O)CH_3$, $N(CH_3)C(O)CH_3$, $CH_2OH$, $CH_2OCH_3$, $CH_2NH_2$, $CH_2NHCH_3$, $CH_2N(CH_3)_2$, $CH_2NHC(O)CH_3$, $CH_2N(CH_3)C(O)CH_3$, $CH_2NHC(O)OCH_3$, $CH_2N(CH_3)C(O)OCH_3$, $CH_2$-piperidyl, or $CH_2$-morpholinyl.

11. The method of claim 8, wherein $R^2$ is cyclohexyl, substituted with $NH_2$, OH, CN, $NHC(O)CH_3$, $CH_2OH$, $CH_2NH_2$, $CH_2NHCH_3$, $CH_2N(CH_3)_2$, $CH_2NHC(O)CH_3$, $CH_2NHC(O)OCH_3$, $CH_2$-piperidyl, or $CH_2$-morpholinyl.

12. The method of claim 1, wherein $R^2$ is aryl, substituted with at least one $NR_2$, OR, CN, NRC(O)R, $CH_2OR$, $CH_2NR_2$, $CH_2NRCOR$, or $CH_2NRCOOR'$.

13. The method of claim 12, wherein $R^2$ is phenyl, substituted with at least one $NH_2$, $NHCH_3$, $N(CH_3)_2$, OH, $OCH_3$, CN, $NHC(O)CH_3$, $N(CH_3)C(O)CH_3$, $CH_2OH$, $CH_2OCH_3$, $CH_2NH_2$, $CH_2NHCH_3$, $CH_2N(CH_3)_2$, $CH_2NHC(O)CH_3$, $CH_2N(CH_3)C(O)CH_3$, $CH_2NHC(O)OCH_3$, or $CH_2N(CH_3)C(O)OCH_3$.

14. The method of claim 12, wherein $R^2$ is phenyl, substituted with $CH_2NH_2$.

15. The method of claim 1, wherein $R^3$ is phenyl substituted with at least one halogen, fluorinated $(C_{1-2})$alkyl, or O-fluorinated$(C_{1-2})$alkyl.

16. The method of claim 15, wherein $R^3$ is substituted with at least one F, Cl, $CHF_2$, $CF_3$, or $OCF_3$.

17. The method of claim 15, wherein $R^3$ is meta-substituted phenyl.

18. The method of claim 1, wherein $R^3$ is pyridyl, substituted with at least one halogen, fluorinated $(C_{1-2})$alkyl, or O-fluorinated$(C_{1-2})$alkyl.

19. The method of claim 18, wherein $R^3$ is substituted with at least one F, Cl, $CHF_2$, $CF_3$, or $OCF_3$.

20. The method of claim 18, wherein $R^3$ is substituted with at least one Cl, or $CF_3$.

21. The method of claim 1, wherein the compound is:

9-((1s,4s)-4-(aminomethyl)cyclohexyl)-N8-(3-chlorophenyl)-N2-(4-methyltetrahydro-2H-pyran-4-yl)-9H-purine-2,8-diamine, 9-((1s,4s)-4-(aminomethyl)cyclohexyl)-N8-(3-chlorophenyl)-N2-(1-methylcyclobutyl)-9H-purine-2,8-diamine, 9-((1s,4s)-4-(aminomethyl)cyclohexyl)-N8-(3-chlorophenyl)-N2-tert-pentyl-9H-purine-2,8-diamine, 9-((1s,4s)-4-(aminomethyl)cyclohexyl)-N8-(3-chlorophenyl)-N2-(1-methylcyclopentyl)-9H-purine-2,8-diamine, N8-(3-chlorophenyl)-9-((1s,4s)-4-((dimethylamino)methyl)cyclohexyl)-N2-(4-methyltetrahydro-2H-pyran-4-yl)-9H-purine-2,8-diamine, 9-((1s,4s)-4-(aminomethyl)cyclohexyl)-N2-tert-butyl-N8-(pyridin-2-yl)-9H-purine-2,8-diamine, 9-((1r,4r)-4-(aminomethyl)cyclohexyl)-N8-(3-chlorophenyl)-N2-(4-methyltetrahydro-2H-pyran-4-yl)-9H-purine-2,8-diamine, 9-((1s,4s)-4-(aminomethyl)cyclohexyl)-N2-(4-methyltetrahydro-2H-pyran-4-yl)-N8-(pyridin-2-yl)-9H-purine-2,8-diamine, 9-((1s,4s)-4-(aminomethyl)cyclohexyl)-N8-(2,3-difluorophenyl)-N2-(4-methyltetrahydro-2H-pyran-4-yl)-9H-purine-2,8-diamine, (1s,4s)-4-(8-(3-chlorophenylamino)-2-(1-methylcyclopentylamino)-9H-purin-9-yl)cyclohexanol, N-(((1s,4s)-4-(8-(3-chlorophenylamino)-2-(4-methyltetrahydro-2H-pyran-4-ylamino)-9H-purin-9-yl)cyclohexyl)methyl)acetamide, 9-((1s,4s)-4-(aminomethyl)cyclohexyl)-N2-(1-methylcyclopentyl)-N8-(3-(trifluoromethyl)phenyl)-9H-purine-2,8-diamine, 9-((1s,4s)-4-(aminomethyl)cyclohexyl)-N2-tert-pentyl-N8-(3-(trifluoromethyl)phenyl)-9H-purine-2,8-diamine, methyl ((1s,4s)-4-(8-(3-chlorophenylamino)-2-(4-methyltetrahydro-2H-pyran-4-ylamino)-9H-purin-9-yl)cyclohexyl)methylcarbamate, 9-((1s,4s)-4-(aminomethyl)cyclohexyl)-N2-tert-butyl-N8-(3-(trifluoromethyl)phenyl)-9H-purine-2,8-diamine, 9-((1s,4s)-4-(aminomethyl)cyclohexyl)-N2-(1-methylcyclopentyl)-N8-(4-(trifluoromethyl)phenyl)-9H-purine-2,8-diamine, 9-((1r,4r)-4-(aminomethyl)cyclohexyl)-N2-tert-butyl-N8-(3-(trifluoromethyl)phenyl)-9H-purine-2,8-diamine, 9-((1 r,4r)-4-(aminomethyl)cyclohexyl)-N2-tert-butyl-N8-p-tolyl-9H-purine-2,8-diamine, ((1s,4 s)-4-(8-(3-chlorophenylamino)-2-(4-methyltetrahydro-2H-pyran-4-ylamino)-9H-purin-9-yl)cyclohexyl)methanol, 9-((1R, 3 S)-3-(aminomethyl)cyclohexyl)-N8-(3-chlorophenyl)-N2-(4-methyltetrahydro-2H-pyran-4-yl)-9H-purine-2,8-diamine, N8-(3-chlorophenyl)-9-((1s,4s)-4-((methylamino)methyl)cyclohexyl)-N2-(4-methyltetrahydro-2H-pyran-4-yl)-9H-purine-2,8-diamine, 9-((1s,4s)-4-(aminomethyl)cyclohexyl)-N2-tert-butyl-N8-(4-(trifluoromethyl)phenyl)-9H-purine-2,8-diamine, 9-((1s,4s)-4-(aminomethyl)cyclohexyl)-N2-tert-pentyl-N8-(4-(trifluoromethyl)phenyl)-9H-purine-2,8-diamine, (1s,4s)-4-(2-(4-methyltetrahydro-2H-pyran-4-ylamino)-8-(3-(trifluoromethyl)phenylamino)-9H-purin-9-yl)cyclohexanecarbonitrile, N-((1s,4s)-4-(8-(3-chlorophenylamino)-2-(4-methyltetrahydro-2H-pyran-4-ylamino)-9H-purin-9-yl)cyclohexyl)acetamide, ((1r,4r)-4-(8-(3-chlorophenylamino)-2-(4-methyltetrahydro-2H-pyran-4-ylamino)-9H-purin-9-yl)cyclohexyl)methanol, 9-((1s,4s)-4-aminocyclohexyl)-N8-(3-chlorophenyl)-N2-(4-methyltetrahydro-2H-pyran-4-yl)-9H-purine-2,8-diamine, 9-((1s,4s)-4-(aminomethyl)cyclohexyl)-N2-(4-methyltetrahydro-2H-pyran-4-yl)-N8-(3-(trifluoromethyl)phenyl)-9H-purine-2,8-diamine, 9-((1s,4s)-4-aminocyclohexyl)-N2-tert-butyl-N8-(3-(trifluoromethyl)phenyl)-9H-purine-2,8-diamine, 9-((1r,4r)-4-aminocyclohexyl)-N2-tert-butyl-N8-(3-(trifluoromethyl)phenyl)-9H-purine-2,8-diamine, 9-((1s,4s)-4-(aminomethyl)cyclohexyl)-N2-(4-methyltetrahydro-2H-pyran-4-yl)-N8-(4-(trifluoromethyl)phenyl)-9H-purine-2,8-diamine, 9-(4-(aminomethyl)phenyl)-N8-(3-chlorophenyl)-N2-(4-methyltetrahydro-2H-pyran-4-yl)-9H-purine-2,8-diamine, 9-((1s,4s)-4-(aminomethyl)cyclohexyl)-N8-(5-chloropyridin-3-yl)-N2-(4-methyltetrahydro-2H-pyran-4-yl)-9H-purine-2,8-diamine, 9-((1s,4s)-4-(aminomethyl)cyclohexyl)-N2-(4-methyltetrahydro-2H-pyran-4-yl)-N8-(2-(trifluoromethyl)pyridin-4-yl)-9H-purine-2,8-diamine, 9-(3-aminocyclobutyl)-N8-(3-chlorophenyl)-N2-(4-methyltetrahydro-2H-pyran-4-yl)-9H-purine-2,8-diamine, 9-((1s,4s)-4-(aminomethyl)cyclohexyl)-N8-(3-chloro-5-(trifluoromethyl)phenyl)-N2-(4-methyltetrahydro-2H-pyran-4-yl)-9H-purine-2,8-diamine, 9-((1s,4s)-4-(aminomethyl)cyclohexyl)-N2-(4-methyltetrahydro-2H-pyran-4-yl)-N8-(3-(trifluoromethoxy)phenyl)-9H-purine-2,8-diamine, 9-((1s,4s)-4-(aminomethyl)cyclohexyl)-N2-(4-methyltetrahydro-2H-pyran-4-yl)-N8-(4-(trifluoromethoxy)phenyl)-9H-purine-2,8-diamine, 9-(3-aminocyclobutyl)-N2-tert-butyl-N8-(3,4-dichlorophenyl)-9H-purine-2,8-diamine, N8-(3-chlorophenyl)-N2-(4-methyltetrahydro-2H-pyran-4-yl)-9-((1s,4s)-4-(piperidin-1-ylmethyl)cyclohexyl)-9H-purine-2,8-diamine, N8-(3-chlorophenyl)-N2-(4-methyltetrahydro-2H-pyran-4-yl)-9-((1s,4s)-4-(morpholinomethyl)cyclohexyl)-9H-purine-2,8-diamine, 9-((1s,4s)-4-(aminomethyl)cyclohexyl)-N8-(2-fluoro-5-(trifluoromethyl)phenyl)-N2-(4-methyltetrahydro-2H-pyran-4-yl)-9H-purine-2,8-diamine, 9-((1s,4s)-4-(aminomethyl)cyclohexyl)-N8-(3,5-dichlorophenyl)-N2-(4-methyltetrahydro-2H-pyran-4-yl)-9H-purine-2,8-diamine, 9-((1s,4s)-4-(aminomethyl)cyclohexyl)-N8-(3,5-difluorophenyl)-N2-(4-methyltetrahydro-2H-pyran-4-yl)-9H-purine-2,8-diamine, 9-((1s,4s)-4-(aminomethyl)cyclohexyl)-N2-(4-methyltetrahydro-2H-pyran-4-yl)-N8-(6-(trifluoromethyl)pyridin-2-yl)-9H-purine-2,8-diamine, 9-((1s,4s)-4-(aminomethyl)cyclohexyl)-N8-(2-fluoro-3-(trifluoromethyl)phenyl)-N2-(4-methyltetrahydro-2H-pyran-4-yl)-9H-purine-2,8-diamine, 9-((1s,4s)-4-(aminomethyl)cyclohexyl)-N8-(3-chloro-5-fluorophenyl)-N2-(4-methyltetrahydro-2H-pyran-4-yl)-9H-purine-2,8-diamine,
9-((1s,4s)-4-(aminomethyl)cyclohexyl)-N2-tert-butyl-N8-(3,5-dichlorophenyl)-9H-purine-2,8-diamine,
9-((1s,4s)-4-(aminomethyl)cyclohexyl)-N8-(3-chloro-2-fluorophenyl)-N2-(4-methyltetrahydro-2H-pyran-4-yl)-9H-purine-2,8-diamine,
9-((1s,4s)-4-(aminomethyl)cyclohexyl)-N8-(5-chloro-2-fluorophenyl)-N2-(4-methyltetrahydro-2H-pyran-4-yl)-9H-purine-2,8-diamine,
9-((1s,4s)-4-(aminomethyl)cyclohexyl)-N8-(3-chlorophenyl)-N2-(1-methylcyclopropyl)-9H-purine-2,8-diamine,
3-(9-((1r,4r)-4-aminocyclohexyl)-2-(tert-butylamino)-9H-purin-8-ylamino)benzonitrile,
9-((1r,4r)-4-aminocyclohexyl)-N2-tert-butyl-N8-(3-chloro-5-(trifluoromethyl)phenyl)-9H-purine-2,8-diamine,
2-(9-((1s,4s)-4-(aminomethyl)cyclohexyl)-8-(3-chlorophenylamino)-9H-purin-2-ylamino)-2-methylpropan-1-ol,
9-((1s,4s)-4-(aminomethyl)cyclohexyl)-N8-(3-chloro-5-(trifluoromethyl)phenyl)-N2-(1-methylcyclobutyl)-9H-purine-2,8-diamine,
9-((1s,4s)-4-((dimethylamino)methyl)cyclohexyl)-N2-(4-methyltetrahydro-2H-pyran-4-yl)-N8-(3-(trifluoromethyl)phenyl)-9H-purine-2,8-diamine,
9-((1s,4s)-4-(aminomethyl)cyclohexyl)-N2-(1-methylcyclobutyl)-N8-(3-(trifluoromethyl)phenyl)-9H-purine-2,8-diamine,
9-((1s,4s)-4-((methylamino)methyl)cyclohexyl)-N2-(4-methyltetrahydro-2H-pyran-4-yl)-N8-(3-(trifluoromethyl)phenyl)-9H-purine-2,8-diamine,
9-(4-aminocyclohexyl)-N8-(2-fluoro-5-(trifluoromethyl)phenyl)-N2-(4-methyltetrahydro-2H-pyran-4-yl)-9H-purine-2,8-diamine,
N2-tert-butyl-N8-(3-chloro-2-fluorophenyl)-9-((1s,4s)-4-((dimethylamino)methyl)cyclohexyl)-9H-purine-2,8-diamine, or
9-((1s,4s)-4-(aminomethyl)cyclohexyl)-N8-(2-fluoro-5-(trifluoromethyl)phenyl)-N2-(1-methylcyclobutyl)-9H-purine-2,8-diamine,
or a pharmaceutically acceptable salt, tautomer, isotopologue, or stereoisomer thereof.

22. A method for the treatment of trypanosomosis, trypanosomiasis, or leishmaniasis, the method comprising administering to a subject having trypanosomosis, trypanosomiasis, or leishmaniasis an effective amount of a compound, wherein the compound is:
9-((1s,4s)-4-(aminomethyl)cyclohexyl)-N8-(3-chlorophenyl)-N2-(tetrahydro-2H-pyran-4-yl)-9H-purine-2,8-diamine,
9-((1r,4r)-4-aminocyclohexyl)-N8-(3-chlorophenyl)-N2-cyclopropyl-9H-purine-2,8-diamine,
9-((1r,4r)-4-aminocyclohexyl)-N8-(3-chlorophenyl)-N2-(cyclopropylmethyl)-9H-purine-2,8-diamine,
9-((1r,4r)-4-aminocyclohexyl)-N8-(3-chlorophenyl)-N2-(2,2,2-trifluoroethyl)-9H-purine-2,8-diamine,
9-((1s,4s)-4-(aminomethyl)cyclohexyl)-N8-(3-chlorophenyl)-N2-methyl-N2-(tetrahydro-2H-pyran-4-yl)-9H-purine-2,8-diamine,
((1s,4s)-4-(8-(3-chlorophenylamino)-2-(tetrahydro-2H-pyran-4-ylamino)-9H-purin-9-yl)cyclohexyl)methanol,
9-((1s,4s)-4-(aminomethyl)cyclohexyl)-N8-(3-chlorophenyl)-N2,N2-dimethyl-9H-purine-2,8-diamine,
9-((1s,4s)-4-(aminomethyl)cyclohexyl)-N8-(3-chlorophenyl)-N2-(2,2-dimethyltetrahydro-2H-pyran-4-yl)-9H-purine-2,8-diamine,
9-((1s,4s)-4-(aminomethyl)cyclohexyl)-N8-(3-chlorophenyl)-N2-methyl-9H-purine-2,8-diamine,
9-((1s,4s)-4-(aminomethyl)cyclohexyl)-N8-(3-chlorophenyl)-N2-(2,2,2-trifluoroethyl)-9H-purine-2,8-diamine,
4-(9-((1s,4s)-4-(aminomethyl)cyclohexyl)-8-(3-chlorophenylamino)-9H-purin-2-ylamino)-1-methylcyclohexanol,
9-((1s,4s)-4-(aminomethyl)cyclohexyl)-N8-(3-chloro-5-(trifluoromethyl)phenyl)-N2-(tetrahydro-2H-pyran-4-yl)-9H-purine-2,8-diamine,
9-((1s,4s)-4-(aminomethyl)cyclohexyl)-N8-(3-chloro-2-fluorophenyl)-N2-(tetrahydro-2H-pyran-4-yl)-9H-purine-2,8-diamine,
9-((1s,4s)-4-(aminomethyl)cyclohexyl)-N8-(2-fluoro-5-(trifluoromethyl)phenyl)-N2,N2-dimethyl-9H-purine-2,8-diamine,
9-((1s,4s)-4-(aminomethyl)cyclohexyl)-N-(2-fluoro-5-(trifluoromethyl)phenyl)-2-(pyrrolidin-1-yl)-9H-purin-8-amine,
9-((1s,4s)-4-(aminomethyl)cyclohexyl)-N8-(2-fluoro-5-(trifluoromethyl)phenyl)-N2-(tetrahydro-2H-pyran-4-yl)-9H-purine-2,8-diamine, or
9-((1s,4s)-4-(aminomethyl)cyclohexyl)-N8-(5-chloro-2-fluorophenyl)-N2-(tetrahydro-2H-pyran-4-yl)-9H-purine-2,8-diamine,
or a pharmaceutically acceptable salt, tautomer, isotopologue, or stereoisomer thereof.

23. The method of claim 1, wherein the trypanosomosis or trypanosomiasis is caused by *T. avium, T. boissoni, T. brucei, T. b. gambiense, T. b. rhodesiense, T. b. evansi, T. carassii, T. cruzi, T. congolense, T. equinum, T. equiperdum, T. evansi, T. godfreyi, T. hosei, T. levisi, T. melophagium, T. parroti, T. percae, T. rangeli, T. rotatorium, T. rugosae, T. sergenti, T. simiae, T. sinipercae, T. suis, T. theileri, T. triglae* or *T. vivax*.

24. The method of claim 1, wherein the trypanosomosis is Animal trypanosomosis or African animal trypanosomosis (AAT).

25. The method of claim 24, further comprising the administration of a second active agent.

26. The method of claim 25, wherein the second active agent is at least one of diminazene di-aceturate, quinapyramine sulphate, melarsomine, isometamidium, homidium chloride or bromide.

27. The method of claim 1, wherein the trypanosomiasis is Human African trypanosomiasis (HAT).

28. The method of claim 27, further comprising the administration of a second active agent.

29. The method of claim 28, wherein the second active agent is pentamidine, suramin, melarsoprol, eflornithine or nifurtimox.

30. The method of claim 1, wherein the trypanosomiasis is American trypanosomiasis or Chagas disease.

31. The method of claim 30, further comprising the administration of a second active agent.

32. The method of claim 31, wherein the second active agent is benznidazole or nifurtimox.

33. The method of claim 1, wherein leishmaniasis is treated or prevented.

34. The method of claim 33, further comprising the administration of a second active agent.

35. The method of claim 34, wherein the second active agent is pentavalent antimonials, Amphotericin B deoxycholate, pentamidine, paromomycin sulfate, miltefosine or ketoconazole.

* * * * *